US005670675A

United States Patent [19]

Kempf et al.

[11] Patent Number: 5,670,675
[45] Date of Patent: *Sep. 23, 1997

[54] RETROVIRAL PROTEASE INHIBITING COMPOUNDS

[75] Inventors: Dale J. Kempf, Lake Villa; Daniel W. Norbeck, Lindenhurst, both of Ill.

[73] Assignee: Abbott Laboratories, Abbott Park, Ill.

[ * ] Notice: The term of this patent shall not extend beyond the expiration date of Pat. No. 5,552,558.

[21] Appl. No.: 409,365

[22] Filed: Mar. 23, 1995

Related U.S. Application Data

[62] Division of Ser. No. 358,648, Dec. 19, 1994, which is a continuation of Ser. No. 164,979, Feb. 7, 1993, abandoned, which is a continuation of Ser. No. 880,729, May 8, 1992, abandoned, which is a division of Ser. No. 518,730, May 9, 1990, Pat. No. 5,142,056, which is a continuation-in-part of Ser. No. 456,124, Dec. 22, 1989, abandoned, which is a continuation-in-part of Ser. No. 405,604, Sep. 8, 1989, abandoned, which is a continuation-in-part of Ser. No. 355,945, May 23, 1989, abandoned.

[51] Int. Cl.$^6$ .................................................... C07D 303/36
[52] U.S. Cl. ............................................... 549/552; 549/553
[58] Field of Search ....................................... 549/553, 552

[56] References Cited

U.S. PATENT DOCUMENTS

| 5,142,056 | 8/1992 | Kempf et al. | 546/265 |
| 5,354,866 | 10/1994 | Kempf et al. | 546/265 |

FOREIGN PATENT DOCUMENTS

| 337714 | 10/1989 | European Pat. Off. |
| 346847 | 12/1989 | European Pat. Off. |
| 357332 | 3/1990 | European Pat. Off. |
| 356223 | 4/1990 | European Pat. Off. |
| 361341 | 4/1990 | European Pat. Off. |
| 362002 | 4/1990 | European Pat. Off. |
| WO89/10752 | 11/1989 | WIPO |
| WO90/00399 | 1/1990 | WIPO |

OTHER PUBLICATIONS

Moore, Biochem. Biophy. Res. Commun. 159, 420 (1989).
Billich, J. Biol. Chem. 263 1790S (1988).
Richards, FEBS Lett., 247, 113 (1989).
Miller, Science 246 1148 (1989).
Meek, Nature 343 90 (1990).
McQuade, Science 247 454 (1990).

*Primary Examiner*—Jane Fan
*Attorney, Agent, or Firm*—Steven R. Crowley

[57] ABSTRACT

A retroviral protease inhibiting compound of the formula
A-X-B
or a pharmaceutically acceptable salt, prodrug or ester thereof, wherein X is a linking group;

A is
(1) substituted amino,
(2) substituted carbonyl,
(3) functionalized imino,
(4) functionalized alkyl,
(5) functionalized acyl,
(6) functionalized heterocyclic or
(7) functionalized (heterocyclic)alkyl; and B is
(1) substituted carbonyl independently defined as herein,
(2) substituted amino independently defined as herein,
(3) functionalized imino independently defined as herein,
(4) functionalized alkyl independently defined as herein,
(5) functionalized acyl independently defined as herein,
(6) functionalized heterocyclic independently defined as herein or
(7) functionalized (heterocyclic)alkyl independently defined as herein.

4 Claims, No Drawings

RETROVIRAL PROTEASE INHIBITING COMPOUNDS

This is a division of U.S. patent application Ser. No. 08/358,648, filed Dec. 19, 1994, which is a continuation of U.S. patent application Ser. No. 08/164,979, filed Dec. 7, 1993, now abandoned which is a continuation of U.S. patent application Ser. No. 07/880,729, filed May 8, 1992, now abandoned which is a division of U.S. patent application Ser. No. 07/518,730, filed May 9, 1990, now U.S. Pat. No. 5,142,056 which is a continuation-in-part of U.S. patent application Ser. No. 07/456,124, filed Dec. 22, 1989, now abandoned which is a continuation-in-part of U.S. patent application Ser. No. 07/405,604, filed Sep. 8, 1989, now abandoned which is a continuation-in-part of U.S. patent application Ser. No. 355,945, filed May 23, 1989 now abandoned.

TECHNICAL FIELD

This invention was made with Government support under contract number AI27220-01 awarded by the National Institute of Allergy and Infectious Diseases. The Government has certain rights in this invention.

The present invention relates to novel compounds and a composition and method for inhibiting retroviral proteases and in particular for inhibiting human immunodeficiency virus (HIV) protease, a composition and method for treating a retroviral infection and in particular an HIV infection, processes for making such compounds and synthetic intermediates employed in these processes.

BACKGROUND ART

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease should provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit vital DNA synthesis. Current treatments for AIDS (Dagani, Chem. Eng. News, Nov. 23, 1987 pp. 41–49) involve administration of compounds such as 2',3'-dideoxycytidine, trisodium phosphonoformate, ammonium 21-tungsto-9-antimoniate, 1-beta-D-ribofuranosyl-1,2,4-triazole-3-carboxamide, 3'-azido-3'-deoxythymidine, and adriamycin that inhibit vital DNA synthesis; compounds such as AL-721 and polymannoacetate which may prevent HIV from penetrating the host cell; and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

Inhibitors of HIV protease are disclosed by Moore, Biochem. Biophys. Res. Commun., 159 420 (1989); Billich, J. Biol. Chem., 263 1790S (1988); Richards, FEBS Lett., 247 113 (1989); Miller, Science 246 1149 (1989); Meek, Nature 343 90 (1990); McQuade, Science 247 454 (1990); Sigal, et al., European Patent Application No. EP0337714, published Oct. 18, 1989; Kempf, et al., PCT Patent Application No. WO89/10752, published Nov. 16, 1989; Molling, et al., European Patent Application No. EP354522, published Feb. 14, 1990; Sigal, et al., European Patent Application No. EP357332, published Mar. 7, 1990; Handa, et al., European Patent Application No. EP346847, published Dec. 20, 1989; Desolms, et al, European Patent Application No. EP356223, published Feb. 28, 1990; Schirlin, et al., European Patent Application No. EP362002, published Apr. 4, 1990; Dreyer, et al., PCT Patent Application No. WO90/00399, published Jan. 25, 1990; and Hanko, et al., European Patent Application No. EP361341, published Apr. 4, 1990.

U.S. Pat. No. 4,652,552 discloses methyl ketone derivatives of tetrapeptides as inhibitors of vital proteases. U.S. Pat. No. 4,644,055 discloses halomethylketone derivatives of peptides as inhibitors of viral proteases.

None of the references mentioned above disclose or suggest the invention claimed herein.

The compounds (A-X-B) shown in Table 1 are disclosed in the following list of references. None of these references disclose or suggest the use of these compounds as inhibitors of retroviral protease or as antiviral agents.

1. S. Apparao, et al., Synthesis, 896 (1987).
2. A. Padwa, et al., J. Chem. Soc. Perkin Trans. I, 2639 (1988).
3. M. McKervey, et al., Tet. Let., 23 2509 (1982).
4. M. Fujiwara, et al., Chem. Abstr. 91:149446.
5. C. Piantadosi, et al., J. Med. Chem., 19 222 (1976).
6. M. Midland, et al., J. Org. Chem., 39 732 (1974).
7. R. Dybas, et al., U.S. Pat. No. 4,172,094, published Oct. 23, 1979.
8. A. Hosomi, et al., Chem. Pharm. Bull., 36 3736 (1988).
9. K. Taniguchi, et al., Chem. Abstr. 108:29541.
10. R Freidlina, et al., Chem. Abstr. 57:16464.

11. T Morikawa, Chem. Abstr. 54:19588.
12. M Sorokin, et al., Chem. Abstr. 108:111518.
13. G Ostroumova, Chem. Abstr. 72:56187.
14. T Kamijo, et al., Chem. Pharm. Bull., 31 4189 (1983).
15. T Takeda, et al., Bull. Chem. Soc. Jpn., 57 1863 (1984).
16. S. Kukalenko, et al., Chem. Abstr. 78:71621.
17. K. Ito, et al., Chem. Pharm. Bull., 27 1691 (1979).
18. H. Kleiner, Chem. Abstr. 73:45598.
19. G. Rawson, et al., Tetrahedron, 26 5653 (1970).
20. M. Il'ina, et al., Chem. Abstr. 70:37885.
21. E. Regel, et al., U.S. Pat. No. 4,618,619, issued Oct. 21, 1986.
22. V. Plakhov, et al., Chem. Abstr. 73:30312.
23. K. Dathe, et al., Chem. Abstr. 84:73203.
24. W. Wegener, et al., Chem. Abstr. 77:101763.
25. E. Mukhametzyanova, et al., Chem. Abstr. 71:39096.
26. K. Petrov, et al., Chem. Abstr. 74:141977.
27. H. Gilman, et al., Chem. Abstr. 89:172760.
28. T. Hosokawa, et al., Bull. Chem. Soc. Jpn., 58 194 (1985).
29. G. Olah, et al., Synthesis, 221 (1980).
(In the table "Ph" represents phenyl).

TABLE 1

| A | X | B |
|---|---|---|
| PhOCH$_2$— | —C(O)— | PhSCH$_2$— |
| PhS(O)$_2$CH$_2$— | —C(O)— | PhCH$_2$CH$_2$— |
| PhCH$_2$CH$_2$— | —C(O)— | PhSCH$_2$— |
| PhS(O)$_2$CH$_2$— | —C(O)— | PhS(O)$_2$CH$_2$— |
| PhOCH$_2$— | —C(O)— | PhOCH$_2$— |
| PhS(O)CH$_2$— | —C(O)— | PhCH$_2$CH$_2$— |
| PhSCH$_2$— | —C(O)— | PhSCH$_2$— |
| PhCH$_2$CH$_2$— | —C(O)— | PhCH$_2$CH$_2$— |
| PhCH$_2$CH$_2$— | —CH(OH)— | PhSCH$_2$— |
| PhOCH$_2$— | —CH(OH)— | PhOCH$_2$— |
| PhS(O)$_2$CH$_2$— | —CH(OH)— | PhS(O)$_2$CH$_2$— |
| PhCH$_2$CH$_2$— | —CH(NH$_2$)— | PhCH$_2$CH$_2$— |
| PhNHCH$_2$— | —CH(OH)— | PhOCH$_2$— |
| PhNHCH$_2$— | —CH(OH)— | PhNHCH$_2$— |
| PhCH$_2$CH$_2$— | —CH(OH)— | PhCH$_2$CH$_2$— |
| PhCH$_2$CH$_2$— | —CH(OH)— | PhSCH$_2$— |
| PhOCH$_2$— | —CH(OH)— | PhSCH$_2$— |
| PhNHCH$_2$— | —CH(OH)— | PhSCH$_2$— |
| PhSCH$_2$— | —CH(OH)— | PhSCH$_2$— |
| PhCH$_2$CH$_2$— | —N(OH)— | PhCH$_2$CH$_2$— |
| PhSCH$_2$— | —N(OH)— | PhSCH$_2$— |
| PhCH$_2$CH$_2$— | —P(OH)(H)— | PhCH$_2$CH$_2$— |
| PhS(O)$_2$CH$_2$— | —N(OH)— | PhS(O)$_2$CH$_2$— |
| PhNHCH$_2$— | —P(O)(OH)— | PhNHCH$_2$— |
| PhOCH$_2$— |  | PhOCH$_2$— |
| PhCH$_2$CH$_2$— | —S(O)$_2$— | PhCH$_2$CH$_2$— |
| PhS(O)$_2$CH$_2$— | —S(O)$_2$— | PhS(O)$_2$CH$_2$— |
| PhSCH$_2$— | —P(O)(OH)— | PhSCH$_2$— |
| PhOCH$_2$— | —P(O)(OH)— | PhOCH$_2$— |
| PhCH$_2$CH$_2$— | —P(O)(OH)— | PhCH$_2$CH$_2$— |
| PhNHCH$_2$— | —P(O)(OH)— | PhNHCH$_2$— |
| PhCH$_2$CH$_2$— | —S(O)— | PhCH$_2$CH$_2$— |
| PhCH$_2$CH$_2$— | —C(=N—OH)— | PhCH$_2$CH$_2$— |

DISCLOSURE OF THE INVENTION

In accordance with the present invention, there are retroviral protease inhibiting compounds of the formula:

A-X-B    (I)

or a pharmaceutically acceptable salt, prodrug or ester thereof.

X is

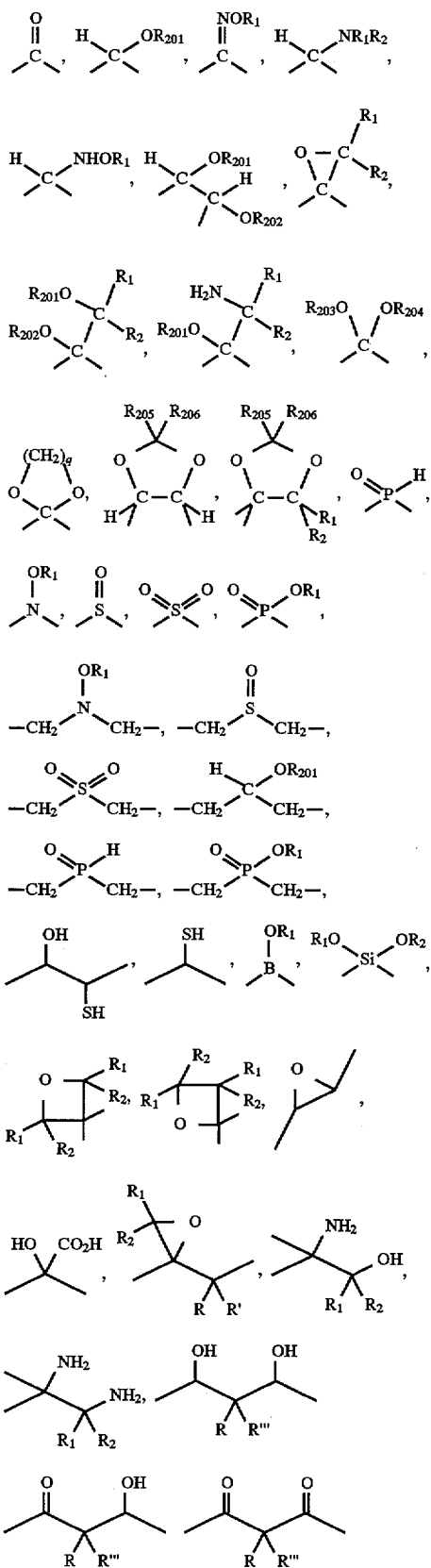

-continued

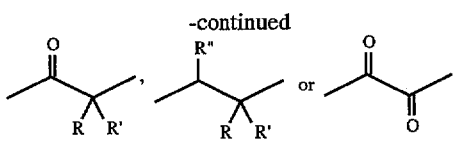

wherein $R_1$ and $R_2$ are independently selected from
(1) hydrogen,
(2) loweralkyl,
(3) hydroxyalkyl and
(4) alkoxyalkyl; and $R_{201}$ and $R_{202}$ are independently selected from
(1) hydrogen,
(2) alkoxyalkyl,
(3) thioalkoxyalkyl and
(4) alkoxyalkoxyalkyl;

$R_{203}$ is loweralkyl;
$R_{204}$ is loweralkyl;
$R_{205}$ and $R_{206}$ are independently selected from
(1) hydrogen
(2) loweralkyl
(3) alkoxyalkyl;

R is hydrogen or halogen;
R' is hydrogen, halogen, loweralkyl, —$NH_2$, —NH(loweralkyl) or —$OR_{206}$ wherein $R_{206}$ is defined as above;
R" is —$NH_2$, —NH(loweralkyl) or —$OR_{206}$ wherein $R_{206}$ is independently defined as above;
R'" is halogen; and
q is 2 or 3.

A is
(1) substituted amino,
(2) substituted carbonyl,
(3) functionalized imino,
(4) functionalized alkyl,
(5) functionalized acyl,
(6) functionalized heterocyclic or
(7) functionalized (heterocyclic)alkyl.

B is:
(1) substituted carbonyl independently defined as herein,
(2) substituted amino independently defined as herein,
(3) functionalized imino independently defined as herein,
(4) functionalized alkyl independently defined as herein,
(5) functionalized acyl independently defined as herein,
(6) functionalized heterocyclic independently defined as herein or
(7) functionalized (heterocyclic) alkyl independently defined as herein.

The term "substituted amino" as used herein includes -$NR_{300}CH(R_3)C(O)$-L-$R_4$ wherein $R_{300}$ is hydrogen or loweralkyl, L is absent or represents a peptide chain containing 1–4 amino acids wherein $R_4$ is bonded to the carboxy terminus of the peptide chain and $R_4$ is hydroxy, alkoxy or functionalized amino and "substituted amino" also includes -N($R_{207}$)($R_3$) wherein $R_3$ and $R_{207}$ are independently selected from
(i) loweralkyl,
(ii) aryl,
(iii) thioalkoxyalkyl
(iv) (aryl)alkyl,
(v) cycloalkyl,
(vi) cycloalkylalkyl,
(vii) hydroxyalkyl,
(viii) alkoxyalkyl,
(ix) aryloxyalkyl,
(x) haloalkyl,
(xi) carboxyalkyl,
(xii) alkoxycarbonylalkyl,
(xiii) aminoalkyl,
(xiv) (N-protected)aminoalkyl,
(xv) alkylaminoalkyl,
(xvi) ((N-protected)(alkyl)amino)alkyl,
(xvii) dialkylaminoalkyl,
(xviii) guanidinoalkyl,
(xix) loweralkenyl,
(xx) heterocyclic,
(xxi) (heterocyclic)alkyl,
(xxii) hydrogen,
(xxiii) arylthioalkyl,
(xxiv) arylsulfonylalkyl,
(xxv) (heterocyclic)thioalkyl,
(xxvi) (heterocyclic) sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cyloalkylsulfonylalkyl,
(xxxvii) cycloalkylalkoxyalkyl,
(xxxviii cycloalkylthioalkoxyalkyl,
(xxxiv) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl and
(xlviii) dialkylaminocarbonylalkyl;
with the proviso that $R_3$ and $R_{207}$ are not both hydrogen.

The term "substituted carbonyl" as used herein includes —C(O) ($R_3$) wherein $R_3$ is independently defined as above.

The term "functionalized imino" as used herein includes —C(=$NOR_1$)($R_3$) wherein $R_1$ is independently defined as above and $R_3$ is independently defined as above, or —C(=$NNR_1R_2$)($R_3$) wherein $R_1$ and $R_2$ are independently defined as above and $R_3$ is independently defined as above.

The term "functionalized alkyl" as used herein includes:
(1) —CH(Z)(($CH_2R_{500}$)$_d$—$R_3$) wherein $R_3$ is independently defined as above; d is 0 or 1;
$R_{500}$ is
(i) —S—,
(ii) —O—,
(iii) —NH—,
(iv) —N(loweralkyl)—, (v) —S(O)—,
(vi) —S(O)$_2$— or
(vii) —CH$_2$—; and Z is
(i) hydrogen,
(ii) fluoro,
(iii) azido,
(iv) —CH(G)(R$_9$) wherein R$_9$ is hydrogen, loweralkyl, aryl, arylalkyl, heterocyclic or (heterocyclic) alkyl; and G is (a) functionalized carbonyl, (b) functionalized sulfonyl, (c) functionalized phosphonyl, (d) loweralkyl substituted with functionalized carbonyl, functionalized sulfonyl or functionalized phosphonyl, (e)-J-H or (f)-J-R$_3$ wherein R$_3$ is independently defined as above and J is absent or represents a peptide chain containing 1–4 amino acids wherein H or R$_3$ is bonded to the amino terminus of the peptide chain,
(v) —N(G)(R$_9$) wherein R$_9$ and G are defined as above,
(vi) —OG wherein G is defined as above;
(vii) —SG wherein G is defined as above; or
(viii) heterocyclic;
(2) —CF(Z)(R$_3$) wherein R$_3$ and Z are defined as above,
(3) —CH(Z)(OR$_3$) wherein R$_3$ and Z are defined as above,
(4) —CH(Z)(NR$_3$R$_9$) wherein R$_3$, R$_9$ and Z are defined as above,
(5) —CH(Z)(SR$_3$) wherein R$_3$ and Z are defined as above,
(6) —CH(Z)(S(O)R$_3$) wherein R$_3$ and Z are defined as above or
(7) —CH(Z)(S(O)$_2$R$_3$) wherein R$_3$ and Z are defined as above.

The term "functionalized acyl" as used herein includes:

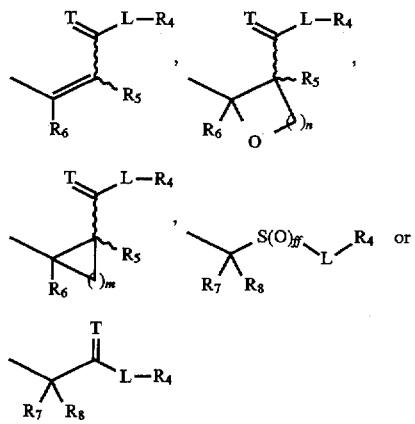

wherein L is absent or represents a peptide chain containing 1–4 amino acids wherein R$_4$ is bonded to the carboxy terminus of the peptide chain, T is O or S;

R$_4$ is
(1) hydroxy,
(2) alkoxy or
(3) functionalized amino,

R$_5$ and R$_6$ are independently selected from
(1) hydrogen,
(2) loweralkyl,
(3) aryl,
(4) heterocyclic,
(5) arylalkyl and
(6) (heterocyclic) alkyl, R$_7$ is
(1) hydrogen,
(2) fluoro,
(3) loweralkyl,
(4) hydroxyalkyl,
(5) alkoxyalkyl,
(6) aryl,
(7) heterocyclic,
(8) arylalkyl or
(9) (heterocyclic)alkyl, R$_8$ is
(1) hydrogen or
(2) fluoro;

ff is 1 or 2;

n is 0–3; and m is 1–4.

The term "functionalized carbonyl" as used herein includes:
(1) R$_{501}$-(CH(R$_3$))$_i$-(C(T))$_a$-(CH(R$_3$))$_b$-(E)$_c$-(CH(R$_3$))$_g$-C(T)-W- wherein W is absent or represents a peptide chain containing 1–3 amino acids wherein R$_{501}$-(C(T))$_a$-(CH(R$_3$))$_b$-(E)$_c$-(CH(R$_3$))$_g$-C(T)- is bonded to the amino terminus of the peptide chain; T is independently O or S; R$_3$ at each occurrence is independently defined as above; E is O, S or N(R$_3$) wherein R$_3$ is independently defined as above; a is 0–1; b is 0–3; c is 0–1; g is 0–3; i is 0–3; and R$_{501}$ is
(a) R$_{17}$-(R$_{800}$)$_h$- wherein R$_{800}$ is N(R$_{17}$), O or S and h is 0 or 1,
(b) (R$_{17}$)$_2$N—O— or
(c) R$_{17}$S(O)$_2$N(R$_3$)-
wherein R$_3$ is independently defined as above and at each occurrence R$_{17}$ is independently selected from:
(i) hydrogen,
(ii) loweralkyl,
(iii) cycloalkyl,
(iv) aryl,
(v) arylalkyl,
(vi)(aryl)alkoxyalkyl
(vii)(aryl)alkoxyalkyl,
(viii) aminoalkyl,
(ix) N-protected-aminoalkyl,
(x) alkylaminoalkyl,
(xi)(N-protected)(alkyl)aminoalkyl,
(xii) dialkylaminoalkyl,
(xiii) carboxyalkoxyalkyl,
(xiv)(alkoxycarbonyl)alkoxyalkyl,
(xv) carboxyalkyl,
(xvi) alkoxycarbonylalkyl,
(xvii)(amino)carboxyalkyl,
(xviii)((N-protected)amino)carboxyalkyl,
(xix)(alkylamino) carboxyalkyl,
(xx)((N-protected)alkylamino)carboxyalkyl,
(xxi)(dialkylamino)carboxyalkyl,
(xxii)(amino)alkoxycarbonylalkyl,
(xxiii)((N-protected)amino)alkoxycarbonylalkyl,
(xxiv)(alkylamino)alkoxycarbonylalkyl,
(xxv)((N-protected)alkylamino)alkoxycarbonylalkyl,
(xxvi)(dialkylamino)alkoxycarbonylalkyl,
(xxviix) aminocycloalkyl,
(xxviii) alkoxyalkyl,
(xxix)(polyalkoxy)alkyl,
(xxx) heterocyclic,
(xxxi)(heterocyclic)alkyl, (xxxii) N-protecting group,
(xxxiii)(hydroxyamino)alkyl,
(xxxiv)(alkoxyamino)alkyl,
(xxxv) cycloalkylalkyl,
(xxxvi) loweralkenyl,
(xxxvii) hydroxyalkyl,
(xxxviii) dihydroxyalkyl,
(xxxix)(alkoxy)(alkyl)aminoalkyl,
(xl) alkylaminocycloalkyl,
(xli) dialkylaminocycloalkyl and
(xlii) polyhydroxyalkyl;
and (2) $R_{501}$-$(CH(R_3))_i$-$(S(O)_p)_a$-$(CH(R_3))_b$-$(E)_c$-$(CH(R_3))_g$-C(T)-W- wherein W is absent or represents a peptide chain containing 1–3 amino acids wherein $R_{501}$-$(S(O)_p)_a$-$(CH(R_3))_b$-$(E)_c$-$(CH(R_3))_g$-C(T)- is bonded to the amino terminus of the peptide chain; T is independently O or S; $R_3$ at each occurrence is independently defined as above; E is O, S or $N(R_3)$ wherein $R_3$ is independently defined as above; a is 0–1; b is 0–3; c is 0–1; f is 1 or 2; g is 0–3; i is 0–3; and $R_{501}$ is defined as above.

The term "functionalized sulfonyl" as used herein includes:

(1) $R_{501}$-$(CH(R_3))_i$-$(C(T))_a$-$(CH(R_3))_b$-$(E)_c$-$(CH(R_3))_g$-$S(O)_f$-W- wherein W is absent or represents a peptide chain containing 1–3 amino acids wherein $R_{501}$-$(C(T))_a$-$(CH(R_3))_b$-$(E)_{c\text{-}(CH(R3))})_g$-$S(O)_f$- is bonded to the amino terminus of the peptide chain; T is independently O or S; $R_3$ at each occurrence is independently defined as above; E is O, S or $N(R_3)$ wherein $R_3$ is independently defined as above; a is 0–1; b is 0–3; c is 0–1; f is 1 or 2; g is 0–3; i is 0–3; and $R_{501}$ is defined as above; and (2) $R_{501}$-$(CH(R_3))_i$-$(S(O)_p)_a$-$(CH(R_3))_b$-$(E)_c$-$(CH(R_3))_g$-$S(O)f$-W- wherein W is absent or represents a peptide chain containing 1–3 amino acids wherein $R_{501}$-$(S(O)_p)_a$-$(CH(R_3))_b$-$(E)_c$-$(CH(R_3))_g$-$S(O)_f$- is bonded to the amino terminus of the peptide chain; $R_3$ at each occurrence is independently defined as above; E is O, S or $N(R_3)$ wherein $R_3$ is independently defined as above; a is 0–1; b is 0–3; c is 0–1; f at each occurrence is 1 or 2; g is 0–3; i is 0–3; and $R_{501}$ is defined as above.

The term "functionalized phosphonyl" as used herein includes:

(1) $R_{501}$-$(CH(R_3))_i$-$(C(T))_a$-$(CH(R_3))_b$-$(E)_c$-$(CH(R_3))_g$-P(=E)-W- wherein W is absent or represents a peptide chain containing 1–3 amino acids wherein $R_{501}$-$(C(T))_a$-$(CH(R_3))_b$-$(E)_c$-$(CH(R_3))_g$-$S(O)_f$- is bonded to the amino terminus of the peptide chain; T is independently O or S; $R_3$ at each occurrence is independently defined as above; E at each occurrence is independently O, S or $N(R_3)$ wherein $R_3$ is independently defined as above; a is 0–1; b is 0–3; c is 0–1; g is 0–3; i is 0–3; and $R_{501}$ is defined as above; and (2) $R_{501}$-$(CH(R_3))_i$-$(S(O)_p)_a$-$(CH(R_3))_b$-$(E)_c$-$(CH(R_3))_g$-P(=E)-W- wherein W is absent or represents a peptide chain containing 1–3 amino acids wherein $R_{501}$-$(S(O)_p)_a$-$(CH(R_3))_b$-$(E)_c$-$(CH(R_3))_g$-$S(O)_f$- is bonded to the amino terminus of the peptide chain; $R_3$ at each occurrence is independently defined as above; E at each occurrence is independently O, S or $N(R_3)$ wherein $R_3$ is independently defined as above; a is 0–1; b is 0–3; c is 0–1; f at each occurrence is 1 or 2; g is 0–3; i is 0–3; and $R_{501}$ is defined as above.

The term "a peptide chain of 1–3 amino acids" as used herein includes —$(N(R_{208})$—$CH(R_3)$—$C(O))_u$— wherein at each occurrence $R_3$ is independently defined as above, u is 1–3, and at each occurrence $R_{208}$ is hydrogen or loweralkyl, or $R_3$ and $R_{208}$ taken together is —$(CH_2)_v$— wherein v is 3–5.

The term "functionalized amino" as used herein includes: —$NR_{15}R_{16}$ wherein $R_{15}$ and $R_{16}$ are independently selected from hydrogen, loweralkyl, hydroxyalkyl, alkoxyalkyl, dihydroxyalkyl, haloalkyl, aminoalkyl, alkylaminoalkyl, aryl, arylalkyl, (heterocyclic)alkyl, heterocyclic, dialkylaminoalkyl, (N-protected) aminoalkyl, (N-protected)alkylaminoalkyl, cyanoalkyl, hydroxyalkyl, carboxyalkyl, alkoxycarbonylalkyl, (amino)carboxyalkyl, ((N-protected) amino) carboxyalkyl, (alkylamino)carboxyalkyl, ((N-protected)alkylamino)carboxyalkyl, (dialkylamino) carboxyalkyl, (amino)alkoxycarbonylalkyl, ((N-protected)amino)alkoxycarbonylalkyl, (alkylamino) alkoxycarbonylalkyl, ((N-protected)alkylamino) alkoxycarbonylalkyl and (dialkylamino) alkoxycarbonylalkyl.

The term "functionalized heterocyclic" as used herein refers to a heterocyclic group indepedently defined as herein which is substituted with a functional group G wherein G is independently defined as herein.

The term "functionalized (heterocyclic)alkyl" as used herein refers to a (heterocyclic)alkyl group independently defined as herein in which the heterocyclic group is substituted with a functional group G wherein G is independently defined as herein.

The chiral centers of the compounds of the invention may be racemic or asymmetric. Racemic mixtures, mixtures of diastereomers, as well as single diastereomers of the compounds of the invention are included in the present invention. The terms "S" and "R" configuration are as defined by the IUPAC 1974 Recommendations for Section E, Fundamental Stereochemistry, Pure Appl. Chem. (1976) 45, 13–30.

The terms "Ala", "Asn", "Gly", "Ile", "Leu", "Lys", "Phe", "Pro", "Ser", and "Val" as used herein refer to alanine, asparagine, glycine, isoleucine, leucine, lysine, phenylalanine, proline, serine and valine, respectively. In general, the amino acid abbreviations used herein follow the IUPAC-IUB Joint Commission on Biochemical Nomenclature for amino acids and peptides (Eur. J. Biochem. 1984, 158, 9–31).

The term "N-protecting group" or "N-protected" as used herein refers to those groups intended to protect nitrogen atoms against undesirable reactions during synthetic procedures or to prevent the attack of exopeptidases on the final compounds or to increase the solubility of the final compounds and includes but is not limited to acyl, acetyl, pivaloyl, t-butylacetyl, t-butyloxycarbonyl (Boc), benzyloxycarbonyl (Cbz) or benzoyl groups or an L- or D-aminoacyl residue, which may itself be N-protected similarly.

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "alkylene" as used herein refers to a straight or branched chain carbon diradical containing from 1 to 6 carbon atoms including, but not limited to, —$CH_2$—, —$CH_2CH_2$—, —$CH(CH_3)CH_2$—, —$CH_2CH_2CH_2$— and the like.

The term "loweralkenyl" as used herein refers to a loweralkyl radical which contains at least one carbon-carbon double bond including, but not limited to, propenyl, butenyl and the like. Alkenyl groups can be unsubstituted or substituted with one or more substituents independently selected from loweralkyl, haloalkyl, cycloalkyl, aryl, heterocyclic, alkoxy, thioalkoxy, amino, alkylamino, dialkylamino, hydroxy, halo, mercapto, nitro, carboxaldehyde, carboxy, carboalkoxy and carboxamide.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide. In addition, substituted aryl groups include tetrafluorophenyl and pentafluorophenyl.

The term "arylalkyl" as used herein refers to an aryl group appended to a loweralkyl radical including, but not limited to, benzyl, 4-hydroxybenzyl, 1-naphthylmethyl and the like.

The term "aminoalkyl" as used herein refers to —$NH_2$ appended to a loweralkyl radical.

The term "cyanoalkyl" as used herein refers to —CN appended to a loweralkyl radical.

The term "hydroxyalkyl" as used herein refers to —OH appended to a loweralkyl radical.

The term "dihydroxyalkyl" as used herein refers to a loweralkyl radical disubstituted with —OH groups.

The term "polyhydroxyalkyl" as used herein refers to a loweralkyl radical substituted with more than two —OH groups.

The term "hydroxyaminoalkyl" as used herein refers to a hydroxyamino group (—NHOH) appended to a loweralkyl radical.

The term "alkoxyaminoalkyl" as used herein refers to —$NHR_{250}$ (wherein $R_{250}$ is an alkoxy group) appended to a loweralkyl radical.

The term "(alkoxy)(alkyl)aminoalkyl" as used herein refers to $(R_{270})(R_{271})N$— wherein $R_{270}$ is alkoxy and $R_{271}$ is loweralkyl appended to a loweralkyl radical.

The term "alkylamino" as used herein refers to a loweralkyl radical appended to an NH radical.

The term "hydroxyalkylamino" as used herein refers to a hydroxyalkyl group appended to an NH radical.

The term "dihydroxyalkylamino" as used herein refers to a dihydroxyalkyl group appended to an NH radical.

The term "(hydroxyamino)alkylamino" as used herein refers to —$NHR_{251}$ wherein $R_{251}$ is a hydroxyaminoalkyl group.

The term "(alkoxyamino)alkylamino" as used herein refers to —$NHR_{252}$ wherein $R_{252}$ is an alkoxyaminoalkyl group.

The term "((hydroxyamino)alkyl)(alkyl)amino" as used herein refers to —$NR_{253}R_{254}$ wherein $R_{253}$ is a hydroxyaminoalkyl group and $R_{254}$ is a loweralkyl group.

The term "((alkoxyamino)alkyl)(alkyl)amino" as used herein refers to —$NR_{255}R_{256}$ wherein $R_{255}$ is an alkoxyaminoalkyl group and $R_{256}$ is a loweralkyl group.

The term "(N-protected) aminoalkylamino" as used herein refers to an N-protected amino group which is appended to a loweralkyl group which in turn is appended to an —NH radical.

The term "cycloalkyl" as used herein refers to an aliphatic ring having 3 to 7 carbon atoms including, but not limited to, cyclopropyl, cyclopentyl, cyclohexyl and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide.

The term "cycloalkylalkyl" as used herein refers to a cycloalkyl group appended to a loweralkyl radical, including but not limited to cyclohexylmethyl.

The term "alkylaminocycloalkyl" as used herein refers to an alkylamino group appended to a cycloalkyl radical.

The term "dialkylaminocycloalkyl" as used herein refers to a dialkylamino group appended to a cycloalkyl radical.

The terms "alkoxy" and "thioalkoxy" as used herein refer to $R_{18}O$— and $R_{18}S$—, respectively, wherein $R_{18}$ is a loweralkyl group or benzyl.

The term "(hydroxyamino)alkoxy" as used herein refers to $R_{257}O$— wherein $R_{257}$ is a hydroxyaminoalkyl group.

The term "(alkoxyamino)alkoxy" as used herein refers to $R_{258}O$— wherein $R_{258}$ is an alkoxyaminoalkyl group.

The term "alkoxyalkyl" as used herein refers to an alkoxy group appended to a loweralkyl radical.

The term "thioalkoxyalkyl" as used herein refers to a thioalkoxy group appended to a loweralkyl radical.

The term "alkoxyalkoxyalkyl" as used herein refers to an alkoxy group appended to an alkoxy group which is in turn appended to a loweralkyl radical including, but not limited to, methoxyethoxymethyl and the like.

The term "guanidinoalkyl" as used herein refers to a guanidino group (—NHC(=NH)$NH_2$) appended to a loweralkyl radical.

The term "alkenyloxy" as used herein refers to $R_{19}O$— wherein $R_{19}$ is a loweralkenyl group.

The term "hydroxyalkoxy" as used herein refers to —OH appended to an alkoxy radical.

The term "dihydroxyalkoxy" as used herein refers to an alkoxy radical which is disubstituted with —OH groups.

The term "arylalkoxy" as used herein refers $R_{90}O$— wherein $R_{90}$ is a arylalkyl group as defined above.

The term "(heterocyclic)alkoxy" as used herein refers to $R_{301}O$— wherein $R_{301}$ is a (heterocyclic)alkyl group.

The term "arylalkoxyalkyl" as used herein refers to a arylalkoxy group as defined above appended to a loweralkyl radical.

The term "aryloxyalkyl" as used herein refers to a $R_{220}O$— group appended to a loweralkyl radical, wherein $R_{220}$ is an aryl group.

The term "dialkylamino" as used herein refers to —$NR_{20}R_{21}$ wherein $R_{20}$ and $R_{21}$ are independently selected from loweralkyl groups.

The term "(hydroxyalkyl)(alkyl)amino" as used herein refers to —$NR_{22}R_{23}$ wherein $R_{22}$ is hydroxyalkyl and $R_{23}$ is loweralkyl.

The term "N-protected aminoalkyl" as used herein refers to —$NHR_{24}$ appended to a loweralkyl group, wherein $R_{24}$ is an N-protecting group.

The term "alkylaminoalkyl" as used herein refers to $NHR_{25}$ appended to a loweralkyl radical, wherein $R_{25}$ is a loweralkyl group.

The term "(N-protected)(alkyl)aminoalkyl" as used herein refers to —$NR_{24}R_{25}$, which is appended to a loweralkyl radical, wherein $R_{24}$ and $R_{25}$ are as defined above.

The term "dialkylaminoalkyl" as used herein refers to —$NR_{26}R_{27}$ which is appended to a loweralkyl radical wherein $R_{26}$ and $R_{27}$ are independently selected from loweralkyl.

The term "azidoalkyl" as used herein refers to a —$N_3$ group appended to a loweralkyl radical.

The term "carboxyalkyl" as used herein refers to a carboxylic acid group (—COOH) appended to a loweralkyl radical.

The term "alkoxycarbonylalkyl" as used herein refers to a $R_{28}C(O)$— group appended to a loweralkyl radical, wherein $R_{28}$ is an alkoxy group The term "carboxyalkoxyalkyl" as used herein refers to a carboxylic acid group (—COOH) appended to an alkoxy group which is appended to a loweralkyl radical.

The term "alkoxycarbonylalkoxyalkyl" as used herein refers to an alkoxycarbonyl group ($R_{30}C(O)$— wherein $R_{30}$ is an alkoxy group) appended to an alkoxy group which is appended to a loweralkyl radical.

The term "(amino)carboxyalkyl" as used herein refers to a loweralkyl radical to which is appended a carboxylic acid group (—COOH) and an amino group (—$NH_2$).

The term "((N-protected)amino)carboxyalkyl" as used herein refers to a loweralkyl radical to which is appended a carboxylic acid group (—COOH) and —$NHR_{31}$ wherein $R_{31}$ is an N-protecting group.

The term "(alkylamino)carboxyalkyl" as used herein refers to a loweralkyl radical to which is appended a carboxylic acid group (—COOH) and an alkylamino group.

The term "((N-protected)alkylamino)carboxyalkyl" as used herein refers to a loweralkyl radical to which is appended a carboxylic acid group (—COOH) and an —$NR_{31}R_{32}$ wherein $R_{31}$ is as defined above and $R_{32}$ is a loweralkyl group.

The term "(dialkylamino)carboxyalkyl" as used herein refers to a loweralkyl radical to which is appended a carboxylic acid group (—COOH) and —$NR_{32}R_{32}$ wherein $R_{32}$ is as defined above.

The term "(amino)alkoxycarbonylalkyl" as used herein refers to a loweralkyl radical to which is appended an alkoxycarbonyl group as defined above and an amino group (—$NH_2$).

The term "((N-protected) amino)alkoxycarbonylalkyl" as used herein refers to a loweralkyl radical to which is appended an alkoxycarbonyl group as defined above and —$NHR_{31}$ wherein $R_{31}$ is as defined above.

The term "(alkylamino) alkoxycarbonylalkyl" as used herein refers to a loweralkyl radical to which is appended an alkoxycarbonyl group as defined above and an alkylamino group as defined above.

The term "((N-protected)alkylamino) alkoxycarbonylalkyl" as used herein refers to a loweralkyl radical to which is appended an alkoxycarbonyl group as defined above and —$NR_{31}R_{32}$ wherein $R_{31}$ and $R_{32}$ are as defined above.

The term "(dialkylamino)alkoxycarbonylalkyl" as used herein refers to a loweralkyl radical to which is appended an alkoxycarbonyl group as defined above and —$NR_{32}R_{32}$ wherein $R_{32}$ is as defined above.

The term "carboxyalkylamino" as used herein refers to —$NHR_{33}$ wherein $R_{33}$ is a carboxyalkyl group.

The term "alkoxycarbonylalkylamino" as used herein refers to —$NHR_{34}$ wherein $R_{34}$ is an alkoxycarbonylakyl group.

The term "(amino)carboxyalkylamino" as used herein refers to —$NHR_{35}$ wherein $R_{35}$ is an (amino)carboxyalkyl group.

The term "((N-protected)amino)carboxyalkylamino" as used herein refers to —$NHR_{36}$ wherein $R_{36}$ is an [(N-protected)amino] carboxyalkyl group.

The term "(alkylamino)carboxyalkylamino" as used herein refers to —$NHR_{37}$ wherein $R_{37}$ is an (alkylamino) carboxyalkyl group.

The term "((N-protected)alkylamino)-carboxyalkylamino" as used herein refers to —$NHR_{38}$ wherein $R_{38}$ is an ((N-protected) alkylamino)carboxyalkyl group.

The term "(dialkylamino)carboxyalkylamino" as used herein refers to —$NHR_{39}$ wherein $R_{39}$ is a (dialkylamino) carboxyalkyl group.

The term "(amino)alkoxycarbonylalkylamino" as used herein refers to —$NHR_{40}$ wherein $R_{40}$ is an (amino) alkoxycarbonylalkyl group.

The term "((N-protected)amino) alkoxycarbonylalkylamino" as used herein refers to —$NHR_{41}$ wherein $R_{41}$ is an ((N-protected)amino)- alkoxycarbonylalkyl group.

The term "(alkylamino)alkoxycarbonylalkylamino" as used herein refers to —$NHR_{42}$ wherein $R_{42}$ is an (alkylamino)alkoxycarbonylalkyl group.

The term "((N-protected) alkylamino) alkoxycarbonylalkylamino" as used herein refers to —$NHR_{43}$ wherein $R_{43}$ is an ((N-protected) alkylamino) alkoxycarbonylalkyl group.

The term "(dialkylamino)alkoxycarbonylalkylamino" as used herein refers to —$NHR_{44}$ wherein $R_{44}$ is a (dialkylamino)alkoxycarbonylalkyl group.

The term "aminocycloalkyl" as used herein refers to an $NH_2$ appended to a cycloalkyl radical.

The term "((alkoxy)alkoxy)alkyl" as used herein refers to an alkoxy group appended to an alkoxy group which is appended to a loweralkyl radical.

The term "polyalkoxyalkyl" as used herein refers to a polyalkoxy residue appended to a loweralkyl radical.

The term "polyalkoxy" as used herein refers to —$OR_{45}$ wherein $R_{45}$ is a straight or branched chain containing 1–5, $C_{n'}$—O—$C_{n''}$ linkages wherein n' and n" are independently selected from 1 to 3, including but not limited to methoxyethoxymethoxy, methoxymethoxy and the like.

The term "(arylalkyl)amino" as used herein refers to $R_{100}NH$— wherein $R_{100}$ is an arylalkyl group as defined above.

The term "(arylalkyl)(alkyl)amino" as used herein refers to $R_{104}R_{105}N$— wherein $R_{104}$ is an arylalkyl group as defined above and $R_{105}$ is a loweralkyl group.

The term "(heterocyclic)alkylamino" as used herein refers to $R_{900}NH$— wherein $R_{900}$ is a (heterocyclic)alkyl group.

The term "((heterocyclic)alkyl)(alkyl)amino" as used herein refers to $R_{900}R_{901}N$— wherein $R_{900}$ is a (heterocyclic)alkyl group and $R_{901}$ is a loweralkyl group.

The term "dialkylaminoalkyl(alkyl)amino" as used herein refers to —$NR_{49}R_{50}$ wherein $R_{49}$ is a dialkylamino residue appended to a loweralkyl residue and $R_{50}$ is a loweralkyl residue.

The term "alkylaminoalkylamino" as used herein refers to —$NHR_{50a}$ wherein $R_{50a}$ is an alkylaminoalkyl group as previously defined.

The term "dialkylaminoalkylamino" as used herein refers to —$NHR_{50b}$ wherein $R_{50b}$ is a dialkylaminoalkyl group as previously defined.

The term "aminoalkylamino" as used herein refers to —$NHR_{51}$ wherein $R_{51}$ is an aminoalkyl residue.

The term "(dihydroxyalkyl)(alkyl)amino" as used herein refers to a loweralkyl group which is disubstituted with —OH radicals, appended to an amino group, which amino group also has appended another loweralkyl group, including but not limited to N-(2,3-dihydroxypropyl)-N-(methyl) amine.

The term "di-(hydroxyalkyl)amino" as used herein refers to —$NR_{52}R_{53}$ wherein $R_{52}$ and $R_{53}$ are hydroxyalkyl residues.

The term "alkoxyalkyl(alkyl)amino" as used herein refers to —$NR_{54}R_{55}$ wherein $R_{54}$ is an alkoxyalkyl group and $R_{55}$ is a loweralkyl group.

The term "di-(alkoxyalkyl)amino" as used herein refers to —$NR_{56}R_{57}$ wherein $R_{56}$ and $R_{57}$ are alkoxyalkyl groups.

The term "di-(polyalkoxyalkyl)amino" as used herein refers to —$NR_{58}R_{59}$ wherein $R_{58}$ and $R_{59}$ are polyalkoxy residues appended to loweralkyl residues.

The term "((polyalkoxy)alkyl))(alkyl)amino" as used herein refers to —$NR_{60}R_{61}$ wherein $R_{60}$ is a polyalkoxy residue appended to a loweralkyl residue and $R_{61}$ is a loweralkyl residue.

The term "halo" or "halogen" as used herein refers to —Cl, —Br, —I or —F.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The term "thioalkoxyalkyl" as used herein refers to a thioalkoxy group appended to a loweralkyl radical.

The term "alkylsulfonyl" as used herein refers to $R_{62}SO_2$— wherein $R_{62}$ is loweralkyl group.

The term "arylthioalkyl" as used herein refers to $R_{505}$—S—$R_{506}$— wherein $R_{505}$ is an aryl group and $R_{506}$ is an alkylene group.

The term "arylsulfonylalkyl" as used herein refers to $R_{507}$—$S(O)_2$—$R_{508}$— wherein $R_{507}$ is any aryl group and $R_{508}$ is an alkylene group.

The term "(heterocyclic)oxyalkyl" as used herein refers to $R_{509}$—O—$R_{510}$— wherein $R_{509}$ is an aryl group and $R_{510}$ is an alkylene group.

The term "(heterocyclic)thioalkyl" as used herein refers to $R_{511}$—S—$R_{512}$— wherein $R_{511}$ is an aryl group and $R_{512}$ is an alkylene group.

The term "(heterocyclic)sulfonylalkyl" as used herein refers to $R_{513}$—$S(O)_2$—$R_{514}$— wherein $R_{513}$ is an aryl group and $R_{514}$ is an alkylene group.

The "arylalkoxyalkyl" as used herein refers to $R_{515}$—O—$R_{516}$— wherein $R_{515}$ is an arylalkyl group and $R_{516}$ is an alkylene group.

The "arylthioalkoxyalkyl" as used herein refers to $R_{517}$—S—$R_{518}$— wherein $R_{517}$ is an arylalkyl group and $R_{518}$ is an alkylene group.

The "arylalkylsulfonylalkyl" as used herein refers to $R_{519}$—$S(O)_2$—$R_{520}$— wherein $R_{519}$ is an arylalkyl group and $R_{520}$ is an alkylene group.

The term "(heterocyclic)alkoxyalkyl" as used herein refers to $R_{521}$—O—$R_{522}$— wherein $R_{521}$ is a (heterocyclic)alkyl group and $R_{522}$ is an alkylene group.

The term "(heterocyclic)thioalkoxyalkyl" as used herein refers to $R_{523}$—S—$R_{524}$— wherein $R_{523}$ is a (heterocyclic)alkyl group and $R_{524}$ is an alkylene group.

The term "(heterocyclic)alkylsulfonylalkyl" as used herein refers to $R_{525}$—$S(O)_2$—$R_{526}$— wherein $R_{525}$ is a (heterocyclic)alkyl group and $R_{526}$ is an alkylene group.

The term "cycloalkyloxyalkyl" as used herein refers to $R_{527}$—O—$R_{528}$— wherein $R_{527}$ is a cycloalkyl group and $R_{528}$ is an alkylene group.

The term "cycloalkylthioalkyl" as used herein refers to $R_{529}$—S—$R_{530}$— wherein $R_{529}$ is a cycloalkyl group and $R_{530}$ is an alkylene group.

The term "cycloalkylsulfonylalkyl" as used herein refers to $R_{531}$—$S(O)_2$—$R_{532}$— wherein $R_{531}$ is a cycloalkyl group and $R_{532}$ is an alkylene group.

The term "cycloalkylalkoxyalkyl" as used herein refers to $R_{533}$—O—$R_{534}$— wherein $R_{533}$ is a cycloalkylalkyl group and $R_{534}$ is an alkylene group.

The term "cycloalkylthioalkoxyalkyl" as used herein refers to $R_{535}$—S—$R_{536}$— wherein $R_{535}$ is a cycloalkylalkyl group and $R_{536}$ is an alkylene group.

The term "cycloalkylalkylsulfonylalkyl" as used herein refers to $R_{537}$—$S(O)_2$—$R_{538}$— wherein $R_{537}$ is a cycloalkylalkyl group and $R_{538}$ is an alkylene group.

The term "aminocarbonyl" as used herein refers to —$C(O)NH_2$.

The term "aminocarbonylalkyl" as used herein refers to an aminocarbonyl group appended to a loweralkyl radical.

The term "alkylaminocarbonyl" as used herein refers to —$C(O)NHR_{539}$ wherein $R_{539}$ is loweralkyl.

The term "alkylaminocarbonylalkyl" as used herein refers to an alkylaminocarbonyl group appended to a loweralkyl radical.

The term "dialkylaminocarbonyl" as used herein refers to —$C(O)NR_{540}R_{541}$ wherein $R_{540}$ and $R_{541}$ are independently selected from loweralkyl.

The term "dialkylaminocarbonylalkyl" as used herein refers to a dialkylaminocarbonyl group appended to a loweralkyl group.

The term "aroylalkyl" as used herein refers to $R_{542}$—C(O)—$R_{543}$— wherein $R_{542}$ is an aryl group and $R_{543}$ is an alkylene group.

The term "(heterocyclic)carbonylalkyl" as used herein refers to $R_{544}$—C(O)—$R_{545}$— wherein $R_{544}$ is a heterocyclic group and $R_{545}$ is an alkylene group.

The term "arylamino" as used herein refers to $R_{546}NH$— wherein $R_{546}$ is an aryl group.

The term "(heterocyclic)amino" as used herein refers to $R_{547}NH$— wherein $R_{547}$ is a heterocyclic group.

The term "heterocyclic ring" or "heterocyclic" as used herein refers to any 3- or 4-membered ring containing a heteroatom selected from oxygen, nitrogen and sulfur; or a 5- or 6-membered ring containing one, two or three nitrogen atoms; one nitrogen and one sulfur atom; or one nitrogen and one oxygen atom. The 5-membered ring has 0–2 double bonds and the 6-membered ring has 0–3 double bonds. The nitrogen and sulfur heteroatoms can be optionally oxidized. The nitrogen heteroatoms can be optionally quaternized. The term "heterocyclic" also includes bicyclic groups in which any of the above heterocyclic rings is fused to a benzene ring or or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Heterocyclics also include:

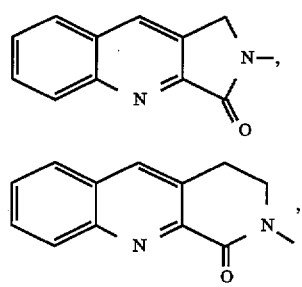

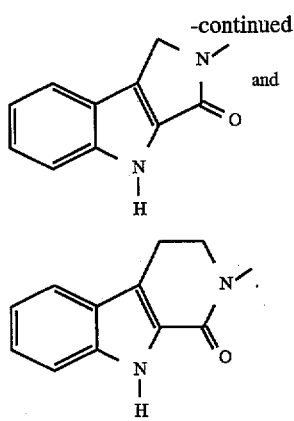

Heterocyclics can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, polyalkoxy, haloalkyl, cycloalkyl, —COOH, —SO₃H and loweralkyl. In addition, nitrogen containing heterocycles can be N-protected.

The term "(heterocyclic)alkyl" as used herein refers to a heterocyclic group appended to a loweralkyl radical, including but not limited to imidazolylmethyl, thiazolylmethyl, pyridylmethyl and morpholinylmethyl.

The term "heterocyclic carbonyloxy" as used herein refers to $R_{304}C(O)O$— wherein $R_{304}$ is a heterocyclic group.

The term "heterocyclic carbonylamino" as used herein refers to $R_{305}C(O)NH$— wherein $R_{305}$ is a heterocyclic group.

In the compounds of the present invention, the A, X and B components may have asymmetric centers and occur as racemates, racemic mixtures, mixtures of diastereomers and as individual diastereomers, with all isomeric forms being included in the invention.

When any variable (i.e., $R_1$, $R_2$, $R_3$, etc.) occurs more than one time in any constituent or in a compound of Formula I, its definition on each occurrence is independent of its definition at every other occurrence. Also, combinations of substituents and/or variables are permissible only if such combinations result in stable compounds.

Representative compounds of the invention include those represented in Table 2. (In the table "Ph" represents phenyl and p-C7H7 represents 4-methylphenyl).

TABLE 2

| Compound of Example | A | X | B |
|---|---|---|---|
| 1B | PhCH₂CH₂— | —S(O)₂— | PhCH₂CH₂— |
| 2 | PhCH₂CH₂— | —S(O)— | PhCH₂CH₂— |
| 3B | PhCH₂CH₂— | —CH(OH)— | PhCH₂CH₂— |
| 3A | PhCH₂CH₂— | —C(O)— | PhCH₂CH₂— |
| 4 | PhOCH₂— | —CH(OH)— | PhOCH₂— |
| 5 | PhOCH₂— | —C(O)— | PhOCH₂— |
| 6G | PhCH₂CH₂— | —CH(OH)— | —CH=CHC(O)NH—(CH₂)₂CH(CH₃)₂ |
| 7B | PhCH₂CH₂— | —CH(OH)— | ⊲—C(O)NH(CH₂)₂CH(CH₃)₂ |
| 8B | PhCH₂CH₂— | —CH(OH)— | ⊲—C(O)NH(CH₂)₂CH(CH₃)₂ |
| 9 | PhCH₂CH₂— | —P(O)H— | PhCH₂CH₂— |
| 10C | PhCH₂CH(NHBoc)— | —CH(OH)— | PhCH₂CH(N₃)— |
| 11 | PhCH₂CH(NHBoc)— | —CH(OH)— | PhCH₂CH(NH₂)— |
| 12 | PhCH₂CH(NH₂)— | —CH(OH)— | PhCH₂CH(NH₂)— |
| 13 | PhCH₂CH(NHSO₂Me)— | —CH(OH)— | PhCH₂CH(NHSO₂Me)— |
| 14 | PhNHCH₂— | —CH(OH)— | PhNHCH₂— |
| 15 | PhSCH₂— | —CH(OH)— | PhSCH₂— |
| 16B | PhCH₂CH₂— | ⊲⊳O | PhCH₂CH₂— |
| 17B | PhCH₂CH(NHBoc)— | —CH(OH)CH(OH)— | PhCH₂CH—(N(CH₂Ph(Cbz)— |
| 18 | PhCH₂CH(NHBoc)— | —CH(OH)CH(OH)— | PhCH₂CH(NHCH₂Ph)— |
| 19 | PhCH₂CH(NH₂)— | —CH(OH)CH(OH)— | PhCH₂CH(NHCH₂Ph)— |
| 20 | PhCH₂CH₂— | —C(OH)(CH₂OH)— | PhCH₂CH₂— |
| 21B | PhOCH₂— | ⊲⊳O | PhOCH₂— |
| 22 | PhCH₂CH(NHBoc)— | —CH(OH)— | PhCH₂CH(CH₂C(O)—NHCH₂CH₂CH(CH₃)₂)— |
| 23B | PhCH₂C(O)— | —CH(OH)CH(OH)— | PhCH₂C(O)— |

TABLE 2-continued

| Compound of Example | A | X | B |
|---|---|---|---|
| 24 | PhCH$_2$CH(OH)— | —CH(OH)CH(OH)— | PhCH$_2$CH(OH)— |
| 25B | PhCH$_2$C(=NOH)— | —CH(OH)CH(OH)— | PhCH$_2$C(=NOH)— |
| 26 | PhCH$_2$C(=NOMe)— | —CH(OH)CH(OH)— | PhCH$_2$C(=NOMe)— |
| 27 | PhCH$_2$C(=NNH$_2$)— | —CH(OH)CH(OH)— | PhCH$_2$C(=NNH$_2$)— |
| 28 | PhCH$_2$CH(CH$_2$CH$_3$)— | —S(O)— | PhCH$_2$CH(CH$_2$CH$_3$)— |
| 29B | PhCH$_2$CH(F)— | —S(O)— | PhCH$_2$CH$_2$— |
| 30B | PhCH$_2$CH$_2$— | —N(OH)— | PhCH$_2$CH$_2$— |
| 31 | PhCH$_2$CH$_2$— | —C(=NOH)— | PhCH$_2$CH$_2$— |
| 32 | PhCH$_2$CH$_2$— | —CH(NH$_2$)— | PhCH$_2$CH$_2$— |
| 33 | PhCH$_2$CH$_2$— | —CH(NH(OH))— | PhCH$_2$CH$_2$— |
| 34C | PhCH$_2$CH(F)— | —C(O)— | PhCH$_2$CH$_2$— |
| 35 | PhCH$_2$CH(NHC(O)Me)— | —CH(OH)— | PhCH$_2$CH(NHC(O)Me)— |
| 36G | PhCH$_2$CH(NH$_2$)— | —CH(OH)— | —CH=CHC(O)NH—CH$_2$CH$_2$CH(CH$_3$)$_2$ |
| 37 | PhCH$_2$CH(NHC(O)Me)— | —CH(OH)— | —CH=CHC(O)NH—CH$_2$CH$_2$CH(CH$_3$)$_2$ |
| 38 | PhCH$_2$CH(NHSO$_2$NMe$_2$)— | —CH(OH)— | PhCH$_2$CH(NHSO$_2$NMe$_2$)— |
| 39 | PhCH$_2$CH(NHC(O)NH$_2$)— | —CH(OH)— | PhCH$_2$CH(NHC(O)NH$_2$)— |
| 40 | PhCH$_2$CH$_2$— | —P(O)(OH)— | PhCH$_2$CH$_2$— |
| 41B | PhCH$_2$CH$_2$— | —C(OH)(CH$_2$NH$_2$)— | PhCH$_2$CH$_2$— |
| 42 | (CH$_3$)$_2$CHCH$_2$CH$_2$— | —CH(OH)— | (CH$_3$)$_2$CHCH$_2$CH$_2$— |
| 43C | PhCH$_2$CF$_2$— | —C(O)— | PhCH$_2$CH$_2$— |
| 44 | PhCH$_2$CH$_2$— | —CH(OH)— | CH$_3$CH$_2$OC(O)CF$_2$— |
| 45 | PhCH$_2$CH$_2$— | —CH(OH)— | HOC(O)CF$_2$— |
| 46 | PhCH$_2$CH$_2$— | —CH(OH)— | (CH$_3$)$_2$CHCH$_2$CH$_2$NHC(O)CF$_2$— |
| 47 | PhCH$_2$CH$_2$— | —C(O)— | (CH$_3$)$_2$CHCH$_2$CH$_2$NHC(O)CF$_2$— |
| 48 | PhCH$_2$CH(NHC(O)—C(CH$_3$)$_2$CH$_2$C(O)OCH$_2$Ph)— | —CH(OH)— | PhCH$_2$CH(NHC(O)—C(CH$_3$)$_2$CH$_2$C(O)OCH$_2$Ph)— |
| 49 | PhCH$_2$CH(NHC(O)—C(CH$_3$)$_2$CH$_2$COOH)— | —CH(OH)— | PhCH$_2$CH(NHC(O)—C(CH$_3$)$_2$CH$_2$COOH)— |
| 50 | 4-NO$_2$—C$_6$H$_4$OCH$_2$— | —CH(OH)— | 4-NO$_2$—C$_6$H$_4$OCH$_2$— |
| 51 | PhCH$_2$CH$_2$— | —CH(OCH$_2$OCH$_3$)— | PhCH$_2$CH$_2$— |
| 52B | PhCH$_2$CH$_2$— | —C(O)— | PhCH$_2$CH$_2$— |
| 53 | PhCH$_2$CH$_2$CH$_2$— | —CH(OH)— | PhCH$_2$CH$_2$CH$_2$— |
| 54B | PhCH$_2$CH$_2$— | —CH(OH)— | —CH=CHC(O)—Val—Val—NH$_2$ |
| 55 | BocNH–CH(CH$_2$Ph)– | —CH(OH)— | Cbz—Val—NH–CH(CH$_2$Ph)– |
| 56 | N$_3$–CH(CH$_2$Ph)– | —CH(OH)— | H$_2$N–CH(CH$_2$Ph)– |
| 57 | N$_3$–CH(CH$_2$Ph)– | —CH(OH)— | Ac—Val—Val—NH–CH(CH$_2$Ph)– |
| 58 | H$_2$N–CH(CH$_2$Ph)– | —CH(OH)— | Ac—Val—Val—NH–CH(CH$_2$Ph)– |
| 59 | Ac—Val—Val—NH–CH(CH$_2$Ph)– | —CH(OH)— | Ac—Val—Val—NH–CH(CH$_2$Ph)– |
| 60 | Ac—Val—Val—NH–CH(CH$_2$Ph)– | —C(O)— | Ac—Val—Val—NH–CH(CH$_2$Ph)– |
| 61E | N$_3$–CH(CH$_2$Ph)– | epoxide | Cbz—Val—NH–CH(CH$_2$Ph)– |

TABLE 2-continued

| Compound of Example | A | X | B |
|---|---|---|---|
| 62 | PhCH$_2$NH—CH(CH$_2$Ph)— | —CH(OH)CH(OH)— | Ac—Val—Val—NH—CH(CH$_2$Ph)— |
| 63 | N$_3$—CH(CH$_2$Ph)— | —C(OH)(CH$_2$OH)— | Cbz—Val—NH—CH(CH$_2$Ph)— |
| 64C | Cbz—Val—O—CH(CH$_2$Ph)— | —CH(OH)CH(OH)— | Cbz—Val—O—CH(CH$_2$Ph)— |
| 65 | BocNH—CH(CH$_2$Ph)— | —CH(OH)— | Cbz—Leu—Asn—NH—CH(CH$_2$Ph)— |
| 66 | BocNH—CH(CH$_2$Ph)— | —CH(OH)— | Cbz—Asn—NH—CH(CH$_2$Ph)— |
| 67 | H$_2$N—CH(CH$_2$Ph)— | —CH(OH)— | Cbz—Asn—NH—CH(CH$_2$Ph)— |
| 68 | Cbz—Asn—NH—CH(CH$_2$Ph)— | —CH(OH)— | Cbz—Asn—NH—CH(CH$_2$Ph)— |
| 69 | H$_2$N—CH(CH$_2$Ph)— | —CH(OH)— | Cbz—Val—NH—CH(CH$_2$Ph)— |
| 70 | Cbz—Val—NH—CH(CH$_2$Ph)— | —CH(OH)— | Cbz—Val—NH—CH(CH$_2$Ph)— |
| 71D | N$_3$—CH(CH$_2$Ph)— | —CH(OH)— | R$_{400}$—Val—Val—NH—CH(CH$_2$Ph)— (R$_{400}$ = CH$_3$OC(O)—(CH$_2$)$_4$—C(O)—) |
| 72 | H$_2$N—CH(CH$_2$Ph)— | —CH(OH)— | R$_{300}$—Val—Val—NH—CH(CH$_2$Ph)— (R$_{300}$ = CH$_3$OC(O)—(CH$_2$)$_4$—C(O)—) |
| 73C | R$_{301}$—Val—Val—NH—CH(CH$_2$Ph)— (R$_{301}$ = CbzNH(CH$_2$)$_5$C(O)—) | —CH(OH)— | R$_{302}$—Val—Val—NH—CH(CH$_2$Ph)— (R$_{302}$ = CH$_3$OC(O)—(CH$_2$)$_4$—C(O)—) |
| 74 | R$_{303}$—Val—Val—NH—CH(CH$_2$Ph)— (R$_{303}$ = CbzNH(CH$_2$)$_4$C(O)—) | —CH(OH)— | R$_{304}$—Val—Val—NH—CH(CH$_2$Ph)— (R$_{304}$ = HOC(O)—(CH$_2$)$_4$—C(O)—) |

TABLE 2-continued

| Compound of Example | A | X | B |
|---|---|---|---|
| 75 | PhOCH$_2$— | —CH(OH)— | Cbz—Val—NH—CH(CH$_2$Ph)— |
| 76 | PhSCH$_2$— | —CH(OH)— | Cbz—Val—NH—CH(CH$_2$Ph)— |
| 77 | PhSO$_2$CH$_2$— | —CH(OH)— | Cbz—Val—NH—CH(CH$_2$Ph)— |
| 78D | R$_{305}$—Leu—NH—CH(CH$_2$Ph)— (R$_{305}$ = CbzNHC(CH$_3$)$_2$CH$_2$C(O)—) | —CH(OH)— | BocNH—CH(CH$_2$Ph)— |
| 79C | R$_{306}$—Leu—NH—CH(CH$_2$Ph)— (R$_{306}$ = 3,4-dihydroxypyrrolidinyl-carbonyl) | —CH(OH)— | BocNH—CH(CH$_2$Ph)— |
| 80 | R$_{307}$—Val—Val—NH—CH(CH$_2$Ph)— (R$_{307}$ = H$_2$N(CH$_2$)$_4$C(O)—) | —CH(OH)— | R$_{308}$—Val—Val—NH—CH(CH$_2$Ph)— (R$_{308}$ = HO$_2$C(CH$_2$)$_4$C(O)—) |
| 81 | PhSCH$_2$— | —CH(OCH$_2$OCH$_3$)— | PhSCH$_2$— |
| 82 | PhOCH$_2$— | —CH(OCH$_2$OCH$_3$)— | PhOCH$_2$— |
| 83C | R$_{309}$—Leu—NH—CH(CH$_2$Ph)— (R$_{309}$ = thiomorpholinyl-carbonyl) | —CH(OH)— | BocNH—CH(CH$_2$Ph)— |
| 84C | R$_{310}$—Leu—NH—CH(CH$_2$Ph)— (R$_{310}$ = sulfonylmorpholinyl-carbonyl) | —CH(OH)— | BocNH—CH(CH$_2$Ph)— |
| 85C | R$_{311}$—Leu—NH—CH(CH$_2$Ph)— (R$_{311}$ = (CH$_3$)$_2$N(CH$_2$)$_2$N(CH$_3$)C(O)—) | —CH(OH)— | BocNH—CH(CH$_2$Ph)— |
| 86E | R$_{312}$—Leu—NH—CH(CH$_2$Ph)— (R$_{312}$ = HOCH$_2$CH(OH)CH$_2$N(CH$_3$)C(O)—) | —CH(OH)— | BocNH—CH(CH$_2$Ph)— |
| 87C | R$_{313}$—Leu—NH—CH(CH$_2$Ph)— (R$_{313}$ = Cbz-piperidin-4-yl-carbonyl) | —CH(OH)— | BocNH—CH(CH$_2$Ph)— |

TABLE 2-continued

| Compound of Example | A | X | B |
|---|---|---|---|
| 88D | R$_{314}$—Leu—NH—CH(Ph)— <br> (R$_{314}$ = HOCH$_2$—(CH$_2$)$_2$—OC(O)—) | —CH(OH)— | BocNH—CH(Ph)— |
| 89B | (4-(CH$_3$)$_2$CH)C$_6$H$_4$CH$_2$CH$_2$— | —CH(OH)— | (4-(CH$_3$)$_2$CH)C$_6$H$_4$CH$_2$CH$_2$— |
| 90B | 4-HOC$_6$H$_4$CH$_2$CH$_2$— | —CH(OH)— | 4-HOC$_6$H$_4$CH$_2$CH$_2$— |
| 91B | (1-naphthyl)CH$_2$CH$_2$— | —CH(OH)— | (1-naphthyl)CH$_2$CH$_2$— |
| 92B | 4-CH$_3$OC$_6$H$_4$CH$_2$CH$_2$— | —CH(OH)— | 4-CH$_3$OC$_6$H$_4$CH$_2$CH$_2$— |
| 93B | 4-BrC$_6$H$_4$CH$_2$CH$_2$— | —CH(OH)— | 4-BrC$_6$H$_4$CH$_2$CH$_2$— |
| 94B | PhCH$_2$CH$_2$— | —(H.Ala—O)CH— | PhCH$_2$CH$_2$— |
| 95B | PhCH$_2$CH$_2$— | —(H.Gly—O)CH— | PhCH$_2$CH$_2$— |
| 96B | PhCH$_2$CH$_2$— | —(H.Lys—O)CH— | PhCH$_2$CH$_2$— |
| 97 | CbzNH(CH$_2$)$_4$C(O)NH—CH(Ph)— | —CH(OH)— | BocNH—CH(Ph)— |
| 98 | CbzNH(CH$_2$)$_4$C(O)NH—CH(Ph)— | —CH(OH)— | PhCH$_2$O$_2$CCH$_2$C(CH$_3$)$_2$C(O)NH—CH(Ph)— |
| 99 | H$_2$N(CH$_2$)$_4$C(O)NH—CH(Ph)— | —CH(OH)— | HO$_2$CCH$_2$C(CH$_3$)$_2$C(O)NH—CH(Ph)— |
| 100G | R$_{315}$—C(O)NH—CH(Ph)— (iBu) <br> (R$_{315}$ = 4-morpholinylC(O)CH$_2$—) | —CH(OH)— | BocNH—CH(Ph)— |
| 101C | R$_{316}$—C(O)NH—CH(Ph)— (iBu) <br> (R$_{316}$ = 4-morpholinylC(O)O—) | —CH(OH)— | BocNH—CH(Ph)— |
| 102C | R$_{317}$—C(O)NH—CH(Ph)— (iBu) <br> (R$_{317}$ = PhCH$_2$NHC(O)CH$_2$—) | —CH(OH)— | BocNH—CH(Ph)— |
| 103 | R$_{318}$—C(O)NH—CH(Ph)— (iBu) <br> (R$_{318}$ = PhCH$_2$NHC(O)CH$_2$—) | —CH(OH)— | H$_2$N—CH(Ph)— |
| 104 | R$_{319}$—C(O)NH—CH(Ph)— (iBu) <br> (R$_{319}$ = PhCH$_2$NHC(O)CH$_2$—) | —CH(OH)— | R$_{320}$—C(O)NH—CH(Ph)— (iBu) <br> (R$_{320}$ = PhCH$_2$NHC(O)CH$_2$—) |

TABLE 2-continued

| Compound of Example | A | X | B |
|---|---|---|---|
| 105C | R$_{321}$—CH(CH$_2$CH(CH$_3$)$_2$)—C(O)NH—CH(CH$_2$Ph)— (R$_{321}$ = PhCH$_2$NHC(O)NHCH$_2$—) | —CH(OH)— | BocNH—CH(CH$_2$Ph)— |
| 106C | R$_{322}$—CH(CH$_2$CH(CH$_3$)$_2$)—C(O)NH—CH(CH$_2$Ph)— (R$_{322}$ = CH$_3$CH$_2$OC(O)NHCH$_2$—) | —CH(OH)— | BocNH—CH(CH$_2$Ph)— |
| 107F | R$_{323}$—CH(CH$_2$CH(CH$_3$)$_2$)—C(O)NH—CH(CH$_2$Ph)— (R$_{323}$ = CH$_3$OCH$_2$CH$_2$OCH$_2$OCH$_2$CH$_2$N(CH$_3$)C(O)CH$_2$—) | —CH(OH)— | BocNH—CH(CH$_2$Ph)— |
| 108 | p-C$_7$H$_7$S(O)$_2$—NH—CH(CH$_2$Ph)— | —CH(OH)— | BocNH—CH(CH$_2$Ph)— |
| 109 | p-C$_7$H$_7$S(O)$_2$—NH—CH(CH$_2$Ph)— | —CH(OH)— | H$_2$N—CH(CH$_2$Ph)— |
| 110 | p-C$_7$H$_7$S(O)$_2$—NH—CH(CH$_2$Ph)— | —CH(OH)— | p-C$_7$H$_7$S(O)$_2$—NH—CH(CH$_2$Ph)— |
| 111 | p-C$_7$H$_7$S(O)$_2$—Val—NH—CH(CH$_2$Ph)— | —CH(OH)— | BocNH—CH(CH$_2$Ph)— |
| 112 | p-C$_7$H$_7$S(O)$_2$—Val—NH—CH(CH$_2$Ph)— | —CH(OH)— | H$_2$N—CH(CH$_2$Ph)— |
| 113 | p-C$_7$H$_7$S(O)$_2$—Val—NH—CH(CH$_2$Ph)— | —CH(OH)— | p-C$_7$H$_7$S(O)$_2$—Val—NH—CH(CH$_2$Ph)— |
| 114D | R$_{324}$—CH(CH$_2$CH(CH$_3$)$_2$)—C(O)NH—CH(CH$_2$Ph)— (R$_{324}$ = CbzNH(CH$_2$)$_3$NH—) | —CH(OH)— | BocNH—CH(CH$_2$Ph)— |
| 115 | R$_{325}$—CH(CH$_2$CH(CH$_3$)$_2$)—C(O)NH—CH(CH$_2$Ph)— (R$_{325}$ = H$_2$N(CH$_2$)$_3$NH—) | —CH(OH)— | BocNH—CH(CH$_2$Ph)— |

TABLE 2-continued

| Compound of Example | A | X | B |
|---|---|---|---|
| 116D | R$_{326}$-CH(CH$_2$Ph)-C(O)NH-CH(CH$_2$Ph)- (R$_{326}$ = CH$_3$ON(CH$_3$)CH$_2$—) | —CH(OH)— | BocNH-CH(CH$_2$Ph)- |
| 117C | R$_{327}$-CH(CH$_2$Ph)-C(O)NH-CH(CH$_2$Ph)- (R$_{327}$ = 1-pyrazolyl-CH$_2$—) | —CH(OH)— | BocNH-CH(CH$_2$Ph)- |
| 118D | R$_{328}$-CH(CH$_2$Ph)-C(O)NH-CH(CH$_2$Ph)- (R$_{328}$ = (CH$_3$)$_3$CS(O)$_2$CH$_2$—) | —CH(OH)— | BocNH-CH(CH$_2$Ph)- |
| 119 | PhCH$_2$-CH(CH$_2$Ph)-C(O)NH-CH(CH$_2$Ph)- | —CH(OH)— | BocNH-CH(CH$_2$Ph)- |
| 120 | (4-(CH$_3$)$_2$CH)C$_6$H$_4$CH$_2$CH$_2$— | —CH(OCH$_2$OCH$_3$)— | (4-(CH$_3$)$_2$CH)C$_6$H$_4$CH$_2$CH$_2$— |
| 121 | (1-naphthyl)CH$_2$CH$_2$— | —CH(OCH$_2$OCH$_3$)— | (1-naphthyl)CH$_2$CH$_2$— |
| 122 | 4-CH$_3$OC$_6$H$_4$CH$_2$CH$_2$— | —CH(OCH$_2$OCH$_3$)— | 4-CH$_3$OC$_6$H$_4$CH$_2$CH$_2$— |
| 123 | 4-BrC$_6$H$_4$CH$_2$CH$_2$— | —CH(OCH$_2$OCH$_3$)— | 4-BrC$_6$H$_4$CH$_2$CH$_2$— |
| 124 | PhCH$_2$CH$_2$— | —CH(OCH$_2$SCH$_3$)— | PhCH$_2$CH$_2$— |
| 125 | PhCH$_2$CH$_2$— | —CH(OCH$_2$OCH$_2$CH$_2$OCH$_3$)— | PhCH$_2$CH$_2$— |
| 126C | PhCH$_2$CHF— | —CH(OH)— | PhCH$_2$CH(N$_3$)— |
| 127 | PhCH$_2$CHF— | —CH(OH)— | PhCH$_2$CH(NH$_2$)— |
| 128 | PhCH$_2$CHF | —CH(OH)— | Cbz—Val—NH-CH(CH$_2$Ph)- |
| 129 | PhCH$_2$CHF | —C(O)— | Cbz—Val—NH-CH(CH$_2$Ph)- |
| 130F | R$_{329}$-CH(iPr)-C(O)NH-CH(Ph)- (R$_{329}$ = 4-methylpiperizinyl-S(O)$_2$CH$_2$—) | —CH(OH)— | BocNH-CH(CH$_2$Ph)- |
| 131C | R$_{330}$-CH(iPr)-C(O)NH-CH(Ph)- (R$_{330}$ = 4-morpholinyl-S(O)$_2$CH$_2$—) | —CH(OH)— | BocNH-CH(CH$_2$Ph)- |
| 132C | R$_{331}$-CH(iPr)-C(O)NH-CH(Ph)- (R$_{331}$ = PhCH$_2$NHS(O)$_2$CH$_2$—) | —CH(OH)— | BocNH-CH(CH$_2$Ph)- |
| 133 | R$_{332}$-CH(iPr)-C(O)NH-CH(Ph)- (R$_{332}$ = 4-methylpiperizinyl-S(O)$_2$CH$_2$—) | —CH(OH)— | H$_2$N-CH(CH$_2$Ph)- |

TABLE 2-continued

| Compound of Example | A | X | B |
|---|---|---|---|
| 134 | R₃₃₃-C(O)NH-CH(iPr)- with Ph branch (R₃₃₃ = 4-methylpiperizinyl-S(O)₂CH₂—) | —CH(OH)— | R₃₃₄-C(O)NH-CH(iPr)- with Ph branch (R₃₃₄ = 4-methylpiperizinyl-S(O)₂CH₂—) |
| 135 | R₃₃₅-C(O)NH-CH(iPr)- with Ph branch (R₃₃₅ = PhCH₂NHS(O)₂CH₂—) | —CH(OH)— | H₂N-CH(CH₂Ph)- |
| 136 | R₃₃₆-C(O)NH-CH(iPr)- with Ph branch (R₃₃₆ = PhCH₂NHS(O)₂CH₂—) | —CH(OH)— | R₃₃₇-C(O)NH-CH(iPr)- with Ph branch (R₃₃₇ = PhCH₂NHS(O)₂CH₂—) |
| 137C | R₃₃₈—Val—NH-CH(CH₂Ph)- (R₃₃₈ = 4-methylpiperizinyl-S(O)₂—) | —CH(OH)— | BocNH-CH(CH₂Ph)- |
| 138 | R₃₃₉—Val—NH-CH(CH₂Ph)- (R₃₃₉ = 4-methylpiperizinyl-S(O)₂—) | —CH(OH)— | H₂N-CH(CH₂Ph)- |
| 139 | R₃₄₀—Val—NH-CH(CH₂Ph)- (R₃₄₀ = 4-methylpiperizinyl-S(O)₂—) | —CH(OH)— | R₃₄₁—Val—NH-CH(CH₂Ph)- (R₃₄₁ = 4-methylpiperizinyl-S(O)₂—) |
| 140 | H—Val—NH-CH(CH₂Ph)- | —CH(OH)— | H—Val—NH-CH(CH₂Ph)- |
| 141 | BocNH-CH(CH₂Ph)- | —CH(OH)CH(OH)— | H₂N-CH(CH₂Ph)- |
| 142C | R₃₄₂—Val—NH-CH(CH₂Ph)- (R₃₄₂ = PhCH₂CH₂C(O)—) | —CH(OH)— | BocNH-CH(CH₂Ph)- |
| 143 | PhCH₂CH₂— | —N(OCH₂OCH₃)— | PhCH₂CH₂— |
| 144C | R₃₄₃—Val—NH-CH(CH₂Ph)- (R₃₄₃ = PhCH₂NHC(O)—) | —CH(OH)— | BocNH-CH(CH₂Ph)- |
| 145C | R₃₄₄—Val—NH-CH(CH₂Ph)- (R₃₃₄ = PhCH₂CH₂CH₂—) | —CH(OH)— | BocNH-CH(CH₂Ph)- |

TABLE 2-continued

| Compound of Example | A | X | B |
|---|---|---|---|
| 146 | Cbz—Val—NH—CH(CH₂Ph)— | —CH(OCH₂OCH₃)— | Cbz—Val—NH—CH(CH₂Ph)— |
| 147 | PhCH₂CH₂— | 2,2-disubstituted-1,3-dioxolane (C linked to two O in 5-membered ring) | PhCH₂CH₂— |
| 148 | BocNH—CH(CH₂Ph)— | —CH(OH)— | CH₃C(O)NH—CH(CH₂Ph)— |
| 149B | PhCH₂CH₂— | —CH(OH)CH(OH)— | PhCH₂CH₂— |
| 150 | PhCH₂CH₂— | 1,3-dioxolane-4,5-diyl (H—C—C—H with two O's) | PhCH₂CH₂— |
| 151 | PhCH₂CH₂— | 1,3-dioxolane-4,5-diyl (H—C—C—H(H) with two O's) | PhCH₂CH₂— |
| 152 | PhCH₂CH₂— | —C(OCH₃)₂— | PhCH₂CH₂— |
| 153 | R₃₄₅—Leu—NH—CH(CH₂Ph)— (R₃₄₅ = H₂NC(CH₃)₂CH₂C(O)—) | —CH(OH)— | BocNH—CH(CH₂Ph)— |
| 154 | Cbz—Leu—Asn—NH—CH(CH₂Ph)— | —CH(OH)— | Cbz—Leu—Asn—NH—CH(CH₂Ph)— |
| 155B | BocNH—CH(CH₂Ph)— | —CH₂S(O)₂CH₂— | BocNH—CH(CH₂Ph)— |
| 156B | PhOC(O)—CH(CH₂Ph)— | —CH₂S(O)₂CH₂— | PhOC(O)—CH(CH₂Ph)— |
| 157 | BocNH—CH(CH₂Ph)— | —CH₂S(O)CH₂— | BocNH—CH(CH₂Ph)— |
| 158 | PhOC(O)—CH(CH₂Ph)— | —CH₂S(O)CH₂— | PhOC(O)—CH(CH₂Ph)— |
| 159B | CH₃OC(O)—CH(CH₂Ph)— | —CH₂N(OH)CH₂— | CH₃OC(O)—CH(CH₂Ph)— |

TABLE 2-continued

| Compound of Example | A | X | B |
|---|---|---|---|
| 160D | R$_{346}$—Val—NH—CH(Ph)— <br> (R$_{346}$ = (4-PyridylCH$_2$OC(O)—) | —CH(OH)— | Cbz—Val—NH—CH(Ph)— |
| 161C | R$_{347}$—Val—NH—CH(Ph)— <br> (R$_{347}$ = (3-PyridylCH$_2$OC(O)—) | —CH(OH)— | Cbz—Val—NH—CH(Ph)— |
| 162C | R$_{348}$—Val—NH—CH(Ph)— <br> (R$_{348}$ = (2-PridylCH$_2$OC(O)—) | —CH(OH)— | Cbz—Val—NH—CH(Ph)— |
| 163C | R$_{349}$—Val—NH—CH(Ph)— <br> (R$_{349}$ = (3-Pyridyl-C(O)—) | —CH(OH)— | Cbz—Val—NH—CH(Ph)— |
| 164C | R$_{350}$—Val—NH—CH(Ph)— <br> (R$_{350}$ = (4-Pyridyl-C(O)—) | —CH(OH)— | Cbz—Val—NH—CH(Ph)— |
| 165C | R$_{351}$—Val—NH—CH(Ph)— <br> (R$_{351}$ = (4-MorpholinylCH$_2$CH$_2$OC(O)—) | —CH(OH)— | Cbz—Val—NH—CH(Ph)— |
| 166C | R$_{352}$—Val—NH—CH(Ph)— <br> (R$_{352}$ = (1-PyrrolidinylCH$_2$CH$_2$OC(O)—) | —CH(OH)— | Cbz—Val—NH—CH(Ph)— |
| 167C | R$_{353}$—Val—NH—CH(Ph)— <br> (R$_{353}$ = (2-FuranylCH$_2$OC(O)—) | —CH(OH)— | Cbz—Val—NH—CH(Ph)— |
| 168C | R$_{354}$—Val—NH—CH(Ph)— <br> (R$_{354}$ = ((1-Methyl)pyrrolidin-2-ylCH$_2$OC(O)—) | —CH(OH)— | Cbz—Val—NH—CH(Ph)— |
| 169C | R$_{355}$—Val—NH—CH(Ph)— <br> (R$_{355}$ = ((1-Methyl)piperazin-4-ylC(O)—) | —CH(OH)— | Cbz—Val—NH—CH(Ph)— |
| 170B | BocNH—CH(Ph)— | —CH(OH)CH(OH)— | BocNH—CH(Ph)— |
| 171 | H$_2$N—CH(Ph)— | —CH(OH)CH(OH)— | H$_2$N—CH(Ph)— |

TABLE 2-continued

| Compound of Example | A | X | B |
|---|---|---|---|
| 172B | Cbz—Val—NH—CH(CH₂Ph)— | —CH(OH)CH(OH)— | Cbz—Val—NH—CH(CH₂Ph)— |
| 173 | H—Val—NH—CH(CH₂Ph)— | —CH(OH)CH(OH)— | H—Val—NH—CH(CH₂Ph)— |
| 174B | R₃₅₆—Val—NH—CH(CH₂Ph)— (R₃₅₆ = 4-Pyridyl-CH₂OC(O)—) | —CH(OH)— | R₃₅₆—Val—NH—CH(CH₂Ph)— |
| 175B | R₃₅₇—Val—NH—CH(CH₂Ph)— (R₃₅₇ = 3-Pyridyl-CH₂OC(O)—) | —CH(OH)— | R₃₅₇—Val—NH—CH(CH₂Ph)— |
| 176B | R₃₅₈—Val—NH—CH(CH₂Ph)— (R₃₅₈ = 2-Pyridyl-CH₂OC(O)—) | —CH(OH)— | R₃₅₈—Val—NH—CH(CH₂Ph)— |
| 177 | R₃₅₉—Val—NH—CH(CH₂Ph)— (R₃₅₉ = 3-Pyridyl-C(O)—) | —CH(OH)— | R₃₅₉—Val—NH—CH(CH₂Ph)— |
| 178 | R₃₆₀—Val—NH—CH(CH₂Ph)— (R₃₆₀ = 3-Pyridyl-C(O)—) | —CH(OH)CH(OH)— | R₃₆₀—Val—NH—CH(CH₂Ph)— |
| 179 | R₃₆₁—NH—CH(CH₂Ph)— (R₃₆₁ = 3-Pyridyl-C(O)—) | —CH(OH)CH(OH)— | R₃₆₁—NH—CH(CH₂Ph)— |
| 180 | R₃₆₂—NH—CH(CH₂Ph)— (R₃₆₂ = 4-Pyridyl-C(O)—) | —CH(OH)CH(OH)— | R₃₆₂—NH—CH(CH₂Ph)— |
| 181F | H₂N—CH(CH₂-cyclohexyl)— | —CH(OH)CF₂— | H₂N—CH(iPr)— |
| 182 | Cbz—Val—NH—CH(CH₂-cyclohexyl)— | —CH(OH)CF₂— | Cbz—Val—NH—CH(iPr)— |

TABLE 2-continued

| Compound of Example | A | X | B |
|---|---|---|---|
| 183 | Cbz—Val—NH—CH(CH₂-cyclohexyl)— | —C(O)CF₂— | Cbz—Val—NH—CH(iPr)— |
| 184 | Cbz—(O—Me)Ser—NH—CH(CH₂-cyclohexyl)— | —CH(OH)CF₂— | Cbz—(O—Me)Ser—NH—CH(iPr)— |
| 185 | Cbz—(O—Me)Ser—NH—CH(CH₂-cyclohexyl)— | —C(O)CF₂— | Cbz—(O—Me)Ser—NH—CH(iPr)— |
| 186 | Ac—(O—Me)Ser—NH—CH(CH₂-cyclohexyl)— | —CH(OH)CF₂— | Ac—(O—Me)Ser—NH—CH(iPr)— |
| 187 | Cbz—Val—NH—CH(CH₂Ph)— | —(H.Gly—O)CH— | Cbz—Val—NH—CH(CH₂Ph)— |
| 188 | Boc—NH—CH(CH₂-thiazol-4-yl)— | —CH(OH)CH(OH)— | Boc—NH—CH(CH₂-thiazol-4-yl)— |
| 189C | R₃₆₃—Val—NH—CH(CH₂Ph)—<br>(R₃₆₃ = 4-Morpholinyl-CH₂C(O)—) | —CH(OH)CH(OH)— | R₃₆₃—Val—NH—CH(CH₂Ph)— |
| 190 | R₃₆₄—Val—NH—CH(CH₂Ph)—<br>(R₃₆₄ = 1-Imidazolyl-CH₂C(O)—) | —CH(OH)CH(OH)— | R₃₆₄—Val—NH—CH(CH₂Ph)— |
| 191B | R₃₆₅C(O)—NH—CH(n-Pr)—CH₂—NH—CH(CH₂Ph)—<br>(R₃₆₅ = (4-Methyl)piperazin-1-yl) | —CH(OH)CH(OH)— | R₃₆₅C(O)—NH—CH(n-Pr)—CH₂—NH—CH(CH₂Ph)— |
| 192 | CH₃OC(O)—NH—CH(CH₂Ph)—CH₂NH—CH(CH₂Ph)— | —CH(OH)CH(OH)— | CH₃OC(O)—NH—CH(CH₂Ph)—CH₂NH—CH(CH₂Ph)— |

TABLE 2-continued

| Compound of Example | A | X | B |
|---|---|---|---|
| 193C | R₃₆₆—C(O)NH—CH(iPr)—CH(CH₂Ph)— (R₃₆₆ = 1,1-Dioxothiazin-4-yl) | —CH(OH)CH(OH)— | R₃₆₆—C(O)NH—CH(iPr)—CH(CH₂Ph)— |
| 194C | R₃₆₇—C(O)NH—CH(iPr)—CH(CH₂Ph)— (R₃₆₇ = Morpholin-4-yl) | —CH(OH)CH(OH)— | R₃₆₇—C(O)NH—CH(iPr)—CH(CH₂Ph)— |
| 195 | R₃₆₈—CH(CH₂Ph)— (R₃₆₈ = 1,1-Dioxothiazin-4-yl) | —CH(OH)CH(OH)— | R₃₆₈—CH(CH₂Ph)— |
| 196 | Cbz—Val—NH—CH(CH₂SPh)— | —CH(OH)CH(OH)— | Cbz—Val—NH—CH(CH₂SPh)— |
| 197 | Cbz—Ile—NH—CH(CH₂Ph)— | —CH(OH)CH(OH)— | Cbz—Ile—NH—CH(CH₂Ph)— |
| 198 | Cbz—Ala—NH—CH(CH₂Ph)— | —CH(OH)CH(OH)— | Cbz—Ala—NH—CH(CH₂Ph)— |
| 199 | Cbz—Phe—NH—CH(CH₂Ph)— | —CH(OH)CH(OH)— | Cbz—Phe—NH—CH(CH₂Ph)— |
| 200 | Cbz—Leu—NH—CH(CH₂Ph)— | —CH(OH)CH(OH)— | Cbz—Leu—NH—CH(CH₂Ph)— |
| 201E | R₃₆₉—Val—NH—CH(CH₂Ph)— (R₃₆₉ = (4-methylpiperazinyl)-C(O)—CH₂—) | —CH(OH)— | Cbz—Val—NH—CH(CH₂Ph)— |
| 202C | R₃₇₀—Val—NH—CH(CH₂Ph)— (R₃₇₀ = (4-morpholinyl)-CH₂CH₂OC(O)—) | —CH(OH)— | Cbz—Val—NH—CH(CH₂Ph)— |
| 203 | R₃₇₁—Val—NH—CH(CH₂Ph)— (R₃₇₁ = (3-pyridinyl)-CH₂C(O)—) | —CH(OH)— | R₃₇₁—Val—NH—CH(CH₂Ph)— |
| 204 | H₂N—CH(CH₂Ph)— | —CH(OH)CH(OH)— | H₂N—CH(CH₂Ph)— |

TABLE 2-continued

| Compound of Example | A | X | B |
|---|---|---|---|
| 205 | BocNH-CH(CH2Ph)- | -CH(OH)CH(OH)- | BocNH-CH(CH2Ph)- |
| 206 | BocNH-CH(CH2Ph)- | -CH(OH)CH(OH)- | BocNH-CH(CH2Ph)- |
| 207 | $R_{372}$-CH(CH2Ph)- ($R_{372}$ = (4-morpholinyl)-CH$_2$C(O)—) | -CH(OH)CH(OH)- | $R_{372}$-CH(CH2Ph)- |
| 208 | $R_{373}$-CH(CH2Ph)- ($R_{373}$ = (4-morpholinyl)-CH$_2$CH$_2$OC(O)—) | -CH(OH)CH(OH)- | $R_{373}$-CH(CH2Ph)- |
| 209 | Cbz—Val—NH-CH(CH2Ph)- | -CH(OH)CH(OH)- | Cbz—Val—NH-CH(CH2Ph)- |
| 210 | Cbz—Val—NH-CH(CH2Ph)- | -CH(OH)CH(OH)- | Cbz—Val—NH-CH(CH2Ph)- |
| 211 | BocNH-CH(CH2Ph)- | -CH(OH)CH(OH)- | BocNH-CH(CH2Ph)- |
| 212 | BocNH-CH(CH2Ph)- | -CH(OH)CH(OH)- | H$_2$N-CH(CH2Ph)- |
| 213 | BocNH-CH(CH2Ph)- | -CH(OH)CH(OH)- | Cbz—Val—NH-CH(CH2Ph)- |
| 214 | $R_{374}$-CH(iPr)-C(O)NH-CH(CH2Ph)- ($R_{374}$ = (CH$_3$)$_2$N—) | -CH(OH)CH(OH)- | $R_{374}$-CH(iPr)-C(O)NH-CH(CH2Ph)- |
| 215B | $R_{375}$—Val—NH-CH(CH2Ph)- ($R_{375}$ = (2-pyridinyl)-CH$_2$OC(O)—) | -CH(OH)CH(OH)- | $R_{375}$—Val—NH-CH(CH2Ph)- |
| 216 | $R_{376}$—Val—NH-CH(CH2Ph)- ($R_{376}$ = (2-pyridinyl)-CH$_2$OC(O)—) | -CH(OH)CH(OH)- | $R_{376}$—Val—NH-CH(CH2Ph)- |

TABLE 2-continued

| Compound of Example | A | X | B |
|---|---|---|---|
| 217 | $R_{377}$—Val—NH—CH(CH$_2$Ph)—<br>($R_{377}$ = (2-pyridinyl)-CH$_2$OC(O)—) | —CH(OH)CH(OH)— | $R_{377}$—Val—NH—CH(CH$_2$Ph)— |
| 218F | $R_{378}$—Val—NH—CH(CH$_2$Ph)—<br>($R_{378}$ = (2-pyridinyl)-CH$_2$N(CH$_3$)C(O)—) | —CH(OH)CH(OH)— | $R_{378}$—Val—NH—CH(CH$_2$Ph)— |
| 219 | $R_{379}$—Val—NH—CH(CH$_2$Ph)—<br>($R_{379}$ = (2-pyridinyl)-CH$_2$N(CH$_3$)C(O)—) | —CH(OH)CH(OH)— | $R_{379}$—Val—NH—CH(CH$_2$Ph)— |
| 220 | $R_{380}$—Val—NH—CH(CH$_2$Ph)—<br>($R_{380}$ = (2-pyridinyl)-CH$_2$N(CH$_3$)C(O)—) | —CH(OH)CH(OH)— | $R_{380}$—Val—NH—CH(CH$_2$Ph)— |
| 221 | $R_{381}$—Val—NH—CH(CH$_2$Ph)—<br>($R_{381}$ = (2-pyridinyl)-CH$_2$N(CH$_3$)C(O)—) | —CH(OH)— | $R_{381}$—Val—NH—CH(CH$_2$Ph)— |
| 222 | $R_{382}$—Val—NH—CH(CH$_2$Ph)—<br>($R_{382}$ = (2-pyridinyl)-C(O)—) | —CH(OH)CH(OH)— | $R_{382}$—Val—NH—CH(CH$_2$Ph)— |
| 223 | $R_{383}$—Val—NH—CH(CH$_2$Ph)—<br>($R_{383}$ = (3-pyridinyl)-CH$_2$CH$_2$C(O)—) | —CH(OH)CH(OH)— | $R_{383}$—Val—NH—CH(CH$_2$Ph)— |
| 224 | $R_{384}$—Val—NH—CH(CH$_2$Ph)—<br>($R_{384}$ = (2-pyridinyl)-CH$_2$C(O)—) | —CH(OH)CH(OH)— | $R_{384}$—Val—NH—CH(CH$_2$Ph)— |
| 225 | $R_{385}$—Val—NH—CH(CH$_2$Ph)—<br>($R_{385}$ = (4-pyridinyl)-CH$_2$OC(O)—) | —CH(OH)CH(OH)— | $R_{385}$—Val—NH—CH(CH$_2$Ph)— |
| 226 | $R_{386}$—CH(CH$_2$Ph)—<br>($R_{386}$ = t-butyl-NHC(O)NH—) | —CH(OH)CH(OH)— | $R_{386}$—CH(CH$_2$Ph)— |
| 227 | $R_{387}$—CH(CH$_2$Ph)—<br>($R_{387}$ = t-butyl-NHC(O)NH—) | —CH(OH)CH(OH)— | $R_{387}$—CH(CH$_2$Ph)— |

TABLE 2-continued

| Compound of Example | A | X | B |
|---|---|---|---|
| 228 | $R_{388}$—Val—NH—CH(CH$_2$Ph)— <br> ($R_{388}$ = (4-pyridinyl)-CH$_2$OC(O)—) | —CH(OH)CH(OH)— | $R_{388}$—Val—NH—CH(CH$_2$Ph)— |
| 229 | $R_{389}$—Val—NH—CH(CH$_2$Ph)— <br> ($R_{389}$ = (3-pyridinyl)-CH$_2$OC(O)—) | —CH(OH)CH(OH)— | $R_{389}$—Val—NH—CH(CH$_2$Ph)— |
| 230 | $R_{389}$—Val—NH—CH(CH$_2$Ph)— <br> ($R_{390}$ = (3-pyridinyl)-CH$_2$OC(O)—) | —CH(OH)CH(OH)— | $R_{389}$—Val—NH—CH(CH$_2$Ph)— |
| 231 | $R_{391}$—Val—NH—CH(CH$_2$Ph)— <br> ($R_{391}$ = (2-pyridinyl)-CH$_2$OC(O)—) | —CH(OH)CH(OH)— | BocNH—CH(CH$_2$Ph)— |
| 232 | $R_{392}$—Val—NH—CH(CH$_2$Ph)— <br> ($R_{392}$ = (2-pyridinyl)-CH$_2$OC(O)—) | —CH(OH)CH(OH)— | H$_2$N—CH(CH$_2$Ph)— |
| 233 | $R_{393}$—Val—NH—CH(CH$_2$Ph)— <br> HOC(O)CH$_2$CH$_2$C(O)NH—CH(CH$_2$Ph)— <br> ($R_{393}$ = (2-pyridinyl)-CH$_2$OC(O)—) | —CH(OH)CH(OH)— | |
| 234D | $R_{394}$—Val—NH—CH(CH$_2$Ph)— <br> ($R_{394}$ = (2-pyridinyl)-CH$_2$N(CH$_3$)S(O)$_2$—) | —CH(OH)CH(OH)— | $R_{394}$—Val—NH—CH(CH$_2$Ph)— |
| 235G | $R_{395}$\C(O)NH—CH(CH$_2$Ph)CH(CH$_3$)$_2$ <br> ($R_{395}$ = (2-pyridinyl)-CH$_2$N(CH$_3$)C(O)CH$_2$—) | —CH(OH)CH(OH)— | $R_{395}$\C(O)NH—CH(CH$_2$Ph)CH(CH$_3$)$_2$ |
| 236 | $R_{396}$—Val—NH—CH(CH$_2$Ph)— <br> ($R_{396}$ = (2-pyridinyl)-CH=CH—C(O)—) | —CH(OH)CH(OH)— | $R_{396}$—Val—NH—CH(CH$_2$Ph)— |
| 237 | $R_{397}$—Val—NH—CH(CH$_2$Ph)— <br> ($R_{397}$ = (2-pyridinyl)-CH$_2$CH$_2$C(O)—) | —CH(OH)CH(OH)— | $R_{397}$—Val—NH—CH(CH$_2$Ph)— |
| 238 | $R_{398}$—Val—NH—CH(CH$_2$Ph)— <br> ($R_{398}$ = (4-morpholinyl)-CH$_2$CH$_2$OC(O)—) | —CH(OH)— | $R_{398}$—Val—NH—CH(CH$_2$Ph)— |

TABLE 2-continued

| Compound of Example | A | X | B |
|---|---|---|---|
| 239 | Cbz—Val—NH—CH(CH₂Ph)— | —CH(OH)— | Boc—Val—NH—CH(CH₂Ph)— |
| 240 | Cbz—Val—NH—CH(CH₂Ph)— | —CH(OH)— | H—Val—NH—CH(CH₂Ph)— |
| 241B | R$_{399}$—Val—NH—CH(CH₂Ph)— (R$_{399}$ = (2-thiazolyl)-CH₂OC(O)—) | —CH(OH)— | R$_{399}$—Val—NH—CH(CH₂Ph)— |
| 242 | R$_{400}$—Val—NH—CH(CH₂Ph)— (R$_{400}$ = (1-imidazolyl)-CH₂C(O)—) | —CH(OH)— | Cbz—Val—NH—CH(CH₂Ph)— |
| 243 | R$_{401}$—Val—NH—CH(CH₂Ph)— (R$_{401}$ = (4-morpholinyl)-CH₂C(O)—) | —CH(OH)— | Cbz—Val—NH—CH(CH₂Ph)— |
| 244 | R$_{402}$—Val—NH—CH(CH₂Ph)— (R$_{402}$ = (2-pyridinyl)-CH₂NHC(O)—) | —CH(OH)— | R$_{402}$—Val—NH—CH(CH₂Ph)— |
| 245 | R$_{403}$—Val—NH—CH(CH₂Ph)— (R$_{403}$ = (4-pyridinyl)-C(O)—) | —CH(OH)— | R$_{403}$—Val—NH—CH(CH₂Ph)— |
| 246 | R$_{404}$—Val—NH—CH(CH₂Ph)— (R$_{404}$ = (3-pyridinyl)-CH₂CH₂C(O)—) | —CH(OH)— | R$_{404}$—Val—NH—CH(CH₂Ph)— |
| 247 | R$_{405}$—Val—NH—CH(CH₂Ph)— (R$_{405}$ = (3-pyridinyl)-CH₂OC(O)—) | —CH(OH)CH(OH)— | R$_{405}$—Val—NH—CH(CH₂Ph)— |
| 248 | R$_{406}$—Val—NH—CH(CH₂Ph)— (R$_{406}$ = (4-morpholinyl)-CH₂CH₂OC(O)—) | —CH(OH)CH(OH)— | R$_{398}$—Val—NH—CH(CH₂Ph)— |
| 249 | R$_{407}$—Val—NH—CH(CH₂Ph)— (R$_{407}$ = (3-pyridinyl)-CH₂OC(O)—) | —CH(OH)CH(OH)— | BocNH—CH(CH₂Ph)— |
| 250 | Cbz—Val—NH—CH(CH₂Ph)— | —CH₂SO₂CH₂— | Cbz—Val—NH—CH(CH₂Ph)— |

TABLE 2-continued

| Compound of Example | A | X | B |
|---|---|---|---|
| 251 | $R_{408}$—Val—NH—CH(CH$_3$)—CH$_2$—Ph<br>($R_{408}$ = (2-pyridinyl)-CH$_2$N(CH$_3$)S(O)$_2$—) | —CH(OH)CH(OH)— | $R_{408}$—Val—NH—CH(CH$_3$)—CH$_2$—Ph |
| 252 | $R_{409}$—Val—NH—CH(CH$_3$)—CH$_2$—Ph<br>($R_{409}$ = (2-pyridinyl)-CH$_2$N(CH$_3$)S(O)$_2$—) | —CH(OH)CH(OH)— | $R_{409}$—Val—NH—CH(CH$_3$)—CH$_2$—Ph |
| 253 | HO—CH(CH(CH$_3$)CH$_2$CH$_3$)—C(O)NH—CH(CH$_3$)—CH$_2$—Ph | —CH(OH)CH(OH)— | HO—CH(CH(CH$_3$)CH$_2$CH$_3$)—C(O)NH—CH(CH$_3$)—CH$_2$—Ph |
| 254 | $R_{410}$—Val—NH—CH(CH$_3$)—CH$_2$—Ph<br>($R_{410}$ = (1-methyl-3-piperidinyl)-CH$_2$OC(O)—) | —CH(OH)— | Cbz—Val—NH—CH(CH$_3$)—CH$_2$—Ph |
| 255 | $R_{411}$—Val—NH—CH(CH$_3$)—CH$_2$—Ph<br>($R_{411}$ = (1-methyl-2-piperidinyl)-CH$_2$OC(O)—) | —CH(OH)— | Cbz—Val—NH—CH(CH$_3$)—CH$_2$—Ph |
| 256 | $R_{412}$—Val—NH—CH(CH$_3$)—CH$_2$—Ph<br>($R_{412}$ = (1-imidazolyl)-CH$_2$C(O)—) | —CH(OH)— | $R_{412}$—Val—NH—CH(CH$_3$)—CH$_2$—Ph |
| 257 | $R_{413}$—Val—NH—CH(CH$_3$)—CH$_2$—Ph<br>($R_{413}$ = (2-pyridinyl)-CH$_2$OC(O)—) | —CH(OH)CH(OH)— | HOC(O)CH$_2$—CH(CH(CH$_3$)$_2$)—C(O)NH—CH(CH$_3$)—CH$_2$—Ph |
| 258 | $R_{414}$—Val—NH—CH(CH$_3$)—CH$_2$—Ph<br>($R_{414}$ = (2-pyridinyl)-CH$_2$CH$_2$C(O)—) | —CH(OH)— | $R_{414}$—Val—NH—CH(CH$_3$)—CH$_2$—Ph |
| 259 | $R_{415}$—Val—NH—CH(CH$_3$)—CH$_2$—Ph<br>($R_{415}$ = PhCH$_2$NHC(O)—) | —CH(OH)— | $R_{415}$—Val—NH—CH(CH$_3$)—CH$_2$—Ph |
| 260 | $R_{416}$—Val—NH—CH(CH$_3$)—CH$_2$—Ph<br>($R_{416}$ = (2-pyridinyl)-CH$_2$NHC(O)—) | —CH(OH)— | $R_{416}$—Val—NH—CH(CH$_3$)—CH$_2$—Ph |
| 261 | $R_{417}$—Val—NH—CH(CH$_3$)—CH$_2$—Ph<br>($R_{417}$ = (3-pyridinyl)-CH$_2$NHC(O)—) | —CH(OH)— | $R_{417}$—Val—NH—CH(CH$_3$)—CH$_2$—Ph |

TABLE 2-continued

| Compound of Example | A | X | B |
|---|---|---|---|
| 262 | CH$_3$OCH$_2$O-CH(CH(CH$_3$)CH$_2$CH$_3$)-C(O)NH-CH(CH$_2$Ph)- | -CH(OH)CH(OH)- | CH$_3$OCH$_2$O-CH(CH(CH$_3$)CH$_2$CH$_3$)-C(O)NH-CH(CH$_2$Ph)- |
| 263 | NH-CH(CH$_2$CH(CH$_3$)$_2$)- | -CH(OH)CF$_2$- | NH-CH(CH(CH$_3$)$_2$)- |
| 264 | Cbz—Val—NH-CH(CH$_2$CH(CH$_3$)$_2$)- | -CH(OH)CF$_2$- | Cbz—Val—NH-CH(CH(CH$_3$)$_2$)- |
| 265 | Cbz—Val—NH-CH(CH$_2$CH(CH$_3$)$_2$)- | -C(O)CF$_2$- | Cbz—Val—NH-CH(CH(CH$_3$)$_2$)- |
| 266C | NH-CH(CH$_2$Ph)- | -CH(OH)CF$_2$- | NH-CH(CH$_2$Ph)- |
| 267 | Cbz—Val—NH-CH(CH$_2$Ph)- | -CH(OH)CF$_2$- | Cbz—Val—NH-CH(CH$_2$Ph)- |
| 268 | R$_{418}$—Val—NH-CH(CH$_2$Ph)-  (R$_{418}$ = (2-pyridinyl)-CH$_2$OC(O)—) | -CH(OH)CF$_2$- | R$_{418}$—Val—NH-CH(CH$_2$Ph)- |
| 269 | R$_{419}$—Val—NH-CH(CH$_2$Ph)-  (R$_{419}$ = (2-pyridinyl)-CH$_2$OC(O)—) | -CH(OH)CF$_2$- | H$_2$N-CH(CH$_2$Ph)- |
| 270 | R$_{420}$—Val—NH-CH(CH$_2$Ph)-  (R$_{420}$ = (2-pyridinyl)-CH$_2$OC(O)—) | -CH(OH)CF$_2$- | Boc—NH-CH(CH$_2$Ph)- |
| 271 | R$_{421}$—Val—NH-CH(CH$_2$Ph)-  (R$_{421}$ = (2-pyridinyl)-CH$_2$OC(O)—) | -CH(OH)CF$_2$- | n-Pr—S(O)$_2$NH-CH(CH$_2$Ph)- |
| 272B | Cba—NH-CH(CH$_2$Ph)- | -CH(OH)CF$_2$- | HO-CH(CH$_2$Ph)- |
| 273 | Cbz—Val—NH-CH(CH$_2$Ph)- | -CH(OH)CF$_2$- | HO-CH(CH$_2$Ph)- |

TABLE 2-continued

| Compound of Example | A | X | B |
|---|---|---|---|
| 274 | Cbz—Val—NH—CH(Ph)—CH₂— | —CH(OH)CF₂— | —C(O)—CH₂—Ph |
| 275D | Cbz—Val—NH—CH(Ph)—CH₂— | —CH(OH)CF₂— | PhCH₂CH₂— |
| 276 | Cbz—Val—NH—CH(Ph)—CH₂— | —C(O)CF₂— | PhCH₂CH₂— |
| 277 | Cbz—Val—NH—CH(Ph)—CH₂— | —CH(OH)CF₂— | (CH₃)₂CHCH₂—C(O)O—CH(CH₃)—CH(Ph)— |
| 278 | Cbz—Val—NH—CH(Ph)—CH₂— | —CH(OH)CF₂— | (CH₃)₂CH—NH—C(O)O—CH(CH₃)—CH(Ph)— |
| 279 | Cbz—Val—NH—CH(Ph)—CH₂— | —CH(OH)CF₂— | CH₃O—CH(CH₃)—CH(Ph)— |
| 280 | Cbz—Val—NH—CH(Ph)—CH₂— | —C(O)—CF₂— | CH₃O—CH(CH₃)—CH(Ph)— |
| 281B | Cbz—Val—NH—CH(CH₂SR₄₂₂)— (R₄₂₂ = 2-pyridinyl) | —CH(OH)CH(OH)— | Cbz—Val—NH—CH(CH₂SR₄₂₂)— |
| 282B | Cbz—Val—NH—CH(CH₂SR₄₂₃)— (R₄₂₃ = 1-methylimidazol-2-yl) | —CH(OH)CH(OH)— | Cbz—Val—NH—CH(CH₂SR₄₂₃)— |
| 283B | Cbz—Val—NH—CH(CH₂SR₄₂₄)— (R₄₂₄ = 2-pyrimidinyl) | —CH(OH)CH(OH)— | Cbz—Val—NH—CH(CH₂SR₄₂₄)— |
| 284B | Cbz—Val—NH—CH(CH₂SR₄₂₅)— (R₄₂₅ = cyclohexyl) | —CH(OH)CH(OH)— | Cbz—Val—NH—CH(CH₂SR₄₂₅)— |
| 285B | Cbz—Val—NH—CH(CH₂SR₄₂₆)— (R₄₂₆ = 4-pyridinyl) | —CH(OH)CH(OH)— | Cbz—Val—NH—CH(CH₂SR₄₂₆)— |

TABLE 2-continued

| Compound of Example | A | X | B |
|---|---|---|---|
| 286B | Cbz—Val—NH—CH(CH₃)—CH₂—S—R₄₂₇ (R₄₂₇ = tert-butyl) | —CH(OH)CH(OH)— | Cbz—Val—NH—CH(CH₃)—CH₂—S—R₄₂₇ |
| 287B | Cbz—Val—NH—CH(CH₃)—CH₂—S—R₄₂₈ (R₄₂₈ = ethyl) | —CH(OH)CH(OH)— | Cbz—Val—NH—CH(CH₃)—CH₂—S—R₄₂₈ |
| 288C | Cbz—Val—NH—CH(CH₃)—CH₂CH₂CH₂CH₃ | —CH(OH)CH(OH)— | Cbz—Val—NH—CH(CH₃)—CH₂CH₂CH₂CH₃ |
| 289B | Cbz—Val—NH—CH(CH₃)—CH₂—Ph | —CH(OH)CH(OH)— | Cbz—Val—NH—CH(CH₃)—CH₂—Ph |
| 290B | Cbz—Val—NH—CH(CH₃)—CH₂—(p-HO)—C₆H₄ | —CH(OH)CH(OH)— | Cbz—Val—NH—CH(CH₃)—CH₂—(p-HO)—C₆H₄ |
| 291 | Cbz—Ile—NH—CH(CH₃)—CH₂—Ph | —CH(OH)— | Cbz—Ile—NH—CH(CH₃)—CH₂—Ph |
| 292 | Cbz—Ile—NH—CH(CH₃)—CH₂—Ph | —CH(OH)— | Boc—NH—CH(CH₃)—CH₂—Ph |
| 293B | Cbz—Val—NH—CH(CH₃)—CH₂—Ph (R₄₂₉ = (4-methylpiperazin-1-yl)CH₂C(O)—) | —CH(OR₄₂₉)— | Cbz—Val—NH—CH(CH₃)—CH₂—Ph |
| 294 | Cbz—Val—NH—CH(CH₃)—CH₂—Ph (R₄₃₀ = (morpholin-4-yl)CH₂C(O)—) | —CH(OR₄₃₀)— | Cbz—Val—NH—CH(CH₃)—CH₂—Ph |
| 295B | Cbz—Val—NH—CH(CH₃)—CH₂—Ph (R₄₃₁ = m-((4-methylpiperazin-1-yl)CH₂)C₆H₄C(O)—) | —CH(OR₄₃₁)— | Cbz—Val—NH—CH(CH₃)—CH₂—Ph |
| 296 | Cbz—Val—NH—CH(CH₃)—CH₂—Ph (R₄₃₂ = m-((morpholin-4-yl)CH₂)C₆H₄C(O)—) | —CH(OR₄₃₂)— | Cbz—Val—NH—CH(CH₃)—CH₂—Ph |
| 297C | Cbz—Val—NH—CH(CH₃)—CH₂—Ph | —CH(OR₄₃₃) | Cbz—Val—NH—CH(CH₃)—CH₂—Ph |

TABLE 2-continued

| Compound of Example | A | X | B |
|---|---|---|---|
| | ($R_{433}$ = p-((4-methylpiperazin-1-yl)CH$_2$)C$_6$H$_4$C(O)—) | | |
| 298 | Cbz—Val—NH—CH(CH$_2$Ph)— | —CH(OR$_{434}$)— | Cbz—Val—NH—CH(CH$_2$Ph)— |
| | ($R_{434}$ = p-((morpholin-4-yl)CH$_2$)C$_6$H$_4$C(O)—) | | |
| 299C | Boc—NH—CH(CH$_2$Ph)— | —C(=NOH)— | Boc—NH—CH(CH$_2$Ph)— |
| 300 | Boc—NH—CH(CH$_2$Ph)— | —CH(NH$_2$)— | Boc—NH—CH(CH$_2$Ph)— |
| 301 | Boc—NH—CH(CH$_2$Ph)— | epoxide | Boc—NH—CH(CH$_2$Ph)— |
| 302B | Cbz—Val—NH—CH(CH$_2$Ph)— | epoxide | Cbz—Val—NH—CH(CH$_2$Ph)— |
| 303B | CH(CH$_2$Ph)—C(O)OCH$_3$ | —CH(OH)— | CH(CH$_2$Ph)—C(O)OCH$_3$ |
| 304B | CH(CH$_2$Ph)—C(O)—Val—OCH$_2$Ph | —CH(OH)— | CH(CH$_2$Ph)—C(O)—Val—OCH$_2$Ph |
| 305 | C(OH)(CH$_2$Ph)—C(O)—Val—OCH$_2$Ph | —CH(OH)CH(OH)— | C(OH)(CH$_2$Ph)—C(O)—Val—OCH$_2$Ph |
| 306 | CH(CH$_2$Ph)—C(O)—Val—OCH$_2$Ph | —CH(OH)CH(OH)— | CH(CH$_2$Ph)—C(O)—Val—OCH$_2$Ph |
| 307D | CH(SPh)(CH$_2$Ph)—C(O)—Val—OCH$_2$Ph | —CH(OH)CH(OH)— | CH(SPh)(CH$_2$Ph)—C(O)—Val—OCH$_2$Ph |
| 308 | Cbz—Val—NH—CH(CH$_2$Ph)— | —CH(OC(O)CH$_2$NH$_2$)— | Cbz—Val—NH—CH(CH$_2$Ph)— |
| 309 | Cbz—Val—NH—CH(CH$_2$Ph)— | epoxide with CF$_2$ | Cbz—Val—NH—CH(CH$_2$Ph)— |
| 310 | Cbz—Val—NH—CH(CH$_2$Ph)— | —CH(OH)CH(OH)— | Cbz—Val—NH—CH(CH$_2$Ph)— |

TABLE 2-continued

| Compound of Example | A | X | B |
|---|---|---|---|
| 311 | Boc—NH—CH(CH2Ph)— | epoxide (O) | (Cbz)(PhCH2)N—CH(CH2Ph)— |
| 312 | Boc—NH—CH(CH2Ph)— | epoxide (O) | H2N—CH(CH2Ph)— |
| 313 | Boc—NH—CH(CH2Ph)— | epoxide (O) | Boc—NH—CH(CH2Ph)— |
| 314 | Boc—NH—CH(CH2Ph)— | —CH(OH)CH2— | Boc—NH—CH(CH2Ph)— |
| 315B | Boc—NH—CH(CH2Ph)— | —CH(OH)CH(NH2)— | Boc—NH—CH(CH2Ph)— |
| 316 | R435—Val—NH—CH(CH2Ph)— (R435 = quinolin-2-carbonyl) | —CH(OH)CH(OH)— | R435—Val—NH—CH(CH2Ph)— |
| 317 | H—Val—NH—CH(CH2Ph)— | —CH(OH)CH(OH)— | H—Val—NH—CH(CH2Ph)— |
| 318 | R436—Val—NH—CH(CH2Ph)— (R436 = quinolin-2-carbonyl) | —CH(OH)CH(OH)— | R436—Val—NH—CH(CH2Ph)— |
| 319 | H—Val—NH—CH(CH2Ph)— | —CH(OH)CH(OH)— | H—Val—NH—CH(CH2Ph)— |
| 320 | R437—Val—NH—CH(CH2Ph)— (R437 = quinolin-2-carbonyl) | —CH(OH)CH(OH)— | R437—Val—NH—CH(CH2Ph)— |
| 321 | R438—Val—NH—CH(CH2Ph)— (R438 = indole-2-carbonyl) | —CH(OH)CH(OH)— | R438—Val—NH—CH(CH2Ph)— |
| 322 | R439—Val—NH—CH(CH2Ph)— (R439 = indole-2-carbonyl) | —CH(OH)CH(OH)— | R439—Val—NH—CH(CH2Ph)— |

TABLE 2-continued

| Compound of Example | A | X | B |
|---|---|---|---|
| 323 | R440—Val—NH—CH(CH3)—CH2—Ph (R440 = indole-2-carbonyl) | —CH(OH)CH(OH)— | R440—Val—NH—CH(CH3)—CH2—Ph |
| 324 | R441—CH(C(O)NH—CH(CH3)—CH2—Ph)—CH2CH(CH3)2 | —CH(OH)CH(OH)— | R441—CH(C(O)NH—CH(CH3)—CH2—Ph)—CH2CH(CH3)2 |
| | R441 = 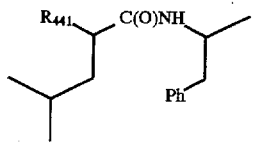 | | |
| 325 | R442—CH(C(O)NH—CH(CH3)—CH2—Ph)—CH(CH3)2 | —CH(OH)CH(OH)— | R442—CH(C(O)NH—CH(CH3)—CH2—Ph)—CH(CH3)2 |
| | | R442 = 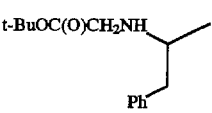 | |
| 326 | t-BuOC(O)CH2NH—CH(CH3)—CH2—Ph | —CH(OH)CH(OH)— | t-BuOC(O)CH2NH—CH(CH3)—CH2—Ph |
| 327C | H2N—CH(CH3)—CH2—R443 (R443 = 2-formylphenyl) | —CH(OH)CH(OH)— | H2N—CH(CH3)—CH2—R443 |
| 328 | 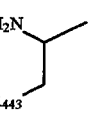 | —CH(OH)CH(OH)— | 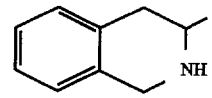 |
| 329 | 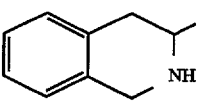 (R444 = —C(O)NH-t-butyl) | —CH(OH)CH(OH)— | 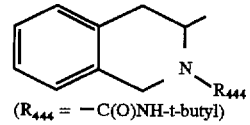 |
| 330E | 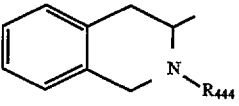 (R445 = —C(O)NH-t-butyl) | —CH(OH)— | 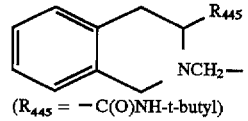 |
| 331 | 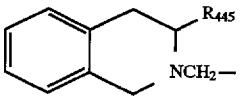 (R446 = —C(O)NH-t-butyl) | —CH(OH)— | 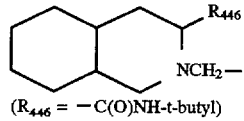 |

TABLE 2-continued

| Compound of Example | A | X | B |
|---|---|---|---|
| 332B | benzene-fused cyclohexane with $R_{447}$, $NCH_2-$ ($R_{447} = -C(O)NH\text{-}t\text{-butyl}$) | $-CH(OH)CH(OH)-$ | benzene-fused cyclohexane with $R_{447}$, $NCH_2-$ |
| 333 | decalin with $R_{448}$, $NCH_2-$ ($R_{448} = -C(O)NH\text{-}t\text{-butyl}$) | $-CH(OH)CH(OH)-$ | decalin with $R_{448}$, $NCH_2-$ |

The compounds of the invention can be prepared as shown in Schemes 1-13. The syntheses of segments (II), (III), (IV), and (V) are described in the Examples. The process shown in Scheme 1 discloses the condensation of carboxylic or sulfonic acid G—OH to segments (II) and (III) in the presence of a coupling reagent to give (VI) and (VII), respectively. The process shown in Scheme 1 also discloses the condensation of segments (IV) and (V) to $NR_{15}R_{16}$ in the presence of a coupling reagent to give (VIII) and (IX), respectively. Coupling reagents known in the art which can be used include, but are not limited to, dicyclohexylcarbodiimide (DCC), 3-ethyl-3'-(dimethylamino)propylcarbodiimide (EDC), bis(2-oxo-3-oxazolidinyl)phosphinic chloride (BOP-Cl), dipenylphosphoryl azide (DPPA) and the like.

In addition to the use of the carboxylic acids or sulfonic acids shown in the scheme, acid halide and other activated ester derivatives of the carboxylic acid or sulfonic acid are useful for the coupling reactions with (II), (III), and $HNR_{15}R_{16}$. Acid halide derivatives include the acid chloride. Activated ester derivatives include activated esters commonly used by those skilled in the art for activating carboxylic acid groups for coupling with an amine to form an amide bond or for coupling with an alcohol to form an ester bond including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

The compounds of the invention having a fluorinated X group can be prepared as shown in the synthetic Scheme 2. The process shown in the synthetic scheme shows the preparation of the key intermediate XV. The synthesis starts with a protected amino alcohol X, which was oxidized by Swern oxidation to the corresponding aldehyde XI. Reformatsky reaction with ethyl bromodifluoroacetate provided XII. Deprotection of XII, followed by treatment with phosgene gave XIII which upon hydrolysis of the ester and treatment with an organometallic such as an alkyllithium or alkyl Grignard provided compound XIV. Oxime formation from XIV and hydrogenation, followed by basic hydrolysis of the oxazolidinone ring gave the key intermediate XV. Coupling of protected amino acid, or amino acid derivatives or peptidyl fragments J to the intermediate XV provides the compounds of the invention XVI. Oxidation of XVI provided the compounds of the invention XVII.

Compounds of the invention wherein X is —CH(OR$_{201}$)— can be prepared as shown in Scheme 3. The process shown in Scheme 3 discloses the reduction and subsequent addition of vinylmagnesium bromide to protected aminoester XVIII. The resulting allylic alcohol XIX is mesylated to provide XX, which is treated with a Grignard reagent and catalytic CuCN to provide olefin XXI. Epoxidation of XXI leads to XXII which is regioselectively opened with azide anion to provide XXIII. Reduction of the azide gives XXIV and deprotection provides XXV, both of which can be coupled according to Scheme 1 to provide compounds of the invention.

Compounds of the invention wherein X is —CH(OR$_{201}$)—CH(OR$_{202}$)— can be prepared as shown in Scheme 4. The process shown in Scheme 4 discloses the oxidation of XXVI to protected aminoaldehyde XXVII. Reductive dimerization of XXVII provides the doubly protected diaminodiol XXVIII, which is deprotected to give diaminodiol XXIX. Coupling of XXIX according to Scheme 1 provides compounds of the invention.

Compounds of the invention of the the type XXXII, in which d=0 or 1 and $R_3$ and $R_{500}$ are as defined above, may be prepared as outlined in Scheme 5. Thus the known aziridine XXX (Y. L. Merrer, et al *Heterocycles*, 1987, 25, 541–548) is acylated (e.g. with G=Cbz-valine), sulfonated (e.g. with G=p-toluene sulfonic acid), or phosphorylated (e.g. with G=diphenylphosphinic acid), to provide compounds of the formula XXXI. These compounds are in turn treated with various nucleophiles, such as thiols, alcohols, amines, or organometallic reagents, which serve to open the aziridine ring. The acetonide can be removed by acid hydrolysis. When G is a sulfonic acid residue, e.g. p-toluenesulfonyl, this group may be removed reductively, for example, with sodium in liquid ammonia or with sodium napthalenide, to provide compounds of the formula XXXII wherein G is hydrogen. These compounds, in turn, can be N-acylated with protected amino acids, e.g. Cbz-valine, to provide additional compounds of the formula XXXII.

As outlined in Scheme 6, compounds of the invention of the formula XXXVI and XXXVII may be prepared by acylation of XXXIII with bromoacetyl bromide, followed by displacement of the bromide with various amine nucleophiles. $R_{800}$ and $R_{801}$ may be selected independently from hyrodgen and alkyl, or may consititute a heterocyclic ring incorporating the nitrogen to which the are appended, e.g., rings such as morpholine, piperidine, and piperazine. Compounds of the invention of formula XL and XLI may be prepared by acylation of XXXIII with (chloromethyl) benzoyl chloride, followed by displacement of the benzylic chloride group with various amine nucleophiles.

As outlined in Scheme 7, compounds of the invention of formula XLV and XLVI, and L and LI, are prepared in analogous fashion from compounds XLII and XLVII.

As outlined in Scheme 8, compounds of the invention of the formula LIII are prepared from compounds of the formula LII by treatment with diazomethane. Compounds of the formula LIV may be oxidized to ketones of the formula LV by treatment with the oxalyl chloride/DMSO reagent followed by treatment with triethylamine. Ketones of the formula LV may be converted to epoxides of the formula LVI by treatment with diazomethane.

As outlined in Scheme 9, the compound of the formula LVII (C. H. Chen, et al, *J. Org. Chem.*, 1981, 46, 2752–2757.) is converted to the compound of the formula LVIII by hydrogenation, reduction with sodium borohydride, followed by saponification of the ester to provide the diacid. This compound is in turn, coupled with various amino acid esters or amides to provide compounds of the formula LIX, wherein $R_{803}$ may be NH or O, and $R_3$ is as defined above.

As outlined in Scheme 10, compounds of the formula LX (W. N. Haworth, et al, *J. Chem. Soc.*, 1944, 217.) are treated with amino acid esters or amides, followed by acetone with an acid catalyst, followed by triflic anhydride to provide compounds of the formula LXI, wherein $R_{803}$ may be NH or O, and $R_3$ is as defined above. These compounds are in turn treated with various alcohol, thiol, or amine nucleophiles, followed by acid catalyzed hydrolysis of the acetonide, to provide compounds of the formula LXII, wherein $R_{803}$ may be NH or O, and $R_3$ and $R_{500}$ are as defined above.

As outlined in Scheme 11, the diepoxide LXIII (R. S. Tipson, et al, *Carbohydrate Research*, 1968, 7, 232–243.) is converted to the diester of the formula LXIV by oxidation, first with the DMSO/oxalyl chloride/triethylamine reagent (Swern reagent) to the dialdehyde, and then with bromine in methanol/aqueous sodium bicarbonate. This compound is in turn treated with various alcohol, thiol, or amine nucleophiles, or with organometallic nucleophiles, followed by protection of the alcohols with a protecting group P', to provide compounds of the formula LXV, wherein d=0 or 1, and $R_{500}$ and $R_3$ are as defined above. Saponification of LXV followed by coupling with various amino acid esters or amides and deprotection of the alcohol protecting groups provides compounds of the formula LXVI, wherein $R_{803}$ may be NH or O, d=0 or 1, and $R_{500}$ and $R_3$ are as defined above.

As outlined in Scheme 12, the compound of the formula LXIII may be oxidized with the Swern reagent in a solvent like THF, and without isolation, treated with an organometallic reagent, such as a Grignard reagent, to provide compounds of the formula LXVII. These compounds, may in turn, be converted to the carbamates LXVIII with an isocyante, wherein $R_{804}$ is hydrogen or benzyl or subsituted benzyl. These carbamates may then be treated with a strong base such as potassium t-butoxide or sodium hydride in a suitable solvent such as THF, and the resulting cyclic carbamates treated with hydrogen over a palladium catalyst to provide compounds of the formula LXIX.

As outlined in Scheme 13, compounds of the formula LV may be converted to the oxime LXX with hydroxylamine hydrochloride in the presence of pyridine. These compounds may then be reduced with hydrogen over a catalyst to provide compounds of the formula LXXI.

Scheme 1

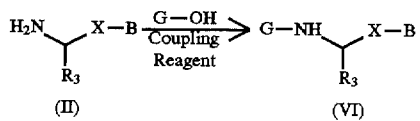

-continued
Scheme 1

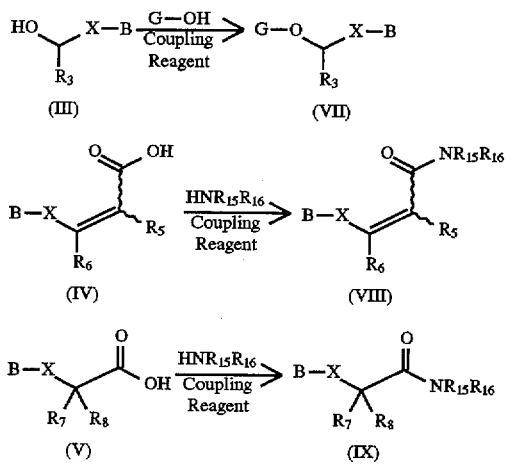

Scheme 2

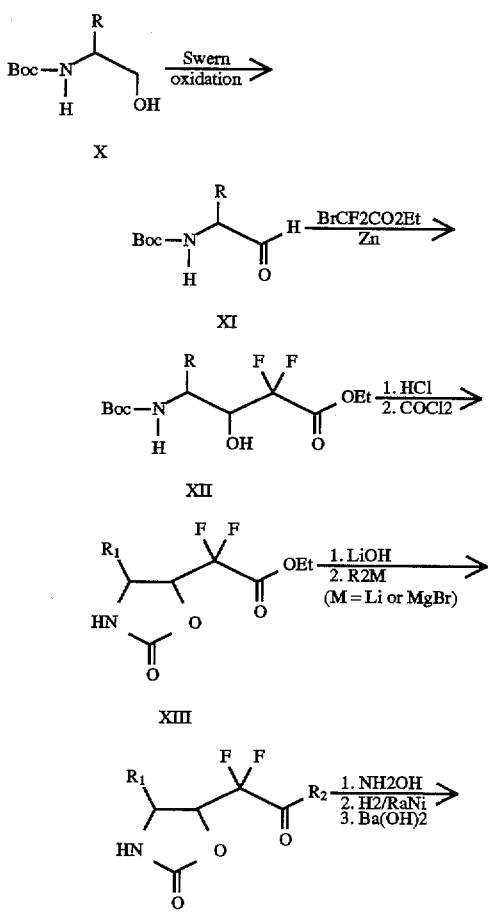

69
-continued
Scheme 2
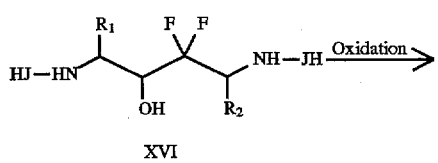
XVI
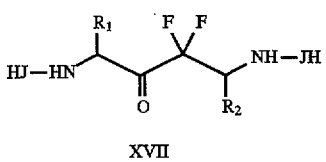
XVII
Scheme 3
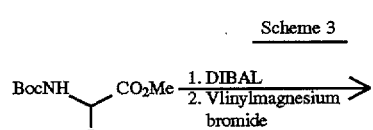
XVIII
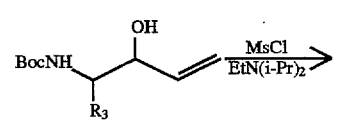
XIX
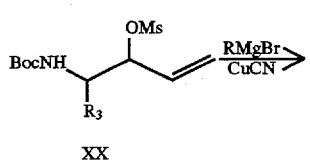
XX
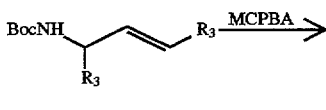
XXI
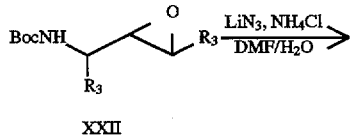
XXII
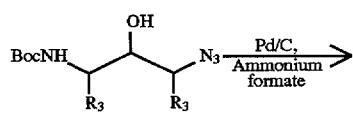
XXIII
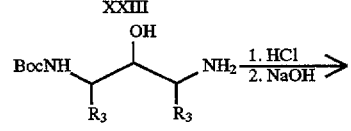
XXIV
70
-continued
Scheme 3
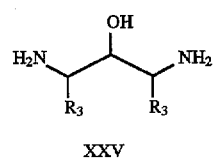
XXV
Scheme 4
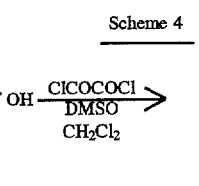
XXVI
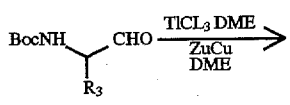
XXVII
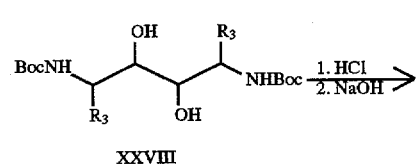
XXVIII
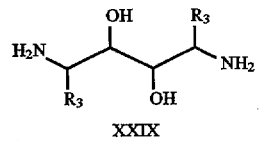
XXIX
Scheme 5
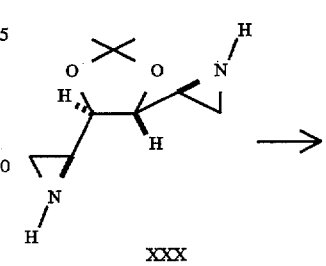
XXX
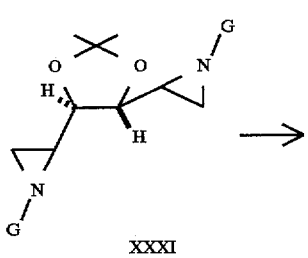
XXXI 5,670,675
-continued
Scheme 5
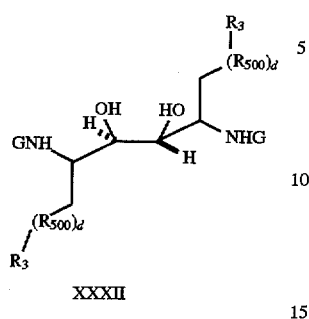
XXXII
SCHEME 6
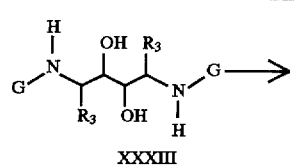
XXXIII
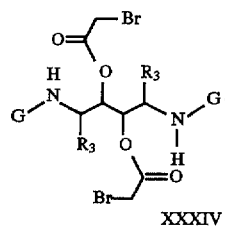
XXXIV    XXXIV
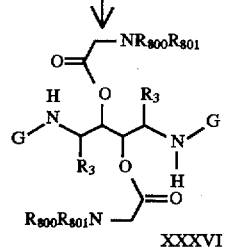
XXXVI    XXXVII
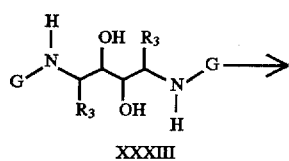
XXXIII
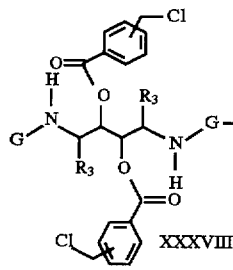
XXXVIII    XXXIX
-continued
SCHEME 6
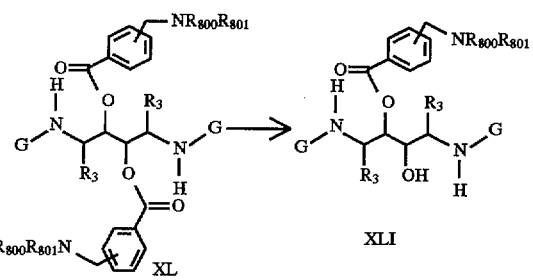
XL    XLI
SCHEME 7
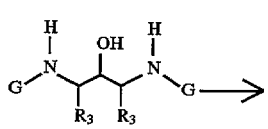
XLII
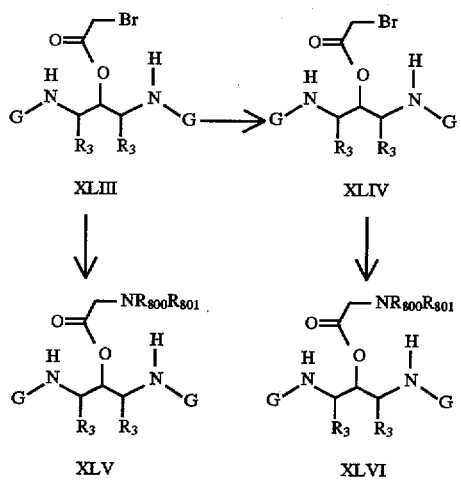
XLIII    XLIV
XLV    XLVI
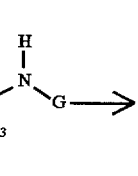
XLVII
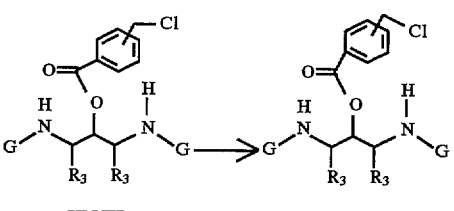
XLVIII    XLIX

SCHEME 7
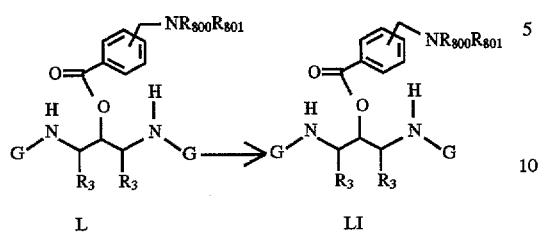
SCHEME 8
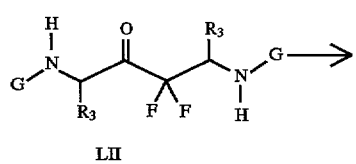
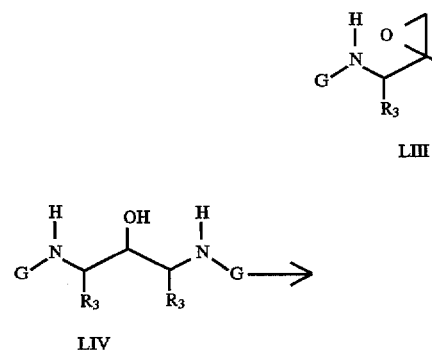
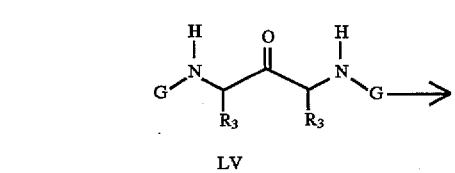
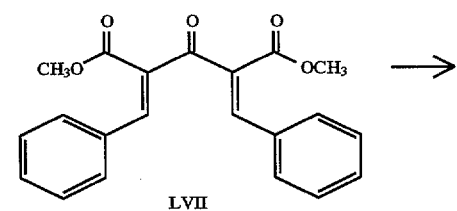
SCHEME 9
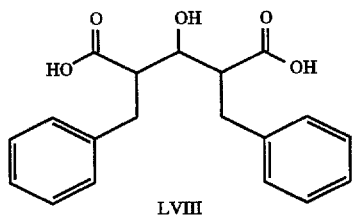
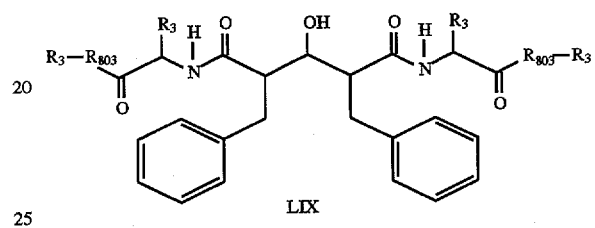
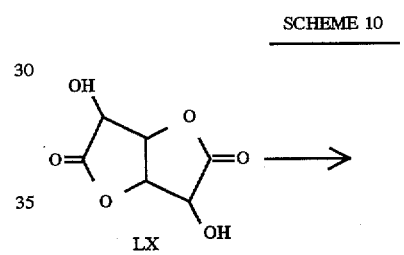
SCHEME 10
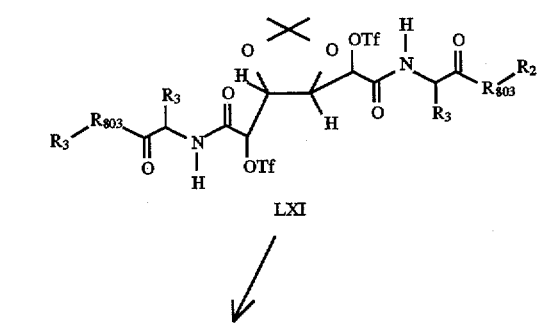
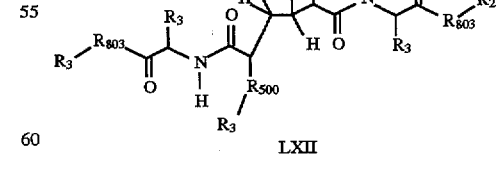

SCHEME 11

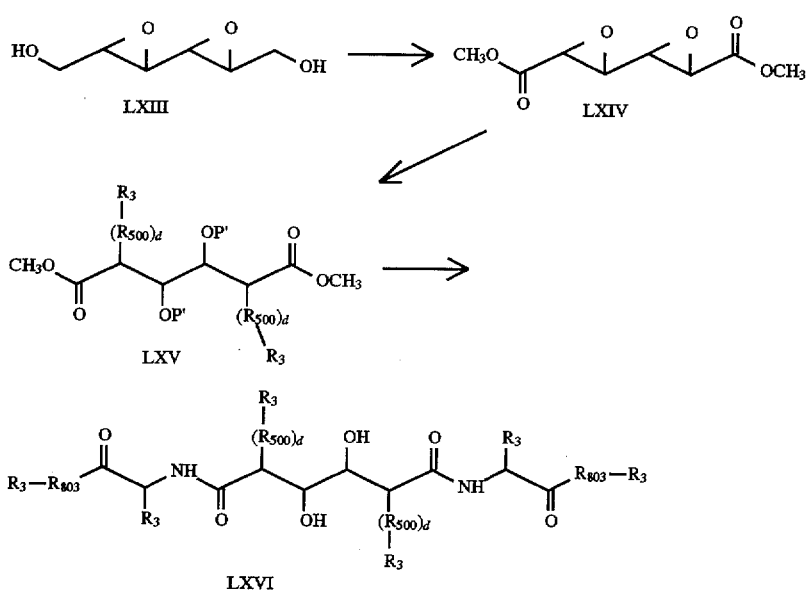

SCHEME 12

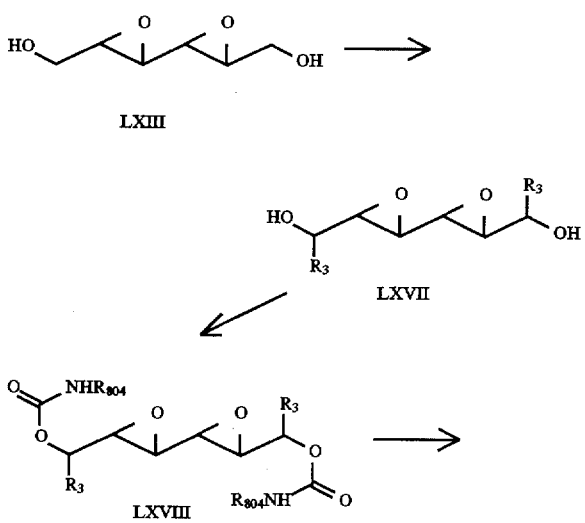

SCHEME 13

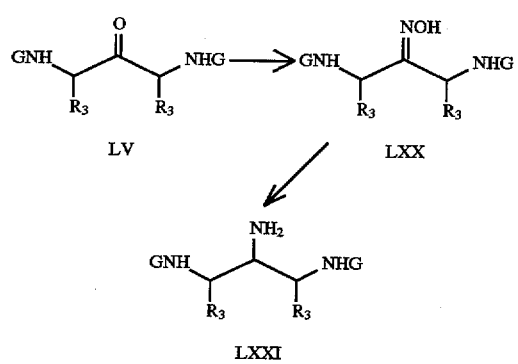

The following examples will serve to further illustrate preparation of the novel compounds of the invention.

EXAMPLE 1

A. Bis-(2-phenylethyl)sulfide

A solution of 7.65 g (32 mmol) of sodium sulfide nonahydrate and 8.7 ml (64 mmol) of 2-bromoethylbenzene in 150 ml of 1:1 tetrahydrofuran:methanol was heated at reflux under inert atmosphere. After 24 h, the solution was allowed to cool and concentrated in vacuo to give the crude desired compound.

B. Bis-(2-phenylethylsulfone

A solution of the resultant compound of Example 1A (32 mmol) in 100 ml of methanol and 50 ml of water was cooled to 0° C. and treated with 29 g (42 mmol) of OXONE. The resulting mixture was stirred at ambient temperature for 6 h, partitioned between dichloromethane and water, and the aqueous layer was washed with dichloromethane. The combined organic layers were concentrated in vacuo, taken up in dichloromethane, washed with water, dried over $MgSO_4$, and concentrated to give 7.57 g (87%) of the desired compound ($R_f$ 0.24, 25% ethyl acetate in hexane) as a pure white solid, m.p. 98°–99° C. $^1$H NMR (CDCl$_3$) δ 3.1–3.2 (m, 8 H), 7.15–7.2 (m, 4H), 7.25–7.35 (m, 6H). Mass spectrum (M+NH$_4$)$^+$=292.

Anal. Calcd. for C$_{16}$H$_{18}$O$_2$S: C, 70.04; H, 6.61; S, 11.68. Found: C, 70.07; H, 6.63; S, 11.44.

EXAMPLE 2

Bis-(2-phenylethyl)sulfoxide

A solution of 7.25 mmol of the resultant compound of Example 1A in 40 ml of methanol and 10 ml of water was cooled to 0° C. and treated with 2.23 g (3.63 mmol) of OXONE. After being stirred at 0° C. for 2.5 h, the solution was partially concentrated in vacuo, diluted with water, extracted with three portions of chloroform, dried over MgSO$_4$, and concentrated. Flash chromatography using 30% ethyl acetate in chloroform gave 1.37 g (73%) of the desired compound ($R_f$ 0.30, 30% ethyl acetate in chloroform) as a pure white solid, m.p. 70°–71° C. $^1$H NMR (CDCl$_3$) δ 2.8–3.0 (m, 4H), 3.0–3.2 (m, 4H), 7.2–7.4 (m, 10H). Mass spectrum: (M+H)$^+$=259.

Anal. Calcd. for C$_{16}$H$_{18}$O2S: C, 74.38; H, 7.02; S, 12.41. Found: C, 74.26; H, 7.04; S, 12.16.

EXAMPLE 3A AND 3B

1,5-Diphenyl-3-pentanone (3A) and 1,5-Diphenyl-3-pentanol (3B).

A mixture of 1.00 g (4.27 mmol) of dibenzylidene acetone and 0.15 g of 10% palladium on carbon in 150 ml of methyl cellusolve was shaken under 4 atm. of hydrogen for 2 h. The solution was filtered and concentrated in vacuo. Flash chromatography using 10–20% ethyl acetate in hexane gave 0.60 g (59%) of 1,5-diphenyl-3-pentanone ($R_f$ 0.43, 20% ethyl acetate in hexane) as a colorless oil and 0.29 g (28%) of 1,5-diphenyl-3-pentanol ($R_f$ 0.36) as a white solid, m.p. 43°–45° C. 1,5-Diphenyl-3-pentanone: $^1$H NMR (CDCl$_3$) δ 2.71 (t, J=7 Hz, 4H), 2.89 (t, J=7 Hz, 4H), 7.1–7.3 (m, 10H). Mass spectrum (M+NH$_4$)$^+$=256.

Anal. Calcd. for C$_{17}$H$_{18}$O: C, 85.67; H, 7.61. Found: C, 85.39; H, 7.63.

1,5-Diphenyl-3-pentanol: $^1$H NMR (CDCl$_3$) δ 1.39 (d, J=5 Hz, 1H), 1.7–1.9 (m, 4H), 2.6–2.9 (m, 4H), 3.68 (m, 1H), 7.1–7.3 (m, 10H). Mass spectrum (M+NH$_4$)$^+$=258.

Anal. Calcd. for C$_{17}$H$_{20}$O: C, 84.96; H, 8.39. Found: C, 84.89; H, 8.18.

EXAMPLE 4

1,3-Diphenoxy-2-propanol

According to the procedure of Piantadosi et. al. (*J. Med. Chem.*, 1976, 19, 222) a solution of 4.0 ml (45 mmol) of phenol in 30 ml of dioxane was treated with 0.95 g (24 mmol) of powdered sodium hydroxide and heated to reflux. Upon dissolution of the solid, the brown, refluxing solution was treated dropwise with 1.69 ml (22 mmol) of epichlorohydrin over a period of 10 min. After being heated at reflux for 5 h, the solution was cooled, concentrated in vacuo, taken up into ether, washed with several portions of water, dried over MgSO$_4$, and concentrated. Recrystallization from 2-propanol gave 1.87 g (35%) of the desired compound ($R_f$ 0.33, 30% ethyl acetate in hexane). $^1$H NMR (CDCl$_3$) δ 2.58 (d, J=5 Hz, 1H), 4.16 (dd, J=10, 6 Hz, 2H), 4.17 (dd, J=10, 6 Hz, 2H), 4.40 (sextet, J=6 Hz, 1H), 6.9–7.0 (m, 6H), 7.2–7.35 (m, 4 H). Mass spectrum (M+NH$_4$)$^+$=262.

EXAMPLE 5

1,3-Diphenoxyacetone

A solution of 0.44 ml (6.2 mmol) of dimethylsulfoxide in 25 ml of dichloromethane was cooled under inert atmosphere to −63° C., treated with 2.3 ml (4.6 mmol) of oxalyl chloride (2M in dichloromethane), and stirred for 15 min. A solution of 0.75 g (3.1 mmol) of the resultant compound of Example 4 in 10 ml of dichloromethane was subsequently added, the solution was stirred for 30 min, and 1.73 ml (12.4 mmol) of triethylamine was added. After stirring for an additional 15 min, the solution was quenched with 10% aqueous citric acid, poured into a mixture of 1:1 ether:hexane and 10% citric acid, extracted with ether, washed with aqueous brine, dried over MgSO$_4$, and concentrated to a yellow oil. Purification by flash chromatography using 20% ethyl acetate in hexane gave 0.62 g (83%) of the desired compound as a white, crystalline solid, m.p. 55°–57° C. $^1$H NMR (CDCl$_3$) δ 4.89 (s, 4H), 6.92 (m, 4H), 7.02 (m, 2H), 7.30 (m, 4H). Mass spectrum (M+NH$_4$)$^+$=260.

EXAMPLE 6

A. 3-Hydroxy-5-phenyl-1-pentene

Vinylmagnesium Bromide (120 mmol, 1M) in ether was added to 80 ml of dry tetrahydrofuran and cooled under inert atmosphere to 0° C. Hydrocinnamaldehyde (8.0 ml, 61 mmol) was added dropwise, and the solution was stirred for 10 min, quenched cautiously with saturated aqueous ammonium chloride, extracted with ether, washed with saturated brine, dried over MgSO$_4$, and concentrated to give 9.82 g (98.6%) of the crude desired product.

B. 3-(t-Butyldimethylsilyloxy)-5-phenyl-1-pentene

A solution of the resultant compound of Example 6A (9.82 g, 60.6 mmol) and 8.2 g (120 mmol) of imidazole in 30 ml of dimethylformamide was treated with cooling (cold water bath) with 10 g (66 mmol) of t-butyldimethylsilyl chloride and stirred at ambient temperature. After 1 h, the solution was diluted with 1:1 ether:hexane, washed with three portions of water, dried over MgSO$_4$, and concentrated in vacuo. Flash chromatography using 3% ethyl acetate in hexane gave 13.2 g (79%) of the desired compound as a colorless oil. $^1$H NMR (CDCl$_3$) δ 0.04 (s, 3H), 0.07 (s, 3 H), 0.90 (s, 9H), 1.81 (m, 2H), 2.66 (m, 2H), 4.16 (q, J=6 Hz, 1H), 5.07 (dt, J=10, 1 Hz, 1H), 5.18 (dt, J=17, 1 Hz, 1H), 5.84 (ddd, J=17, 10, 6 Hz, 1H), 7.1–7.3 (m, 5H). Mass spectrum: (M+H)$^+$=277.

C. 2-(t-Butyldimethylsilyoxy)-4-phenylbutyraldehyde

A solution of 0.81 g (2.93 mmol) of the resultant compound of Example 6B in 20 ml of dichloromethane and 10 ml of methanol was cooled to −78° C. A mixture of ozone in air was bubbled through the solution until a blue color persisted. Air was bubbled through the solution to discharge excess ozone, and the solution was treated with dimethylsulfide. After being stirred overnight at ambient temperature, the solution was diluted with dichloromethane, washed with water, dried over MgSO$_4$, and concentrated in vacuo to give 0.81 g (100%) of the crude desired product.

D. (Z)-Methyl 4-(t-Butyldimethylsilyoxy)-6-phenyl-2-hexenoate

A suspension of 120 mg (3.0 mmol) of sodium hydride (60% suspension in oil) in 20 ml of tetrahydrofuran was cooled to 0° C. and treated with a solution of 937 mg (2.95 mmol) of bis(2,2,2-trifluoroethyl)(methoxycarbonylmethyl) phosphate in 5 ml of tetrahydrofuran. The resulting solution was stirred for 10 min at 0° C., treated with a solution of 2.93 mmol of the resultant compound of Example 6C in 5 ml of tetrahydrofuran, and stirred at ambient temperature for 1 h. The solution was subsequently quenched with aqueous ammonium chloride, extracted with ether, washed with saturated brine, dried over MgSO$_4$, and concentrated in vacuo. Flash chromatography using 3% ethyl acetate in hexane gave 578 mg (59%) of the desired compound. $^1$H NMR (CDCl$_3$) δ 0.02 (s, 3H), 0.08 (s, 3H), 0.90 (s, 9H), 1.83 (m, 2H), 2.64, (ddd, J=13, 11, 6 Hz, 1H), 2.77 (ddd, J=13, 11, 6 Hz, 1H), 3.70 (s, 3H), 5.38 (br q, J=7 Hz, 1H), 5.72 (dd, J=11, 1 Hz, 1H), 6.21 (dd, J=11, 8 Hz, 1H), 7.15–7.3 (m, 5H). Mass spectrum (M+H)$^+$=335.

E. (Z)-4-(t-Butyldimethylsilyoxy)-6phenyl-2-hexenoic Acid

A solution of 567 mg (1.69 mmol) of the resultant compound of Example 6D in 13 ml of dioxane was cooled to 0° C., treated with 6.5 ml (3.2 mmol) of 0.5M aqueous lithium hydroxide, and stirred at ambient temperature for 24 h. The resulting solution was poured into chloroform/1N HCl, separated, dried over MgSO$_4$, and concentrated to give the desired product. $^1$H NMR (CDCl$_3$) δ 0.04 (s, 3H), 0.09 (s, 3H), 0.91 (s, 9H), 1.88 (m, 2H), 2.66, (m, 1 H), 2.78 (m, 1H), 5.31 (br q, J=7 Hz, 1H), 5.78 (dd, J=12, 1 Hz, 1H), 6.34 (dd, J=12, 8 Hz, 1H), 7.15–7.3 (m, 5H). Mass spectrum (M+H)$^+$=321.

F. (Z)-N-(3-Methylbutyl)-4-(t-Butyldimethylsilyloxy)-6-phenyl-2-hexenamide

A solution of the resultant compound of Example 6E (225 rag, 0.70 mmol) and 0.85 ml of 4-methylmorpholine in 15 ml of dichloromethane was cooled to 0° C. and treated with 0.10 ml (0.77 mmol) of isobutyl chloroformate. The resulting solution was stirred for 10 min, treated with 0.089 ml (0.77 mmol) of isoamylamine, and stirred at ambient temperature for 2 h. The solution was subsequently diluted with dichloromethane, washed sequentially with 10% aqueous citric acid and aqueous NaHCO$_3$, dried over Na$_2$SO$_4$, and concentrated. Flash chromatography using 15% ethyl acetate in hexane gave 245 mg (90%) of the desired compound as an oil. $^1$H NMR (CDCl$_3$) δ 0.04 (s, 3H), 0.09 (s, 3H), 0.90 (s, 9H), 0.92 (d, J=7 Hz, 6H), 1.41 (br q, J=7 Hz, 2H), 1.63 (heptet, J=7 Hz, 1H), 1.86 (m, 2H), 2.63 (m, 1H), 2.78 (m, 1H), 3.30 (m, 2H), 5.50 (br q, 1H), 5.59 (dd, J=11, 1 Hz, 1H), 5.98 (dd, J=11, 8 Hz, 1H), 7.15–7.3 (m, 5H). Mass spectrum (M+H)$^+$=391.

G. (Z)-N-(3-Methylbutyl)-4-hydroxy-6-phenyl-2-hexenamide

A solution of 58.7 mg (0.151 mmol) of the resultant compound of Example 6F in 1 ml of tetrahydrofuran was treated with 0.18 ml (0.18 mmol) of tetra-n-butylammonium fluoride (1M in tetrahydrofuran). After being stirred for 1 h, the solution was concentrated in vacuo. Flash chromatography using 60% ethyl acetate in chloroform gave 26.9 mg (65%) of the desired compound as an oil. $^1$H NMR (CDCl$_3$) δ 0.93 (d, J=7 Hz, 6H), 1.43 (q, J=7 Hz, 2H), 1.63 (heptet, J=7 Hz, 1H), 1.93 (m, 2H), 2.80 (m, 2H), 3.32 (m, 2H), 4.58 (m, 1H), 5.69 (br, 1H), 5.73 (dd, J=12, 1 Hz, 1H), 6.19 (dd, J=12, 6 Hz, 1H), 7.15–7.3 (m, 5H). Mass spectrum (M+H)$^+$=276.

EXAMPLE 7

A. N-(3-Methylbutyl)-2-(1-(t-Butyldimethylsilyloxy)-3-phenylpropyl)-cyclopropane-1-carboxamide The resultant compound of Example 6F was treated with diiodomethane and diethylzinc according to the procedure of Ito (*Organic Synthesis*, 1980, 59, 113) to give the desired compound.

B. N-(3-Methylbutyl)-2-(1-hydroxy-3-phenylpropyl)-cyclopropane-1-carboxamide Using the procedure of Example 6G with the resultant compound of Example 7A gave the desired compound.

EXAMPLE 8

A. cis-N-(3-Methylbutyl)-4-(t-butyldimethylsilyloxy)-6-phenyl-2-hexenamide-2,3-oxide A solution of 235 mg (0.59 mmol) of the resultant compound of Example 6F and 270 mg (1.25 mmol) of m-chloroperbenzoic acid in 5 ml of dichloromethane was allowed to stand at ambient temperature for 6 d. The resulting solution was diluted with ether, washed sequentially with 10% aqueous Na$_2$S$_2$O$_3$ and aqueous NaOH then with saturated brine, dried over MgSO$_4$, and concentrated in vacuo. Flash chromatography using 20% ethyl acetate in hexane gave the desired compound as a ca. 2:1 mixture of diastereomers. Major diastereomer: $^1$H NMR (CDCl$_3$) δ 0.07 (s, 3H), 0.13 (s, 3H), 0.90 (d, J=7 Hz, 3H), 0.91 (d, J=7 Hz, 3H), 0.96 (s, 9H), 1.29 (br q, J=7 Hz, 2H), 1.58 (heptet, J=7 Hz, 1H), 1.82 (m, 2H), 2.60 (m, 1H), 2.76 (m, 1H), 3.16 (m, 2H), 3.35 (td, J=8, 5 Hz, 1H), 3.51 (d, J=5 Hz, 1H), 5.98 (br, 1H), 7.15–7.3 (m, 5H). Mass spectrum (M+H)$^+$=406.

Minor diastereomer: $^1$H NMR (CDCl$_3$) δ 0.01 (s, 3H), 0.07 (s, 3H), 0.90 (d, J=7 Hz, 6H), 0.91 (s, 9H), 1.27 (br q, J=7 Hz, 2H), 1.56 (heptet, J=7 Hz, 1H), 1.99 (m, 2H), 2.73 (m, 1H), 2.84 (m, 1H), 3.09 (m, 1 H), 3.11 (dd, J=8, 4 Hz, 1H), 3.20 (m, 1H), 3.41 (dt, J=9, 6 Hz, 1H), 3.51 (d, J=4 Hz, 1H), 5.81 (br, 1H), 7.2–7.35 (m, 5H). Mass spectrum (M+H)$^+$=406.

B. cis-N-(3-Methylbutyl)-4-hydroxy-6-phenyl-2-hexenamide-2,3-oxide

Using the procedure of Example 6G separately with the major and minor diastereomers of Example 8A gave, after flash chromatography using 60% ethyl acetate in chloroform, 90% and 86% yields of the desired compounds, respectively. Major diastereomer: $^1$H NMR (CDCl$_3$) δ 0.90 (d, J=7 Hz, 3 H), 0.91 (d, J=7 Hz, 3H), 1.29 (br q, J=7 Hz, 2H), 1.57 (heptet, J=7 Hz, 1H), 1.89 (m, 2H), 1.96 (d, J=4 Hz, 1H), 2.69 (m, 1H), 2.80 (m, 1H), 3.03 (m, 1H), 3.19 (dd, J=8, 5, Hz, 1H), 3.22 (m, 1H), 3.35 (m, 1H), 3.58 (d, J=5 Hz, 1H), 6.01 (br, 1H), 7.15–7.3 (m, 5H). Mass spectrum (M+H)$^+$=292.

Minor diastereomer: $^1$H NMR (CDCl$_3$) δ 0.90 (d, J=7 Hz, 3H), 0.91 (d, J=7 Hz, 3H), 1.26 (m, 2H), 1.55 (heptet, J=7 Hz, 1H), 2.02 (m, 2H), 2.47 (d, J=3 Hz, 1H), 2.77 (m, 1H), 2.85 (m, 1H), 3.11 (m, 1H), 3.13 (dd, J=9, 5 Hz, 1H), 3.24 (m, 2H), 3.56 (d, J=5 Hz, 1 H), 5.96 (br, 1H), 7.2–7.35 (m, 5H). Mass spectrum (M+H)$^+$=292.

EXAMPLE 9

Di-(2-phenylethyl)phosphine Oxide

To a solution of 25 mmol of (2-phenyl)ethylmagnesium bromide in 25 ml of diethyl ether was added dropwise with cooling (ice bath) 0.92 ml (7.14 mmol) of diethyl phosphite. The resulting solution was heated at reflux for 2 h, cooled, and treated with aqueous ammonium chloride. The product was extracted with ether, dried over MgSO$_4$, and concentrated in vacuo. Flash chromatography using ethyl acetate gave 1.23 g (64%) of the desired compound (R$_f$ 0.64, 10% methanol in chloroform) as a colorless oil. $^1$H NMR (CDCl$_3$) δ 2.0–2.2 (m, 4H), 2.85–3.1 (m, 4H), 6.89 (dm, J=455 Hz, 1H), 7.15–7.4 (m, 10H). Mass spectrum (M+H)$^+$ =259.

EXAMPLE 10

A. 2-(t-Butyloxycarbonylamino)-1,5-diphenylpent-3-ene

A solution of 15.1 g (54.5 mmol) of the resultant compound of Example 36A and 38 ml (220 mmol) of diisopropylethylamine in 450 ml of dry dichloromethane was cooled under N$_2$ atmosphere in an acetone/ice bath and treated dropwise with 8.5 ml (110 mmol) of methanesulfonyl chloride. The solution was stirred for 7 min after addition was complete, then was quenched with 400 ml of 10% citric acid. The bath was removed, and the mixture was extracted with 800 ml of ether. The organic layer was washed sequentially with 500 ml of water and 300 ml of saturated brine, dried over MgSO$_4$, and concentrated in vacuo to give the crude mesylate as an off-white solid. To a flame-dried 3-neck 1000 mL flask equipped with an internal low-temperature thermometer was added 1.45 g (16 mmol) of anhydrous cuprous cyanide. The flask was then charged with 500 ml of anhydrous tetrahydrofuran. The suspension was cooled under N$_2$ altmosphere in a dry ice/acetone bath. A solution of phenylmagnesium bromide (55 ml, 165 mmol) in ether (3M) was added via syringe. The bath was removed, and the resulting beige suspension was warmed with stirring by use of a water bath. As the internal temperature reached −5° C., the solid began to dissolve, and the solution began to turn darker. By the time the internal temperature reached −1° C., the solution was homogenous, and was immediately recooled by placement of the flask in a dry ice/acetone bath. AS the internal temperature reached −65° C., addition of a solution of the above crude mesylate in 75 ml of tetrahydrofuran was added via cannula. The resulting solution was stirred at ca. −70° C. for 15 min. The bath was then removed, and the solution was immediately treated with 100 ml of saturated aqueous ammonium chloride followed by 300 ml of ether. As the mixture warmed, 100 ml of 1N NH$_4$OH was added, and the mixture was stirred under air atmosphere for several hours while the aqueous layer turned dark blue. The mixture was then extracted with 500 ml of ether. The organic layer was washed with saturated brine and concentrated in vacuo without drying to give a yellow oil. The combined aqueous layers were extracted with 500 ml of additional ether, which was added to the above oil. The resulting solution was washed with saturated brine, dried over MgSO$_4$, and concentrated to a yellow oil. The oil was taken up in 100 ml of dichloromethane, treated with 50 g of silica gel, and concentrated in vacuo until the residue was a freely flowing solid. The solid was placed on top of a 60 mm column containing 300 g of silica gel and eluted sequentially with 1200 ml of hexane (to bring out biphenyl formed as a side product) followed by 5000 ml of 5% ethyl acetate in hexane. Combination of the pure fractions gave 11.95 g (65%) of the desired compound. $^1$H NMR (CDCl$_3$, major isomer) δ 1.40 (s, 9H), 2.7–2.9 (m, 2H), 3.32 (d, J=7 Hz, 2H), 4.4 (br, 2H), 5.43 (dd, J=15, 6 Hz, 1H), 5.64 (dt, J=15, 7 Hz, 1H), 7.0–7.3 (m, 10H).

B. 2-(t-Butyloxycarbonylamino)-1,5-diphenylpent-3-ene-3,4-oxide

A solution of 11.71 g (34.75 mmol) of the resultant compound of Example 10A in 200 ml of dichloromethane was treated with 15 g (174 mmol) of solid sodium bicarbonate, cooled to 0° C., and treated with 24 g (69 mmol) of m-chloroperbenzoic acid (50%). The resulting suspension was sealed with a septum and stirred in a cold room (5° C.) for three days. The resulting mixture, which contained much precipitate, was decanted into a 1000 ml flask. The white residue was broken up and washed out with 400 ml of 10% sodium thiosulfate solution and 300 ml of ether. The two-phase mixture was stirred for 2 hours, and the layers were separated. The organic layer was washed sequentially with 200 ml portions of 2M NaOH, water, and saturated brine. The combined aqueous layers were extracted with 200 ml of ether, which was washed sequentially with 50 ml of water and 50 mL of aqueous brine, combined with the original organic phase, dried over MgSO$_4$, and concentrated in vacuo. The resulting oil was taken up in 100 ml of dichloromethane, treated with 50 g of silica gel, and concentrated in vacuo until the residue was a freely flowing solid. The solid was placed on top of a 60 mm column containing 300 g of silica gel and eluted sequentially with 1000 ml of 5% ethyl acetate in hexane followed by 3500 ml of 12% ethyl acetate in hexane. Concentration of the combined fractions gave 9.36 g (76%) of the desired compound (ca. 4:1 mixture of diastereomers) as an oil which solidified upon standing.

C. 4-Azido-2-(t-butyloxycarbonylamino)-1,5-diphenyl-3-hydroxypentane

A solution of 9.12g (25.84 mmol) of the resultant compound of Example 10B, 7.0 g (140 mmol) of lithium azide, and 1.73 g (32 mmol) of ammonium chloride in 75 ml of dimethylformamide and 7.5 ml of water was heated in an oil bath at 70° C. for 32 hours. After being allowed to cool, the resulting solution was treated with 1000 ml of 1:1 ether/hexane and 800 ml of water. The layers were separated, and the aqueous layer was extracted with 500 ml of additional 1:1 ether/hexane. The combined organic layers were washed sequentially with 400 ml of water and 200 ml of saturated brine, dried over MgSO$_4$, and concentrated in vacuo to a solid. The solid was taken up in 100 ml of dichloromethane, treated with 50 g of silica gel, and concentrated in vacuo until the residue was a freely flowing solid. The solid was placed on top of a 60 mm column containing 300 g of silica gel and eluted sequentially with 1000 ml of 10% ethyl acetate in hexane, 1000 ml of 15% ethyl acetate in hexane, and 2000 ml of 25% ethyl acetate in hexane. Concentration of the fractions gave 9.26 g (91%) of the desired compound as a ca. 4:1 mixture of diastereomers. $^1$H NMR (CDCl$_3$) δ 1.42 (s, 9H), 2.78 (m, 1H), 2.89 (m, 1H), 3.13 (m, 1H), 3.29 (m, 1H), 3.41 (m, 1H), 3.53 (m, 1H), 3.80 (m, 1H), 4.06 (m, 1H), 4.83 (m, 1H), 7.2–7.35 (m, 10H). Mass spectrum (M+H)$^+$=338.

EXAMPLE 11

4-Amino-2-(t-butyloxycarbonylamino)-1,5-diphenyl-3-hydroxypentane

A rapidly stirring suspension of 10 mg of 10% palladium on carbon in 0.3 ml of methanol was treated under inert atmosphere with 60 mg (0.95 mmol) of solid ammonium formate. After 3 min, a solution of 52 mg (0.13 mmol) of the resultant compound of Example 10C in 0.4 ml of methanol was added. The resulting mixture was stirred for 2 h, diluted with methanol and 1N ammonium hydroxide, filtered through Celite, and concentrated in vacuo. The residue was treated with 1N NaOH, extracted with two portions of chloroform, dried over sodium sulfate, and concentrated. Flash chromatography using 7.5% methanol in chloroform gave 37 mg (76%) of the desired compound (R$_f$ 0.38, 2.5% methanol/2% isopropylamine in chloroform) as a white solid, m.p. 134°–135° C. $^1$H NMR (CDCl$_3$) δ 1.48 (s, 9H), 2.50 (dd, J=13, 10 Hz, 1H), 2.8–3.1 (m, 4H), 3.41 (br d, J=7 Hz, 1H), 4.11 (br q, J=8 Hz, 1H), 4.83 (br d, J=9 Hz, 1 H), 7.15–7.35 (m, 10H). Mass spectrum (M+H)$^+$=370.

Anal. Calcd. for C$_{22}$H$_{30}$N$_2$O$_3$·0.15H$_2$O: C, 70.81; H, 8.18; N, 7.51. Found: C, 70.89; H, 8.15; N, 7.43.

EXAMPLE 12

2,4-Diamino-1,5-diphenyl-3-hydroxypentane

The resultant compound of Example 11 (18 mg, 0.049 mmol) was treated with 1 ml of 4M HCl in dioxane, stirred for 0.5 h at ambient temperature, and concentrated in vacuo. The residue was partitioned between chloroform and aqueous NaHCO$_3$, dried over Na$_2$SO$_4$ and concentrated to provide the desired compound (R$_f$ 0.12, 10% methanol in chloroform) as a white solid, m.p. 106°–107° C. $^1$H NMR (CDCl$_3$) δ 2.51 (dd, J=13, 10 Hz, 1H), 2.67 (dd, J=13, 9 Hz, 1H), 2.85–3.0 (m, 2H), 3.19 (m, 1H), 3.38 (m, 2H), 7.15–7.35 (m, 10H). Mass spectrum: (M+H)$^+$=271.

EXAMPLE 13

2,4-Bis-((methyl)sulfonyl)amino-1,5-diphenyl-3-hydroxypentane

A solution of the resultant compound of Example 12 (0.049 mmol) and 0.032 ml (0.29 mmol) of 4-methylmorpholine in 1 ml of dichloromethane was cooled to 0° C. and treated with 0.008 ml (0.10 mmol) of methanesulfonyl chloride. After 0.5 h, the solution was washed with 10% aqueous citric acid, dried over Na$_2$SO$_4$, and concentrated. Flash chromatography using 5% methanol in chloroform gave 2.6 mg (13%) of the desired compound. $^1$H NMR (CDCl$_3$) δ 2.16 (s, 3 H), 2.34 (s, 3H), 2.93 (m, 4H), 3.41 (d, J=4 Hz, 1H), 3.7–3.8 (m, 2H), 3.92 (m, 1H), 5.06 (d, J=9 Hz, 1H), 5.42 (d, J=9 Hz, 1H), 7.2–7.4 (m, 10H). Mass spectrum (M+NH$_4$)$^+$=444.

EXAMPLE 14

2-Hydroxy-1,3-di(N-phenylamino)propane

A mixture of 0.25 ml (2.74 mmol) of aniline, 0.107 ml (1.37 mmol) of epichlorohydrin, and 60.4 mg (1.51 mmol) of sodium hydroxide in 2 ml of dimethylformamide was heated at 110° C. for 20 h. The solvent was removed in vacuo and the residue was purified by flash chromatography using 5% ethyl acetate in chloroform to give 21 mg (6%) of the desired compound (R$_f$ 0.63, 40% ethyl acetate in chloroform). $^1$H NMR (CDCl$_3$) δ 3.21 (dd, J=13, 8 Hz, 2H), 3.37 (dd, J=13, 4 Hz, 2H), 4.13 (m, 1H), 6.65–6.8 (m, 6H), 7.15–7.3 (m, 6H). Mass spectrum (M+H)$^+$=243.

EXAMPLE 15

2-Hydroxy-1,3-di(S-phenylthio)propane

Using the procedure of Example 4 but replacing phenol with thiophenol gave, after flash chromatography using 10% ethyl acetate in hexane, the desired compound (1.21 g, 56%, R$_f$ 0.20, 10% ethyl acetate in hexane) as a colorless oil. $^1$H NMR (CDCl$_3$) δ 2.77 (d, J=4 Hz, 1H), 3.05 (dd, J=14, 7 Hz, 2H), 3.20 (dd, J=14, 5 Hz, 2H), 3.82 (m, 1H), 7.15–7.4 (m, 10H). Mass spectrum (M+NH$_4$)$^+$=294.

EXAMPLE 16

A. 2-(2-Phenylethyl)-4-phenylbut-1-ene

A suspension of 1.59 g (4.45 mmol) of methyltriphenylphosphonium bromide in 100 ml of tetrahydrofuran was cooled to −78° C., treated with 2.2 ml (4.5 mmol) of n-butyllithium, warmed to 0° C., and recooled to −78° C. The resulting solution was treated via cannula with a solution of 1.59 g (4.45 mmol) of 1,5-diphenyl-3-pentanone in 20 ml of tetrahydrofuran. After being allowed to stir at ambient temperature for 2 h, the solution was diluted with hexane, washed sequentially with water and saturated brine, dried over MgSO$_4$, and concentrated in vacuo. The mixture was purified by flash chromatography to give 0.90 g (86%) of the desired compound as a colorless oil. $^1$H NMR (CDCl$_3$) δ 2.37 (t, J=8 Hz, 4H), 2.76 (t, J=8 Hz, 4H), 4.81 (s, 2H), 7.15–7.3 (m, 10H). Mass spectrum (M+NH$_4$)$^+$=254.

Anal. Calcd for C$_{18}$H$_{20}$: C, 91.47; H, 8.53. Found: C, 90.93; H, 8.56.

B. 2-(2-Phenylethyl)-4-phenylbut-1-ene-1,2-oxide

A solution of 107 mg (0.453 mmol) of the resultant compound of Example 16A in 2 ml of dichloromethane was treated with 150 mg (0.68 mmol) of m-chloroperbenzoic acid (80%). After being stirred for 40 min, the solution was treated with 10% aqueous sodium thiosulfate, stirred for 1 h, partitioned between ethyl acetate and aqueous NaOH, washed sequentially with water and saturated brine, dried over MgSO$_4$, and concentrated. The residue was purified by flash chromatography using 10% ethyl acetate in hexane to give 133 mg (99%) of the desired compound (R$_f$ 0.25, 10% ethyl acetate in hexane) as a colorless oil. $^1$H NMR (CDCl$_3$) δ 1.95 (m, 4H), 2.60 (s, 2H), 2.71 (t, J=9 Hz, 4H), 7.15–7–3 (m, 10H). Mass spectrum (M+NH$_4$)$^+$=270.

Anal. Calcd. for C$_{18}$H$_{20}$O·0.3H$_2$O: C, 83.88; H, 8.06. Found: C, 83.62; H, 7.94.

EXAMPLE 17

A. trans-2-(N-Benzyl-N-(benzyloxycarbonyl)amino)-5-(t-butyloxycarbonylamino)-1,6-diphenyl-3-hexene Using the procedure of Example 10A but replacing phenylacetaldehyde with N-benzyl-N-(benzyloxycarbonyl) phenylalaninal gave, after flash chromatography using 20% ethyl acetate in hexane, 45 mg (30%) of the desired compound. $^1$H NMR (d$_6$-DMSO, 100° C.) δ 1.32 (s, 9H), 2.54 (dd, J=14, 7 Hz, 1H), 2.62 (dd, J=14, 7 Hz, 1H), 2.77 (dd, J=14, 7 Hz, 1H), 2.83 (dd, J=14, 7 Hz, 1H), 4.04 (br pentet, J=7 Hz, 1H), 4.20 (d, J=16 Hz, 1H), 4.33 (d, J=16 Hz, 1H), 4.48 (br q, J=7 Hz, 1H), 5.03 (AA', 2H), 5.44 (dd, J=16, 6 Hz, 1H), 5.61 (dd, J=16, 7 Hz, 1H), 7.0–7.4 (m, 20H). Mass spectrum (M+H)$^+$=591.

B. 2-(N-Benzyl-N-(benzyloxycarbonyl)amino)-5-(t-butyloxycarbonylamino-3,4-dihydroxy-1,6-diphenyl-3-hexane A solution of 40 mg (0.068 mmol) of the resultant compound of Example 17A in 1 ml of tetrahydrofuran was treated sequentially with 0.034 ml (0.0034 mmol) of osmium tetroxide (2.5% in t-butanol) and 20 mg (0.14 mmol) of 4-methylmorpholine-N-oxide. After 20 h, the solution was treated with 10% Na$_2$S$_2$O$_3$, stirred for 15 min, diluted with ether, washed with two portions of 10% Na$_2$S$_2$O$_3$, one portion of water, and one portion of saturated aqueous NaHCO$_3$, dried over Na$_2$SO$_4$, and concentrated in vacuo. Flash chromatography using 30% ethyl acetate in hexane gave the desired compound (R$_f$ 0.43, 30% ethyl acetate in hexane) as a 2:1 mixture of diastereomers. Mass spectrum (M+H)$^+$=625.

EXAMPLE 18

2-(N-Benzylamino)-5-(t-butyloxycarbonylamino)-3,4-dihydroxy-1,6-diphenyl-3-hexane Ammonia (ca. 3 ml) was condensed into a precooled (−78° C.) mixture of excess sodium metal in 2 ml of tetrahydrofuran. A solution of 25 mg (0.040 mmol) of the resultant compound of Example 17B in 1 ml of tetrahydrofuran was added, and the resulting solution was stirred for 10 min, quenched with saturated aqueous ammonium chloride, allowed to warm to ambient temperature, extracted with ether, dried over $Na_2SO_4$, and concentrated to give the crude desired product. Mass spectrum: $(M+H)^+=491$.

EXAMPLE 19

5-Amino-2-(N-benzylamino)-3,4-dihydroxy-1,6-diphenyl-3-hexane Dihydrochloride The resultant compound of Example 18 (18.5 mg, 0.038 mmol) was treated with 1 ml of 4M HCl in dioxane. After 1 h, the solution was concentrated in vacuo to give the desired compound.

EXAMPLE 20

1,5-Diphenyl-3-hydroxy-3-(hydroxymethyl)pentane

Using the procedure of Example 17B with 166 mg (0.70 mmol) of the resultant compound of Example 16A gave, after purification by flash chromatography using 40% ethyl acetate in hexane, 114 mg (60%) of the desired compound ($R_f$ 0.27, 50% ethyl acetate in hexane). $^1H$ NMR ($CDCl_3$) δ 1.77 (t, J=6 Hz, 1H), 1.89 (m, 4H), 1.91 (s, 1H), 2.70 (m, 4H), 3.59 (d, J=6 Hz, 2H), 7.15–7.35 (m, 10H). Mass spectrum $(M+NH_4)^+=288$.

Anal. Calcd. for $C_{18}H_{22}O_2$: C, 79.96; H, 8.20. Found: C, 80.19; H, 8.06.

EXAMPLE 21

A. 1,1-Di-(phenoxymethyl)ethene

A solution of 2.0 ml (22.7 mmol) of phenol in 40 ml of dioxane was heated to reflux and treated with 0.96 g (23.8 mmol) of sodium hydroxide. After the solid had dissolved, the solution was treated dropwise over a period of 15 min with 1.25 ml (10.8 mmol) of 2-chloromethyl-3-chloro-1-propene. The resulting solution was heated at reflux for 6 h, allowed to cool, and concentrated in vacuo. The residue was taken up in ether, washed with several portions of water, dried over $MgSO_4$, and concentrated to a yellow liquid. Flash chromatography using 10% ethyl acetate in hexane gave 1.72 g (65%) of the desired compound as a colorless oil. $^1H$ NMR ($CDCl_3$) δ 4.63 (m, 4H), 5.35–5.45 (m, 2H), 6.9–7.0 (m, 6H), 7.25–7.35 (m, 4H). Mass spectrum $(M+NH_4)^+=258$.

B. 1,1-Di-(phenoxymethyl)ethene-1,2-oxide

A solution of 0.74 g (3.1 mmol) of the resultant compound of Example 21A in 15 ml of dichloromethane was treated with 0.52 g (6.2 mmol) of sodium bicarbonate, cooled to 0° C., and treated with a solution of 0.8 g (4.6 mmol) of m-chloroperbenzoic acid (80%). The resulting solution was stirred at ambient temperature for 16 h, treated with aqueous sodium bisulfite, stirred for 30 min, extracted with dichloromethane, washed sequentially with 1N NaOH, water, and saturated brine, and dried over $MgSO_4$. Concentration of the solution gave an oil which was purified by flash chromatography using 10% ethyl acetate in hexane to give 0.44 g (56%) of the desired compound ($R_f$ 0.50, 10% ethyl acetate in hexane). $^1H$ NMR ($CDCl_3$) δ 3.02 (s, 2H), 4.26 (AA', 4H), 6.9–7.0 (m, 6H), 7.25–7.35 (m, 4H). Mass spectrum $(M+NH_4)^+=274$.

EXAMPLE 22

N-(3-Methylbutyl)-5-(t-butyloxycarbonylamino)-6-phenyl-3-(phenylmethyl)-4-hydroxyhexanamide Using the procedures of Evans et. al. (*J. Org. Chem.* 1985, 50, 4615) with the resultant compound of 11B and isoamylamine gave the desired compound.

EXAMPLE 23

A. 2,2-Dimethyl-4,5-di-(2-phenyl-1-oxoethyl)-1,3-dioxolane

A solution of 7.5 g (20.5 mmol) of N,N,N',N',-tetramethyl-O,O'-isopropylidene-d-tartaric diamide (Briggs, et. al., *J. Chem. Soc. Perkin Trans. I*, 1985, 795) in 150 ml of tetrahydrofuran was treated over a period of 20 min with 41 ml (82 mmol) of benzylmagnesium chloride. The resulting solution was stirred overnight at ambient temperature, poured over ice/saturated ammonium chloride, extracted with ethyl acetate, dried over $MgSO_4$, and concentrated in vacuo. Flash chromatography using 20% ethyl acetate in hexane gave 0.83 g (12%) of the desired compound as an oil. $^1H$ NMR ($CDCl_3$) δ 1.45 (s, 6H), 3.94 (s, 4H), 4.70 (s, 2H), 7.2–7.4 (m, 10H). Mass spectrum $(M+H)^+=339$.

B. 3,4-Dihydroxy-1,6-diphenylhexan-2,5-dione

The resultant compound of Example 23A (100 mg, 0.3 mmol) was treated with 10 ml of 80% aqueous acetic acid, heated at reflux for 5 min, allowed to cool, and concentrated in vacuo. The crude product was purified by flash chromatography using 20% ethyl acetate in hexane to give 65 mg (74%) of the desired compound ($R_f$ 0.15, 30% ethyl acetate in hexane). $^1H$ NMR ($CDCl_3$) δ 2.39 (d, J=5 Hz, 1H), 2.81 (d, J=3 Hz, 1H), 3.89 (d, J=15 Hz, 2 H), 4.13 (d, J=15 Hz, 2H), 4.40 (br t, J=3 Hz, 1H), 4.66 (m, 1H), 7.15–7.5 (m, 10H). Mass spectrum $(M+H)^+=299$.

EXAMPLE 24

1,6-Diphenyl-2,3,4,5-tetrahydroxyhexane

According to the procedure of Achmatowicz and Wicha (*Tetrahedron Lett.,* 1987, 28, 2999) the resultant compound of Example 23A was treated with sodium borohydride in ethanol and deprotected according to the procedure of 23B to give the desired compound as a mixture of stereoisomers.

EXAMPLE 25

A. 2,2-Dimethyl-4,5-di-(2-phenyl-1-(N-hydroxyimino)ethyl-1,3-dioxolane

A solution of the resultant compound of Example 23A (0.5 g, 1.5 mmol) in 10 ml of pyridine was treated with 0.22 g (3.2 mmol) of hydroxylamine hydrochloride and stirred overnight at ambient temperature. The resulting solution was partitioned between ethyl acetate and water, dried over $MgSO_4$, and concentrated in vacuo. Flash chromatography using 10% ethyl acetate in hexane gave 0.53 g (92%) of the desired compound as an apparent 4:1:1 mixture of isomers. $^1H$ NMR ($CDCl_3$, major isomer) δ 1.40 (s, 6H), 3.70 (d, J=14 Hz, 2H), 3.83 (d, J=14 Hz, 2 H), 4.56 (s, 2H), 7.15–7.35 (m, 10H). Mass spectrum $(M+H)^+=369$.

B. 3,4-Dihydroxy-1,6-diphenylhexan-2,5-dione Dioxime

The resultant compound of Example 25A was deprotected according to the procedure of 23B to give the desired compound.

EXAMPLE 26

3,4-Dihydroxy-1,6-diphenylhexan-2,5-dione Dimethyl Dioxime

Using the procedures of Example 25A and 25B but replacing hydroxylamine hydrochloride with methoxyamine hydrochloride gave the desired compound.

EXAMPLE 27

3,4-Dihydroxy-1,6-diphenylhexan-2,5-dione Dihydrazide

Using the procedures of Example 25A and 25B but replacing hydroxylamine hydrochloride with hydrazine hydrate gave the desired compound.

EXAMPLE 28

Bis-(1-phenylbut-2-yl)sulfoxide

Using the procedures of Example 1A and Example 2 but replacing (2-bromoethyl)benzene with (2-bromobut-1-yl) benzene gave the desired compound.

EXAMPLE 29

A. (2-Phenylethyl)-(1-fluoro-2-phenylethyl)sulfide

According to the procedure of McCarthy et. al. (*J. Amer. Chem. Soc.* 1985, 107, 735), the resultant compound of Example 2 was treated with diethylaminosulfur trifluoride in dichloromethane to give the desired compound.

B. (2-Phenylethyl)-(1-fluoro-2-phenylethyl) sulfoxide

Using the procedure of Example 2 with the resultant compound of Example 29A gave the desired compound.

EXAMPLE 30

A. O-Benzoyl-N,N-di-(2-phenylethyl) hydroxylamine

According to the procedure of Vaouanc et. al. (*Synthesis*, 1985, 807), N,N-di-(2-phenylethyl)amine was treated with bis(diphenylphosphinyl)peroxide to give the desired compound.

B. N,N-Di-(2-phenylethyl)hydroxylamine

According to the procedure of Vaouanc et. al. (*Synthesis*, 1985, 807), the resultant compound of Example 30A was treated with sodium ethoxide to give the desired compound. $^1$H NMR (CDCl$_3$) δ 2.9–3.0 (m, 8H), 5.62 (br s, 1 H), 7.15–7.3 (m, 10H). Mass spectrum: (M+H)$^+$=242.

EXAMPLE 31

1,5-Diphenyl-3-pentanone Oxime

Using the procedure of Example 25A with 1,5-diphenyl-3-pentanone gave the desired compound.

EXAMPLE 32

3-Amino-1,5-Diphenylpentane

According to the procedure of Feuer and Braunstein (*J. Org. Chem.* 1969, 34, 1817), the resultant compound of Example 31 was treated with borane to give the desired compound.

EXAMPLE 33

N-(1,5-Diphenylpent-3-yl)hydroxylamine

A solution of 0.37 g (1.55 mmol) of 1,5-diphenyl-3-pentanone in 20 ml of 2-propanol was treated with 0.22 g (3.1 mmol) of hydroxylamine hydrochloride and 0.31 g (4.7 mmol) of anhydrous sodium acetate. After being stirred for 10 min, the mixture was treated with 0.20 g (3.2 mmol) of sodium cyanoborohydride and stirred at ambient temperature for 16 h. After concentration in vacuo, the residue was taken up in ethyl acetate, washed sequentially with aqueous NaHCO$_3$ and saturated brine, dried over MgSO$_4$, and concentrated. Flash chromatography using 40% ethyl acetate in chloroform gave 121 mg (31%) of the desired compound (R$_f$ 0.16, 30% ethyl acetate in chloroform) as a white solid, m.p. 54°–55° C. $^1$H NMR (CDCl$_3$) δ 1.7–1.85 (m, 2H), 1.85–2.0 (m, 2H), 2.6–2.75 (m, 4H), 2.90 (pentet, J=6 Hz, 1H), 5.22 (br, 2H), 7.1–7.35 (m, 10H). Mass spectrum (M+H)$^+$=256.

Anal. Calcd. for C$_{17}$H$_{21}$NO: C, 79.96; H, 8.29; N, 5.49. Found: C, 79.82; H, 8.39; N, 5.50.

EXAMPLE 34

A. N-Methyl-N-methoxy-2-hydroxy-3-phenylpropanamide

A solution of 2.0 g (12 mmol) of phenyllactic acid, 1.17 g (12 mmol) of N,O-dimethylhydroxylamine hydrochloride, and 1.78 g (13 mmol) of 1-hydroxybenzotriazole in 20 ml of dimethylformamide was treated sequentially with 2.77 ml (25 mmol) of 4-methylmorpholine and 2.53 g (13 mmol) of N-ethyl-N'-(dimethylaminoethyl)carbodiimide. After being stirred at ambient temperature overnight, the solution was diluted with ethyl acetate; washed sequentially with water, 10% citric acid, aqueous NaHCO$_3$, and saturated brine; dried over MgSO$_4$; and concentrated in vacuo to give 2.5 g (100%) of the crude desired compound. $^1$H NMR (CDCl$_3$) δ 2.85 (dd, J=14, 7 Hz, 1H), 3.08 (dd, J=14, 4 Hz, 1H), 3.23 (s, 3H), 3.72 (s, 3H), 4.62 (m, 1H), 7.2–7.3 (m, 5H). Mass spectrum (M+H)$^+$=210.

B. N-Methyl-N-methoxy-2-fluoro-3-phenylpropanamide

The resultant compound of Example 34A (0.5 g, 2.4 mmol) in 5 ml of dichloromethane was treated with 0.63 ml (4.8 mmol) of diethylaminosulfur trifluoride and stirred at ambient temperature. After 16 h, the solution was quenched with water, washed with aqueous NaHCO$_3$, dried over MgSO$_4$, and concentrated. Flash chromatography using 20% ethyl acetate in hexane gave 210 mg (42%) of the desired compound. $^1$H NMR (CDCl$_3$) δ 3.1–3.2 (m, 2H), 3.21 (s, 3 H), 3.68 (s, 3H), 5.37 (dm, J=50 Hz, 1H), 7.2–7.4 (m, 5 H). Mass spectrum (M+NH$_4$)$^+$=229.

C. 1,5-Diphenyl-2-fluoro-3-pentanone

A solution of 200 mg (0.1 mmol) of the resultant compound of Example 34B in 3 ml of tetrahydrofuran was treated with 0.36 ml (0.36 mmol) of 2-phenylethylmagnesium bromide and stirred at ambient temperature for 16 h. The resulting solution was treated with water, extracted with ethyl acetate, washed sequentially with aqueous ammonium chloride, water, and saturated brine, dried over MgSO$_4$, and concentrated. Flash chromatography using 5% ethyl acetate in hexane gave 108 mg (44%) of the desired compound (R$_f$ 0.60, 15% ethyl acetate in hexane) as an oil. $^1$H NMR (CDCl$_3$) δ 2.5–3.3 (m, 6H), 4.96 (ddd, J=50, 8, 4 Hz, 1 H), 7.1–7.3 (m, 10H). Mass spectrum (M+NH$_4$)$^+$ =274, (M+NH$_4$+H$_2$O)$^+$=290.

EXAMPLE 35

2,4-Bis-(N-acetylamino)-1,5-diphenyl-3-hydroxypentane

A suspension of 0.037 mmol of the resultant compound of Example 12 in 1 ml of aqueous NaHCO$_3$ was cooled to 0°

C. and treated with 0.04 ml of acetic anhydride. After being stirred for 40 min, the solution was extracted with dichloromethane. The organic phase was washed with saturated brine, dried over $Na_2SO_4$, and concentrated. The crude material was recrystallized from dichloromethane/ethyl acetate to give the desired compound ($R_f$ 0.7, 10% methanol in chloroform, 90% yield) as a white solid, m.p. 125°–126° C. Mass spectrum: $(M+H)^+=355$.

EXAMPLE 36

A. 4-(t-Butyloxycarbonylamino)-3-hydroxy-5-phenyl-1-pentene

A solution of 10.25 g (36.7 mmol) of N-(t-butyloxycarbonyl)phenylalanine methyl ester in 60 ml of toluene was cooled to −78° C. under inert atmosphere and treated dropwise over a period of 45 min with 35 ml (52.5 mmol) of diisobutylaluminum hydride in toluene. The resulting solution was stirred for 5 min, treated with 200 ml (200 mmol) of vinylmagnesium bromide, and allowed to warm to 0° C. for 16 h. The solution was subsequently quenched cautiously with methanol, treated with aqueous Rochelle salts, stirred for a few min, and filtered. The residue was digested several times with ethyl acetate and filtered; and the combined filtrates were washed with saturated brine, dried over $MgSo_4$, and concentrated. Silica gel chromatography using 20% ethyl acetate in hexane gave 5.46 g (54%) of the pure desired compound.

B. 4-Benzyl-3-(t-butyloxycarbonyl)-2,2-dimethyl-5-vinyloxazolidine

A solution of 5.00 g (18.0 mmol) of the resultant compound of Example 36A and 17 ml (180 mmol) of 2-methoxypropene in 50 ml of dichloromethane was cooled to 0° C. and treated with 0.21 g (0.83 mmol) of pyridinium p-toluenesulfonate. After several h at ambient temperature, the solution was treated with aqueous $NaHCO_3$, extracted with dichloromethane, dried over $MgSO_4$, and concentrated. Flash chromatography using 8% ethyl acetate in hexane gave 5.29 g (92%) of the desired compound as an oil.

C. 4-Benzyl-3-(t-butyloxycarbonyl)-2,2-dimethyloxazolidine-5-carboxaldehyde

A solution of 5.28 g (16.7 mmol) of the resultant compound of Example 36B in 60 ml of dichloromethane and 30 ml of methanol was cooled to −78° C. and treated with a stream of ozone in air until a blue color persisted. Dry nitrogen was bubbled through the solution until the blue color was discharged, and the resulting solution was transferred via cannula to a precooled (−45° C.) suspension of 4.5 g of zinc metal in 4.5 ml of acetic acid, 100 ml of water, and 100 ml of methanol. The resulting mixture was stirred for 5 min, allowed to warm to ambient temperature over 2.5 h, quenched with saturated brine, extracted twice with dichloromethane, dried over $MgSO_4$, and concentrated. Flash chromatography using 30% ethyl acetate in hexane gave 4.41 g (83%) of the desired compound as an oil which crystallized. $^1H$ NMR ($CDCl_3$) δ 1.52 (s, 9H), 1.54 (br, 6 H), 2.8 (br, 1H), 3.3 (br, 1H), 4.19 (br, 1H), 4.42 (br, 1H), 7.2–7.35 (m, 5H), 9.65 (br, 1H). Mass spectrum: $(M+H)^+=320$.

D. (cis)-Methyl 3-(4-Benzyl-3-(t-butyloxycarbonyl)-2,2-dimethyloxazolidin-5-yl)propenoate A suspension of 0.21 g (5.2 mmol) of sodium hydride (60% dispersion in mineral oil) in 15 ml of dry tetrahydrofuran was cooled to 0° C., treated with 1.52 g (4.8 mmol) of bis(2,2,2-trifluoroethyl) (methoxycarbonylmethyl) phosphonate in 5 ml of tetrahydrofuran, stirred for 10 min at 0° C., treated with a solution of 1.0 g (3.13 mmol) of the resultant compound of Example 36C in 5 ml of tetrahydrofuran, and stirred at ambient temperature for 1 h. The resulting solution was quenched with aqueous $NH_4Cl$, extracted with ether, washed with saturated brine, dried over $MgSO_4$, and concentrated. Flash chromatography using 15% ethyl acetate in hexane gave 0.82 g (69%) of the desired compound. Mass spectrum: $(M+H)^+=376$.

E. (cis)-3-(4-Benzyl-3-(t-butyloxycarbonyl)-2,2-dimethyl-oxazolidin-5-yl)propenoic Acid A solution of 218 mg (0.58 mmol) of the resultant compound of Example 36D in 4.6 ml of dioxane was treated with 2.3 ml (1.2 mmol) of 0.5M aqueous lithium hydroxide. After 2 h, the solution was diluted with chloroform, acidified with 1N HCl, partitioned, and the aqueous layer was washed with additional chloroform. The combined organic layers were dried over $MgSO_4$ and concentrated to give the desired compound as a colorless oil.

F. (cis)-N-(3-Methylbutyl)-3-(4-benzyl-3-(t-butyloxycarbonyl)-2,2-dimethyl-oxazolidin-5-yl) propenamide According to the mixed anhydride procedure of Example 6F, the resultant compound of Example 36E was coupled to isoamylamine to give 251 mg (100%) of the desired compound as a colorless oil. $^1H$ NMR ($CDCl_3$) δ 0.93 (d, J=7 Hz, 6 H), 1.41 (t, J=7 Hz, 2H), 1.51 (s, 9H), 1.57 (s, 6H), 1.62 (heptet, J=7 Hz, 1H), 2.9–3.4 (m, 4H), 3.96 (m, 1 H), 5.20 (m, 1H), 5.7–6.1 (m, 3H), 7.15–7.3 (m, 5H). Mass spectrum: $(M+H)^+=431$.

G. (cis)-N-(3-Methylbutyl)-5-amino-4-hydroxy-6-phenyl-2-hexenamide

A solution of 48 mg (0.11 mmol) of the resultant compound of Example 36F in 1 ml of dichloromethane was treated with 1 ml of trifluoroacetic acid. After being stirred for 1.75 h, the solution was concentrated in vacuo, taken up in 3 ml of 2:1 tetrahydrofuran:water, stirred for 45 min, treated with solid $K_2CO_3$, extracted with chloroform, dried over $MgSO_4$, and concentrated to give 21 mg (64%) of the desired compound. $^1H$ NMR ($CDCl_3$) δ 0.92 (d, J=7 Hz, 6H), 1.43 (m, 2H), 1.63 (heptet, J=7 Hz, 1H), 2.9–3.1 (m, 3H), 3.33 (m, 2H), 4.50 (m, 1H), 5.36 (dd, J=12, 2 Hz, 1H), 5.43 (br, 1H), 6.22 (dd, J=12, 6 Hz, 1H), 7.2–7.35 (m, 5H). Mass spectrum: $(M+H)^+=291$.

EXAMPLE 37

(cis)-N-(3-Methylbutyl)-5-(acetylamino)-4-hydroxy-6-phenyl-2-hexenamide

A solution of 28.2 mg (0.092 mmol) of the resultant compound of Example 36G in 1 ml of dichloromethane was cooled to 0° C. and treated sequentially with 0.010 ml (0.092 mmol) of 4-methylmorpholine and 0.087 ml (0.092 mmol) of acetic anhydride. After being stirred at ambient temperature for 1 h, the solution was partitioned between dichloromethane and water, dried over $Na_2SO_4$, and concentrated. Flash chromatography using 5% methanol in chloroform gave the desired compound ($R_f$ 0.15, 5% methanol in chloroform). $^1H$ NMR ($CDCl_3$) δ 0.92 (d, J=7 Hz, 6H), 1.42 (q, J=7 Hz, 2H), 1.62 (heptet, J=7 Hz, 1H), 1.94 (s, 3H), 2.92 (dd, J=13, 7 Hz, 1H), 2.99 (dd, J=13, 5 Hz, 1H), 3.32 (m, 2H), 4.38 (m, 1H), 4.43 (m, 1H), 5.74 (dd, J=12, 2 Hz, 1H), 5.75 (br, 1H), 6.07 (br, 1H), 6.13 (dd, J=12, 5 Hz, 1H), 6.90 (d, J=4 Hz, 1H), 7.2–7.35 (m, 5H). Mass spectrum: $(M+H)^+$ =333.

EXAMPLE 38

2,4-Bis-((N,N-dimethylamino)sulfamoyl)amino)-1,5-diphenyl-3-hydroxypentane

The resultant compound of Example 12B (0.1 mmol) was dissolved in 1 ml of dichloromethane and treated sequentially with 0.5 mmol of triethylamine and 0.2 mmol of (N,N-dimethyl)aminosulfamoyl chloride. After being stirred for 3 h, extractive workup gave the desired compound.

EXAMPLE 39

2,4-Bis-(N-(aminocarbonyl)amino)-1,5-diphenyl-3-hydroxypentane

A solution of 0.1 mmol of the resultant compound of Example 12B and 0.2 mmol of sodium hydroxide in 1 ml of water was treated with 0.3 mmol of potassium cyanate. After being heated to 60° C. for 1 h, the solution was cooled, extracted with chloroform, dried over $Na_2SO_4$, and concentrated to give the desired compound.

EXAMPLE 40

Di-(2-phenylethyl)phosphinic Acid

The resultant compound of Example 9 (250 mg, 0.97 mmol) was added to 10 ml of 5.25% sodium hypochlorite. The resulting solution was stirred vigorously for 1 h, acidified, extracted with chloroform, washed with 1N HCl and saturated brine, dried over $MgSO_4$, and concentrated in vacuo to give 217 mg (82%) of the desired compound ($R_f$ 0.12, 20% methanol in chloroform) as a glass. $^1H$ NMR $(CDCl_3)$ δ 2.0–2.1 (m, 4H), 2.9–3.0 (m, 4H), 7.15–7.4 (m, 10H). Mass spectrum $(M+H)^+$=275.

EXAMPLE 41

A. 3-(Azidomethyl)-1,5-diphenyl-3-hydroxypentane

Using the procedure of Example 10C with 242 mg (0.96 mmol) of the resultant compound of Example 16B gave, after silica gel chromatography using 16% ethyl acetate in hexane, 259 mg (84%) of the desired compound. $^1H$ NMR $(CDCl_3)$ δ 1.78 (s, 3H), 1.90 (m, 4H), 2.69 (m, 4H), 3.41 (s, 2H), 7.2–7.35 (m, 10H). Mass spectrum: $(M+NH_4)^+$=313.

B. 3-(Aminomethyl)-1,5-diphenyl-3-hydroxypentane

Using the procedure of Example 11 with 158 mg (0.536 mmol) of the resultant compound of Example 41A gave, after silica gel chromatography using 2.5% methanol/2% isopropylamine in chloroform, 116 mg (81%) of the desired compound ($R_f$ 0.36, 2.5% methanol/2% isopropylamine in chloroform) as a white solid, m.p. 104°–106° C. $^1H$ NMR $(CDCl_3)$ δ 1.1–1.5 (br, 2H), 1.81 (m, 4H), 2.70 (m, 6H), 7.15–7.35 (m, 10H). Mass spectrum: $(M+H)^+$=270.

Anal. Calcd. for $C_{18}H_{23}NO$: C, 80.26; H, 8.61; N, 5.20. Found: C, 83.56; H, 8.99; N, 5.88.

EXAMPLE 42

2,8-Dimethyl-5-hydroxynonane

A solution of 5.63 g (33 mmol) of 2,8-dimethylnonan-5-one in 150 ml of methanol was cooled to 0° C. and treated with 0.8 g (21 mmol) of sodium borohydride. After 1 h, the solution was quenched with 1N HCl; diluted with 1:1 hexane/ether; washed sequentially with 1N NaOH, water, and saturated brine; dried over $MgSO_4$; and concentrated in vacuo. Flash chromatography using 10% ethyl acetate in hexane gave 2.30 g (40%) of the desired compound ($R_f$ 0.36, 20% ethyl acetate in hexane) as a colorless oil. $^1H$ NMR $(CDCl_3)$ δ 0.88 (d, J=7 Hz, 6H), 0.89 (d, J=7 Hz, 6H), 1.1–1.6 (m, 10H), 3.56 (m, 1H).

EXAMPLE 43

A. 2-Benzyl-2-ethoxycarbonyl-1,3-dithiane

A solution of 3.0 g (15.6 mmol) of 2-ethoxycarbonyl-1,3-dithiane in 40 ml of dry tetrahydrofuran was cooled under inert atmosphere to –78° C. and treated with 7.5 ml (15.6 mmol) of n-butyllithium. The resulting solution was warmed to –25° C., stirred for 20 min, recooled to –78° C., treated with 1.8 ml (15.6 mmol) of benzyl chloride, and stirred at ambient temperature for 16 h. After quenching with aqueous ammonium chloride, the mixture was extracted with ether, washed sequentially with water, aqueous sodium thiosulfate, and brine, dried over $MgSO_4$, and concentrated in vacuo. Flash chromatography using 5% ethyl acetate in hexane gave 3.9 g (88%) of the desired compound. $^1H$ NMR $(CDCl_3)$ δ 1.33 (t, J=7 Hz, 3H), 1.85 (qt, J=14, 3 Hz, 1H), 2.11 (dm, J=14 Hz, 1H), 2.69 (dt, J=14, 4 Hz, 2 H), 3.23 (ddd, J=14, 12, 3 Hz, 2H), 3.38 (s, 2H), 4.27 (q, J=7 Hz, 2H), 7.25–7.35 (m, 5H). Mass spectrum $(M+NH_4)^+$=300.

B. Ethyl 2,2-Difluoro-3-phenylpropanoate

A solution of 0.50 g (1.76 mmol) of the resultant compound of Example 43A in 15 ml of acetonitrile was cooled to 0° C. and treated with a solution of 1.8 g (10.5 mmol) of N-bromosuccinimide in 15 ml of acetonitrile and 2 ml of water. After being stirred for 5 min, the solution was added to 1:1 hexane/dichloromethane, washed sequentially with aqueous sodium bisulfite/sodium bicarbonate, water, and saturated brine, dried over $MgSO_4$, and concentrated to give 0.30 g of crude ethyl 3-phenylpyruvate. The crude residue was taken up in 3 ml of dry dichloromethane, treated with 0.83 ml (6.3 mmol) of diethylaminosulfur trifluoride, and stirred at ambient temperature for 3 d. The resulting solution was cooled to 0° C., quenched cautiously with water, extracted with dichloromethane, washed sequentially with water, aqueous sodium bicarbonate, and saturated brine, dried over $MgSO_4$, and concentrated in vacuo. Flash chromatography using 5% ethyl acetate in hexane gave 72 mg (25%) of the desired compound. $^1H$ NMR $(CDCl_3)$ δ 1.25 (t, J=7 Hz, 3H), 3.38 (t, $J_{H-F}$=16 Hz, 2 H), 4.24 (q, J=7 Hz, 2H), 7.25–7.35 (m, 5H). Mass spectrum $(M+NH_4)^+$=232.

C. 2,2-Difluoro-1,5-diphenyl-3-pentanone

A solution of 70 mg (0.33 mmol) of the resultant compound of Example 43B in 3 ml of tetrahydrofuran was cooled to –78° and treated with 0.33 ml (0.33 mmol) of (2-phenylethyl)magnesium bromide (1M in tetrahydrofuran). The resulting solution was allowed to warm to ambient temperature for 1 h, quenched with acetic acid in tetrahydrofuran, taken up in ethyl acetate, washed sequentially with aqueous ammonium chloride, water, and saturated brine, dried over $MgSO_4$, and concentrated. Flash chromatography using 2% ethyl acetate in hexane gave 5.2 mg (6%) of the desired compound ($R_f$ 0.71, 20% ethyl acetate in hexane). $^1H$ NMR $(CDCl_3)$ δ 2.92 (t, J=7 Hz, 2H), 3.31 (t, J=16 Hz, 2H), 4.38 (t, J=7 Hz, 2H), 7.1–7.35 (m, 10H). Mass spectrum $(M+NH_4)^+$=292, $(M+NH_4+H_2O)^+$=308.

EXAMPLE 44

Ethyl 2,2-Difluoro-3-hydroxy-5-phenylpentanoate

According to the procedure of Thaisrivongs et. al. (*J. Med. Chem.*, 1986, 29, 2080), ethyl bromodifluoroacetate was condensed with hydrocinnamaldehyde to give the desired compound.

EXAMPLE 45

2,2-Difluoro-3-hydroxy-5-phenylpentanoic Acid

Using the procedure of Example 6E with the resultant compound of Example 44 gave the desired compound.

EXAMPLE 46

N-(3-Methylbutyl)-2,2-difluoro-3-hydroxy-5-phenylpentanamide

Using the procedure of Example 6F with the resultant compound of Example 45 gave the desired compound.

EXAMPLE 47

N-(3-Methylbutyl)-2,2difluoro-3-oxo-5-phenylpentanamide

According to the procedure of Thaisrivongs et. al. (*J. Med. Chem.*, 1986, 29, 2080), the resultant compound of Example 46 was treated with dimethylsulfoxide and oxalyl chloride to give the desired compound.

EXAMPLE 48

Dibenzyl 5,9-Diaza-6,8-dibenzyl-4,10dioxo-7-hydroxy-3,3,11,11-tetramethyltridecanedicarboxylate The resultant compound of Example 12 (0.1 mmol) was dissolved in 1 ml of dichloromethane and treated sequentially with 0.5 mmol of triethylamine and 0.2 mmol of 3-benzyloxycarbonyl-2,2-dimethylpropanoyl chloride (Matsushita, et. al., Heterocycles, 22, 1403 (1984). After being stirred for 3 h, extractive workup gave the desired compound.

EXAMPLE 49

5,9-Diaza-6,8-dibenzyl-4,10-dioxo-7hydroxy-3,3,11,11-tetramethyltridecanedicarboxylic Acid Using the procedure of Example 11 with the resultant compound of Example 48 gave the desired compound.

EXAMPLE 50

1,3-Di-(4-nitrophenoxy)-2-propanol

A solution of 1 g (7.2 mmol) of 4-nitrophenol, 0.28 ml (3.6 mmol) of epichlorohydrin, and 0.16 g (3.96 mmol) of sodium hydroxide in 2 ml of dimethylformamide was heated at 110° C. for 1 h. The solvent was removed in vacuo, and the residue was purified by flash chromatography using chloroform to give 0.97 g (81%) of the desired compound ($R_f$ 0.42, 40% ethyl acetate in chloroform). $^1$H NMR (CDCl$_3$) δ 2.54 (d, 5 Hz, 1H), 4.28 (dd, J=10, 6 Hz, 2H), 4.29 (dd, J=10, 5 Hz, 2H), 4.50 (br sextet, J=6 Hz, 1H), 7.0–7.05 (m, 4H), 8.2–8.3 (m, 4H). Mass spectrum (M+NH$_4$)$^+$=352.

EXAMPLE 51

1,5Diphenyl-3-((methoxy)pentane

A solution of 101 mg (0.42 mmol) of 1,5-diphenyl-3-pentanol, 0.18 ml (1.0 mmol) of ethyldiisopropylamine, and 0.063 ml (0.84 mmol) of chloromethyl methyl ether in 1 ml of dichloromethane was allowed to stand for 16 h. The resulting solution was taken up in ethyl acetate, washed sequentially with 10% aqueous citric acid, water, and saturated sodium bicarbonate, dried over Na$_2$SO$_4$, and concentrated in vacuo. Flash chromatography using 10% ethyl acetate in hexane gave 109 mg (92%) of the desired compound ($R_f$ 0.51, 25% ethyl acetate in hexane) as an oil. $^1$H NMR (CDCl$_3$) δ 1.88 (m, 4H), 2.70 (m, 4H), 3.44 (s, 3 H), 3.64 (pentet, J=6 Hz, 1H), 4.70 (s, 2H), 7.15–7.3 (m, 10H). Mass spectrum (M+NH$_4$)$^+$=302.

EXAMPLE 52

A. 2,2-Di-(3-phenylpropyl)-1,3-dithiane

A solution of 1.0 g (4.2 mmol) of 2-(3-phenylpropyl)-1,3-dithiane in 25 ml of dry tetrahydrofuran was cooled to −78° C. and treated with 3.23 ml (4.2 mmol) of sec-butyllithium. The resulting solution was stirred at −25° C. for 20 min, recooled to −78° C., and treated with 0.64 ml (4.2 mmol) of 1-bromo-3-phenylpropane. After being stirred at −78° C. for 15 min, the solution was allowed to stir overnight at ambient temperature. The solution was partitioned between ether and aqueous ammonium chloride, and the organic layer was washed sequentially with water, 1M sodium bisulfite, and saturated brine, dried over MgSO$_4$, and concentrated in vacuo to give the desired compound. $^1$H NMR (CDCl$_3$) δ 1.65–1.9 (m, 9H), 2.18 (m, 1H), 2.55–2.75 (m, 6H), 2.78 (t, J=8 Hz, 1H), 3.40 (t, J=6 Hz, 1H), 7.1–7.35 (m, 10H). Mass spectrum (M+H)$^+$=357.

B. 1,7-Diphenylheptan-4-one

A solution of the resultant compound of Example 52A (1.6 g (4.5 mmol) in 20 ml of acetonitrile was cooled to 0° C. and treated dropwise with a solution of 4.8 g (27 mmol) of N-bromosuccinimide in 15 ml of acetonitrile and 15 ml of water. The resulting solution was stirred for 1.5 h, extracted with dichloromethane, washed sequentially with 1M sodium bisulfite, aqueous sodium bicarbonate, and saturated brine; dried over MgSO$_4$, and concentrated in vacuo. Flash chromatography using 7% ethyl acetate in hexane gave 0.56 g (93%) of the desired compound ($R_f$ 0.33, 10% ethyl acetate in hexane) as an oil. $^1$H NMR (CDCl$_3$) δ 1.90 (pentet, J=7 Hz, 4H), 2.39 (t, J=7 Hz, 4H), 2.61 (t, J=7 Hz, 4H), 7.15–7.3 (m, 10H). Mass spectrum (M+H)$^+$=267.

EXAMPLE 53

1,7-Diphenylheptan-4-ol

Using the procedure of Example 42 with the resultant compound of Example 52 gave, after silica gel chromatography using 15% ethyl acetate in hexane, the desired compound ($R_f$ 0.23, 30% ethyl acetate in hexane) as an oil. $^1$H NMR (CDCl$_3$) δ 1.4–1.8 (m, 8H), 2.62 (br t, 4 H), 3.63 (m, 1H), 7.15–7.3 (m, 10H). Mass spectrum (M+NH$_4$)$^+$=286.

EXAMPLE 54

A. (Z)-(4-(t-Butyldimethylsilyloxy)-6-phenyl-2-hexenoyl)-Val-Val Amide

A solution of the resultant compound of Example 6E (57 mg, 0.18 mmol) and 0.022 ml of 4-methylmorpholine in 3 ml of dichloromethane was cooled to 0° C. and treated with 0.026 ml (0.19 mmol) of isobutyl chloroformate. The resulting solution was stirred for 10 min, treated with a solution of 41 mg (0.19 mmol) of H-Val-Val-NH$_2$ in 1.5 ml of dimethylformamide, and stirred at ambient temperature for 2 h. The solution was subsequently diluted with ethyl acetate, washed sequentially with 10% aqueous citric acid and aqueous $NaHCO_3$, dried over $MgSO_4$, and concentrated. Flash chromatography using 60% ethyl acetate in chloroform gave 53 mg (57%) of the desired compound as a 1:1 mixture of diastereomers.

B. (Z)-(4-Hydroxy-6-phenyl-2-hexenoyl)-Val-Val Amide

A solution of 13 mg (0.025 mmol) of the resultant compound of Example 54A in 0.5 ml of tetrahydrofuran was treated with 0.065 ml (0.065 mmol) of tetra-n-butylammonium fluoride (1M in tetrahydrofuran). After being stirred for 16 h, the solution was concentrated in vacuo. Flash chromatography using 7.5% methanol in chloroform gave the desired compound, m.p. 147°–149° C., as a 1:1 mixture of diastereomers ($R_f$ 0.15, 7.5% methanol in chloroform). Mass spectrum: $(M+H)^+=403$.

Anal. Calcd. for $C_{22}H_{33}N_3O_4 \cdot 0.5H_2O$: C, 64.05; H, 8.31; N, 10.19. Found: C, 63.84; H, 7.65; N, 10.06.

EXAMPLE 55

2-(t-Butyloxycarbonylamino)-4-(Cbz-valinyl-amino)-1,5-diphenyl-3-hydroxypentane A solution of 39 mg (0.16 mmol) of Cbz-Val-OH, 52 mg (0.14 mmol) of the resultant compound of Example 11, and 23 mg (0.17 mmol) of 1-hydroxybenzotriazole in 2 ml of dimethylformamide was treated with 0.019 ml (0.17 mmol) of 4-methylmorpholine, cooled to 0° C., and treated with 33 mg (0.17 mmol) of N-ethyl-N'-(dimethylaminopropyl)-carbodiimide hydrochloride. After being stirred at ambient temperature overnight, the solution was diluted with ethyl acetate, washed sequentially with 10% citric acid, water, and aqueous $NaHCO_3$, dried over $Na_2SO_4$, and concentrated in vacuo. Separation of the desired compounds by flash chromatography using methanol in chloroform gave 80 mg (95%) of the desired compound ($R_f$ 0.40, 10% methanol in chloroform) as a white solid, m.p. 187°–187.5° C. Mass spectrum $(M+H)^+=604$.

EXAMPLE 56

A. 2-Amino-4-azido-1,5-diphenyl-3-hydroxypentane Hydrochloride

The resultant compound of Example 10C (25 mg, 0.063 mmol) was treated with 1 ml of 4M HCl in dioxane, stirred for 0.5 h at ambient temperature, and concentrated in vacuo to give the desired compound.

EXAMPLE 57

Acetyl-Val-Val Amide of 2-Amino-4-azido-1,5-diphenyl-3-hydroxypentane

A solution of 18 mg (0.069 mmol) of Ac-Val-Val-OH, 0.063 mmol of the resultant compound of Example 56, and 10 mg (0.076 mmol) of 1-hydroxybenzotriazole in 0.5 ml of dimethylformamide was treated sequentially with 0.015 ml (0.14 mmol) of 4-methylmorpholine and 15 mg (0.076 mmol) of N-ethyl-N'-(dimethylaminoethyl)carbodiimide. After being stirred at ambient temperature overnight, the solution was diluted with ethyl acetate, washed sequentially with aqueous $NaHCO_3$ and water, dried over $MgSO_4$, and concentrated in vacuo to give the desired compound.

EXAMPLE 58

(2N)-Acetyl-Val-Val Amide of 2,4-Diamino-1,5-diphenyl-3-hydroxypentane

Using the procedure of Example 11 with 0.063 mmol of the resultant compound of Example 57 gave, after silica gel chromatography using 7.5% methanol in chloroform, 15.3 mg (48%) of the desired compound.

EXAMPLE 59

2,4-Bis-(N-(acetyl-valinyl-valinyl)amino)-1,5-diphenyl-3-hydroxypentane

A solution of 8.5 mg (0.033 mmol) of Ac-Val-Val-OH, 15.3 mg (0.030 mmol) of the resultant compound of Example 58, and 8 mg (0.059 mmol) of 1-hydroxybenzotriazole in 1 ml of dimethylformamide was treated sequentially with 0.0045 ml (0.04 mmol) of 4-methylmorpholine and 6.5 mg (0.034 mmol) of N-ethyl-N'-(dimethylaminoethyl) carbodiimide. After being stirred at ambient temperature overnight, the solution was diluted with ethyl acetate, washed sequentially with 10% aqueous citric acid, aqueous $NaHCO_3$ and water, and concentrated in vacuo to a solid which was triturated with 1:1 chloroform:methanol, filtered, washed with 1:1 chloroform:methanol, and air-dried to give the desired compound as a white solid, m.p. 271°–272.5° C. Mass spectrum $(M+H)^+=751$.

Anal. Calcd. for $C_{41}H_{62}N_6O_7 \cdot H_2O$: C, 64.04; H, 8.39; N, 10.93. Found: C, 63.89; H, 8.02; N, 10.82.

EXAMPLE 60

2,4-Bis-(N-(acetyl-valinyl-valinyl)amino)-1,5-diphenyl-3-pentanone

A solution of the resultant compound of Example 59 (0.056 mmol) in 10 ml of acetone was cooled to 0° C. and treated with 5 drops of aqueous chromic acid. After 1.25 h, the solution was quenched with 2-propanol and aqueous $NaHCO_3$, filtered through Celite, extracted with 10% methanol in chloroform, and concentrated in vacuo. Flash chromatography using 7.5% methanol in chloroform gave 3.7 mg (9%) of the desired compound ($R_f$ 0.39, 10% methanol in chloroform). Mass spectrum $(M+H)^+=749$.

EXAMPLE 61

A. 4-Azido-2-(t-butyloxycarbonylamino)-1,5-diphenyl-3-pentanone

Using the procedure of Example 60 with the resultant compound of Example 5C gave the desired compound.

B. 4-Azido-2-(t-butyloxycarbonylamino)-1,5-diphenyl-3-methylenepentane

Using the procedure of Example 16A with the resultant compound of Example 61A gave the desired compound.

C. 2-Amino-4-azido-1,5-diphenyl-3-methylenepentane Hydrochloride

Using the procedure of Example 56 with the resultant compound of Example 61B gave the desired compound.

D. Cbz-Val Amide of 2-Amino-4-azido-1,5-diphenyl-3-methylenepentane

Using the procedure of Example 55 with the resultant compound of Example 61C gave the desired compound.

E. Cbz-Val Amide of 3-Amino-2-(1-azido-2-phenylethyl)-4-phenyl-1-butene-1,2-epoxide Using the procedure of Example 16B with the resultant compound of Example 61D gave the desired compound.

EXAMPLE 62

5-((N-Acetyl-valinyl-valinyl)amino)-2-(N-benzylamino)-3,4-dihydroxy-1,6-diphenyl-3-hexane A solution of 10 mg (0.04 mmol) of Ac-Val-Val-OH, 0.039 mmol of the resultant compound of Example 19, and 6 mg (0.044 mmol) of 1-hydroxybenzotriazole in 1 ml of dichloromethane and 0.4 ml of dimethylformamide was treated with 0.009 ml (0.08 mmol) of 4-methylmorpholine, cooled to 0° C., and treated with 9 mg (0.047 mmol) of N-ethyl-N'-(dimethylaminoethyl)carbodiimide. After being stirred at ambient temperature overnight, the solution was diluted with ethyl acetate, washed sequentially with aqueous NaHCO$_3$ and water, dried over Na$_2$SO$_4$, and concentrated in vacuo. Separation of the desired compounds by flash chromatography using 6% methanol in chloroform gave 3.0 mg (13%) of the less polar diastereomer (R$_f$ 0.33, 10% methanol in chloroform), m.p. 154°–156° C., and 4.1 mg (17%) of the more polar diastereomer (R$_f$ 0.28), m.p. 121°–124° C. Mass spectrum (for each diastereomer): (M+H)$^+$=631.

EXAMPLE 63

Cbz-Val Amide of 2-Amino-4-azido-1,5-diphenyl-3-hydroxy-3-(hydroxymethyl)pentane Using the procedure of Example 17B with the resultant compound of Example 61D gave the desired compound.

EXAMPLE 64

A. 2.2-Dimethyl-4,5-di-(1-hydroxy-2-phenylethyl)-1,3-dioxolane

According to the procedure of Achmatowicz and Wicha (*Tetrahedron Lett.*, 1987, 28, 2999) the resultant compound of Example 23 was treated with sodium borohydride in ethanol to give the desired compound as a mixture of stereoisomers.

B. 2.2-Dimethyl-4,5-di-(1-(Cbz-valinyl)oxy-2-phenylethyl)-1,3-dioxolane

Using the procedure of Example 55 with the resultant compound of Example 64A and replacing 1-hydroxybenzotriazole with 4-dimethylaminopyridine gave the desired compound.

C. 2,5-Di-(Cbz-valinyl)oxy-3,4-dihydroxy-1,6-diphenylhexane

The resultant compound of Example 64B was treated with 1 ml of 80% aqueous acetic acid, heated at reflux for 5 min, allowed to cool, and concentrated in vacuo to give the desired compound.

EXAMPLE 65

2-(t-Butyloxycarbonylamino)-4-(Cbz-leucinyl-asparaginyl-amino)-1,5-diphenyl-3-hydroxypentane Using the procedure of Example 55 but replacing Cbz-Val-OH with Cbz-Leu-Asn-OH gave, after silica gel chromatography using methanol/chloroform, the desired compound (R$_F$ 0.4; 2.5% methanol/2% isopropylamine/chloroform) in 98% yield, m.p. 192°–193.5° C. Mass spectrum (M+H)$^+$=732.

Anal. Calcd for C$_{40}$H$_{53}$N$_5$O$_8$: C, 65.64; H, 7.30; N, 9.57. Found: C, 65.31; H, 7.43; N, 9.52.

EXAMPLE 66

2-(t-Butyloxycarbonylamino-4-(Cbz-asparaginyl-amino)-1,5-diphenyl-3-hydroxypentane Using the procedure of Example 55 but replacing Cbz-Val-OH with Cbz-Asn-OH gave, after silica gel chromatography using methanol/chloroform, the desired compound (R$_F$ 0.4; 2.5% methanol/2% isopropylamine/chloroform) in 74% yield, m.p. 216°–217° C. Mass spectrum (M+H)$^+$=619.

EXAMPLE 67

2-Amino-4-(Cbz-asparaginyl-amino)-1,5-diphenyl-3-hydroxypentane

Using the procedure of Example 11 with the resultant compound of Example 66 gave, after silica gel chromatography using methanol/isopropylamine/chloroform, the desired compound (R$_F$ 0.3; 2.5% methanol/2% isopropylamine/chloroform) in 95% yield. Mass spectrum (M+H)$^+$=519.

EXAMPLE 68

2,4-Bis-(Cbz-asparaginyl-amino)-1,5-diphenyl-3-hydroxypentane

Using the procedure of Example 55 but replacing Cbz-Val-OH with Cbz-Asn-OH and replacing the resultant compound of Example 11 with the resultant compound of Example 67 gave, after silica gel chromatography using methanol/chloroform, the desired compound (R$_F$ 0.4; 2.5% methanol/2% isopropylamine/chloroform) in 75% yield, m.p. 234°–236° C. (dec). Mass spectrum (M+H)$^+$=767.

Anal. Calcd for C$_{41}$H$_{46}$N$_6$O$_9$·0.75H$_2$O: 63.10; H, 6.14; N, 10.77. Found: C, 63.03; H, 6.03; N, 10.50.

EXAMPLE 69

2Amino-4-(Cbz-valinyl-amino)-1,5-diphenyl-3hydroxypentane

Using the procedure of Example 56 with the resultant compound of Example 55 gave, after silica gel chromatography using methanol/isopropylamine/chloroform, the desired compound (R$_F$ 0.3; 2.5% methanol/2% isopropylamine/chloroform) in 100% yield, m.p. 158°–160° C. Mass spectrum (M+H)$^+$=504.

EXAMPLE 70

2,4-Bis-(Cbz-valinyl-amino)-1,5-diphenyl-3-hydroxypentane

Using the procedure of Example 55 but replacing the resultant compound of Example 11 with the resultant compound of Example 69 gave, after silica gel chromatography using methanol/chloroform, the desired compound (R$_F$ 0.4; 2.5% methanol/2% isopropylamine/chloroform) in 98% yield, m.p. 198°–200° C. Mass spectrum (M+H)$^+$=737.

Anal. Calcd. for C$_{43}$H$_{52}$N$_4$O$_7$·0.5H$_2$O: C, 69.24; H, 7.16; N, 7.51. Found: C, 69.40; H, 7.29; N, 7.47.

EXAMPLE 71

A. N-Boc-valinyl-valine benzyl ester

Boc-Val-OH (2.86 g, 13.2 mmol) was coupled to valine benzyl ester p-toluenesulfonate (5.0 g, 13.2 mmol) using the procedure of Example 55 to give 5.41 g, (100%) of the desired product (R$_F$ 0.15; 20% ethyl acetate in hexane) as a colorless gum. Mass spectrum (M+H)$^+$=407.

B. N-(5-Carbomethoxypentanoyl)-valinyl-valine benzyl ester

The resultant compound of Example 71A (0.50 g, 1.23 mmol) was deprotected according to the procedure of Example 56 and coupled to adipic acid monomethyl ester (0.21 g, 1.28 mmol) using the mixed anhydride procedure of Example 54A to give, after flash chromatography using 40% ethyl acetate in chloroform, 0.53 g (96%) of the desired compound.

C. N-(5-Carbomethoxypentanoyl)-valinyl-valine

A mixture of the resultant compound of Example 71B (0.53 g, 1.18 mmol) and 100 mg of 10% palladium on carbon in 30 ml of methanol was stirred under one atmosphere of hydrogen. After 5 h, the mixture was filtered through Celite and concentrated to give 0.40 g (93%) of the desired compound as a solid.

D. 2-Azido-4-((5-Carbomethoxypentanoyl)-valinyl-valinyl)amino-1,5-diphenyl-3-hyroxypentane The resultant compound of Example 71C (91 mg, 0.25 mmol) was coupled to the resultant compound of Example 56 (0.25 mmol) using the carbodiimide coupling procedure of Example 55 to give, after flash chromatography using 60% ethyl acetate in chloroform, 104 mg (64%) of the desired compound ($R_f$ 0.32, 75% ethyl acetate in chloroform). Mass spectrum $(M+H)^+=637$.

EXAMPLE 72

2-Amino-4-((5-carbomethoxypentanoyl)-valinyl-valinyl)amino-1,5-diphenyl-3-hydroxypentane Using the procedure of Example 11 with the resultant compound of Example 71D gave, after flash chromatography using 5% methanol in chloroform, the desired compound ($R_f$ 0.28, 10% methanol in chloroform) in 63% yield. Mass spectrum $(M+H)^+=611$.

Anal. Calcd. for $C_{34}H_{50}N_4O_6 \cdot 4H_2O$: C, 59.80; H, 8.56; N, 8.20. Found: C, 60.08; H, 7.36; N, 8.21.

EXAMPLE 73

A. N-(6-(Benzyloxycarbonylamino)hexanoyl)-valinyl-valine methyl ester

N-(6-(Benzyloxycarbonylamino)hexanoic acid was coupled to Val-Val methyl ester using the mixed anhydride procedure of Example 54A to give the desired compound.

B. N-(6-(Benzyloxycarbonylamino)hexanoyl)-valinyl-valine

The resultant compound of Example 73A was hydrolyzed according to the procedure of Example 6E to give the desired compound. Mass spectrum $(M+H)^+=464$.

C. 2-(N-(6-Benzyloxycarbonylamino)hexanoyl-valinyl-valinyl-amino)-4-(N-(5-carbomethoxypentanoyl)-valinyl-valinyl-amino)-1,5-diphenyl-3-hydroxypentane The resultant compound of Example 73B (37 mg, 0.079 mmol) was coupled to the resultant compound of Example 72 (48 mg, 0.079 mmol) using the carbodiimide coupling procedure of Example 55 to give, after flash chromatography using 4% methanol in chloroform, 31 mg (37%) of the desired compound ($R_f$ 0.19, 5% methanol in chloroform). Mass spectrum $(M+H)^+=1056$.

Anal. Calcd. for $C_{58}H_{85}N_7O_{11} \cdot 3.5H_2O$: C, 62.23; H, 8.28; N, 8.76. Found: 62.12; H, 7.33; N, 8.75.

EXAMPLE 74

2-(N-(6-(Benzyloxycarbonylamino)hexanoyl)-valinyl-valinyl-amino)-4-(N-(5-carboxypentanoyl)-valinyl-valinyl-amino)-1,5-diphenyl-3-hydroxypentane A solution of 31 mg (0.029 mmol) of the resultant compound of Example 73C in 5 ml of dioxane was treated with 1 ml of 0.5M aqueous lithium hydroxide. After being stirred for 24 h at ambient temperature, the solution was concentrated in vacuo, diluted with ethyl acetate and 1M hydrochloric acid, stirred for 2 h, and separated. The organic phase was washed with water, allowed to evaporate slowly to a small volume. The mixture was then filtered to give the desired compound as a solid.

EXAMPLE 75

Cbz-Val Amide of 3-Amino-2-hydroxy-5-methyl-1-phenoxyhexane

Cbz-valine was coupled to 3-amino-2-hydroxy-5-methyl-1-phenoxyhexane (J. Med. Chem. 1987, 30, 1609) using the carbodiimide coupling procedure of Example 55 to give the desired compound.

EXAMPLE 76

Cbz-Val Amide of 3-Amino-2-hydroxy-5-methyl-1-(phenylthio)hexane

Cbz-valine was coupled to 3-amino-2-hydroxy-5-methyl-1-(phenylthio)hexane (J. Med. Chem. 1987, 30, 1609) using the carbodiimide coupling procedure of Example 55 to give the desired compound.

EXAMPLE 77

Cbz-Val Amide of 3-Amino-2-hydroxy-5-methyl-1-(phenylsulfonyl)hexane

Cbz-valine was coupled to 3-amino-2-hydroxy-5-methyl-1-(phenylsulfonyl)hexane (J. Med. Chem. 1987, 30, 1609) using the carbodiimide coupling procedure of Example 55 to give the desired compound.

EXAMPLE 78

A. 3-(Benzyloxycarbonylamino)-3-methylbutanoic Acid

A solution of 2,2-dimethyl-3-carbomethoxypropionic acid (LeMaul, Bull. Soc. Chim. Fr., 828 (1965), 20 g, 0.125 mol), diphenylphosphorylazide (34.3 g, 0.125 mol) and triethylamine was heated in toluene (150 ml) at 100° C. for 2 h. After cooling to 5° C., the toluene solution was washed successively with 0.5M HCl, aqueous $NaHCO_3$ and brine. Evaporation of the dried solution gave a residue which was chromatographed on silica gel eluting with 60/40 hexane-ether. There was obtained 13 g of methyl 3-isocyanato-3-methylbutanoate as a mobile liquid. A solution of this material in toluene (20 ml) was treated with benzyl alcohol (13 ml) and the resulting mixture heated at reflux for 40 h. Evaporation of the toluene left a residue which was dissolved in methanol (125 ml) and then treated with a solution of NaOH (6.6 g, 0.165 mol) in 22 ml of water. After 5 h, the reaction mixture was partially evaporated, washed with ether and acidified with 6N HCl. Extraction with methylene chloride and evaporation gave 21 g of the desired product. NMR (300 MHz, $CDCl_3$): 1.42 (s,6H), 2.78 (s,2H), 5.08 (s,2H).

B. Cbz-((β,β-di-Me)-βAla)-Leu-$OCH_3$

A 4.0 g sample of 3-benzyloxycarbonylamino-3-methylbutanoic acid was coupled to leucine methyl ester hydrochloride using the mixed anhydride procedure described in Example 6F. Purification of the crude product by silica gel chromatography gave the desired compound.

C. Cbz-((β,β-di-Me)-β-Ala)-Leu-OH

To a 0° C. solution of Cbz-(β,β-di-Me)-β-Ala)-Leu-OMe (3.63 mmol) in dioxane (15 ml) was added a solution of lithium hydroxide (0.174 g, 4.15 mmol) in water (7.5 ml). After stirring for 1 h at 0°–5° C., the reaction mixture was diluted with cold water and extracted 2× with ether. The aqueous portion was acidified with 6N HCl and extracted with ether. The organic extract was washed with brine and evaporated to give the desired compound.

D. 2-(t-Butyloxycarbonylamino)-4-(Cbz-((β,β-di-Me)-β-Ala-leucinyl-amino)-1,5-diphenyl-3-hydroxypentane According to the carbodiimide coupling procedure of Example 55, the resultant compound of Example 78C was coupled to the resultant compound of Example 11 to give the desired compound.

EXAMPLE 79

A. (3,4-cis-Dihydroxypyrrolidinylcarbonyl)-leucine Methyl Ester

A suspension of L-leucine methyl ester hydrochloride (10 g) in toluene (f200 ml) was heated to 100° C. while phosgene gas was bubbled into the reaction mixture. After approximately 2 h the mixture became homogeneous. The bubbling of phosgene was continued for 15 more minutes keeping the temperature at 100° C. The toluene was then evaporated and the residue chased with benzene several times. The isocyanate from L-Leu-OCH$_3$ was then dissolved in 100 ml of methylene chloride and 1.1 equivalent of 3-pyrroline (75% pure) was added dropwise at 0° C. After 15 min, the reaction mixture was washed with 0.5N HCl and methylene chloride. The organic layer was washed with aqueous NaHCO$_3$ and dried over MgSO$_4$. Evaporation of the solvent gave 3-pyrrolinylcarbonyl-Leu-methyl ester which was cis-hydroxylated under the following conditions: 2.5 g of the 3-pyrrolinylcarbonyl-Leu-methyl ester was dissolved in 50 ml of THF and 1 ml of a 2.5% solution of OsO$_4$ in t-butanol was added, followed by 1.15 g of N-methylmorpholine-N-oxide. After 1 h, the solvent was evaporated and the residue dissolved in 150 ml of ethyl acetate, washed with dilute Na$_2$SO$_3$ solution and satd. NaHCO$_3$ solution, and then dried over MgSO$_4$. Evaporation of the solvent gave a crude compound which was purified by SiO$_2$ column chromatography to give the desired compound.

B. (3.4-cis-Dihydroxypyrrolidinylcarbonyl)-leucine

The resultant compound of Example 79A was hydrolyzed according to the procedure of Example 78C to provide the desired compound.

C. 2-(t-Butyloxycarbonylamino)-4-((3,4-cis-dihydroxypyrrolidinylcarbonyl)-leucinyl-amino)-1,5-diphenyl-3-hydroxypentane According to the carbodiimide coupling procedure of Example 55, the resultant compound of Example 79B was coupled to the resultant compound of Example 11 to give the desired compound.

EXAMPLE 80

2-(N-(6-Aminohexanoyl)-valinyl-valinyl-amino)-4-(N-(5-carboxypentanoyl)-valinyl-valinyl-amino)-1,5-diphenyl-3-hydroxypentane Using the procedure of Example 71C with the resultant compound of Example 74 gave the desired compound.

EXAMPLE 81

1,3-Di-(S-phenylthio)-2-((methoxy)methoxy)propane

Using the procedure of Example 51 but replacing 1,5-diphenyl-3-pentanol with the resultant compound of Example 15 gave, after silica gel chromatography using 15% ethyl acetate in hexane, 44 mg (31%) of the desired compound (R$_f$ 0.27, 20% ethyl acetate in hexane). $^1$H NMR (CDCl$_3$) δ 3.21 (dd, J=15, 6 Hz, 2H), 3.26 (dd, J=15, 6 Hz, 2H), 3.40 (s, 3H), 3.91 (pentet, J=6 Hz, 1H), 4.68 (s, 2H), 7.15–7.35 (m, 10H). Mass spectrum (M+NH$_4$)$^+$=338.

EXAMPLE 82

1,3-Diphenoxy-2-((methoxy)methoxy)propane

Using the procedure of Example 51 but replacing 1,5-diphenyl-3-pentanol with the resultant compound of Example 4 gave, after silica gel chromatography using 10% ethyl acetate in hexane, 80 mg (49%) of the desired compound (R$_f$ 0.42, 20% ethyl acetate in hexane). $^1$H NMR (CDCl$_3$) δ 3.44 (s, 3H), 4.18 (dd, J=10, 6 Hz, 2H), 4.22 (dd, J=15, 6 Hz, 2H), 4.33 (pentet, J=6 Hz, 1H), 4.85 (s, 2H), 6.9–7.0 (m, 6H), 7.25–7.35 (m, 4H). Mass spectrum (M+NH$_4$)$^+$=306.

EXAMPLE 83

A. ((4-Thiomorpholinyl)carbonyl)-leucine Methyl Ester

A suspension of L-leucine methyl ester hydrochloride (6 g) in toluene (125 ml) was heated to 100° C. and phosgene gas was bubbled into the reaction mixture. After approximately 1.5 h, the mixture became homogeneous. The bubbling of phosgene was continued for 10 more min. The solvent was then evaporated and the residue chased with benzene several times. The residue was then dissolved in 100 ml of methylene chloride, cooled to 0° C., and treated dropwise with 1.1 equivalent of thiomorpholine. After 10 min the solution was washed with 1N HCl and the organic layer was dried with MgSO$_4$. Evaporation of solvent gave the desired compound.

B. (4-Thiomorpholinylcarbonyl)-leucine

The resultant compound of Example 83A ws hydrolyzed according to the procedure of Example 6E to provide the desired compound.

C. 2-(t-Butyloxycarbonylamino)-4-((4-thiomorpholinylcarbonyl)-leucinyl-amino)-1,5-diphenyl-3-hydroxypentane According to the carbodiimide coupling procedure of Example 55, the resultant compound of Example 83B was coupled to the resultant compound of Example 11 to give the desired compound.

EXAMPLE 84

A. ((4-Sulphonylmorpholinyl)carbonyl)-leucine Methyl Ester

To 2 g of the resultant compound of Example 83A in 100 ml of methylene chloride was added 2.94 g of a metachloroperbenzoic acid at 0° C. After 30 min the solvent was evaporated and the ether solution was washed with 10% sodium sulfite solution and then with satd. sodium bicarbonate several times. The organic layer was dried with MgSO$_4$ and evaporation of the solvent gave the crude product which was purified by silica gel column chromatography to give the desired compound.

B. (4-Sulphonylmorpholinylcarbonyl)-leucine

The resultant compound of Example 84A was hydrolyzed according to the procedure of Example 6E to provide the desired compound.

C. 2-(t-Butyloxycarbonylamino)-4-((4-sulphonylmorpholinylcarbonyl)-leucinyl-amino)-1, 5-diphenyl-3-hydroxypentane According to the carbodiimide coupling procedure of Example 55, the resultant compound of Example 84B was coupled to the resultant compound of Example 11 to give the desired compound.

EXAMPLE 85

A. N-Methyl-N-(2-(N,N-dimethylamino)ethyl) carbamoyl-leucine Methyl Ester

A solution of 2.1 mmol of a-isocyanoto-leucine methyl ester (prepared according to the procedure of Example 79A) in 50 ml of dichloromethane was cooled to 0° C. and treated with 0.3 ml (2.3 mmol) of N,N,N'-trimethylethylenediamine. After being allowed to stir for 16 h, the solution was concentrated and the desired compound was isolated by flash column chromatography.

B. N-Methyl-N-(2-(N,N-dimethylamino)ethyl) carbamoyl-leucine Lithium Salt

A solution of the resultant compound of Example 85A in dioxane was cooled to 0° C., treated with 1.05 equiv. of aqueous lithium hydroxide (0.5M) and stirred for 1.5 h. The resulting solution was concentrated in vacuo to give the desired compound as a white solid.

C. 2-(t-Butyloxycarbonylamino)-4-(N-methyl-N-(2-(N,N-dimethylamino)ethyl)carbamoyl)leucinyl-amino)-1,5-diphenyl-3-hydroxypentane According to the carbodiimide coupling procedure of Example 55, the resultant compound of Example 85B was coupled to the resultant compound of Example 11 to give the desired compound.

EXAMPLE 86

A. 1-Benzyloxycarbonylamino-2,3-propanediol

1-Amino-2,3-propanediol (15.2 g, 167 mmol) and NaOH (8.1 g, 204 mmol) in water (70 ml) at −10° C. was treated dropwise with benzyl chloroformate (28.5 ml, 200 mmol) in ether (30 ml) over 20 min. The reaction was stirred at 0° C. for 30 min then at room temperature for 2 h. The mixture was acidified with 2M HCl and extracted with ethyl acetate which was washed with 0.5M H$_3$PO$_4$ and brine, then dried over Na$_2$SO$_4$ and evaporated. Recrystallization of the residue from benzene afforded 16.59 g (44%) of the desired product as a white powder. NMR (300 MHz, CD$_3$OD, ppm): 3.12 (dd, 1H), 3.28 (dd, 1H), 3.50 (m, 2H), 3.68 (m, 1H), 5.08 (s,2H), 7.35 (m, 5H).

B. 1Methylamino-2,3-propanediol

Lithium aluminum hydride (7.20 g, 189 mmol) in tetrahydrofuran (THF, 300 ml) was heated to reflux and the resultant compound from Example 86A (17.0 g, 75.5 mmol) in THF (150 ml) was added dropwise over 10 min. The mixture was refluxed for 2 h, cooled, quenched sequentially with water (10 ml), 3M NaOH (40 ml) and water (20 ml), then filtered and concentrated. The residue was dissolved in water which was washed with ether and evaporated. Bulb to bulb distillation of the residue afforded 2.0 g (25%) of the desired compound as an oil. NMR (300 MHz, CDCl$_3$, ppm): 2.45 (s,3H), 2.68 (dd, 1H), 2.77 (dd, 1H), 3.61 (dd, 1H), 3.72 (dd, 1H), 3.78 (m, 1H).

C. (N-Methyl-2,3-dihydroxypropylamino)carbonyl-leucine Methyl Ester

Using the procedure of Example 83A but replacing thiomorpholine with the resultant compound of Example 86B gave the desired compound.

D. (N-Methyl-2,3-dihydroxypropylamino)carbonyl-leucine

The resultant compound of Example 86C was hydrolyzed according to the procedure of Example 6E to give the desired compound.

E. 2-(t-Butyloxycarbonylamino)-4-(((N-methyl-2,3-dihydroxypropylamino)carbonyl)leucinyl-amino)-1, 5diphenyl-3-hydroxypentane According to the carbodiimide coupling procedure of Example 55, the resultant compound of Example 86D was coupled to the resultant compound of Example 11 to give the desired compound.

EXAMPLE 87

A. (N-(Benzyloxycarbonyl)pipiridin-4-yl)carbonyl-leucine Methyl Ester

Cbz-isonipecotic acid was coupled to leucine methyl ester using the mixed anhydride procedure of Example 6F to give the desired compound.

B. (N-(Benzyloxycarbonyl)pipiridine-4-yl)carbonyl-leucine

The resultant compound of Example 87A was hydrolyzed according to the procedure of Example 6E to give the desired compound.

C. 2-(t-Butyloxycarbonylamino)-4-(((N-(benzyloxycarbonyl)pipiridin-4-yl)carbonyl) leucinyl-amino)-1,5-diphenyl-3-hydroxypentane According to the carbodiimide coupling procedure of Example 55, the resultant compound of Example 87B was coupled to the resultant compound of Example 11 to give the desired compound.

EXAMPLE 88

A. N-(Allyloxycarbonyl)-leucine Methyl Ester

A solution of leucine methyl ester (5 mmol) and triethylamine (10 mmol) in dichloromethane (50 ml) was cooled to 0° C. and treated dropwise with allyl chloroformate. After addition, the solution was stirred at ambient temperature for 2 h, diluted with dichloromethane, washed successively with 1N HCl and aqueous NaHCO$_3$, dried over Na$_2$SO$_4$, and concentrated to give the desired compound.

B. N-(3-Hydroxypropyloxycarbonyl)-leucine Methyl Ester

To a stirred 0° C. solution of the resultant compound of Example 88A (2.13 mmol) in dry tetrahydrofuran (THF, 50 ml) was added 9-borabicyclo(3.3.1)nonane (9-BBN, 25.5 ml of a 0.5M solution in THF). The mixture was warmed to room temperature for 12 h and then cooled to 0° C. Water (15 ml) and 3M NaOH (4.5 ml) were added followed 2 min later by 30% $H_2O_2$ (5 ml). The mixture was partitioned between brine (20 ml) and ethyl acetate (100 ml). The organic phase was washed (brine), dried ($Na_2SO_4$), filtered, and evaporated. Silica gel chromatography provided the desired compound.

C. N-(3-Hydroxypropyloxycarbonyl)-leucine

The resultant compound of Example 88B was hydrolyzed according to the procedure of Example 6E to give the desired compound.

D. 2-(t-Butyloxycarbonylamino)-4-(N-(3-hydroxyproploxycarbonyl)leucinyl-amino)-1,5-diphenyl-3-hydroxypentane According to the carbodiimide coupling procedure of Example 55, the resultant compound of Example 88C was coupled to the resultant compound of Example 11 to give the desired compound.

EXAMPLE 89

A. 1,5-Di-(4-isopropylphenyl)-1,4-penten-3-one

A solution of 3.30 g (82 mmol) of NaOH in 33 ml of water and 165 ml of 95% ethanol was treated with a mixture of 5.0 ml (33 mmol) of 4-isopropylbenzaldehyde and 1.21 ml (16.5 mmol) of acetone. The resulting solution was stirred at ambient temperature for 16 h, diluted with water, and filtered. The solid was taken up in dichloromethane, and the solution was washed with water, dried over $MgSO_4$, and concentrated to a light yellow solid. Recrystallization from hexane/ethyl acetate gave 2.15 g (41%) of the desired compound. $^1$H NMR ($CDCl_3$) δ 1.27 (d, J=7 Hz, 12H), 2.94 (heptet, J=7 Hz, 2H), 7.05 (d, J=16 Hz, 2H), 7.28 (d, J=10 Hz, 4H), 7.56 (d, J=10 Hz, 4H), 7.72 (d, J=16 Hz, 2H).

B. 1,5-Di-(4-isopropylphenyl)-3hydroxypentane

Using the procedure of Example 3 with the resultant compound of Example 89A but replacing methyl cellusolve with methanol gave the desired compound.

EXAMPLE 90

A. 1.5-Di-(4-benzyloxyphenyl)-1,4-penten-3-one

Using the procedure of Example 89A but replacing 4-isopropylbenzaldehyde with 4-benzyloxybenzylaldehyde gave the desired compound in 70% yield after recrystallization from dichloromethane/hexane. $^1$H NMR ($CDCl_3$) δ 6.95 (d, J=16 Hz, 2H), 7.00 (d, J=8 Hz, 4H), 7.3–7.5 (m, 10H), 7.58 (d, J=8 Hz, 4H), 7.70 (d, J=16 Hz, 2H). Mass spectrum: $(M+H)^+=447$.

B. 1.5-Di-(4-hydroxyphenyl)-3-hydroxypentane

Using the procedure of Example 89B with the resultant compound of Example 90A gave the desired compound ($R_f$ 0.25, 40% ethyl acetate in chloroform) in 30% yield after silica gel chromatography using 40% ethyl acetate in chloroform. $^1$H NMR ($CDCl_3$) δ 1.76 (m, 4H), 2.55–2.7 (m, 4H), 3.63 (m, 1H), 4.59 (s, 2H), 6.25 (d, J=9 Hz, 4H), 7.05 (d, J=9 Hz, 4H). Mass spectrum: $(M+NH_4)^+=290$.

EXAMPLE 91

A. Di-(1-naphthyl)-1,4-penten-3-one

Using the procedure of Example 89A but replacing 4-isopropylbenzaldehyde with 1-naphthaldehyde gave the desired compound in 39% yield after recrystallization from ethyl acetate/hexane. $^1$H NMR ($CDCl_3$) δ 7.24 (d, J=16 Hz, 2H), 7.5–7.7 (m, 6H), 7.9–8.0 (m, 6H), 8.29 (d, J=8 Hz, 2H), 8.66 (d, J=16 Hz, 2H).

B. 1,5-Di-(1-napthyl)-3-hydroxypentane

Using the procedure of Example 89B with the resultant compound of Example 91A but replacing palladium on carbon with Raney nickel gave the desired compound after silica gel chromatography.

EXAMPLE 92

A. Di-(4-methoxyphenyl)-1,4-penten-3-one

Using the procedure of Example 89A but replacing 4-isopropylbenzaldehyde with p-anisaldehyde gave the desired compound in 61% yield after recrystallization from ethyl acetate/hexane. $^1$H NMR ($CDCl_3$) δ 3.87 is, 6H), 6.92 (d, J=9 Hz, 4H), 6.96 (d, J=16 Hz, 2H), 7.58 (d, J=9 Hz, 4H), 7.71 (d, J=16 Hz, 2H).

B. 1,5-Di-(4-methoxyphenyl)-3-hydroxypentane

Using the procedure of Example 89B with the resultant compound of Example 92A gave the desired compound after silica gel chromatography.

EXAMPLE 93

A. Di-(4-bromophenyl)-1,4-penten-3-one

Using the procedure of Example 89A but replacing 4-isopropylbenzaldehyde with 4-bromobenzaldehyde gave the desired compound in 79% yield after recrystallization from ethyl acetate/hexane. $^1$H NMR ($CDCl_3$) δ 7.05 (d, J=16 Hz, 2H), 7.48 (dt, J=9, 2 Hz, 4H), 7.57 (dt, J=9, 2 Hz, 4 H), 7.68 (d, J=16 Hz, 2H).

B. 1,5-Di-(4-bromophenyl)-3-hydroxypentane

Using the procedure of Example 89B with the resultant compound of Example 93A but replacing palladium on carbon with 5% platinum on carbon gave the desired compound after silica gel chromatography.

EXAMPLE 94

A. Cbz-alanine Ester of 3-Hydroxy-1,5-diphenylpentane

A solution of 100 mg (0.42 mmol) of 3-hydroxy-1,5-diphenylpentane, 94 mg (0.42 mmol) of Cbz-alanine, and 10 mg (0.08 mmol) of 4-dimethylaminopyridine in 4 ml of dichloromethane was treated with 99 mg (0.51 mmol) of N-ethyl-N'-(dimethylaminoethyl) carbodiimide hydrochloride. After being stirred at ambient temperature for 7 h, the solution was diluted with ethyl acetate, washed sequentially with 10% aqueous citric acid, water, aqueous $NaHCO_3$ and saturated brine, dried over $MgSO_4$, and concentrated to give the desired compound.

B. Alanine Ester of 3-Hydroxy-1,5-diphenylpentane

Using the procedure of Example 11 with the resultant compound of Example 94A gave the desired compound in 73% yield after silica gel chromatography using 5% methanol in chloroform. $^1$H NMR ($CDCl_3$) δ 1.35 (d, J=7 Hz, 3H), 1.9–2.0 (m, 4H), 2.6–2.7 (m, 2H), 3.48 (q, J=7 Hz, 1H), 5.02 (tt, J=7, 5 Hz, 1H), 7.1–7.3 (m, 10H).

Anal. Calcd. for $C_{20}H_{26}ClNO_2 \cdot 0.5H_2O$: C, 67.31; H, 7.63; N, 3.92. Found: C, 67.19; H, 7.25; N, 3.85.

EXAMPLE 95

A. Boc-glycine Ester of 3-Hydroxy-1,5-diphenylpentane

Using the procedure of Example 94A but replacing Cbz-alanine with Boc-glycine gave the desired compound.

Using the procedure of Example 12 with the resultant compound of Example 95A gave a white solid which was taken up in dichloromethane, washed with aqueous $NaHCO_3$, dried over $Na_2SO_4$, and concentrated. Silica gel chromatography using 1.5% methanol in chloroform followed by treatment with acetic acid in chloroform gave, after concentration, the desired compounded in 79% yield. $^1H$ NMR ($CDCl_3$) δ 1.9–2.0 (m, 4H), 2.09 (s, 3H), 2.6–2.7 (m, 4H), 3.32 (br s, 2H), 3.6–3.8 (m, 2H), 5.06 (tt, J=7, 5 Hz, 1H), 7.1–7.3 (m, 10H). Mass spectrum: $(M+H)^+=298$.

EXAMPLE 96

A. $N^\alpha$, $N^\epsilon$-Di Cbz-lysine Ester of 3-Hydroxy-1,5-diphenylpentane Using the procedure of Example 94A but replacing Cbz-alanine with $N^\alpha$, $N^\epsilon$-Di-Cbz-lysine gave the desired compound.

B. Lysine Ester of 3-Hydroxy-1,5-diphenylpentane Diacetate

A mixture of 180 mg (0.28 mmol) of the resultant compound of Example 96B and 50 mg of 10% palladium on carbon in 5 ml of methanol and 0.3 ml of acetic acid was stirred under an $H_2$ atmosphere for 16 h. The solution was filtered through Celite and concentrated to give 135 mg (98%) of the desired compound as a white solid. Mass spectrum: $(M+H)^+=369$.

Anal. Calcd. for $C_{27}H_{40}N_2O_6 \cdot H_2O$: C, 64.01; H, 8.36; N, 5.53. Found: C, 63.97; H, 8.13; N, 5.36.

EXAMPLE 97

2-(t-Butyloxycarbonylamino)-4-((6-(Cbz-amino)hexanoyl)amino)-1,5-diphenyl-3-hydroxypentane N-(6-(Benzyloxycarbonylamino)hexanoic acid was coupled to the resultant compound of Example 11 using the mixed anhydride procedure of Example 54A to give the desired compound after silica gel chromatography using 75% ethyl acetate in chloroform.

EXAMPLE 98

2-((3-(Benzyloxycarbonyl)-3-methylpropanoyl)amino-4-((6-(Cbz-amino)hexanoyl)amino)1,5-diphenyl-3-hydroxypentane The resultant compound of Example 97 (32 mg) was deprotected according to the procedure of Example 12 and coupled to 3-benzyloxycarbonyl-2,2-dimethylpropanoic acid (Matsushita, et. al., Heterocycles, 22, 1403 (1984) according to the mixed anhydride coupling procedure of Example 54A to give the desired compound in 28% yield after silica gel chromatography using 60% ethyl acetate in chloroform. Mass spectrum: $(M-PhCH_2O)^+=628$.

EXAMPLE 99

2-((3-Carboxy-3-methylpropanoyl)amino)-4-6aminohexanoyl)amino-1,5-diphenyl-3-hydroxypentane Using the procedure of Example 71C with the resultant compound of Example 98 gave the desired compound in 100% yield. Mass spectrum: $(M+H)^+=512$.

EXAMPLE 100

A. (4S)-3-(4-Methylpentanoyl)-4-(2-propyl)oxazolidine-2-one

To a stirred solution of 4-(2-propyl)-oxazolidine-2-one in anhydrous tetrahydrofuran (250 ml) under a nitrogen atmosphere at –78° C. was added in a dropwise fashion a solution of n-butyllithium in hexane (50 ml, 77.4 mmol) over 5 to 10 min. After stirring an additional 20 min at –78° C., 4-methylpentanoyl chloride (85.2 mmol) was added neat. The reaction was warmed to room temperature and stirred 1 to 2 h at the temperature. The reaction was quenched by adding 100 ml of saturated aqueous ammonium chloride and the volatiles were removed by rotary evaporation. The resulting aqueous residue was extracted three times with ether and the combined organic phases were washed with brine, dried ($Na_2SO_4$), filtered and concentrated in vacuo. Recrystallization from hexanes/ethyl acetate provided the desired compound.

B. (4R)-3-((2-R)-2-(t-Butyloxycarbonyl)methyl-4-methylpentanoyl)-4-(2-propyl)oxazolidine-2-one To a stirred solution of the resultant compound of Example 100A (8.72 mmol) in anhydrous tetrahydrofuran (30 ml) under a nitrogen atmosphere at –78° C. was added a solution of sodium hexamethyldisilylamide (9.6 ml, 9.59 mmol) in tetrahydrofuran. After stirring for 30 min at –78° C., t-butyl bromoacetate (2.21 g, 11.34 mmol) was added in anhydrous tetrahydrofuran and the resulting solution stirred 1 h at –78° C. The reaction was quenched by adding 20 ml of saturated aqueous ammonium chloride and partitioned between water and ether. The aqueous layer was drawn off and extracted with ether. The combined organic phases were washed with 10% aqueous HCl, saturated aqueous $NaHCO_3$, and brine, dried ($Na_2SO_4$), filtered, and concentrated in vacuo. Recrystallization from acetone/hexanes provided the desired compound.

C. Benzyl-(2R)-2-(t-Butyloxycarbonyl)methyl-4-methylpentanoate

To a stirred solution of dry benzyl alcohol (0.55 ml, 5.33 mmol) in anhydrous tetrahydrofuran (18 ml) under a nitrogen atmosphere at 0° C. was added a hexane solution of n-butyllithium (2.58 ml; 4.00 mmol). To this solution was added the resultant compound of Example 100B in anhydrous tetrahydrofuran (10 ml). After stirring 1 h at 0° C. the reaction was quenched by adding excess saturated aqueous ammonium chloride. The volatiles were removed by rotary evaporation and the resulting aqueous residue was extracted two times with ether. The combined organic layers were washed with brine, dried ($Na_2SO_4$), filtered, and concentrated in vacuo to provide an oil which was purified by chromatography on $SiO_2$ to give the desired compound.

D. Benzyl (2R)-2-(Carboxymethyl)-4-methylpentanoate

The resultant compound of Example 100C (1.47 mmol) was dissolved in a 1:1 (v:v) solution (6 ml) of trifluoroacetic acid and dichloromethane and stirred at room temperature for 1 h. The volatiles were removed in vacuo to provide the desired compound. The unpurified material was of sufficient purity to employ in subsequent steps.

E. Benzyl(2R)-2-Isobutyl-3-morpholinocarbonylpropionate

The resultant compound of Example 100D was coupled to morpholine using the mixed anhydride procedure as described in Example 6F to give the desired compound.

F. (2R)-2-Isobutyl-3-morpholinocarbonylpropionic Acid

The resultant compound of Example 100E was hydrogenolyzed according to the procedure of Example 71C to provide the desired compound.

G. 2-(t-Butyloxycarbonylamino)-4-(N-(2-isobutyl-3-morpholinocarbonylpropionyl)amino)-1,5-diphenyl-3-hydroxypentane According to the carbodiimide coupling procedure of Example 55, the resultant compound of Example 100F was coupled to the resultant compound of Example 11 to give the desired compound.

EXAMPLE 101

A. (((4-Morpholinyl)carbonyl)oxy)-4-methylpentanoic Acid Methyl Ester

To 2-hydroxy-4-methylpentanoic acid methyl ester was added 150 ml of 12.5% phosgene in toluene and 25 drops of dimethylformamide. After stirring for 16 h at room temperature, the solvent was evaporated and the residue chased several times with benzene. The resulting product was dissolved in methylene chloride (50 ml), cooled to 0° C. and treated by dropwise addition with 3.86 g (0.044 mol) of morpholine. The reaction mixture was stirred for 2 h at 0°–5° C. and then distributed between 0.5N HCl and methylene chloride. The organic phase was washed with aqueous NaHCO$_3$ and brine and evaporated to a residue. Flash chromatography on silica gel gave the desired compound.

B. (((4-Morpholinyl)carbonyl)oxy)-4-methylpentanoic Acid

The resultant compound of Example 101A was hydrolyzed according to the procedure of Example 6E to provide the desired compound.

C. 2-(t-Butyloxycarbonylamino)-4-(N-((((4-morpholinyl)carbonyl)oxy)-4-methylpentanoyl)amino-1,5-diphenyl-3-hydroxypentane According to the carbodiimide coupling procedure of Example 55, the resultant compound of Example 101B was coupled to the resultant compound of Example 11 to give the desired compound.

EXAMPLE 102

A. Benzyl (2R)-2-Isobutyl-3-((N-benzyl-N-methylamino)carbonyl)propionate

The resultant compound of Example 100D was coupled to benzylamine using the mixed anhydride procedure as described in Example 6F to give the desired compound.

B. (2R)-2-Isobutyl-3-((N-benzyl-N-methylamino)carbonyl)propionic Acid

The resultant compound of Example 102A was hydrolyzed according to the procedure of Example 6E to provide the desired compound.

C. 2-(t-Butyloxycarbonylamino)-4-(N-(2-isobutyl-3-((N-benzyl-N-methylamino)carbonyl)propionyl)amino)-1,5-diphenyl-3-hydroxypentane According to the carbodiimide coupling procedure of Example 55, the resultant compound of Example 102B was coupled to the resultant compound of Example 11 to give the desired compound.

EXAMPLE 103

2-Amino-4-(N-(2-isobutyl-3-((N-benzyl-N-methylamino)carbonyl)propionyl)amino)-1,5-diphenyl-3-hydroxypentane Hydrochloride Using the procedure of Example 12 with the resultant compound of Example 102C gave the desired compound.

EXAMPLE 104

2,4-Bis-(N-(2-isobutyl-3-((N-benzyl-N-methylamino)carbonyl)propionyl)amino)-1,5-diphenyl-3-hydroxypentane According to the carbodiimide coupling procedure of Example 55, the resultant compound of Example 102B was coupled to the resultant compound of Example 103 to give the desired compound.

EXAMPLE 105

A. Benzyl (2R)-2-Isobutyl-3-(((4-N-benzyl-N-methylamino)carbonyl)amino)propionate The resultant compound of Example 100D (1.47 mmol), diphenylphosphoryl azide (1.47 mmol), and triethylamine (1.47 mmol) in dry benzene (6 ml) were refluxed for 5 h to provide a solution of the derived isocyanate which was cooled to 0° C. and treated with benzylamine (1.6 mmol). The cooling bath was removed and the reaction stirred for 1 h. The reaction mixture was poured into 10% aqueous HCl and extracted two times with ether. The combined organic layers were washed successively with saturated aqueous NaHCO$_3$ and brine, dried (Na$_2$SO$_4$), filtered and concentrated in vacuo to provide the unpurified product. The desired product was obtained in pure form after chromatography on SiO$_2$.

B. (2R)-2-Isobutyl-3-(((N-benzyl-N-methylamino)carbonyl)amino)propionic Acid The resultant compound of Example 105A was hydrolyzed according to the procedures of Example 6E to give the desired compound.

C. 2-(t-Butyloxycarbonylamino)-4-(N-(2-isobutyl-3-(((N-benzyl-N-methylamino)carbonyl)amino)propionyl)amino)-1,5-diphenyl-3-hydroxypentane According to the carbodiimide coupling procedure of Example 55, the resultant compound of Example 105B was coupled to the resultant compound of Example 11 to give the desired compound.

EXAMPLE 106

A. Benzyl (2R)-2-Isobutyl-3-((ethoxycarbonyl)amino)-propionate

Using the procedure of Example 105A but replacing benzylamine with ethanol gave the desired compound.

B. (2R)-2-Isobutyl-3-((ethoxycarbonyl)amino)propionic Acid

The resultant compound of Example 106A was hydrogenolyzed according to the procedure of Example 71C to give the desired compound.

C. 2-(t-Butyloxycarbonylamino)-4-(N-(2-isobutyl-3-((ethoxycarbonyl)amino)propionyl)amino)-1,5-diphenyl-3-hydroxypentane According to the carbodiimide coupling procedure of Example 55, the resultant compound of Example 106B was coupled to the resultant compound of Example 11 to give the desired compound.

EXAMPLE 107

A. N-Benzyloxycarbonyl-N-methyl-2-aminoethanol

To N-methylethanolamine (149 mmol) in methylene chloride (100 ml) at 0° C. was added benzyl chloroformate (70 mmol). The mixture was stirred at 0° C. for 30 min, then at room temperature for 1 h, poured into ethyl acetate, washed with 2M HCl, saturated $NaHCO_3$ solution, and brine, then dried over $Na_2SO_4$ and evaporated to provide the desired compound. $^1H$ NMR ($CDCl_3$,TMS) δ 7.36 (m, 5H), 5.14 (s,2H), 3.78 (m, 2H), 3.47 (m, 2H), 3.01 (s, 3H).

B. 1-Methoxyethoxymethoxy-2-(N-methyl-N-benzyloxycarbonylamino)ethane

To the resultant compound from Example 107A (66 mmol) in methylene chloride (100 ml) was added diisopropylethylamine (138 mmol) and 2-methoxyethoxymethyl chloride (132 mmol). After 4 h the mixture was evaporated, dissolved in ethyl acetate, washed with 0.5M $H_3PO_4$, saturated $NaHCO_3$ solution, and brine, then dried over $Na_2SO_4$, and evaporated to afford the desired product as an oil, b.p. 150°–170° C. (0.3 mm).

C. 1-Methylamino-2-methoxyethoxymethoxyethane

The resultant compound from Example 107B (31 mmol) and 10% palladium on carbon (3 g) in methanol (60 ml) were stirred under a hydrogen atmosphere for 24 h. The mixture was filtered, evaporated and distilled to afford the desired product as an oil, b.p. 130°–140° C. (45 mm).

D. Benzyl (2R)-2-Isobutyl-3-(N-methyl-N-(2-methoxyethoxymethoxyethyl)aminocarbonyl)propionate The resultant compound of Example 100D was coupled to the resultant compound of Example 107C using the mixed anhydride procedure of Example 6F to give the desired compound.

E. (2R)-2-Isobutyl-3-(N-methyl-N-(2-methoxyethoxy methoxyethyl)aminocarbonyl) propionic Acid The resultant compound of Example 107D was hydrogenolyzed according to the procedure of Example 71C to give the desired compound.

F. 2-(t-Butyloxcarbonylamino)-4-(N-(2-isobutyl-3-(N-methyl-N-(2-methoxyethoxymethoxyethyl) aminocarbonyl)-propionyl)amino-1,5-diphenyl-3-hydroxypentane According to the carbodiimide coupling procedure of Example 55, the resultant compound of Example 106B was coupled to the resultant compound of Example 11 to give the desired compound.

EXAMPLE 108

2-(t-Butyloxycarbonylamino)-4-(p-toluenesulfonylamino)-1,5-diphenyl-3-hydroxypentane The resultant compound of Example 11 (0.05 mmol) in 2 ml of pyridine was cooled to 0° C. and treated with 0.05 mmol of p-toluenesulfonyl chloride. After 2 h, the solution was diluted with ether, washed sequentially with 1N HCl, aqueous $NaHCO_3$, and saturated brine, dried over $MgSO_4$, and concentrated. Silica gel chromatography gave the desired compound.

EXAMPLE 109

2-Amino-4-(p-toluenesulfonylamino)-1,5-diphenyl-3-hydroxypentane Hydrochloride

Using the procedure of Example 12 with the resultant compound of Example 108 gave the desired compound.

EXAMPLE 110

2.4-Bis-(p-toluenesulfonylamino)-1,5-diphenyl-3-hydroxypentane

Using the procedure of Example 108 with the resultant compound of Example 109 gave the desired compound.

EXAMPLE 111

2-(t-Butyloxycarbonylamino)-4-(N-((p-toluenesulfonyl)valinyl)amino)-1,5-diphenyl-3-hydroxypentane According to the carbodiimide coupling procedure of Example 55, N-(p-toluenesulfonyl)valine was coupled to the resultant compound of Example 11 to give the desired compound.

EXAMPLE 112

2-Amino-4-(N-((p-toluenesulfonyl)valinyl)amino)-1, 5-diphenyl-3-hydroxypentane Hydrochloride Using the procedure of Example 12 with the resultant compound of Example 111 gave the desired compound.

EXAMPLE 113

2,4-Bis-(N-((p-toluenesulfonyl)valinyl)amino)-1,5-diphenyl-3-hydroxypentane

According to the carbodiimide coupling procedure of Example 55, N-(p-toluenesulfonyl)valine was coupled to the resultant compound of Example 112 to give the desired compound.

EXAMPLE 114

A. N-(2-Cyanoethyl)leucine Methyl Ester

A solution of leucine methyl ester (0.590 mmol) in acrylonitrile (2 ml) was heated at reflux. Evaporation provided a residue which was chromatographed on silica gel to give desired compound.

B. N-(3-Benzyloxycarbonylaminopropyl)leucine Methyl Ester

The resultant compound of Example 114A (0.135 mmol) was hydrogenated (4 atmospheres $H_2$) over Raney Nickel (85 mg) in anhydrous methanol/ammonia (20 ml/5 ml) for 3 h. Filtration and evaporation provided the crude amine which was taken up in dichloromethane and treated with 0.14 mmol of N-(benzyloxycarbonyloxy)succinimide. After 2 h, the solution was washed with aqueous $NaHCO_3$, dried over $Na_2SO_4$, and concentrated. Silica gel chromatography gave the desired compound.

C. N-(3-Benzyloxycarbonylaminopropyl)leucine

The resultant compound of Example 114B was hydrolyzed according to the procedure of Example 6E to give the desired compound.

D. 2-(t-Butyloxycarbonylamino)-4-(N-(((3-benzyloxycarbonyl)aminopropyl)leucinyl)amino)-1,5-diphenyl-3-hydroxypentane According to the carbodiimide coupling procedure of Example 55, the resultant compound of Example 114C was coupled to the resultant compound of Example 11 to give the desired compound.

EXAMPLE 115

2-(t-Butyloxycarbonylamino)-4-(N-((3-aminopropyl)leucinyl)amino)-1,5-diphenyl-3-hydroxypentane The resultant compound of Example 114D was hydrogenolyzed according to the procedure of Example 71C to provide the desired compound.

EXAMPLE 116

A. Methyl a-Benzylacrylate a-Benzylacrylic acid (1.00 g, 6.17 mmol) in methanol (20 ml) was treated with $BF_3 \cdot Et_2O$ (2 ml). The mixture was heated to reflux for 14 h, cooled, and poured into saturated $NaHCO_3$ solution. Extraction with ether followed by drying over $Na_2SO_4$ and evaporation afforded 1.03 g (95%) of a mobile oil. $^1H$ NMR ($CDCl_3$) δ 7.17–7.35 (m, 5H), 6.23 (m, 1H), 5.47 (m, 1H), 3.74 (s, 3H), 3.63 (s,2H).

B. Methyl 2-Benzyl-3-(N-methoxyl-N-methylamino)propionate

The resultant compound from Example 116A (800 mg, 4.54 mmol), N-methyl,O-methylhydroxylamine hydrochloride (0.57 g, 5.4 mmol), and $NaHCO_3$ (0.46 g, 5.48 mmol) in dimethylsulfoxide (5 ml) were heated at 130° C. for 20 h. The mixture was diluted with ethyl acetate, washed with water, saturated $NaHCO_3$ solution and brine, and then was dried over $Na_2SO_3$ and evaporated. Chromatography of the residue on silica gel with 10% ethyl acetate in hexane afforded 226 mg (21%) of a mobile oil. $^1H$ NMR ($CDCl_3$) δ 7.10–7.30 (m, 5H), 3.60 (s,3H), 3.47 (s,3H), 2.80–3.10 (m, 4H), 2.60 (dd, 1H), 2.55 (s, 3H).

C. 2-Benzyl-3-(N-methoxyl-N-methylamino)propionic Acid

Using the procedure of Example 117B with the resultant compound from Example 116B gave the desired product. $^1H$ NMR ($CDCl_3$) δ 7.10–7.35 (m, 5H), 3.58 (s,3H), 2.62 (s,3H).

D. 2-(t-Butyloxycarbonylamino)-4-(N-(2-benzyl-3-(N-methoxyl-N-methylamino)propionyl)amino)-1,5-diphenyl-3-hydroxypentane According to the carbodiimide coupling procedure of Example 55, the resultant compound of Example 116C was coupled to the resultant compound of Example 11 to give the desired compound.

EXAMPLE 117

A. Methyl 2-Benzyl-3-pyrazol-1-ylpropionate

Using the procedure of Example 116B but replacing N-methyl,O-methylhydroxylamine hydrochloride and $NaHCO_3$ with pyrazole provided the desired product as an oil. $^1H$ NMR ($CDCl_3$) δ 7.52 (d, 1H), 7.10–7.35 (m, 6H), 6.10 (dd, 1H), 4.38 (dd, 1H), 4.24 (dd, 1H), 3.57 (s,3H), 3.37 (m, 1H), 2.98 (dd, 1H), 2.82 (dd, 1H).

B. 2-Benzyl-3-pyrazol-1-ylpropionic Acid

The resultant compound from Example 117A (100.0 mg, 0.409 mmol) in dioxane (2 ml) at 0° C. was treated with $LiOH \cdot H_2O$ (22.0 mg, 0.524 mmol) in water (1 ml). After 1 h at 0° C. and 30 min at room temperature the solvent was evaporated and the residue was taken up in water, the pH was adjusted to pH 3–4, and the mixture was extracted with $CHCl_3$ which was dried over $Na_2SO_4$ and evaporated to afford 96 mg (100%) of a solid. $^1H$ NMR ($CDCl_3$) δ 7.56 (d, 1H), 7.10–7.35 (m, 6H), 6.26 (dd, 1H), 4.30 (m, 2H), 3.34 (m, 1H), 3.12 (dd, 1H), 2.72 (dd, 1H).

C. 2-(t-Butyloxycarbonylamino)-4-(N-(2-benzyl-3-pyrazol-1-ylpropionyl)amino)-1,5-diphenyl-3-hydroxypentane According to the carbodiimide coupling procedure of Example 55, the resultant compound of Example 117B was coupled to the resultant compound of Example 11 to give the desired compound.

EXAMPLE 118

A. Methyl 2-Benzyl-3-tert-butylmercaptopropionate

To sodium (3.05 g, 133 mmol) in methanol (135 ml) was added tert-butylmercaptan (17.0 ml, 151 mmol). After 20 min methyl a-benzylacrylate (17.05 g, 96.8 mmol) in methanol (100 ml) was added and after 1 h at room temperature the mixture was heated at reflux for 17 h. After cooling, the mixture was acidified with 2M HCl (70 ml), concentrated, taken up in ether, washed with water and brine, then dried over $MgSO_4$ and evaporated to 23.59 g (92%) of an oil. $^1H$ NMR ($CDCl_3$) δ 7.15–7.35 (m, 5H), 3.63 (S, 3H), 2.60–3.05 (m, 5H), 1.28 (s, 9H).

B. Methyl 2-Benzyl-3-tert-butylsulfonylpropionate

To the resultant compound from Example 118A (270 mg, 1.01 mmol) in methanol (6 ml) and water (5 ml) at 0° C. was added potassium peroxymonosulfate (1.845 g, 6 mmol) in portions. After 15 min at 0° C. and 24 h at room temperature the mixture was filtered, diluted with water, and extracted with $CH_2Cl_2$ which was washed with brine, dried over $MgSO_4$, and evaporated to 300 mg (99%) of an oil. $^1H$ NMR δ 7.15–7.35 (m, 5H), 3.68 (s, 3H), 3.45 (m, 2H), 3.12 (dd, 1H), 2.98 (m, 2H), 1.37 (s, 9H).

C. 2-Benzyl-3-tert-butylsulfonylpropionic Acid

The resultant compound from Example 118B (282 mg, 0.95 mmol) in 6M HCl (2 ml) and acetic acid (0.4 ml) was heated at reflux for 16 h. The mixture was cooled and filtered and the resulting solid was recrystallized from methycyclohexane/ethyl acetate to afford 152 mg (56%) of the desired product, m.p. 147°–148° C.

D. 2-(t-Butyloxycarbonylamino)-4-(N-(2-benzyl-3-tert-butylsulfonylpropionyl)amino)-1,5-diphenyl-3-hydroxypentane According to the carbodiimide coupling procedure of Example 55, the resultant compound of Example 118C was coupled to the resultant compound of Example 11 to give the desired compound.

EXAMPLE 119

2-(t-Butyloxycarbonylamino)-4-(N-(3-phenyl-2-(phenylmethyl)propionyl)amino)-1,5-diphenyl-3-hydroxypentane According to the carbodiimide coupling procedure of Example 55, dibenzylacetic acid was coupled to the resultant compound of Example 11 to give the desired compound.

EXAMPLE 120

1,5-Di-(4-isopropylphenyl)-3-(methoxymethyl)pentane

Using the procedure of Example 51 but replacing 1,5-diphenyl-3-pentanol with the resultant compound of Example 89B gave the desired compound.

EXAMPLE 121

1,5-Di-(1-naphthyl)-3-(methoxymethyl)pentane

Using the procedure of Example 51 but replacing 1,5-diphenyl-3-pentanol with the resultant compound of Example 91B gave the desired compound.

EXAMPLE 122

1,5-Di-(4-methoxyphenyl)-3-(methoxymethyl)pentane

Using the procedure of Example 51 but replacing 1,5-diphenyl-3-pentanol with the resultant compound of Example 92B gave the desired compound.

EXAMPLE 123

1,5-Di-(4-bromophenyl)-3-(methoxymethyl)pentane

Using the procedure of Example 51 but replacing 1,5-diphenyl-3-pentanol with the resultant compound of Example 93B gave the desired compound.

EXAMPLE 124

1,5-Diphenyl-3-(thiomethoxymethyl)pentane 1,5-Diphenyl-3-hydroxypropentane was treated with sodium hydride followed by chloromethyl methyl sulfide and sodium iodide according to the procedure of Corey and Bock (*Tetrahedron Lett.* 1975, 3269) to provide the desired compound.

EXAMPLE 125

1,5-Diphenyl-3-(2-methoxyethoxymethyl)pentane

Using the procedure of Example 51 but replacing chloromethyl methyl ether with 2-methoxyethoxymethyl chloride gave the desired compound.

EXAMPLE 126

A. Methyl 2-Fluoro-3-phenylpropanoate

Using the procedure of Example 34B but replacing the resultant compound of Example 34A with methyl 3-phenyllactate provided the desired compound.

B. 2,3-Epoxy-4-fluoro-1,5-diphenylpentane

The resultant compound of Example 126B treated with α-lithio-2-phenylethyl phenyl sulfoxide according to the procedure of Bravo et. al. (*J. Chem. Soc., Perkin Trans. I,* 1989, 1201) to provide the desired compound.

C. 2-Azido-1,5-diphenyl-4-fluoro-3-hydroxypentane

Using the procedure of Example 10C with the resultant compound of Example 126B gave the desired compound.

EXAMPLE 127

2-Amino-1,5-diphenyl-4-fluoro-3-hydroxypentane

Using the procedure of Example 10D with the resultant compound of Example 126C gave the desired compound.

EXAMPLE 128

2-(N-Cbz-valinyl)amino-1,5-diphenyl-4-fluoro-3-hydroxypentane

Using the procedure of Example 55 but replacing the resultant compound of Example 11 with the resultant compound of Example 127 gave the desired compound.

EXAMPLE 129

2-(N-Cbz-valinyl)amino-1,5-diphenyl-4-fluoro-3-pentanone

According to the procedure of Thaisrivongs et. al. (*J. Med. Chem.* 1986, 29, 2080), the resultant compound of Example 128 was oxidized with oxalyl chloride/dimethyl sulfoxide to provide the desired compound.

EXAMPLE 130

A. Benzyl α-Isopropylacrylate

α-Isopropylacrylic acid (13 mmol) in dry ether (40 ml) was treated with dicyclohexylcarbodiimide (12 mmol), benzyl alcohol (12 mmol) and 4-dimethylaminopyridine (2.5 mmol). After stirring at ambient temperature for 44 h, the mixture was filtered and evaporated. Silica gel chromatography provided the desired compound.

B. Benzyl 3-Acetylmercapto-2-isopropylpropionate

The resultant compound of Example 130A (27 mmol) in dry ether (10 ml) was treated with thiolacetic acid (42 mmol) and pyridine (28 mmol). After 5 days, the mixture was concentrated in vacuo and chromatographed on silica gel to provide the desired compound.

C. 2-Benzyloxycarbonyl-3-methylbut-1-ylsulfonyl Chloride

Chlorine was bubbled into a mixture of the resultant compound of Example 130B (25 mmol) in water (250 ml) for 30 min at ambient temperature followed by nitrogen which was bubbled through the mixture for 15 min. The mixture was extracted with methylene chloride which was dried over $MgSO_4$ and concentrated to provide the desired compound which was used without further purification.

D. Benzyl 2-Isopropyl-3-(4-methylpiperizin-1-ylsulfonyl)propionate

A solution of the resultant compound of Example 130C (2.8 mmol) in 10 ml of dichloromethane was cooled to −10° C. and treated with 1-methylpiperazine (8.5 mmol). After 30 min, the solution was concentrated in vacuo, taken up in ethyl acetate, washed sequentially with aqueous $NaHCO_3$ and saturated brine, dried over Na$_2$SO$_4$, and concentrated. Silica gel chromatography provided the desired compound.

E. 2-Isopropyl-3-(4-methylpiperizin-1-ylsulfonyl) propionic Acid

The resultant compound of Example 130D was hydrogenolyzed according to the procedure of Example 71C to provide the desired compound.

F. 2-(t-Butyloxycarbonylamino)-4-(N-((2-isopropyl-3-(4-methylpiperizin-1-yl)sulfonyl)propionyl) amino)- 1,5-diphenyl-3-hydroxypentane According to the carbodiimide coupling procedure of Example 55, the resultant compound of Example 130E was coupled to the resultant compound of Example 11 to give the desired compound.

EXAMPLE 131

A. Benzyl 2-Isopropyl-3-(morpholin-4-ylsulfonyl) propionate

Using the procedure of Example 130D but replacing 1-methylpiperazine with morpholine gave the desired compound.

B. 2-Isopropyl-3-(morpholin-4-ylsulfonyl)propionic Acid

The resultant compound of Example 131A was hydrogenolyzed according to the procedure of Example 71C to provide the desired compound.

C. 2-(t-Butyloxycarbonylamino)-4-(N-((2-isopropyl-3-(morpholin-4-yl)sulfonyl)propionyl)amino)-1,5-diphenyl-3-hydroxypentane According to the carbodiimide coupling procedure of Example 55, the resultant compound of Example 131B was coupled to the resultant compound of Example 11 to give the desired compound.

EXAMPLE 132

A. Benzyl 2-Isopropyl-3-((benzylamino)sulfonyl) propionate

Using the procedure of Example 130D but replacing 1-methylpiperazine with benzylamine gave the desired compound.

B. 2-Isopropyl-3-((benzylamino)sulfonyl)propionic Acid

The resultant compound of Example 132A was hydrolyzed according to the procedure of Example 6E to provide the desired compound.

C. 2-(t-Butyloxycarbonylamino)-4-(N-((2-isopropyl-3-(benzylamino)sulfonyl)propionyl)amino)-1,5-diphenyl-3-hydroxypentane According to the carbodiimide coupling procedure of Example 55, the resultant compound of Example 132B was coupled to the resultant compound of Example 11 to give the desired compound.

EXAMPLE 133

2-Amino-4-(N-((2-isopropyl-3-(4-methylpiperizin-1-yl)sulfonyl)propionyl)amino)-1,5diphenyl-3-hydroxypentane Dihydrochloride Using the procedure of Example 12 with the resultant compound of Example 130F provided the desired compound.

EXAMPLE 134

2,4-Bis-(N-((2-isopropyl-3-(4-methylpiperizin-1-yl) sulfonyl)propionyl)amino)-1,5-diphenyl-3-hydroxypentane According to the carbodiimide coupling procedure of Example 55, the resultant compound of Example 130E was coupled to the resultant compound of Example 133 to give the desired compound.

EXAMPLE 135

2-Amino-4-(N-((2-isopropyl-3-(benzylamino) sulfonyl)propionyl)amino)-1,5diphenyl-3-hydroxypentane Dihydrochloride Using the procedure of Example 12 with the resultant compound of Example 132C provided the desired compound.

EXAMPLE 136

2,4-Bis-(N-((2-isopropyl-3-(benzylamino)sulfonyl) propionyl)amino)-1,5-diphenyl-3-hydroxypentane According to the carbodiimide coupling procedure of Example 55, the resultant compound of Example 132B was coupled to the resultant compound of Example 135 to give the desired compound.

EXAMPLE 137

A. N-((4-Methylpiperazin-1-yl)sulfamoyl)valine Benzyl Ester

A solution of valine benzyl ester p-toluenesulfonate (5 mmol) in dichloromethane (50 ml) to 0° C. and treated sequentially with diisopropylethylamine (12 mmol) and 4-methylpiperazinesulfamoyl chloride. After being stirred for 16 h at ambient temperature, the solution was diluted with ethyl acetate, washed sequentially with 1N HCl, water, and aqueous NaHCO$_3$, dried over MgSO$_4$, and concentrated in vacuo. Silica gel chromatography provided the desired compound.

B. N-((4-Methylpiperazin-1-yl)sulfamoyl)valine

The resultant compound of Example 137A was hydrogenolyzed according to the procedure of Example 71C to provide the desired compound.

C. 2-(t-Butyloxycarbonylamino)-4-(N-(((4-methylpiperazin-1-yl)sulfamoyl)valine)amino-1,5-diphenyl-3-hydroxypentane According to the carbodiimide coupling procedure of Example 55, the resultant compound of Example 137B was coupled to the resultant compound of Example 11 to give the desired compound.

EXAMPLE 138

2-Amino-4-(N-(((4methylpiperazin-1-yl)sulfamoyl) valinyl)amino)-1,5-diphenyl-3-hydroxypentane Dihydrochloride Using the procedure of Example 12 with the resultant compound of Example 137C provided the desired compound.

EXAMPLE 139

2,4-Bis-(N-(((4-methylpiperazin-1-yl)sulfamoyl) valinyl)amino)-1,5-diphenyl-3-hydroxypentane According to the carbodiimide coupling procedure of Example 55, the resultant compound of Example 137B was coupled to the resultant compound of Example 138 to give the desired compound.

EXAMPLE 140

2,4-Bis-N-(valinyl)amino-1,5-diphenyl-3-hydroxypentane

The resultant compound of Example 70 was hydrogenolyzed according to the procedure of Example 71C to provide the desired compound ($R_f$ 0.1, 10% methanol in chloroform) as a white solid, m.p. 131°–132° C.

EXAMPLE 141

2-Amino-5-(t-butyloxycarbonylamino)-3,4-dihydroxy-1,6-diphenyl-3-hexane

A mixture of 0.13 g of the resultant compound of Example 17B and 0.13 g of 10% palladium on carbon in 50 ml of ethyl acetate was shaken under 4 atmospheres of $H_2$ for 4 h. The resulting mixture was filtered through Celite and concentrated in vacuo to provide 72 mg (86%) of the desired compound as a 1:1 mixture of diastereomers. Mass spectrum: $(M+H)^+$=401.

EXAMPLE 142

A. N-(3-Phenylpropionyl)valine Benzyl Ester

Using the procedure of Example 137A but replacing 4-methylpiperazinesulfamoyl chloride with dihydrocinnamoyl chloride gave the desired compound.

B. N-(3-Phenylpropionyl)valine

The resultant compound of Example 142A was hydrogenolyzed according to the procedure of Example 71C to provide the desired compound.

C. 2-(t-Butyloxycarbonylamino)-4-(N-((3-phenylpropionyl)valinyl)amino)1,5-diphenyl-3-hydroxypentane According to the carbodiimide coupling procedure of Example 55, the resultant compound of Example 142B was coupled to the resultant compound of Example 11 to give the desired compound.

EXAMPLE 143

N,N-Di-(2-phenylethyl)-O-(methoxymethyl)hydroxylamine

Using the procedure of Example 51 but replacing 1,5-diphenyl-3-pentanol with the resultant compound of Example 30B gave the desired compound.

EXAMPLE 144

A. N-((Benzylamino)carbonyl)valine Methyl Ester

Using the procedure of Example 83A but replacing leucine methyl ester hydrochloride with valine methyl ester hydrochloride and replacing thiomorpholine with benzylamine provided the desired compound.

B. N-((Benzylamino)carbonyl)valine

The resultant compound of Example 144A was hydrolyzed according to the procedure of Example 6E to provide the desired compound.

C. 2-(t-Butyloxycarbonylamino)-4-(N-(((benzylamino)carbonyl)valinyl)amino)-1,5-diphenyl-3-hydroxypentane According to the carbodiimide coupling procedure of Example 55, the resultant compound of Example 144B was coupled to the resultant compound of Example 11 to give the desired compound.

EXAMPLE 145

A. N-(3-Phenylpropyl)valine Benzyl Ester

A mixture of dihydrocinnamaldehyde (7 mmol), valine benzyl ester dihydrochloride (7 mmol), anhydrous sodium acetate (0.7 g, 21 mmol), and sodium cyanoborohydride (11 mmol) in 200 mL of isopropyl alcohol was stirred at ambient temperature. After 16 h, an additional 0.2 g portion of sodium cyanoborohydride was added and stirring was continued for 4.5 h. After removal of the solvent in vacuo, the residue was taken up in ethyl acetate, washed sequentially with saturated aqueous $NaHCO_3$ and saturated brine, dried over $MgSO_4$, and concentrated. Silica gel chromatography gave the desired compound.

B. N-(3-Phenylpropyl)valine

The resultant compound of Example 145A was hydrogenolyzed according to the procedure of Example 71C to provide the desired compound.

C. 2-(t-Butyloxycarbonylamino)-4-(N-((3-phenylpropyl)valinyl)amino)-1,5-diphenyl-3-hydroxypentane According to the carbodiimide coupling procedure of Example 55, the resultant compound of Example 145B was coupled to the resultant compound of Example 11 to give the desired compound.

EXAMPLE 146

2,4-Bis-(Cbz-valinyl-amino)-1,5-diphenyl-3-((methoxy)methoxy)pentane

A solution of 22 mg of the resultant compound of Example 70 in 1 ml of dichloromethane was treated with 0.07 ml of ethyldiisopropylamine and 0.03 ml of chloromethyl methyl ether. The resulting solution was heated at reflux for 1 h. The cooled solution was concentrated in vacuo to give 26 mg of a crude solid which was recrystallized from ethyl acetate/chloroform to provide 15 mg of the desired compound ($R_f$ 0.6, 10% methanol in chloroform) as a white solid, m.p. 197°–198° C. Mass spectrum: $(M+H)^+$=781.

Anal. Calcd for $C_{45}H_{56}N_4O_8 \cdot 1.5H_2O$: C, 66.89; H, 7.36; N, 6.93. Found: 66.96; H, 6.76; N, 6.77.

EXAMPLE 147

2,2-Di-(2-phenylethyl)-1,3-dioxolane

A solution of 135 mg (0.6 mmol) of 1,5-diphenyl-3-pentanone, 0.2 ml of ethylene glycol, and 10 mg of p-toluene sulfonic acid monohydrate was refluxed with azeotropic removal of water. After separation of water was completed, the solution was diluted with ethyl acetate, washed sequentially with aqueous NaHCO and water, dried over $Na_2SO_4$, and concentrated to provide the desired compound. $^1H$ NMR ($CDCl_3$) δ 2.0 (m, 4H), 2.71 (m, 4H), 4.03 (s, 4H), 7.15–7.3 (m, 10H). Mass spectrum: $(M+H)^+$=283.

EXAMPLE 148

2-(Acetylamino)-4-(t-butyloxycarbonylamino)-1,5-diphenyl-3-hydroxypentane

A solution of 20 mg of the resultant compound of Example 11 and 0.05 ml of triethylamine in 1 ml of dichloromethane was cooled to 0° C. and treated with 0.01 ml of acetic anhydride. After 30 min. the solution was partitioned between water and dichloromethane, and the organic phase was dried over $Na_2SO_4$ and concentrated to give 23 mg (100%) of the desired compound ($R_f$ 0.5, 10% methanol in chloroform). Mass spectrum: $(M+H)^+=413$.

EXAMPLE 149

A. 3-(tert-Butyldimethylsilyloxy)-1,6-diphenyl-4-hydroxyhexane

A solution of 2-phenylethylmagnesium bromide (prepared from 0.4 ml of 2-(bromoethyl)benzene and 90 mg of magnesium) in tetrahydrofuran was cooled to 0° C. and treated with a solution of 0.35 g of the resultant compound of Example 6C in tetrahydrofuran. After being stirred at ambient temperature for 1 h, the solution was heated at reflux for 4 h, treated with saturated aqueous ammonium chloride, extracted with ether, washed with saturated brine, dried over $MgSO_4$, and concentrated. Silica gel chromatography using ethyl acetate/hexane gave the desired compound.

B. 3,4-Dihydroxy-1,6-diphenylhexane

A solution of the resultant compound of Example 149A (30 mg, 0.078 mmol) was deprotected according to the procedure of Example 6G to provide the desired compound as a 3:1 mixture of diastereomers. Recrystallization from chloroform/ethyl acetate provided the desired compound as a single isomer, m.p. 128.5°–129° C. $^1$H NMR ($CDCl_3$) $\delta$ 1.76 (m, 4H), 1.82 (d, J=5 Hz, 2H), 2.63 (dr, J=14, 8 Hz, 2 H), 2.85 (ddd, J=14, 9, 6 Hz, 2H), 3.62 (m, 2H), 7.15–7.3 (m, 10H). Mass spectrum: $(M+NH_4)^+=288$.

EXAMPLE 150

4,5-Di-(2-phenylethyl)-1,3-dioxolane

The resultant compound of Example 149 was treated with paraformaldehyde and $H_2SO_4$ in acetic acid according to the procedure of Hough, et. al. (*J. Chem. Soc.*, 1952, 1525) to provide the desired compound.

EXAMPLE 151

4,4-Di-(2-phenylethyl)-1,3-dioxolane

The resultant compound of Example 20 was treated with paraformaldehyde and $H_2SO_4$ in acetic acid according to the procedure of Hough, et. al. (*J. Chem. Soc.*, 1952, 1525) to provide the desired compound.

EXAMPLE 152

3,3-Dimethoxy-1,5-diphenylpentane 1,5-Diphenyl-3-pentanone was treated with HCl in anhydrous methanol according to procedure of Cameron et. al. (*J. Chem. Soc.* 1953, 3864) to provide the desired compound.

EXAMPLE 153

2-(t-Butyloxycarbonylamino)-4-(((β,β,-di-Me)-β-Ala)-leucinyl-amino)-1,5-diphenyl-3-hydroxypentane The resultant compound of Example 78D was hydrogenolyzed according to the procedure of Example 71C to provide the desired compound.

EXAMPLE 154

2,4-Bis-(Cbz-leucinyl-asparaginyl-amino)-1,5-diphenyl-3-hydroxypentane

Using the procdure of Example 12 with the resultant compound of Example 65 gave a crude amine hydrochloride which was coupled to Cbz-Leu-Asn-OH according to the procedure of Example 55 to give, after silica gel chromatography using methanol/chloroform, the desired compound ($R_f$ 0.7, 10% methanol in chloroform) as a white solid, m.p. 250–251. Mass spectrum $(M+H)^+=993$.

EXAMPLE 155

A. Bis-((2-t-butyloxycarbonylamino)-3-phenylpropyl)sulfide

A solution of 2.30 g (7.0 mmol) of 2-(t-butyloxycarbonylamino)-3-phenylpropyl methanesulfonate (*Tetrahedron Lett.* 1986, 27, 2095) and 0.84 g (3.5 mmol) of sodium sulfide nonahydrate in 75 ml of 2:1 tetrahydrofuran/methanol was heated at reflux for 2.5 h. The cooled solution was concentrated in vacuo, partitioned between ethyl acetate and water, washed with saturated brine, dried over $MgSO_4$, and concentrated. Silica gel chromatography using 20% ethyl acetate in hexane provided 0.42 g (24%) of the desired compound. Mass spectrum: $(M+H)^+=501$.

B. Bis-((2-t-butyloxycarbonylamino)-3-phenylpropyl)sulfone

A solution of the resultant compound of Example 155A (404 mg, 0.81 mmol) in 10 ml of dichloromethane was treated with 0.40 g of 80% m-chloroperbenzoic acid. After being stirred for 16 h at ambient temperature, the solution was diluted with dichloromethane, washed sequentially with 10% $Na_2S_2O_3$/3N NaOH and water, dried over $MgSO_4$, and concentrated to give 0.36 g (84%) of the desired compound ($R_f$ 0.25, 15% ethyl acetate in chloroform) as a white solid, m.p. 227°–228° C. (dec). Mass spectrum: $(M+H)^+=533$.

Anal. Calcd. for $C_{28}H_{40}N_2O_6S \cdot 0.75H_2O$: C, 61.57; H, 7.66; N, 5.13. Found: C, 61.65; H, 7.33; N, 4.93.

EXAMPLE 156

A. Bis-((2-benzyloxycarbonyl)-3-phenylpropyl)sulfide

Using the procedure of Example 155A but replacing 2-(t-butyloxycarbonylamino)-3-phenylpropyl methanesulfonate with benzyl α-benzylacrylate provided the desired compound after silica gel chromatography.

B. Bis-((2-benzyloxycarbonyl)-3-phenylpropyl)sulfone

Using the procedure of Example 155B with the resultant compound of Example 156A gave the desired compound.

EXAMPLE 157

Bis-((2-t-butyloxycarbonylamino)-3-phenylpropyl)sulfoxide

Using the procedure of Example 2 with the resultant compound of Example 155A provided the desired compound.

EXAMPLE 158

Bis-((2-benzyloxycarbonyl)-3-phenylpropyl)sulfoxide

Using the procedure of Example 2 with the resultant compound of Example 156A provided the desired compound.

EXAMPLE 159

A. N,N-Bis-((2-methoxycarbonyl)-3-phenylpropyl)-O-benzylhydroxylamine

The resultant compound from Example 116A (4 mmol), O-benzylhydroxylamine hydrochloride (2 mmol), and NaHCO$_3$ (2.2 mmol) in dimethylsulfoxide (5 ml) were heated at 130° C. for 20 h. The mixture was diluted with ethyl acetate, washed with water, saturated NaHCO$_3$ solution and brine, and then was dried over Na$_2$SO$_3$ and evaporated. Silica gel chromatography provided the desired compound.

B. N,N-Bis-((2-methoxycarbonyl)-3-phenylpropyl) hydroxylamine

The resultant compound of Example 159A (1 mmol) was treated with 10 ml of 30% HBr in acetic acid and stirred at ambient temperature for 4 h. After removal of the solvent in vacuo, the residue was partitioned between ethyl acetate and aqueous NaHCO$_3$, dried over Na$_2$SO$_4$, and concentrated. Silica gel chromatography provided the desired compound.

EXAMPLE 160

A. α-Isocyanato-valine Methyl Ester

A suspension of L-valine methyl ester hydrochloride (10 g) in toluene (400 ml) was heated to 100° C. and phosgene gas was bubbled into the reaction mixture. After approximately 6 h, the mixture became homogeneous. The bubbling of phosgene was continued for 10 more min, then the solution was cooled with the bubbling of N$_2$ gas. The solvent was then evaporated and the residue chased with toluene two times. Evaporation of solvent gave 14.2 g of the crude desired compound.

B. N-((4-Pyridinyl)methoxycarbonyl)-valine Methyl Ester

A solution of 0.73 g (4.65 mmol) of the resultant compound of Example 160A and 0.51 g (4.65 mmol) of pyridine-4-methanol in 30 mL of toluene was heated at reflux under N$_2$ atmosphere for 4 h. The solvent was removed in vacuo, and the residue was purified by silica gel chromatography using 2% methanol in chloroform to give 1.01 g (82%) of the desired compound as an oil. $^1$H NMR (CDCl$_3$) δ 0.91 (d, J=7 Hz, 3H), 0.99 (d, J=7 Hz, 3H), 2.19 (m, 1H), 3.76 (s, 3H), 4.31 (dd, J=9, 5 Hz, 1H), 5.12 (s, 2H), 5.37 (br d, 1H), 7.25 (d, J=6 Hz, 2H), 8.60 (d, J=6 Hz, 2H).

C. N-((4-Pyridinyl)methoxycarbonyl)-valine Lithium Salt

A solution of 50.8 mg (0.191 mmol) of the resultant compound of Example 160B in 0.75 ml of dioxane was treated with 0.46 ml (0.23 mmol) of 0.5M aqueous lithium hydroxide. The resulting solution was stirred overnight at ambient temperature and concentrated in vacuo to provide the desired compound.

D. 2-(N-((4-Pyridinyl)methoxycarbonyl)-valinyl-amino)-4-(Cbz-valinyl-amino)-1,5-diphenyl-3-hydroxypentane A solution of the resultant compound of Example 160C (0.191 mmol), 94 mg (0.97 mmol) of the resultant compound of Example 69, and 31 mg (0.23 mmol) of 1-hydroxybenzotriazole in 2 ml of dimethylformamide was treated under N$_2$ atmosphere with 44 mg (0.23 mmol) of N-ethyl-N'-(dimethylaminopropyl) carbodiimide hydrochloride and stirred overnight at ambient temperature. The resulting solution was taken up in ethyl acetate, washed sequentially with aqueous NaHCO$_3$, H$_2$O, and saturated brine, dried over Na$_2$SO$_4$, and concentrated in vacuo. Chromatography on silica gel using 3% methanol in chloroform provided 119 mg (87%) of the desired compound (R$_f$ 0.19, 5% methanol in chloroform) as a white solid, m.p. 170°–172° C. (dec). Mass spectrum: (M+1)$^+$=738.

Anal. Calcd for C$_{42}$H$_{51}$N$_5$O$_7$·0.5H$_2$O: C, 67.54; H, 7.02; N, 9.38. Found: C, 67.53; H, 7.00; N, 9.39.

EXAMPLE 161

A. N-((3-Pyridinyl)methoxycarbonyl)-valine Methyl Ester

Using the procedure of Example 160B but replacing pyridine-4-methanol with pyridine-3-methanol provided the desired compound as an oil after silica gel chromatography using 2% methanol in chloroform. $^1$H NMR (CDCl$_3$) δ 0.90 (d, J=7 Hz, 3H), 0.98 (d, J=7 Hz, 3 H), 2.16 (m, 1H), 3.65 (s, 3H), 4.30 (dd, J=9, 5 Hz, 1H), 5.14 (s, 2H), 5.30 (br d, 1H), 7.30 (dd, J=8, 5 Hz, 1H), 7.70 (br d, J=8 Hz, 1H), 8.58 (dd, J=4, 1 Hz, 1H), 8.63 (br s, 1H).

B. N-((3-Pyridinyl)methoxycarbonyl)-valine Lithium Salt

Using the procedure of Example 160C with the resultant compound of Example 161A provided the desired compound.

C. 2-(N-((3-Pyridinyl)methoxycarbonyl-valinyl-amino)-4-1Cbz-valinyl-amino)-1,5-diphenyl-3-hydroxypentane Using the procedure of Example 160D but replacing the resultant compound of Example 160C with the resultant compound of Example 161B provided, after silica gel chromatography using 3% methanol in chloroform, 113 mg (94%) of the desired compound (R$_f$ 0.21, 5% methanol in chloroform) as a white solid, m.p. 177°–178° C. Mass spectrum: (M+1)$^+$=738.

Anal. Calcd for C$_{42}$H$_{51}$N$_5$O$_7$·0.5H$_2$O: C, 67.54; H, 7.02; N, 9.38. Found: C, 67.35; H, 6.90; N, 9.35.

EXAMPLE 162

A. N-((2-Pyridinyl)methoxycarbonyl)-valine Methyl Ester

Using the procedure of Example 160B but replacing pyridine-4-methanol with pyridine-2-methanol provided 0.72 g (54%) of the desired compound as an oil after silica gel chromatography using 2% methanol in chloroform. $^1$H NMR (CDCl$_3$) δ 0.91 (d, J=7 Hz, 3H), 0.98 (d, J=7 Hz, 3H), 2.19 (m, 1H), 3.75 (s, 3H), 4.32 (dd, J=9, 5 Hz, 1H), 5.24 (s, 2H), 5.39 (br d, 1H), 7.23 (ddd, J=8, 4, 1 Hz, 1H), 7.37 (d, J=8 Hz, 1H), 7.70 (td, J=8, 2 Hz, 1H), 8.60 (br d, 1H).

B. N-(2-Pyridinyl)methoxycarbonyl)-valine Lithium Salt

Using the procedure of Example 160C with the resultant compound of Example 162A provided the desired compound.

C. 2-(N-((2-Pyridinyl)methoxycarbonyl)-valinyl-amino)-4-(Cbz-valinyl-amino)-1,5-diphenyl-3-hydroxypentane Using the procedure of Example 160D but replacing the resultant compound of Example 160C with the resultant compound of Example 162B provided, after silica gel chromatography using 2% methanol in chloroform, 119 mg (99%) of the desired compound28, 5% methanol in chloroform) as a white solid, m.p. 194°–195° C. Mass spectrum: $(M+1)^+=738$.

Anal. Calcd for $C_{42}H_{51}N_5O_7 \cdot 0.5H_2O$: C, 67.54; H, 7.02; N, 9.38. Found: C, 67.31; H, 7.00; N, 9.37.

EXAMPLE 163

A. N-((3-Pyridinyl)carbonyl)-valine Benzyl Ester

A solution of 2.44 g (6.44 mmol) of L-valine benzyl ester p-toluenesulfonate in 100 ml of dichloromethane was cooled under $N_2$ atmosphere to 0° C. and treated sequentially with 1.15 g (6.44 mmol) of nicotinyl chloride hydrochloride and 2.8 ml (26 mmol) of 4-methylmorpholine. After being stirred at ambient temperature overnight, the resulting solution was diluted with 200 ml of diethyl ether, washed sequentially with water, aqueous $NaHCO_3$, and saturated brine, dried over $Na_2SO_4$, and concentrated in vacuo to give 2.09 g (95%) of the desired compound. $^1H$ NMR $(CDCl_3)$ δ 0.96 (d, J=7 Hz, 3H), 1.01 (d, J=7 Hz, 3 H), 2.30 (m, 1H), 4.83 (dd, J=9, 5 Hz, 1H), 5.20 (AA', 2H), 6.67 (br d, 1H), 7.37 (br s, 6H), 8.11 (dd, J=8, 2 Hz, 1H), 8.74 (br, 1H), 9.01 (s, 1H).

B. N-((3-Pyridinyl)carbonyl)-valine

A suspension of 0.16 g of 10% palladium on carbon in 20 ml of methanol was treated with a solution of 1.08 g (3.16 mmol) of the resultant compound of Example 163A in 10 ml of methanol. The resulting mixture was stirred vigorously under $H_2$ atmosphere for 4 h, filtered through Celite, and concentrated in vacuo to provide the desired compound as an off-white solid.

C. 2-(N-((3-Pyridinyl)carbonyl)-valinyl-amino)-4-(Cbz-valinyl-amino)-1,5-diphenyl-3-hydroxypentane Using the procedure of Example 160D but replacing the resultant compound of Example 160C with the resultant compound of Example 163B provided, after silica gel chromatography using 3% methanol in chloroform, 85 mg (72%) of the desired compound ($R_f$ 0.21, 5% methanol in chloroform), m.p. 196°–199° C. Mass spectrum: $(M+1)^+=708$.

Anal. Calcd for $C_{41}H_{49}N_5O_6 \cdot 1.25H_2O$: C, 67.42; H, 7.11; N, 9.59. Found: C, 67.56; H, 6.91; N, 9.66.

EXAMPLE 164

A. N-((4-Pyridinyl)carbonyl)-valine Benzyl Ester

Using the procedure of Example 163A but replacing nicotinyl chloride hydrochloride with isonicotinyl chloride hydrochloride provided 2.32 g (97%) of the desired compound. $^1H$ NMR $(CDCl_3)$ δ 0.94 (d, J=7 Hz, 3 H), 0.99 (d, J=7 Hz, 3H), 2.30 (m, 1H), 4.82 (dd, J=9, 5 Hz, 1H), 5.22 (AA',2H), 6.75 (br d, 1H), 7.38 (br s, 5H), 7.63 (dd, J=6, 2 Hz, 2H), 8.76 (dd, J=6, 2 Hz, 1H).

B. N-((4-Pyridinyl)carbonyl)-valine

Using the procedure of Example 163B with the resultant compound of Example 164A gave the desired compound.

C. 2-(N-((4-Pyridinyl)carbonyl)-valinyl-amino)-4-)Cbz-valinyl-amino)-1,5-diphenyl-3-hydroxypentane Using the procedure of Example 160D but replacing the resultant compound of Example 160C with the resultant compound of Example 164B provided, after silica gel chromatography using 3% methanol in chloroform, the desired compound.

EXAMPLE 165

A. N-(2-(4-Morpholinyl)ethyloxy)carbonyl)-valine Methyl Ester

A solution of 1.04 g (6.60 mmol) of the resultant compound of Example 160A and 0.88 ml (7.25 mmol) of 4-(2-hydroxyethyl)morpholine in 30 mL of toluene was heated at reflux under $N_2$ atmosphere for 12 h. The solvent was removed in vacuo, and the residue was purified by silica gel chromatography using 5% methanol in chloroform to give 1.41 g (71%) of the desired compound as an oil. $^1H$ NMR $(CDCl_3)$ δ 0.89 (d, J=7 Hz, 3H), 0.96 (d, J=7 Hz, 3H), 2.16 (m, 1H), 2.50 (br t, 4H), 2.62 (t, J=6 Hz, 2H), 3.72 (t, J=6 Hz, 4 H), 3.75 (s, 3H), 4.20 (br t, 2H), 4.37 (dd, J=9, 5 Hz, 1H), 5.25 (br d, 1H).

B. N-((2-(4-Morpholinyl)ethyloxy)carbonyl)-valine Lithium Salt

A solution of 77.7 mg (0.27 mmol) of the resultant compound of Example 165A in 1 ml of dioxane was treated with 1.04 ml (0.52 mmol) of 0.5M aqueous lithium hydroxide. After being stirred for 2.5 h at ambient temperature, the resulting solution was treated with 0.26 ml (0.26 mmol) of 1N aqueous HCl and concentrated in vacuo to provide the desired compound as a white solid.

C. 2-(N-((2-(4-Morpholinyl)ethyloxy)carbonyl)-valinyl-amino)-4-(Cbz-valinyl-amino)-1,5-diphenyl-3-hydroxypentane Using the procedure of Example 160D but replacing the resultant compound of Example 160C with the resultant compound of Example 165B provided, after silica gel chromatography using 4% methanol in chloroform, 150 mg (94%) of the desired compound ($R_f$ 0.34, 7.5% methanol in chloroform) as a white solid, m.p. 159°–161° C. Mass spectrum: $(M+1)^+=760$.

Anal. Calcd for $C_{42}H_{57}N_5O_8 \cdot 0.75H_2O$: C, 65.22; H, 7.62; N, 9.05. Found: C, 65.19; H, 7.49; N, 9.08.

EXAMPLE 166

A. N-((2-(1-Pyrrolidinyl)ethyloxy)carbonyl)-valine Methyl Ester

Using the procedure of Example 165A but replacing 4-(2-hydroxyethyl)morpholine with 4-(2-hydroxyethyl)-pyrrolidine provided, after silica gel chromatography using 6% methanol in chloroform, 1.14 g (80%) of the desired compound as an oil. $^1H$ NMR $(CDCl_3)$ δ 0.90 (d, J=7 Hz, 3H), 0.96 (d, J=7 Hz, 3H), 1.80 (m, 4H), 2.15 (m, 1H), 2.57 (m, 4H), 2.63 (t, J=6 Hz, 2H), 3.74 (s, 3H), 4.20 (br t, 2H), 4.28 (dd, J=9, 5 Hz, 1H), 5.30 (br d, 1H).

B. N-((2-(1-Pyrrolidinyl)ethyloxy)carbonyl)-valine Lithium Salt

Using the procedure of Example 165B with the resultant compound of Example 166A provided the desired compound as a white solid.

C. 2-(N-(2-(1-Pyrrolidinyl)ethyloxy)carbonyl)-valinyl-amino)-4-(Cbz-valinyl-amino)-1,5-diphenyl-3-hydroxypentane Using the procedure of Example 160D but replacing the resultant compound of Example 160C with the resultant compound of Example 166B provided, after silica gel chromatography using 7.5% methanol in chloroform, 103 mg (63%) of the desired compound ($R_f$ 0.13, 7.5% methanol in chloroform) as a white solid, m.p. 143°–146° C. Mass spectrum: $(M+1)^+$=744.

Anal. Calcd for $C_{42}H_{57}N_5O_7$: C, 67.81; H, 7.72; N, 8.89. Found: C, 68.20; H, 7.53; N, 8.89.

EXAMPLE 167

A. N-((2-Furanyl)methoxycarbonyl)-valine Methyl Ester

Using the procedure of Example 165A but replacing 4-(2-hydroxyethyl)morpholine with 2-furfuryl alcohol provided, after silica gel chromatography using 20% ethyl acetate in hexane, 0.91 g (70%) of the desired compound as an oil. $^1$H NMR (CDCl$_3$) δ 0.88 (d, J=7 Hz, 3H), 0.96 (d, J=7 Hz, 3H), 2.15 (m, 1H), 3.74 (s, 3 H), 4.29 (dd, J=9, 5 Hz, 1H), 5.07 (s, 2H), 5.25 (br d, 1H) 6.36 (m, 1H), 6.42 (m, 1H), 7.43 (m, 1H).

B. N-((2-Furanyl)methoxycarbonyl)-valine

Using the procedure of Example 165B with the resultant compound of Example 167A provided, after acidification and extraction into chloroform, the desired compound as a white solid.

C. 2-(N-((2-Furanyl)methoxycarbonyl)-valinyl-amino)-4-(Cbz-valinyl-amino)-1,5-diphenyl-3-hydroxypentane Using the procedure of Example 160D but replacing the resultant compound of Example 160C with the resultant compound of Example 167B provided the desired compound.

EXAMPLE 168

A. N-(((1-Methyl)pyrrolidin-2-yl)methoxycarbonyl)-valine Methyl Ester

Using the procedure of Example 165A but replacing 4-(2-hydroxyethyl) morpholine with 1-methyl-2-pyrrolidine-methanol provided, after silica gel chromatography using 5% methanol in chloroform, the desired compound as an oil. $^1$H NMR (CDCl$_3$) δ 0.90 (d, J=7 Hz, 3H), 0.96 (d, J=7 Hz, 3H), 1.6–2.0 (m, 34 H), 2.15 (m, 1H), 2.23 (td, J=9, 8 Hz, 1H), 2.40 (s, 3H), 2.53 (m, 1H), 3.03 (m, 1H), 3.74 (s, 3H), 4.00 (dd, J=12, 6 Hz, 1H), 4.17 (dd, J=12, 5 Hz, 1H), 4.28 (dd, J=9, 5 Hz, 1H), 5.27 (br d, 1H).

B. N-(((1-Methyl)pyrrolidin-2-yl)methoxycarbonyl)-valine Lithium Salt

Using the procedure of Example 165B with the resultant compound of Example 168A provided the desired compound as a white solid.

C. 2-(N-(((1-Methyl)pyrrolidin-2-yl)methoxycarbonyl)-valinyl-amino)-4-(Cbz-valinyl-amino)-1,5-diphenyl-3-hydroxypentane Using the procedure of Example 160D but replacing the resultant compound of Example 160C with the resultant compound of Example 168B provided, after silica gel chromatography using methanol in chloroform, the desired compound.

EXAMPLE 169

A. N-(((1-Methyl)piperazin-4-yl)carbonyl)-valine Methyl Ester

A solution of 0.86 g (5.47 mmol) of the resultant compound of Example 160A in 10 ml of dichloromethane was treated with 0.73 ml (6.6 mmol) of 1-methylpiperazine. The resulting solution was stirred at ambient temperature for 2.5 h, after which it was concentrated in vacuo. The residue was purified by silica gel chromatography using 5% methanol in chloroform to provide 1.40 g (100%) of the desired compound. $^1$H NMR (CDCl$_3$) δ 0.91 (d, J=7 Hz, 3H), 0.95 (d, J=7 Hz, 3 H), 2.13 (m, 1H), 2.31 (s, 3H), 2.41 (t, J=5 Hz, 4 H), 3.43 (m, 4H), 3.74 (s, 3H), 4.46 (dd, J=9, 5 Hz, 1H), 4.93 (br d, 1H).

B. N-(((1-Methyl)piperazin-4-yl)carbonyl)-valine Lithium Salt

Using the procedure of Example 165B with the resultant compound of Example 169A provided the desired compound as a white solid.

C. 2-(N-(((1-Methyl)piperazin-4-yl)carbonyl)-valinyl-amino)-4-(Cbz-valinyl-amino)-1,5-diphenyl-3-hydroxypentane Using the procedure of Example 160D but replacing the resultant compound of Example 160C with the resultant compound of Example 169B provided, after silica gel chromatography using 6% methanol in chloroform, 196 mg (98%) of the desired compound ($R_f$ 0.15, 7.5% methanol in chloroform) as a white solid, m.p. 175°–176° C. Mass spectrum: $(M+1)^+$=729.

Anal. Calcd for $C_{41}H_{56}N_6O_6 \cdot H_2O$: C, 65.93; H, 7.83; N, 11.25. Found: C, 65.58; H, 7.70; N, 11.14.

EXAMPLE 170

A. N-((t-Butyloxy)carbonyl)-phenylalaninal

A solution of 2.8 ml (40 mmol) of dry dimethylsulfoxide in 150 ml of dry dichloromethane was cooled under nitrogen atmosphere in a dry ice/chloroform bath (ca. −60° C.). In a separate flask, a 2M solution of oxalyl chloride in dichloromethane (15 ml, 30 mmol) was precooled to −60° C. and then added via cannula. After 10 min, a solution of 5 g (20 mmol) of N-((t-butyloxy)carbonyl)-phenylalaninol in 30 ml of dry dichloromethane was added via cannula. The resulting solution was stirred at −60° C. for 45 min, and was subsequently treated via syringe with 11 ml (80 mmol) of dry triethylamine. After being stirred for an additional 15 min at −60° C., the solution was quenched by addition of 10% aqueous citric acid, then immediately poured into a rapidly stirred mixture of 200 ml of 1:1 hexane:ether and 100 ml of 10% aqueous citric acid. The reaction flask was rinsed with ether which was added to the above mixture. The mixture was poured into a separatory funnel and the layers were sequentially with dilute layer was washed sequentially with dilute aqueous sodium bicarbonate and saturated brine, dried over MgSO$_4$, and concentrated in vacuo to provide the crude desired compound.

B. 2,5-Di-(N-((t-butyloxy)carbonyl)amino)-3,4-dihydroxy-1,6-diphenylhexane

In a glove bag purged with argon, a 500 ml three-neck flask was charged with 27 g of TiCl$_3$(DME)$_2$ followed by 200 ml of anhydrous dimethoxyethane (DME). A separate flask was charged with 20 g of Zn-Cu couple and connected to one of the side necks of the three-neck flask with Gooch tubing. The flask was sealed with septa, removed from the glove bag, and outfitted under positive argon flow with an overhead mechanical stirrer. Under positive argon pressure, Zn-Cu was added in portions with vigorous stirring. After addition, the Gooch tubing was removed and replaced with a rubber septum. Stirring was continued while the flask was placed in an oil bath and heated to 85° C. for 2.5 h. After being allowed to cool, the flask was placed in an ice bath while stirring was continued, and the mixture was treated via cannula with a solution of the resultant compound of Example 170A (20 mmol) in 20 ml of anhydrous dimethoxyethane. The progress of the reaction was monitered by tlc. After 1 h, the reaction mixture was filtered through Celite, and the residue was washed with ethyl acetate. The filtrate was treated with saturated aqueous sodium bicarbonate, and air was bubbled through the suspension until it became white. The layers were separated, and the organic layer was washed with saturated brine, dried over $MgSO_4$, and concentrated to give 3.7 g of a light yellow solid. The solid was taken up in dichloromethane, treated with silica gel, and concentrated to a freely flowing powder. The powder was placed on the top of a silica gel column and eluted first with 70:30 hexane:ethyl acetate to bring off the more mobile product ($R_f$ 0.26, 70:30 hexane:ethyl acetate) which contained two diastereomers (2S, 3S, 4S, 5S and 2S, 3R, 4S, 5S) followed by 60:40 hexane:ethyl acetate to bring off the less mobile product ($R_f$ 0.10) which contained one major diastereomer (2S, 3R, 4R, 5S).

(2S, 3R, 4R, 5S)-2,5-Di-(N-((t-butyloxy)carbonyl)amino)-3,4-dihydroxy-1,6-diphenylhexane m.p. 200°–202° C. $^1$H NMR δ 1.35 (s, 18H), 2.87 (dd, J=13, 7 Hz, 2H), 2.98 (dd, J=13, 7 Hz, 2H), 3.41 (m, 2H), 3.76 (br q, J=8 Hz, 2 H), 3.96 (m, 2H), 4.77 (br d, J=8 Hz, 2H), 7.15–7.3 (m, 10H). Mass spectrum: $(M+H)^+=501$.

Anal. Calcd for $C_{28}H_{40}N_2O_6 \cdot 0.5H_2O$: C, 65.99; H, 8.11; N, 5.50. Found: 65.96; H, 7.96; N, 5.49.

EXAMPLE 171

(2S,3R, 4R,5S)-2,5-Diamino-3,4-dihydroxy-1,6-diphenylhexane (2S, 3R, 4R, 5S)-2,5-Di-(N-((t-butyloxy)carbonyl)amino)-3,4-dihydroxy-1,6-diphenylhexane (2.7 g, 5.4 mmol) was treated with 200 ml of 6N aqueous hydrochloric acid and heated to 90° C. until the solid had completely dissolved (30 min). The resulting solution was cooled, concentrated in vacuo, treated with saturated brine and 3N aqueous NaOH, extracted with chloroform, dried over $Na_2SO_4$, and concentrated in vacuo. Silica gel chromatography using 3% methanol/2% isopropylamine in chloroform provided the pure desired compound ($R_f$ 0.40, 5% methanol/ 2% isopropylamine in chloroform) as a white solid, m.p. 86°–89° C. $^1$H NMR (CDCl$_3$) δ 2.72 (dd, J=14, 9 Hz, 2H), 2.92 (dd, J=14, 6 Hz, 2H), 3.03 (dd, J=9, 5 Hz, 2H), 3.69 (s, 2H), 7.15–7.35 (m, 10H). Mass spectrum: $(M+H)^+=301$.

Anal. Calcd for $C_{18}H_{24}N_2O_2 \cdot 0.25H_2O$: C, 70.91; H, 8.10; N, 9.19. Found: C, 70.52; H, 7.92; N, 8.93.

EXAMPLE 172

A. N-((Cbz-valinyl)oxy)-succinimide

A suspension of 3.40 g (13.5 mmol) of Cbz-valine and 1.56 g (13.5 mmol) of N-hydroxysuccinimide in 200 ml of dichloromethane was treated with 2.86 g (14.9 mmol) of N-ethyl-N'-(dimethylaminopropyl) carbodiimide hydrochloride and stirred at ambient temperature for 4 h. The resulting solution was washed sequentially with 10% citric acid, aqueous $NaHCO_3$, and water; dried over $Na_2SO_4$, and concentrated in vacuo to provide 4.00 g (85%) of the desired compound.

B. (2S,3R,4R,5S)-2,5-Di-(N-(Cbz-valinyl)amino)-3,4-dihydroxy-1,6-diphenylhexane

A solution of 28.7 mg (0.096 mmol) of the resultant compound of Example 171 in 1 ml of dioxane was treated with 139 mg (0.40 mmol) of the resultant compound of Example 172A and stirred at ambient temperature for 24 h. The resulting solution was treated with 0.5 ml of 3N NaOH, stirred for 15 min, extracted with two portions of 10% methanol in chloroform, dried over $Na_2SO_4$, and concentrated in vacuo. The residue was chromatographed on silica gel using 3% methanol in chloroform to provide 42.4 mg (58%) of the desired compound ($R_f$ 0.35, 5% methanol in chloroform) as a white solid, m.p. 231°–232° C. Mass spectrum: $(M+H)^+=767$.

Anal. Calcd for $C_{44}H_{54}N_4O_8 \cdot 0.25H_2O$: C, 68.51; H, 7.12; N, 7.26. Found: C, 68.48; H, 7.11; N, 7.12.

EXAMPLE 173

(2S,3R,4R,5S)-2,5-Di-(N-(valinyl)amino)-3,4-dihydroxy-1,6-diphenylhexane

Using the procedure of Example 71C with the resultant compound of Example 172B provided the desired compound ($R_f$ 0.07, 10% methanol in chloroform) as a white solid, m.p. 205°–207° C. Mass spectrum: $(M+H)^+=499$.

Anal. Calcd for $C_{28}H_{42}N_4O_4 \cdot 0.75H_2O$: C, 65.66; H, 8.56; N, 10.94. Found: C, 65.47; H, 7.93; N, 10.59.

EXAMPLE 174

A. N-((4-Pyridinyl)methoxycarbonyl)-valine

Using the procedure of Example 160C but adding twice the amount of 1M HCl provided the desired compound.

B. 2,4-Di-(N-((4-pyridinyl)methoxycarbonyl)-valinyl-amino)-1,5-diphenyl-3-hydroxypentane The resultant compound of Example 174A (0.60 mmol) was coupled to the resultant compound of Example 12 (60 mg, 0.22 mmol) using the procedure of Example 55 except that the reaction was allowed to proceed for 2 days at ambient temperature. Silica gel chromatography using methanol/chloroform provided the desired compound ($R_f$ 0.44, 10:1 chloroform:methanol) as a white solid, m.p. 158°–159° C. Mass spectrum: $(M+H)^+=741$.

Anal. Calcd for $C_{41}H_{50}N_6O_7 \cdot 0.5H_2O$: C, 65.85; H, 6.87; N, 11.24. Found: C, 6.76; H, 65.67; N, 11.12.

EXAMPLE 175

A. N-((3-Pyridinyl)methoxycarbonyl)-valine

Using the procedure of Example 161B but adding twice the amount of 1M HCl provided the desired compound.

B. 2,4-Di-(N-((3-pyridinyl)methoxycarbonyl)-valinyl-amino)-1,5-diphenyl-3-hydroxypentane Using the procedure of Example 174B but replacing the resultant compound of Example 174A (0.60 mmol) with the resultant compound of Example 175A gave, after silica gel chromatography using methanol/chloroform, the desired compound ($R_f$ 0.53, 10: 1 chloroform:methanol) as a white solid, m.p. 177°–178° C. Mass spectrum: $(M+H)^+=741$.

Anal. Calcd for $C_{41}H_{50}N_6O_7 \cdot 0.5H_2O$: C, 65.85; H, 6.87; N, 11.24. Found: C, 66.09; H, 6.72; N, 11.24.

EXAMPLE 176

A. N-((2-Pyridinyl)methoxycarbonyl)-valine

Using the procedure of Example 162B but adding twice the amount of 1M HCl provided the desired compound.

B. 2,4-Di-(N-((2-pyridinyl)methoxycarbonyl)-valinyl-amino)-1,5-diphenyl-3-hydroxypentane Using the procedure of Example 174B but replacing the resultant compound of Example 174A (0.60 mmol) with the resultant compound of Example 176A gave, after silica gel chromatography using methanol/chloroform, the desired compound as a white solid, m.p. 155°–156° C. Mass spectrum: $(M+H)^+=741$.

Anal. Calcd for $C_{41}H_{50}N_6O_7 \cdot 0.5H_2O$: C, 65.85; H, 6.87; N, 11.24. Found: C, 65.89; H, 6.90; N, 11.24.

EXAMPLE 177

2,4-Di-(N-(((3-pyridinyl)carbonyl)-valinyl)-amino)-1,5diphenyl-3-hydroxypentane A solution of 15 mg (0.032 mmol) of the resultant compound of Example 140 and 0.01 ml (0.09 mmol) of 4-methylmorpholine in 2 ml of dichloromethane was cooled to 0° C. and treated with 12 mg (0.067 mmol) of nicotinyl chloride hydrochloride. The resulting Solution was stirred at 0° C. for 1 h, washed with aqueous $NaHCO_3$, dried over $Na_2SO_4$, and concentrated in vacuo. The residue was recrystallized from chloroform/ethyl acetate/hexane to afford the desired compound ($R_f$ 0.40, 10% methanol in chloroform) as a white solid, m.p. 228–230. Mass spectrum: $(M+H)^+=679$.

EXAMPLE 178

2,5-Di-(N-(((3-pyridinyl)carbonyl)-valinyl)amino)-3,4-dihydroxy-1,6-diphenylhexane Using the procedure of Example 177 with the resultant compound of Example 173 provided the desired compound.

EXAMPLE 179

2,5-Di-(N-((3-pyridinyl)carbonyl)amino)-3,4-dihydroxy-1,6-diphenylhexane

Using the procedure of Example 177 but replacing the resultant compound of Example 140 with the resultant compound of Example 171 provided the desired compound.

EXAMPLE 180

2,5-Di-(N-((4-pyridinyl)carbonyl)amino)-3,4-dihydroxy-1,6-diphenylhexane

Using the procedure of Example 177 but replacing the resultant compound of Example 140 with the resultant compound of Example 171 and replacing nicotinyl chloride hydrochloride with isonicotinyl chloride hydrochloride provided the desired compound.

EXAMPLE 181

A. Ethyl 4(S)-((t-Butyloxycarbonyl)amino)-5-cyclohexyl-2,2-difluoro-3(R,S)-hydroxypentanoate To a suspension of 1.2 g (17 mmol) of activated zinc in 5 ml of tetrahydrofuran under argon in a sonicating bath was added slowly a solution of 1.7 g (6.8 mmole) of Boc-L-cyclohexylalaninal and 2.34 ml (18.4 mmole) of ethyl bromodifluoroacetate in 30 ml of tetrahydrofuran. After complete addition, the solution was sonicated for an additional 30 min. The mixture was then added to 1M $KHSO_4$ and extracted with dichloromethane (3×100 ml), dried with $Na_2SO_4$, filtered and concentrated in vacuo. The residual oil was purified by silica gel column chromatography (15–30% ethyl acetate in hexane) to give 1.22 g (75%) of two diastereomers.

3(R) diastereomer: $^1H$ NMR ($CDCl_3$) δ 1.37 (t, 3H, J=7.0 Hz), 1.46 (S, 9H), 4.35 (q, 2H, J=7.0 Hz); m.p. 73°–74.5° C. Anal. ($C_{18}H_{31}NO_5F_2$) C,H,N.

3(S) diastereomer: $^1H$ NMR ($CDCl_3$) δ 1.37 (t, 3H, J=7.5 Hz), 1.45 (S, 9H), 4.31 (q, 2H, J=7.5 Hz); m.p. 115°–117° C.

Anal. ($C_{18}H_{31}NO_5F_2$) C,H,N.

B. 2-Oxazolidinone derivative of Ethyl 4-(S)-amino-5-cyclohexyl-2,2-difluoro-3(R)-hydroxypentanoate To 50 mg of the resultant 3(R) isomer of Example 181A was added 1 ml of 4M HCl in dioxane. The solution was stirred at ambient temperature for 30 min. The concentrated residue was dissolved in dichloromethane and treated with 0.1 ml of triethylamine and excess phosgene in toluene (10% solution). After stirring at ambient temperature for 1 hr, the crude product was purified by silica gel column chromatography (10% ethyl acetate in hexane) to give 32 mg of desired compound. $^1H$ NMR ($CDCl_3$) d 1.38 (t, 3H, J=7 Hz), 4.08 (m, 1H), 4.38 (q, 2H, J=7 Hz), 4.58 (ddd, 1H, J=4.5, 6.0, 15 Hz), 6.05 (br S, 1H). Anal. ($C_{14}H_{21}NO_4F_2$) C,H,N.

C. 4(S)-cyclohexylmethyl-5(R)-(4'(4',4'-difluoro-3'-oxo-2'-methyl-butyl))-2-oxazolidinone The hydrolysis of 2.5 g of the resultant compound of Example 181B by lithium hydroxide in aqueous methanol provided 2.3 g of the corresponding carboxylic acid. The acid was dissolved in 40 ml of tetrahydrofuran and cooled to −78° C. To the vigorously stirred solution was added 18 ml of isopropyl lithium solution in pentane (12.4% by wt.). After 30 min, the solution was slowly warmed to 0° C. and stirred for an additional 30 min. The reaction was carefully quenched with water and extracted with ethyl acetate (3×100 ml), dried and concentrated in vacuo. The crude product was purified by silica gel column chromatography (20% ethyl acetate in hexane) to give 1.36 g of desired product. $^1H$ NMR ($CDCl_3$) d 1.20 (t, 6H, J=6.3 Hz), 3.17 (d of heptet, 1H, J=1.8, 6.6 Hz), 4.06 (m, 1H), 4.62 (ddd, 1H, J=4.5, 6.0, 20.4 Hz), 5.63 (br S, 1H). Anal. ($C_{14}H_{23}NO_3F_2$) C,H,N.

D. Oxime derivative of 4(S)-cyclohexylmethyl-5(R)-(4'(4',4'-difluoro-3'oxo-2'-methyl-butyl))-2-oxazolidinone To a solution of 1.2 g of the resultant compound of Example 181C in 20 ml of ethanol was added 0.55 ml of pyridine and then 410 mg of hydroxyamine hydrochloride. The solution was heated to reflux for 5.5 hrs. The solvent was removed in vacuo and the crude product was purified by silica gel column chromatography (10% $EtOAc/CH_2Cl_2$) to give 1.12 g of desired product. Mass spectrum: $M^+=318$.

E. 4(S)-Cyclohexylmethyl-5(R)-(4'(4',4'-difluoro-3'-amino-2-methyl-butyl))2-oxazolidinone To a solution of 1.1 g of the resultant compound of Example 181D in 40 ml of ethanol was added 0.5 g of activated Raney nickel. The reaction mixture was stirred vigorously under a hydrogen atmosphere for 2 h. The catalyst was filtered off and the filtrate concentrated to a oily residue. The crude product was purified by silica gel column chromatography (10% $EtOAc/CH_2Cl_2$) to give 550 mg of desired product. Mass spectrum: $M^+=304$.

F. 3,6-Diamino-7-cyclohexyl-5-hydroxy-4,4-difluoro-2-methylheptane

To a solution of 150 mg of the resultant compound of Example 181E in 10 ml of dioxane and 10 ml of water was added 325 mg of barium hydroxide octahydrate. The reaction mixture was heated to reflux for 0.3 hrs. The suspension was cooled to ambient temperature and filtered and the solid was washed with ethyl acetate. The filtrate was washed with satd. brine and the aqueous phase was extracted with ethyl acetate (2×50 ml). The combined ethyl acetate solution was dried, filtered and concentrated to provide 130 mg of the desired product. Mass spectrum: $M^+=278$.

EXAMPLE 182

3,6-Bis-(Cbz-valinyl-amino)-7-cyclohexyl-5-hydroxy-4,4-difluoro-2-methylheptane

To a solution of 130 ml of the resultant compound of Example 181F in 10 ml of dimethylformamide was added at 0° C. successively 230 mg of Cbz-valine, 220 mg of N-ethyl-N'-(dimethylaminopropyl) carbodiimide hydrochloride, 400 mg of 1-hydroxybenzotriazole and 0.16 ml of triethylamine. The solution was stirred at 0° C. for 3 hrs and at ambient temperature for 12 hrs. The dimethylformamide was removed under vacuum and the residue was dissolved in 50 ml of ethyl acetate and washed with saturated. brine. The aqueous layer was extracted with ethyl acetate (2×50 ml) and dried, filtered and concentrated. The crude product was purified by silica gel column chromatography (2% MeOH/CH$_2$Cl$_2$) to give 220 mg of the desired compound (64%). Mass spectrum: $(M+H)^+=745$. $^1$H NMR (CDCl$_3$) d 0.78–0.90 (m, 18H), 3.60 (m, 1H), 3.85 (m, 1H), 4.00 (m, 1H), 4.40 (m, 1H), 4.55 (m, 1H), 5.03 (S, 4H), 5.78 (d, 1H), 7.25–7.36 (m, 10H), 7.69 (d, 1H).

EXAMPLE 183

3,6-Bis-(Cbz-valinyl-amino)-7-cyclohexyl-5-oxo-4,4-difluoro-2-methylheptane

A solution of oxidant was prepared as follows: to 392 mg of sulfuric acid was added 5 ml of acetic acid and 298 mg of sodium dichromate. To a solution of 150 mg of the resultant compound of Example 182 in 10 ml of acetic acid was added 2 ml of the oxidant. After stirring at ambient temperature for 1 hr, the acetic acid was removed under vacuum and the residue was dissolved in 50 ml of ethyl acetate and washed with 30 ml of water. The aqueous layer was extracted with ethyl acetate (2×40 ml) and the combined ethyl acetate solution was dried, filtered and concentrated. The crude product was purified by silica gel column chromatography (10% EtOAc/CH$_2$Cl$_2$) to give 120 mg of the desired compound (80%). Mass spectrum: $(M+H)^+=743$. $^1$H NMR (CDCl$_3$): d 0.85–0.98 (m, 18H), 3.90–4.02 (m, 2H), 460 (m, 1H), 5.35 (br d, 1H), 6.10 (br d, 1H), 6.20 (br d, 1H), 7.35 (m, 10H).

EXAMPLE 184

3,6-Bis-(Cbz-0-methyl-serinyl-amino)-7-cyclohexyl-5-hydroxy-4,4-difluoro-2-methylheptane To a solution of 90 mg of the resultant compound of Example 181F in 7 ml of dimethylformamide was added at 0° C. 164 mg of Cbz-0-methyl-serine, 160 mg of N-ethyl-N'-(dimethylaminopropyl) carbodiimide hydrochloride, 280 mg of 1-hydroxybenzotriazole and 0.11 ml of triethylamine. The solution was stirred at 0° C. for 3 hrs, then at ambient temperature for 19 hrs. The DMF was removed under vacuum and the residue was dissolved in 50 ml of ethyl acetate and washed with satd. NaHCO$_3$, then brine. The aqueous layer was extracted with EtOAc (2×50 ml) and dried, filtered and concentrated. The crude product was purified by silica gel column chromatography (82%) of the desired compound. Mass spectrum: $(M+H)^+=749$.

EXAMPLE 185

3,6-Bis-(Cbz-0-methylserinyl-amino)-7-cyclohexyl-5-oxo-4,4-difluoro-2-methylheptane The resultant compound of Example 184 (60 mg) was oxidized using the procedure of Example 183 to give 40 mg of desired product. Mass spectrum: $(M+H)=747$.

EXAMPLE 186

3,6-Bis-(acetyl-0-methylserinyl-amino)-7-cyclohexyl-5-hydroxy-4,4-difluoro-2-methylheptane A solution was 50 mg of the resultant compound of Example 185 and 20 mg of 10% Pd/C was stirred vigorously under a hydrogen atmosphere. After 30 minutes, the catalyst was filtered off and the filtrate concentrated to give a colorless oil, which was dissolved in 2 ml of CH$_2$Cl$_2$. The solution was cooled to 0° C., 0.03 ml of triethylamine and 0.01 ml of acetyl chloride were added. After 2 hrs, the solution was concentrated and the crude product purified by silica gel column chromatography (5% MeOH/CH$_2$Cl$_2$) to give 16 mg of the desired compound. Mass spectrum: $(M+H)^+=565$.

EXAMPLE 187

Glycine Ester of 2,4-Bis-(Cbz-valinyl-amino)-1,5-diphenyl-3-hydroxypentane Acetate Salt Using the procedure of Example 95 with the resultant compound of Example 70 provided the desired compound.

EXAMPLE 188

2,5-Di-(N-((t-butyloxy)carbonyl)amino)-3,4-dihydroxy-1,6-di-(4-thiazolyl)hexane

Using the procedures of Example 170A and Example 170B but replacing N-((t-butyloxy)carbonyl)-phenylalaninol with N-((t-butyloxy)carbonyl)-(4-thiazolyl)-alaninol provided the desired compound.

EXAMPLE 189

A. Benzyl 2-(1-morpholinyl)acetate

A solution of 1.5 ml (17 mmol) of morpholine in 40 ml of dichloromethane was treated with 1 ml (6.3 mmol) of benzyl 2-bromoacetate. The resulting solution was stirred at ambient temperature for 16 h. The resulting solution was filtered and concentrated in vacuo. The residue was purified by silica gel chromatography using 3:1 chloroform:ethyl acetate to provide 1.35 g (91%) of the desired compound. $^1$H NMR (CDCl$_3$) δ 2.59 (m, 4H), 3.27 (s, 2H), 3.77 (m, 4H), 5.17 (s, 2H), 7.3–7.4 (m, 5H).

B. 2-(1-Morpholinyl)acetic Acid

Using the procedure of Example 163B with the resultant compound of Example 189A provided the desired compound.

C. 2,5-Di-(N-((2-(1-morpholinyl)acetyl)-valinyl) amino-3,4-dihydroxy-1,6-diphenylhexane The resultant compound of Example 189B was coupled to the resultant compound of Example 173 using the coupling procedure of Example 55 provided, after silica gel chromatography using a gradient of 3–5% methanol in chloroform, the desired compound ($R_f$ 0.31, 10% methanol in chloroform).

EXAMPLE 190

A. Benzyl 2-(1-Imidazolyl)acetate

A solution of 1.4 g (21 mmol) of imidazole and 1.0 ml (6.3 mmol) of benzyl 2-bromoacetate in 40 ml of dichloromethane was stirred at ambient temperature for 16 h. The resulting solution was washed with water, dried over $Na_2SO_4$, and concentrated in vacuo. Silica gel chromotography of the residue using 5% methanol in chloroform provided 1.22 g (89%) of the desired compound as an oil. $^1H$ NMR ($CDCl_3$) δ 4.73 (s, 2H), 5.21 (s, 2 H), 6.96 (t, J=1 Hz, 1H), 7.11 (t, J=1 Hz, 1H), 7.36 (m, 5H), 7.51 (br s, 1H).

B. 2-(1-Imidazolyl)acetic Acid

The resultant compound of Example 190A was hydrogenolyzed according to the procedure of Example 163B except that water was added prior to filtration to solubilize the product. Removal of the solvent after filtration provided the desired compound.

C. 2,5-Di-(N-((2-(1-imidazolyl)acetyl)-valinyl-amino)-1,5-diphenyl-3,4-dihydroxypentane The resultant compound of Example 190B was coupled to the resultant compound of Example 173 using the carbodiimide coupling procedure described in Example 55 to give a crude mixture in which the product was soluble. The mixture was diluted with ethyl acetate, filtered, and the solid was washed sequentially with water and ethyl acetate. The residue was air-dried to provide the desired compound in 40% yield.

EXAMPLE 191

A. 1-(2-Bromohexanoyl)-4-methylpiperazine

Using the mixed anhydride procedure of Example 6F, 2-bromohexanoic acid was coupled to 1-methylpiperazine to provide the desired compound.

B. 2,5-Di-(N-((2-(4-methylpiperazin-1-carbonyl) pent-1-yl)amino)-3,4-dihydroxy-1,6-diphenylhexane Using the procedure of Example 159A but replacing the resultant compound of Example 116A with the resultant compound of Example 191A and replacing O-benzylhydroxylamine hydrochloride with the resultant compound of Example 171 provided the desired compound.

EXAMPLE 192

2,5-Di-(N-(2-methoxycarbonyl-3-phenylprop-1-yl) amino)-3,4-dihydroxy-1,6-diphenylhexane Using the procedure of Example 159A but replacing O-benzylhydroxylamine hydrochloride with the resultant compound of Example 171 provided the desired compound.

EXAMPLE 193

A. 4-(2-(Benzyloxycarbonyl)-3-methylprop-1-yl)-1,1-dioxo-1,4-thiazine

According to the method of Kawaguchi, et. al. (*Agric. Biol. Chem.* 1987, 51, 435), 3-sulfolene was ozonolyzed and aminated with L-valine benzyl ester p-toluenesulfonate to provide the desired compound.

B. 4-(2-Carboxy-3-methylprop-1-yl)-1,1-dioxo-1,4-thiazine

The resultant compound of Example 193A was hydrogenolyzed according to the procedure of Example 163B to provide the desired compound.

C. 2,5-Di-(N-(2-(1,1-dioxothiazin-4-yl)-3-methylbutanoyl)amino)-3,4-dihydroxy-1,6-diphenylhexane The resultant compound of Example 193B was coupled to the resultant compound of Example 171 using the coupling procedure described in Example 160D to provide the desired compound.

EXAMPLE 194

A. 4-(2-(Benzyloxycarbonyl)-3-methylprop-1-yl) morpholine

According to the method of Kawaguchi, et. al. (*Agric. Biol. Chem.* 1987, 51, 435), 2,5-dihydrofuran was ozonolyzed and aminated with L-valine benzyl ester p-toluenesulfonate to provide the desired compound.

B. 4-(2-Carboxy-3-methylprop-1-yl)morpholine

The resultant compound of Example 194A was hydrogenolyzed according to the procedure of Example 163B to provide the desired compound.

C. 2,5-Di-(N-(2-(morpholin-4-yl)-3-methylbutanoyl) amino)-3,4-dihydroxy-1,6-diphenylhexane The resultant compound of Example 194B was coupled to the resultant compound of Example 171 using the coupling procedure described in Example 160D to provide the desired compound.

EXAMPLE 195

2,5-Di-(2-(1,1-dioxothiazin-4-yl)-3,4-dihydroxy-1,6-diphenylhexane

According to the method of Kawaguchi, et. al. (*Agric. Biol. Chem.* 1987, 51, 435), 3-sulfolene was ozonolyzed and aminated with the resultant compound of Example 171 to provide the desired compound.

EXAMPLE 196

A. N, N-Bis-(Cbz-valinyl)-(2S, 3R, 4R, 5S)-1,2:5,6-diimino-3,4-O-isopropylidenehexanediol A solution of (2S,3R, 4R, 5S)-1,2:5,6-diimino-3,4-O-isopropylidenehexanediol (2.72 g, 12.7 mmol, Y. L. Merrer, et al, *Heterocycles*, 1987, 25, 541–548)) and 3.51 g (14 mmol) of N-Cbz-valine in 30 mL of dry THF was cooled in an ice bath. To the cooled solution was added 2.684 g (14 mmol) of 1-(3-dimethylaminopropyl)-3-ethylcarbodiimide hydrochloride, followed by 1.95 mL (14 mmol) of triethylamine. The reaction mixture was stirred overnight in the ice bath. The reaction temperature was 10° C. when the reaction mixture was diluted with ethyl acetate, washed with dilute aqueous sodium bicarbonate solution and brine and dried over anhydrous magnesium sulfate. The solution was filtered and concentrated under reduced pressure. The residue was purified by flash chromatography on a 5×30 cm silica gel column eluted with 50% ethyl acetate in hexane to give 1.20 g (26.3% yield) of the title compound; FAB MS M/Z: 651 (M+H)$^+$; $^1$H NMR (CDCl$_3$) δ 0.96 (d, 6H), 1.03 (d, 6H), 1.33 (s, 6H), 2.15–2.28 (m, 2H), 2.48 (d, 2H), 2.58 (d, 2H), 2.74 (br s, 2H), 3.89 (br s, 2H), 4.27 (dd, 2H), 5.09 (s, 4H), 7.30–7.40 (m, 10H).

Analysis calculated for C$_{35}$H$_{46}$N$_4$O$_8$: C, 64.62; H, 7.08; N, 8.62. Found: C, 64.35; H, 7.07; N, 8.41.

B. N,N-Bis-(Cbz-valinyl)-(2R, 3R, 4R, 5R)-1,6-bis(phenylthio)-2,5-diamino-3,4-O-isopropylidenehexanediol To a slurry of 22.5 mg (0.564 mmol) of 60% sodium hydride in 1 mL of THF cooled in an ice bath, was added 87 μL (0.846 mmol) of thiophenol. The mixture was stirred for 0.5 h and then a solution of 92 mg (0.141 mmol) of the resultant compound of Example 196A in 2.0 mL of DMF was added to the mixture at ambient temperature. The reaction mixture was stirred at ambient temperature overnight and then diluted with ethyl acetate and water. The aqueous mixture was extracted with ethyl acetate. The organic phase was concentrated under reduced pressure. The residue was purified by flash chromatography on a 1.0×30 cm silica gel column eluted with 40% ethyl acetate in hexane to give 55 mg (45% yield) of the title compound; FAB MS M/Z: 871 (M+H)$^+$; $^1$H NMR (CDCl$_3$) δ 0.89 (d, 6H), 0.96 (d, 6H), 1.32 (s, 6H), 2.10–2.21 (m, 2H), 2.88–2.98 (dd, 2H), 3.05–3.15 (dd, 2H), 3.95 (dd, 2H), 4.0 (br s, 2H), 4.11 (dd, 2H), 5.09 (s, 4H), 7.12–7.25 (m, 8H), 7.30–7.40 (m, 10H).

C. N,N-Bis-(Cbz-valinyl)-(2R, 3R, 4R, 5R)-1,6-bis(phenylthio)-2,5-diamino-3,4-hexanediol A solution of the resultant compound of Example 196B (55 mg, 0.063 mmol) in 2.0 mL of trifluoroacetic acid containing 0.2 mL of water at 0° C. was stirred for 4 h. The solvent was evaporated under reduced pressure and ethyl alcohol was added to the residue. The ethanol was removed under reduced pressure and the residue was purified by flash chromatography on a 1.0×35 cm silica gel column eluted with 40% methylene chloride in ethyl acetate to give 38 mg (73% yield)of the title compound; FAB MS M/Z: 831 (M+H)$^+$; $^1$H NMR (CDCl$_3$) δ 0.89 (d, 6H), 0.97 (d, 6H), 2.10–2.20 (m, 2H), 3.08–3.20 (m, 2H), 3.66 (br s, 2H), 3.74 (br s, 2H), 3.92 (dd, 2H), 5.11 (s, 4H), 7.12–7.29 (m, 8H), 7.30–7.40 (m, 12H). Analysis calculated for C$_{44}$H$_{54}$N$_4$O$_8$S$_2$: C, 63.61; H, 6.50; N, 6.75. Found: C, 63.61; H, 6.57; N, 6.69.

EXAMPLE 197

2,5-Di-(N-(Cbz-isoleucinyl)amino)-3,4dihydroxy-1,6-diphenylhexane

A mixture of 10 mg (0.033 mmol) of the resultant compound of Example 171 and 38.6 mg (0.10 mmol) of Cbz-isoleucine p-nitrophenyl ester in 0.2 ml of tetrahydrofuran was stirred at ambient temperature for 21 h. The resulting misture was diluted with 1 ml of tetrahydrofuran, treated with 0.5 ml of 3N NaOH, stirred for 45 min, extracted with chloroform, washed sequentially with 3N NaOH and saturated brine, dried over MgSO$_4$, and concentrated. The residue was purified on silica gel by eluting with 2% methanol in chloroform to provide 23 mg (86%) of the desired compound. Mass spectrum: (M+H)$^+$=795.

EXAMPLE 198

2,5-Di-(N-(Cbz-alaninyl)amino)-3,4-dihydroxy-1,6-diphenylhexane

Using the procedure of Example 197 but replacing Cbz-isoleucine p-nitrophenyl ester with Cbz-alaninyloxysuccinimide provided the desired compound. Mass spectrum: (M+H)$^+$=711.

EXAMPLE 199

2,5-Di-(N-(Cbz-phenylalaninyl)amino)-3,4-dihydroxy-1,6-diphenylhexane

Using the procedure of Example 197 but replacing Cbz-isoleucine p-nitrophenyl ester with Cbz-phenylalanine p-nitrophenyl ester provided the desired compound. Mass spectrum: (M+H)$^+$=863.

EXAMPLE 200

2,5-Di-(N-(Cbz-leucinyl)amino)-3,4-dihydroxy-1,6-diphenylhexane

Using the procedure of Example 197 but replacing Cbz-isoleucine p-nitrophenyl ester with Cbz-leucine p-nitrophenyl ester provided the desired compound. Mass spectrum: (M+H)$^+$=795.

EXAMPLE 201

A. N-((Benzyloxycarbonyl)methyl)-valine Methyl Ester

A solution of 2.12 g (12.6 mmol) of L-valine methyl ester hydrochloride, 2.0 ml (12.6 mmol) of benzyl bromoacetate, and 3.5 ml (31 mmol) of 4-methylmorpholine in 100 ml of dioxane was heated at reflux for 4 h. After being allowed to cool, the solution was concentrated in vacuo and partitioned between ether and water. The organic layer was dried over MgSO$_4$ and concentrated in vacuo. Chromatography on silica gel using 20% ethyl acetate in hexane provided 0.77 g (22%) of the desired compound as a colorless oil (R$_f$ 0.24, 20% ethyl acetate in hexane). $^1$H NMR δ 0.95 (d, J=7 Hz, 6H), 1.96 (br, 1 H), 1.98 (octet, J=7 Hz, 1H), 3.08 (d, J=6 Hz, 1H), 3.43 (AA',2H), 3.71 (s, 3H), 5.16 (s, 2H), 7.36 (m, 5 H).

B. N-(Carboxymethyl)-valine Methyl Ester

The resultant compound of Example 201A (0.7 g, 2.5 mmol) was hydrogenolyzed according to the procedure of Example to provide 0.49 g (100%) of the desired compound as a white solid.

C. N-((((4-Methyl)piperazinyl)carbonyl)methyl)-valine Methyl Ester

Using the carbodiimide coupling procedure of Example the resultant compound of Example 201B (466 mg, 2.46 mmol) was coupled to 1-methylmorpholine to provide, after chromatography on silica gel using 5% methanol in chloroform, 0.61 g (91%) of the desired compound as a colorless oil.

D. N-((((4-Methyl)piperazinyl)carbonyl)methyl)-valine

A solution of 0.59 g (2.2 mmol) of the resultant compound of Example 201C in 16 ml of dioxane was treated with 8.7 ml (4.4 mmol) of 0.5M aqueous lithium hydroxide. The resulting solution was stirred at ambient temperature for 16 h, treated with 4.4 ml of 1M aqueous HCl, and concentrated in vacuo to provide the crude desired compound.

E. 1,5-Diphenyl-3-hydroxy-2-(N-(Cbz-valinyl)amino-4-N-(((4-methyl)piperazinyl)carbonyl)methyl)-valinyl)amino-pentane The resultant compound of Example 201D (80 mg, 0.21 mmol) was coupled to the resultant compound of Example 69 (89 mg, 0.18 mmol) according to the procedure described in Example 55 to provide, after silica gel chromatography using 6% methanol in chloroform, the desired compound ($R_f$ 0.16, 7.5% methanol in chloroform) as a white solid, m.p. 74°–76° C. Mass spectrum: (M+H)$^+$=743.

Anal. Calcd. for $C_{42}H_{58}N_6O_6 \cdot 0.5H_2O$: C, 67.09; H, 7.91; N, 11.18. Found: C, 67.16; H, 7.86; N, 10.87.

EXAMPLE 202

A. Methyl 3-(4-Morpholinyl)propanoate

A solution of 4.9 ml (56 mmol) of morpholine in 50 ml of dichloromethane was treated dropwise with 5.0 ml (56 mmol) of methyl acrylate. The resulting solution was allowed to stand at ambient temperature for 3 days, after which it was concentrated in vacuo to an oil. Chromatography on silica gel using 0.5% methanol/2% isopropylamine in chloroform provided 9.54 g (99%) of the desired compound as a colorless liquid.

B. 3-(4-Morpholinyl)propanoic Acid

A solution of the resultant compound of Example 202A (8.35 g, 48.3 mmol) in 60 ml of dioxane was treated with 40 ml of water and 19.3 ml (58 mmol) of 3N aqueous NaOH. After being stirred for 4 h, the solution was treated with 58 ml (58 mmol) of 1N aqueous HCl and concentrated in vacuo to provide the crude desired compound.

C. (2S,3R,4R,5S)-3,4-Dihydroxy-2,5-di-(N-(N-(3(4-morpholinyl)propanoyl)-valinyl)-amino-1,6-diphenylhexane The resultant compound of Example 202B (0.64 mmol) was coupled to the resultant compound of Example 173 (0.214 mmol) according to the procedure described in Example 55 to provide, after silica gel chromatography using 5% methanol in chloroform, 101.5 mg (61%) of the desired compound ($R_f$ 0.17, 10% methanol in chloroform) as a white solid, m.p. 243°–245° C. (dec). Mass spectrum: (M+H)$^+$=781.

Anal. Calcd. for $C_{42}H_{64}N_6O_8 \cdot H_2O$: C, 63.14; H, 8.33; N, 10.52. Found: C, 63.20; H, 8.16; N, 11.21.

EXAMPLE 203

(2S,3R,4R,5S)-3,4-Dihydroxy-2,5-di-(N-(N-(3-pyridyl-acetyl))-valinyl)-amino-1,6-diphenylhexane 3-Pyridylacetic acid hydrochloride (117 mg, 0.68 mmol) was coupled to the resultant compound of Example 173 (113 mg, 0.226 mmol) according to the procedure described in Example 55 to provide, after silica gel chromatography using 10% methanol in chloroform, the desired compound ($R_f$ 0.16, 10% methanol in chloroform). Mass spectrum: (M+H)$^+$=737.

EXAMPLE 204

(2S,3S,4S,5S)- and (2S,3R,4S,5S)-2,5-Diamino-3,4-dihydroxy-1,6-diphenylhexane Using the procedure of Example 171 with the more mobile mixture of compounds of Example 170B provided a mixture of diamines which were separated by silica gel chromatography using 2% isopropylamine in chloroform containing sequential amounts of 1%, 2% and 5% methanol.

(2S,3S,4S,5S)-2,5-Diamino-3,4-dihydroxy-1,6-diphenylhexane $R_f$ 0.40 (5% methanol/2% isopropylamine in chloroform), $^1$H NMR (CDCl$_3$) δ 2.63 (dd, J=14, 11 Hz, 2 H), 2.85 (dd, J=14, 4 Hz, 2H), 3.60 (dt, J=11, 4 Hz, 2H), 3.92 (d, J=3 Hz, 2H), 7.2–7.4 (m, 10H).

(2S,3R,4S,5S)-2,5Diamino-3,4-dihydroxy-1,6-diphenylhexane $R_f$ 0.23 (5% methanol/2% isopropylamine in chloroform), m.p. 115°–119° C., $^1$H NMR (CDCl$_3$) δ 2.46 (dd, J=14, 9 Hz, 1H), 2.61 (dd, J=14, 11 Hz, 1H), 3.02 (td, J=9, 3 Hz, 1H), 3.19 (dd, J=14, 4 Hz, 1H), 3.35–3.4 (m, 2H), 3.51 (t, J=9 Hz, 1H), 3.76 (dd, J=9, 3 Hz, 1H), 7.2–7.4 (m, 10H).

EXAMPLE 205

(2S,3S,4S,5S)-2,5-Di-(N-((t-butyloxy)carbonyl)amino)-3,4-dihydroxy-1,6-diphenylhexane A solution of 15 mg (0.05 mmol) of (2S,3S,4S,5S)-2,5-diamino-3,4-dihydroxy-1,6-diphenylhexane in 0.5 ml of dichloromethane was treated with 24 mg (0.11 mmol) of di-t-butyldicarbonate and stirred at ambient temperature. After 16 h, the solution was concentrated in vacuo, and the residue was purified by silica gel chromatography using 30% ethyl acetate in hexane to provide 17 mg (68%) of the desired compound, m.p. 216°–218° C. $^1$H NMR δ 1.40 (s, 18H), 2.97 (dd, J=14, 5 Hz, 2H), 3.20 (dd, J=14, 5 Hz, 2H), 3.22 (m, 2H), 4.03 (m, 2H), 4.35 (d, J=5 Hz, H), 4.41 (d, J=9 Hz, 2H), 7.2–7.3 (m, 10H). Mass spectrum: (M+H)$^+$=501.

EXAMPLE 206

(2S,3R,4S,5S)-2,5-Di-(N-((t-butyloxy)carbonyl)amino)-3,4-dihydroxy-1,6-diphenylhexane Using the procedure of Example 205 with (2S, 3S, 4S, 5S)-2,5-diamino-3,4-dihydroxy-1,6-diphenylhexane provided the desired compound ($R_f$ 0.32, 30% ethyl acetate in hexane), as a white solid, m.p. 208°–212° C. $^1$H NMR δ 1.33 (s, 9H), 1.40 (s, 9H), 2.67 (m, 1H), 2.75–2.95 (m, 6H), 3.47 (m, 2H), 4.14 (m, 2H), 4.58 (m, 1H), 4.83 (br d, 1H), 4.93 (br d, 1H), 7.15–7.3 (m, 10H).

EXAMPLE 207

(2S,3R,4R,5S)-2,5-Di-(N-((4-morpholinyl)acetyl)amino)-3,4-dihydroxy-1,6-diphenylhexane The resultant compound of Example 189B (23.5 mg, 0.16 mmol) was coupled to 23.2 mg (0.077 mmol) of the resultant compound of Example 171 using the carbodiimide coupling procedure described in Example 55 to provide, after silica gel chromatography using 5% methanol in chloroform, the desired compound ($R_f$ 0.4, 10% methanol in chloroform) as a white solid, m.p. 172°–177° C., in 55% yield. Mass spectrum: (M+H)$^+$=555.

Anal. Calcd for $C_{30}H_{42}N_4O_6 \cdot 0.5H_2O$: C, 63.92; H, 7.69; N, 9.93. Found: C, 64.10; H, 7.58; N, 9.97.

EXAMPLE 208

(2S,3R,4R,5S)-2,5-Di-(N-((2-pyridinyl)carbonyl)amino)-3,4-dihydroxy-1,6-diphenylhexane Picolinic acid was coupled to the resultant compound of Example 171 using the carbodiimide coupling procedure described in Example 55 to provide, after chromatography on silica gel using 5% methanol in chloroform, 58 mg (60%) of the desired compound ($R_f$ 0.6, 10% methanol in chloroform) as a white solid, m.p. 179°–184° C. Mass spectrum: (M+H)$^+$=511.

EXAMPLE 209

(2S,3R,4S,5S)-2,5-Di-(N-(Cbz-valinyl)amino)-3,4-dihydroxy-1,6-diphenylhexane

Using the procedure of Example 172B with 25 mg (0.083 mmol) of (2S,3R, 4S,5S)-2,5-diamino-3,4-dihydroxy-1,6-diphenylhexane provided the desired compound (31%, $R_f$ 0.3, 5% methanol in chloroform) as a white solid, m.p. 230°–234° C. Mass spectrum: $(M+H)^+=767$.

EXAMPLE 210

(2S,3S,4S,5S)-2,5-Di-(N-(Cbz-valinyl)amino)-3,4-dihydroxy-1,6-diphenylhexane

Cbz-valine p-nitrophenyl ester was coupled to (2S,3S,4S,5S)-2,5-diamino-3,4-dihydroxy-1,6-diphenylhexane using the procedure of Example 172B to provide the desired compound ($R_f$ 0.42, 5% methanol in chloroform) as a white solid, m.p. 239°–242° C. in 86% yield.

EXAMPLE 211

(2S,3R,4R,5S)-2,5-Di-(N-((t-butyloxy)carbonyl)amino)-1,6-dicyclohexyl-3,4-dihydroxyhexane A mixture of 180 mg (0.36mmol) of (2S,3R, 4R, 5S)-2,5-di-(N-((t-butyloxy)carbonyl)amino)-3,4-dihydroxy-1,6-diphenylhexane and 180 mg of 5% rhodium on carbon in 50 ml of methanol was shaken under 4 atmospheres of hydrogen for 24 h. The resulting mixture was filtered and concentrated in vacuo. The residue was purified by silica gel chromatography using 5% ethyl acetate in hexane to provide 120 mg (65%) of the desired compound ($R_f$ 0.35, 30% ethyl acetate in hexane) as a white solid, m.p. 224°–226° C. Mass spectrum: $(M+H)^+=513$.

Anal. Calcd for $C_{28}H_{52}N_2O_6$: C, 65.69; H, 10.22; N, 5.46. Found: C, 65.27; H, 10.16; N, 5.40.

EXAMPLE 212

(2S,3S,4R,5S)-5-Amino-2-(N-((t-butyloxy)carbonyl)amino)-3,4-dihydroxy-1,6-diphenylhexane A solution of 200 mg (0.67 mmol) of (2S,3S,4R,5S)-2,5-diamino-3,4-dihydroxy-1,6-diphenylhexane in 10 ml of dichloromethane was treated with 174 mg (0.8 mmol) of di-t-butyldicarbonate. After being allowed to stir overnight at ambient temperature, the solution was concentrated, and the residue was purified by silica gel chromatography using 10% methanol in chloroform to provide 180 mg (56%) of the desired compound along with 80 mg (20%) of the resultant compound of Example 206.

EXAMPLE 213

(2S, 3S,4R,5S)-2-(N-((t-Butyloxy)carbonyl)amino)-5-(N-(Cbz-valinyl)amino)-3,4-dihydroxy-1,6-diphenylhexane The resultant compound of Example 212 was coupled to Cbz-valine using the carbodiimide coupling procedure of Example 55 to provide the desired compound ($R_f$ 0.48, 5% methanol in chloroform) as a white solid, m.p. 178°–182° C., in 88% yield. Mass spectrum: $(M+H)^+=634$.

Anal. Calcd for $C_{36}H_{47}N_3O_7 \cdot 0.5H_2O$: C, 67.27; H, 7.53; N, 6.54. Found: C, 67.18; H, 7.45; N, 6.71.

Anal. Calcd for $C_{30}H_{30}N_4O_4 \cdot 0.5H_2O$: C, 69.35; H, 6.01; N, 10.78. Found: C, 69.15; H, 5.93; N, 10.53.

EXAMPLE 214

A. N,N-Dimethylvaline

A mixture of 2.5 g of L-valine, 0.5 g of 10% palladium on carbon, in 93 ml of methanol and 7 ml of formalin was shaken under 4 atmospheres of hydrogen. After 24 h, the solution was filtered and concentrated in vacuo to provide the crude desired compound.

B. (2S,3R,4R,5S)-2,5-Bis-(N-(N,N-dimethylvalinyl)amino)-3,4-dihydroxy-1,6-diphenylhexane The resultant compound of Example 214A was coupled to the resultant compound of Example 171 using the carbodiimide coupling procedure of Example 55 to provide the desired compound (20%, $R_f$ 0.3, 10% methanol in chloroform) as a white solid, m.p. 200°–204° C. Mass spectrum: $(M+H)^+=555$.

EXAMPLE 215

A. N-((2-Pyridinyl)methoxycarbonyl)-valine p-Nitrophenyl Ester

A solution of 0.87 mmol of the resultant compound of Example 176A and 133 mg (0.96 mmol) of p-nitrophenol in 4 ml of tetrahydrofuran and 2 ml of dimethylformamide was treated with 183 mg (0.96 mmol) of N-ethyl-N'-(dimethylaminopropyl) carbodiimide hydrochloride and stirred at ambient temperature. After 4 h, the solvent was removed in vacuo, and the residue was partially purified by silica gel chromatography using 20% ethyl acetate in chloroform to give 0.34 mg of the desired compound contaminated with excess p-nitrophenol.

B. (2S,3R,4R,5S)-2,5-Di-(N-((2-pyridinyl)methoxycarbonyl)-valinyl-amino)-3,4-dihydroxy-1,6-diphenylhexane A solution of 230 mg of the crude resultant compound of Example 215A and 70 mg (0.23 mmol) of the resultant compound of Example 171 in 1 ml of 1:1 tetrahydrofuran/dimethylformamide was stirred at ambient temperature for 16 h. The resulting solution was treated with aqueous $NaHCO_3$, stirred for 1 h, diluted with 5% methanol in chloroform, washed with aqueous $NaHCO_3$ until the washes were colorless, dried over $Na_2SO_4$, and concentrated. Chromatography on silica gel using 2% methanol in chloroform followed by 5% methanol in chloroform provided 140.6 mg (80%) of the desired compound ($R_f$ 0.32, 10% methanol in chloroform) as a white solid, m.p. 196°–200° C. Mass spectrum: $(M+H)^+=769$.

Anal. Calcd for $C_{42}H_{52}N_6O_8$: C, 65.61; H, 6.82; N, 10.93. Found: C, 65.68; H, 6.93; N, 10.95.

EXAMPLE 216

(2S,3S,4S,5S)-2,5-Di-(N-((2-pyridinyl)methoxycarbonyl)-valinyl-amino)-3,4-dihydroxy-1,6-diphenylhexane Using the procedure of Example 215B but replacing the resultant compound of Example 171 with (2S,3S,4S,5S)-2,5-diamino-3,4-dihydroxy-1,6-diphenylhexane provided, after silica gel chromatography using a gradient of 2–5% methanol in chloroform, the desired compound ($R_f$ 0.32, 5% methanol in chloroform) as a white solid, m.p. 220°–223° C., in 79% yield. Mass spectrum: $(M+H)^+=769$.

Anal. Calcd for $C_{42}H_{52}N_6O_8 \cdot 0.5H_2O$: C, 64.85; H, 6.87; N, 10.80. Found: C, 64.69; H, 6.84; N, 10.63.

EXAMPLE 217

(2S,3R,4S,5S)-2,5-Di-(N-((2-pyridinyl)methoxycarbonyl)-valinyl-amino)-3,4-dihydroxy-1,6-diphenylhexane Using the procedure of Example 215B but replacing the resultant compound of Example 171 with (2S,3R,4S,5S)-2,5-diamino-3,4-dihydroxy-1,6-diphenylhexane provided, after silica gel chromatography using a gradient of 2–5% methanol in chloroform, the desired compound ($R_f$ 0.23, 5% methanol in chloroform) as a white solid, m.p. 238°–240° C., in 82% yield. Mass spectrum: (M+H)$^+$=769.

Anal. Calcd for $C_{42}H_{52}N_6O_8 \cdot 0.25H_2O$: C, 65.23; H, 6.84; N, 10.87. Found: C, 65.01; H, 6.89; N, 10.92.

EXAMPLE 218

A. 2-(N-(t-Butyloxycarbonyl)aminomethyl)pyridine

A solution of 21.2 g (97 mmol) of di-t-butyldicarbonate in 200 ml of dichloromethane was cooled to 0° C. and treated in portions with 10 ml (97 mmol) of 2-(aminomethyl)pyridine. After being allowed to warm to ambient temperature and stirred overnight, the resulting solution was diluted with 100 ml of dichloromethane, washed with three 100 ml portions of water, dried over $Na_2SO_4$, and concentrated in vacuo to provide 19.8 g (98%) of the desired compound ($R_f$ 0.28, 5% methanol in chloroform). $^1$H NMR (CCDl$_3$) δ 1.47 (s, 9H), 4.45 (d, J=6 Hz, 2H), 5.56 (br, 1H), 7.18 (m, 1H), 7.28 (d, J=8 Hz, 1H), 7.66 (td, J=7, 2 Hz, 1H), 8.53 (m, 1H).

B. 2-((N-(t-Butyloxycarbonyl)-N-methylamino)methyl)pyridine

A solution of 19.8 g (95 mmol) of the resultant compound of Example 218A in anhydrous tetrahydrofuran was cooled under $N_2$ atmosphere to 0° C. and treated with 4.95 g (124 mmol) of sodium hydride (60% dispersion in oil). The solution was stirred for 15 min, treated dropwise with 7.1 ml (114 mmol) of methyl iodide, stirred at ambient temperature for 2 h, and quenched cautiously with water. The resulting mixture was partitioned between ether and water, dried over $Na_2SO_4$, and concentrated. Chromatography on silica gel provided 14.9 g (70%) of the desired compound as a colorless oil.

C. 2-(N-methylamino)methyl)pyridine Dihydrochloride

The resultant compound of Example 218B (3.05 g, 13.7 mmol) was treated with 30 ml of 4N HCl in dioxane and heated at 40° C. for 0.5 h. The solvent was removed in vacuo to provide the crude desired compound as a light brown solid.

D. N-((N-methyl-N-((2-pyridinyl)methyl)amino)carbonyl)-valine Methyl Ester

A mixture of 1.61 g (7.2 mmol) of the resultant compound of Example 218C and 1.14 g (7.2 mmol) of the resultant compound of Example 160A in 40 ml of dichloromethane was treated with 2 ml (18 mmol) of 4-methylmorpholine. After being stirred for 2 h, the solution was partitioned between dichloromethane and water, dried over $Na_2SO_4$, and concentrated. Chromatography on silica gel using 2% methanol in chloroform provided 1.94 g (96%) of the desired compound ($R_f$ 0.32, 5% methanol in chloroform) as a colorless oil. $^1$H NMR (CCDl$_3$) δ 0.93 (d, J=7 Hz, 3H), 0.97 (d, J=7 Hz, 3H), 2.16 (m, 1H), 3.03 (s, 3H), 3.72 (s, 3H), 4.43 (dd, J=8, 5 Hz, 1H), 4.55 (s, 2H), 6.15 (br, 1 H), 7.22 (dd, J=8, 6 Hz, 1H), 7.28 (d, J=6 Hz, 1H), 7.69 (br t, 1H), 8.55 (d, J=5 Hz, 1H).

E. N-((N-methyl-N-((2-pyridinyl)methyl)amino)carbonyl)-valine P-Nitrophenyl Ester Using the procedures of Example 176A and Example 215A but replacing the resultant compound of Example 162A with the resultant compound of Example 218D provided the desired compound.

F. (2S,3R,4R,5S)-2,5-Di-(N-((N-Methyl-N-((2-pyridinyl)methyl)amino)carbonyl)-valinyl-amino)-3,4-dihydroxy-1,6-diphenylhexane Using the procedure of Example 215B but replacing the resultant compound of Example 215A with the resultant compound of Example 218E provided, after silica gel chromatography using a gradient of 2–5% methanol in chloroform, the desired compound ($R_f$ 0.28, 5% methanol in chloroform) as a white solid, m.p. 108°–111° C., in 85% yield. Mass spectrum: (M+H)$^+$=795.

Anal. Calcd for $C_{44}H_{58}N_8O_6 \cdot 1.25H_2O$: C, 64.65; H, 7.46; N, 13.71. Found: C, 64.35; H, 7.06; N, 13.58.

EXAMPLE 219

(2S,3S,4S,5S)-2,5-Di-(N-((N-Methyl-N-((2-pyridinyl)methyl)amino)carbonyl)-valinyl-amino)-3,4-dihydroxy-1,6-diphenylhexane Using the procedure of Example 215B but replacing the resultant compound of Example 215A with the resultant compound of Example 218E and replacing the resultant compound of Example 171 with (2S,3S,4S,5S)-2,5-diamino-3,4-dihydroxy-1,6-diphenylhexane provided, after silica gel chromatography using a gradient of 1–5% methanol in chloroform, the desired compound ($R_f$ 0.38, 5% methanol in chloroform) as a white solid, m.p. 110°–112° C., in 75% yield. Mass spectrum: (M+H)$^+$=795.

Anal. Calcd for $C_{44}H_{58}N_8O_6 \cdot H_2O$: C, 65.00; H, 7.44; N, 13.78. Found: C, 64.61; H, 7.21; N, 13.60.

EXAMPLE 220

(2S,3R,4S,5S)-2,5-Di-(N-((N-Methyl-N-((2-pyridinyl)methyl)amino)carbonyl)-valinyl-amino)-3,4-dihydroxy-1,6-diphenylhexane Using the procedure of Example 215B but replacing the resultant compound of Example 215A with the resultant compound of Example 218E and replacing the resultant compound of Example 171 with (2S,3R,4S,5S)-2,5-diamino-3,4-dihydroxy-1,6-diphenylhexane provided, after silica gel chromatography using a gradient of 1–2% methanol in chloroform, the desired compound ($R_f$ 0.36, 5% methanol in chloroform) as a white solid, m.p. 159°–162° C., in 79% yield. Mass spectrum: (M+H)$^+$=795.

Anal. Calcd for $C_{44}H_{58}N_6O_8$: C, 66.48; H, 7.35; N, 14.09. Found: C, 66.31; H, 7.43; N, 13.95.

EXAMPLE 221

2,4-Di-(N-((N-Methyl-N-((2-pyridinyl)methyl)amino)carbonyl)-valinyl-amino)-1,5-diphenyl-3-hydroxypentane The resultant compound of Example 218D was hydrolyzed according to the procedure of Example 176A and coupled to the resultant compound of Example 12 according to the carbodiimide coupling procedure described in Example 55 to provide, after silica gel chromatography using 3% methanol in chloroform, the desired compound (53%, $R_f$ 0.5, 10% methanol in chloroform) as a white solid, m.p. 70°–72° C. Mass spectrum: $(M+H)^+=765$.

EXAMPLE 222

(2S,3R4R,5S)-2,5-Di-(N-(((2-pyridinyl)carbonyl)-valinyl)amino)-3,4-dihydroxy-1,6-diphenylhexane Picolinic acid was coupled to the resultant compound of Example 173 using the carbodiimide coupling procedure described in Example 55 to provide after silica gel chromatography using a gradient of 5–10% methanol in chloroform, the desired compound ($R_f$ 0.16, 10% methanol in chloroform) as a white solid, m.p. 167°–171° C., in 61% yield. Mass spectrum: $(M+H)^+=709$.

Anal. Calcd for $C_{40}H_{48}N_6O_6$: C, 67.78; H, 6.83; N, 11.86. Found: C, 67.81; H, 6.59; N, 11.78.

EXAMPLE 223

A. 3-(3-Pyridinyl)propanoic Acid

A mixture of 3 g (20 mmol) of 3-(3-pyridinyl)acrylic acid and 0.3 g of 10% palladium on carbon in 150 ml of ethyl acetate was shaken under 4 atmospheres of hydrogen for 24 h. After filtration, the resulting solution was concentrated in vacuo to provide the desired compound.

B. (2S,3R,4R,5S)-2,5-Di-(N-(3-(3-pyridinyl)propanoyl)-valinyl-amino)-3,4-dihydroxy-1,6-diphenylhexane The resultant compound of Example 223A was coupled to the resultant compound of Example 173 using the carbodiimide coupling procedure described in Example 55 to provide after silica gel chromatography using a gradient of 5–10% methanol in chloroform, the desired compound ($R_f$ 0.1, 10% methanol in chloroform) as a white solid, m.p. 260°–263° C., in 37% yield. Mass spectrum: $(M+H)^+=765$.

EXAMPLE 224

(2S,3R,4R,5S)-3,4-Dihydroxy-2,5-di-(N-(N-(2-pyridyl-acetyl))-valinyl)-amino-1,6-diphenylhexane (2-Pyridyl)acetic acid was coupled to the resultant compound of Example 173 using the carbodiimide coupling procedure described in Example 55 to provide after silica gel chromatography using a gradient of 2–5% methanol in chloroform, the desired compound (41%, $R_f$ 0.21, 5% methanol in chloroform) as a white solid, m.p. 208°–213° C. Mass spectrum: $(M+H)^+=737$.

EXAMPLE 225

A. N-((4-Pyridinyl)methoxycarbonyl)-valine p-Nitrophenyl Ester

Using the procedures of Example 176A and Example 215A but replacing the resultant compound of Example 162A with the resultant compound of Example 160B provided the desired compound.

B. (2S,3R,4R,5S)-2,5-Di-(N-((4-pyridinyl)methoxycarbonyl)-valinyl-amino)-3,4-dihydroxy-1,6-diphenylhexane Using the procedure of Example 215B but replacing the resultant compound of Example 215A with the resultant compound of Example 225A provided, after silica gel chromatography using a gradient of 2–5% methanol in chloroform, the desired compound ($R_f$ 0.11, 10% methanol in chloroform) as a white solid, m.p. 221°–224° C. in 48% yield. Mass spectrum: $(M+H)^+=769$.

Anal. Calcd for $C_{42}H_{52}N_6O_8 \cdot 0.5H_2O$: C, 64.85; H, 6.87; N, 10.80. Found: C, 64.91; H, 6.81; N, 10.80.

EXAMPLE 226

(2S,3R,4S,5S)-2,5-Di-(N-(t-butylaminocarbonyl)amino)-3,4-dihydroxy-1,6-diphenylhexane A solution of 30 mg (0.1 mmol) of (2S,3R,4S,5S)-2,5-diamino-3,4-dihydroxy-1,6-diphenylhexane in 1 ml of dichloromethane was treated with 25 µl (0.22 mmol) of t-butylisocyanate. The resulting solution was stirred at ambient temperature, diluted with dichloromethane, washed with brine, dried over $Na_2SO_4$, and concentrated in vacuo. Silica gel chromatography using a gradient of 1–3% methanol in chloroform provided 49 mg (98%) of the desired compound ($R_f$ 0.4, 10% methanol in chloroform) as a white solid, m.p. 193°–196° C. Mass spectrum: $(M+H)^+=499$.

Anal. Calcd for $C_{28}H_{42}N_4O_4 \cdot H_2O$: C, 65.09; H, 8.58; N, 10.84. Found: C, 65.17; H, 8.21; N, 10.77.

EXAMPLE 227

(2S,3R,4S,5S)-2,5-Di-(N-(isopropylaminocarbonyl)amino)-3,4-dihydroxy-1,6-diphenylhexane Using the procedure of Example 226 but replacing t-butylisocyanate with isopropylisocyanate provided the desired compound ($R_f$ 0.24, 10% methanol in chloroform) as a white solid, m.p. 220°–222° C., in 81% yield. Mass spectrum: $(M+H)^+=471$.

Anal. Calcd for $C_{26}H_{38}N_4O_4 \cdot 0.25H_2O$: C, 65.73; H, 8.17; N, 11.79.

EXAMPLE 228

(2S,3S,4S,5S)-2,5-Di-(N-((4-pyridinyl)methoxycarbonyl)-valinyl-amino-3,4-dihydroxy-1,6-diphenylhexane Using the procedure of Example 215B but replacing the resultant compound of Example 215A with the resultant compound of Example 225A and replacing the resultant compound of Example 171 with (2S,3S,4S,5S)-2,5-diamino-3,4-dihydroxy-1,6-diphenylhexane provided, after silica gel chromatography using a gradient of 2–5% methanol in chloroform, the desired compound (35%, $R_f$ 0.25, 10% methanol in chloroform) as a white solid, m.p. 190°–193° C. Mass spectrum: $(M+H)^+=769$.

EXAMPLE 229

A. N-((3-Pyridinyl)methoxycarbonyl)-valine p-Nitrophenyl Ester

Using the procedures of Example 176A and Example 215A but replacing the resultant compound of Example 162A with the resultant compound of Example 161A provided the desired compound.

B. (2S,3S,4S,5S)-2,5-Di-(N-((3-pyridinyl)methoxycarbonyl)-valinyl-amino)-3,4-dihydroxy-1,6-diphenylhexane Using the procedure of Example 215B but replacing the resultant compound of Example 215A with the resultant compound of Example 229A and replacing the resultant compound of Example 171 with (2S,3S,4S,5S)-2,5-diamino-3,4-dihydroxy-1,6-diphenylhexane provided, after silica gel chromatography using a gradient of 5–10% methanol in chloroform, the desired compound ($R_f$ 0.31, 10% methanol in chloroform) as a white solid, m.p. 202°–207° C. Mass spectrum: (M+H)$^+$=769.

EXAMPLE 230

(2S,3R,4S,5S)-2,5-Di-(N-((3-pyridinyl) methoxycarbonyl)-valinyl-amino)-3,4-dihydroxy-1, 6-diphenylhexane Using the procedure of Example 215B but replacing the resultant compound of Example 215A with the resultant compound of Example 229A and replacing the resultant compound of Example 171 with (2S,3R, 4S,5S)-2,5-diamino-3,4-dihydroxy-1,6-diphenylhexane provided, after silica gel chromatography using a gradient of 2–5% methanol in chloroform, the desired compound (31%, $R_f$ 0.28, 10% methanol in chloroform) as a white solid, m.p. 212°–216° C. Mass spectrum: (M+H)$^+$=769.

EXAMPLE 231

(2S,3S,4R,5S)-2-(N-((t-Butyloxy)carbonyl)amino)-5-(N-((2-pyridinyl)methoxycarbonyl)-valinyl-amino)-3,4-dihydroxy-1,6-diphenylhexane Using the procedure of Example 215B but replacing the resultant compound of Example 171 with the resultant compound of Example 212 provided, after silica gel chromatography using a gradient of 0–2% methanol in chloroform, the desired compound ($R_f$ 0.57, 5% methanol in chloroform) as a white solid, m.p. 202°–204° C., in 61% yield. Mass spectrum: (M+H)$^+$=635.

EXAMPLE 232

(2S,3S,4R,5S)-2-Amino-5-(N-((3-pyridinyl) methoxycarbonyl)-valinyl-amino)-3,4-dihydroxy-1, 6-diphenylhexane The resultant compound of Example 231 (200 mg, 0.31 mmol) was treated with 20 ml of 4N HCl in dioxane. After being stirred at ambient temperature for 2 h, the solvent was removed in vacuo. The residue was partitioned between chloroform and aqueous NaHCO$_3$, dried over Na$_2$SO$_4$, and concentrated. Silica gel chromatography using a gradient of 2% methanol/2% isopropylamine in chloroform provided 140 mg (84%) of the desired compound.

EXAMPLE 233

(2S,3S,4R,5S)-2-(N-Succinylamino)-5-(N-((3-pyridinyl)methoxycarbonyl)-valinyl-amino)-3,4-dihydroxy-1,6-diphenylhexane A solution of 50 mg (0.93 mmol) of the resultant compound of Example 232 in 0.5 ml of dichloromethane was treated with 9.3 mg (0.93 mmol) of succinic anhydride. The resulting mixture was stirred overnight at ambient temperature and concentrated in vacuo to a solid which was washed with chloroform. The solvent was decanted to provide the desired compound ($R_f$ 0.91, 1:1:1:1 ethyl acetate/n-butanol/water/acetic acid) as a white solid. Mass spectrum: (M+H)$^+$=635.

EXAMPLE 234

A. N-(Chlorosulfonyl)-valine Methyl Ester

A suspension of 15.3 g (90 mmol) of L-valine methyl ester hydrochloride in 45 ml of acetonitrile was treated with 22 ml (270 mmol) of sulfuryl chloride and heated at reflux for 16 h. The resulting light yellow solution was allowed to cool and concentrated in vacuo to a viscous oil. The oil was treated two times with acetonitrile followed each time by concentration in vacuo. The crude desired product was thus obtained as a viscous oil.

B. N-((N-Methyl-N-((2-pyridinyl)methyl)amino) sulfonyl)-valine Methyl Ester

A mixture of 13.7 mmol of the resultant compound of Example 218C and 3.17 g (13.7 mmol) of the resultant compound of Example 234A in 100 ml of dichloromethane was cooled to 0° C. and treated with 6 ml of 4-methylmorpholine. The resulting solution stirred for 2 h, diluted with dichloromethane, washed with aqueous NaHCO$_3$, dried over Na$_2$SO$_4$, and concentrated in vacuo. Chromatography on silica gel using 30% ethyl acetate in chloroform provided 1.72 g (40%) of the desired compound as a colorless oil. $^1$H NMR (CCDl$_3$, major rotamer) δ 0.95 (d, J=7 Hz, 3H), 1.03 (d, J=7 Hz, 3H), 2.12 (m, 1H), 2.79 (s, 3H), 3.76 (s, 3H), 3.95 (dd, J=8, 4 Hz, 1H), 4.54 (AA',2 H), 6.40 (d, J=8 Hz, 1H), 7.26 (m, 1H), 7.35 (d, 6 Hz, 1H), 7.71 (br t, 1H), 8.59 (d, J=4 Hz, 1H). Mass spectrum: (M+H)$^+$=316.

C. N-((N-Methyl-N-((2-pyridinyl)methyl)amino) sulfonyl)-valine

A solution of 200 mg (0.63 mmol) of the resultant compound of Example 234B in 2.5 ml of dioxane was treated with 2.5 ml of 0.5M LiOH. After being stirred overnight at ambient temperature, the solution was concentrated in vacuo at 30° C., diluted with dioxane and water, neutralized with 1M HCl, and concentrated in vacuo to provide the crude desired compound.

D. (2S,3R,4R,5S)-2,5-Di-(N-((N-Methyl-N-((2-pyridinyl)methyl)amino)sulfonyl)-valinyl-amino)-3, 4-dihydroxy-1,6-diphenylhexane The resultant compound of Example 234C was coupled to the resultant compound of Example 171 using the carbodiimide coupling procedure of Example 55 to provide, after silica gel chromatography using 2% methanol in chloroform, the desired compound (45%, $R_f$ 0.5, 10% methanol in chloroform) as a white solid, m.p. 85°–89° C. Mass spectrum: (M+H)$^+$=867.

Anal. Calcd for C$_{42}$H$_{58}$N$_8$O$_8$S$_2$·H$_2$O: C, 57.00; H, 6.83; N, 12.66. Found: C, 56.78; H, 6.56; N, 12.45.

EXAMPLE 235

A. (4S)4-Benzyl-3-(3-methylbutanoyl)oxazolidine-2-one

Using the procedure of Example 100A but replacing 4-(2-propyl)-oxazolidine-2-one with 4-benzyloxazolidine-2-one and replacing 4-methylpentanoyl chloride with isovaleryl chloride provided the desired compound.

B. (4S,2'S)-3-(2-(t-Butyloxycarbonyl)methyl-4-methylbutanoyl)-4-benzyloxazolidine-2-one Using the procedure of Example 100B with the resultant compound of Example 235A provided, after silica gel chromatography using 15% ethyl acetate in hexane followed by dichloromethane, the desired compound ($R_f$ 0.35, 20% ethyl acetate in hexane) in 88% yield.

C. Benzyl (2S)-2-(t-Butyloxycarbonyl)methyl-4-methylbutanoate

Using the procedure of Example 100C with the resultant compound of Example 235B provided, after silica gel chromatography using 6% ethyl acetate in hexane, the desired compound ($R_f$ 0.43, 10% ethyl acetate in hexane) in 60% yield.

D. Benzyl (2S)-2-Carboxymethyl-4-methylbutanoate

Using the procedure of Example 100D with the resultant compound of Example 235C provided the desired compound as a crude colorless oil.

E. Benzyl (2S)-2-(((N-Methyl-N-((2-pyridinyl)methyl)amino)carbonyl)methyl)-4-methylbutanoate The resultant compound of Example 235D was coupled to the resultant compound of Example 218C using the mixed anhydride coupling method described in Example 6F to provide, after silica gel chromatography using 60% ethyl acetate in chloroform, the desired compound ($R_f$ 0.19, 60% ethyl acetate in chloroform) in 73% yield.

F. (2S)-2-(((N-Methyl-N-((2-pyridinyl)methyl)amino)-carbonyl)methyl)-4-methylbutanoic Acid The resultant compound of Example 235E was hydrogenolyzed according to the procedure described in Example 71C to provide the desired compound.

G. (2S,3R,4R,5S,2'S,2"S)-2,5-Di-(2-(((N-methyl-N-((2-pyridinyl)methyl)amino)carbonyl)methyl)-4-methylbutanoyl-amino)-3,4-dihydroxy-1,6-diphenylhexane The resultant compound of Example 235F was coupled to the resultant compound of Example 171 using the carbodiimide coupling procedure of Example 55 to provide, after silica gel chromatography using 5% methanol in chloroform, the desired compound in 42% yield, m.p. 169°–170° C. Mass spectrum: (M+H)$^+$=793.

Anal. Calcd for $C_{46}H_{60}N_6O_6 \cdot 0.5H_2O$: C, 68.89; H, 7.67; N, 10.48. Found: C, 68.85; H, 7.80; N, 10.16.

EXAMPLE 236

Ethyl 3-(2-Pyridinyl)acrylate

A suspension of 0.43 g (10.7 mmol) of sodium hydride (60% dispersion in oil) in 60 ml of anhydrous tetrahydrofuran was cooled to 0° C. and treated with 2.1 ml (10.5 mmol) of triethylphosphonoacetate. The resulting solution was stirred for 10 min, treated with 1.0 ml (10.5 mmol) of pyridine-2-carboxaldehyde, heated at reflux for 2 h, and stirred overnight at ambient temperature. The resulting mixture was partitioned between ether and aqueous ammonium chloride, washed sequentially with water and saturated brine, dried over $MgSO_4$, and concentrated in vacuo. Chromatography on silica gel using 25% ethyl acetate in hexane provided 1.54 g (83%) of the desired compound as a colorless liquid. $^1$H NMR (CDCl$_3$) δ 1.34 (t, J=7 Hz, 3H), 4.28 (q, J=7 Hz, 2H), 6.92 (d, J=16 Hz, 1H), 7.27 (ddd, J=8, 5, 1 Hz, 1H), 7.43 (d, J=8 Hz, 1H), 7.72 (m, 1H), 8.65 (m, 1H).

B. 3(2-Pyridinyl)acrylic Acid

The resultant compound of Example 236A was hydrolyzed according to the procedure of Example 176A to provide the desired compound.

C. (2S,3R,4R,5S)-2,5-Di-(N-(3-(2-pyridinyl)propenoyl)-valinyl-amino)-3,4-dihydroxy-1,6-diphenylhexane Using the procedures of Example 223A and Example 223B but replacing 3-(3-pyridinyl)acrylic acid with the resultant compound of Example 236B provided the desired compound.

EXAMPLE 237

(2S,3R,4R,5S)-2,5-Di-(N-(3-(2-pyridinyl)propanoyl)-valinyl-amino)3,4-dihydroxy-1,6-diphenylhexane Using the procedures of Example 223A and Example 223B but replacing 3-(3-pyridinyl)acrylic acid with 3-(2-pyridinyl)acrylic acid provided the desired compound ($R_f$ 0.21, 10% methanol in chloroform). Mass spectrum: (M+H)$^+$=765.

EXAMPLE 238

2,4-Di-(N-((2-(4-morpholinyl)ethyloxy)carbonyl)-valinyl-amino)-1,5-diphenyl-3-hydroxypentane The resultant compound of Example 165B was coupled to the resultant compound of Example 12 using the carbodiimide coupling procedure of Example 160D to provide, after silica gel chromatography using 3% methanol in chloroform, the desired compound ($R_f$ 0.6, 10% methanol in chloroform) in 66% yield as a white solid, m.p. 122°–123° C. Mass spectrum: (M+H)$^+$=783.

EXAMPLE 239

2-(Boc-valinyl-amino)-4-(Cbz-valinyl-amino)-1,5-diphenyl-3-hydroxypentane

Boc-valine was coupled to the resultant compound of Example 69 using the carbodiimide coupling procedure of Example 55 to provide, after silica gel chromatography using 3% methanol in chloroform, the desired compound (82%, $R_f$ 0.7, 10% methanol in chloroform) as a white solid, m.p. 184°–184° C. Mass spectrum: (M+H)$^+$=703.

Anal. Calcd for $C_{40}H_{54}N_4O_7 \cdot 0.5H_2O$: C, 67.49; H, 7.79; N, 7.87. Found: C, 67.79; H, 7.63; N, 7.91.

EXAMPLE 240

4-(cbz-valinyl-amino)-amino-2-(valinyl-amino)-1,5-diphenyl-3-hydroxypentane

Using the procedure of Example 12 with the resultant compound of Example 239 provided a crude hydrochloride salt which was partitioned between chloroform and aqueous NaHCO$_3$, dried over Na$_2$SO$_4$, and concentrated. Chromatography of the residue on silica gel using 3% methanol in chloroform provided in 89% yield the desired compound ($R_f$ 0.5, 10% methanol in chloroform) as a white solid, m.p. 126°–127° C. Mass spectrum: (M+H)$^+$=603.

Anal. Calcd for $C_{35}H_{46}N_4O_5 \cdot 1.5H_2O$: C, 66.75; H, 7.84; N, 8.90. Found: C, 66.88; H, 7.25; N, 8.79.

EXAMPLE 241

A. N-((2-Thiazolyl)methoxycarbonyl)-valine Methyl Ester

Using the procedure of Example 160B but replacing pyridine-4-methanol with 2-(hydroxymethyl)thiazole (Dondoni, et. al., *Synthesis*, 1987, 998; *Tetrahedron Lett.* 1983, 24, 2901) provided, after silica gel chromatography using 3% methanol in chloroform, the desired compound in 74% yield. Mass spectrum: (M+H)$^+$=273.

B. 2,4-Di-(N-((2-thiazolyl)methoxycarbonyl)-valinyl-amino)-1,5-diphenyl-3-hydroxypentane The resultant compound of Example 241A was hydrolyzed according to the procedure of Example 176A and coupled to the resultant compound of Example 12 according to the carbodiimide coupling procedure of Example 55 to provide, after silica gel chromatography using 3% methanol in chloroform, the desired compound (72%, $R_f$ 0.7, 10% methanol in chloroform) as a white solid, m.p. 92°–93° C. Mass spectrum: $(M+H)^+=751$.

Anal. Calcd for $C_{37}H_{46}N_6O_7S$: C, 59.18; H, 6.18; N, 11.20. Found: C, 60.42; H, 6.51; N, 10.61.

EXAMPLE 242

4-(Cbz-valinyl-amino)-2-(N-((2-(1-imidazolyl) acetyl)-valinyl-amino)-1,5-diphenyl-3-hydroxypentane The resultant compound of Example 190B was coupled to the resultant compound of Example 240 using the carbodiimide coupling procedure of Example 55 to provide, after silica gel chromatography using 3% methanol in chloroform, the desired compound (70%, $R_f$ 0.3, 10% methanol in chloroform). Mass spectrum: $(M+H)^+=711$.

EXAMPLE 243

4-(Cbz-valinyl-amino)-2(N-((2-(1-morphoninyl) acetyl-valinyl-amino)-1,5-diphenyl-3-hydroxypentane The resultant compound of Example 189B was coupled to the resultant compound of Example 240 using the carbodiimide coupling procedure of Example 55 to provide, after silica gel chromatography using 3% methanol in chloroform, the desired compound (67%, $R_f$ 0.5, 10% methanol in chloroform). Mass spectrum: $(M+H)^+=730$.

EXAMPLE 244

4-(Cbz-valinyl-amino)-2-(N-((N-((3-pyridinyl) methyl)amino)-carbonyl)-valinyl-amino)-1,5-diphenyl-3-hydroxypentane A solution of 3-(aminomethyl)pyridine (12 µl, 0.11 mmol) in 0.5 ml of nitromethane was cooled to –20° C. and treated with 0.23 ml (0.12 mmol) of a 0.5M solution of carbonyl bis(N-methyl)imidazole triflate (Rappoport, et. al., *J. Am. Chem. Soc.* 1989, 111, 6856) in nitromethane. After 30 min, the solution was treated with a solution of 50 mg (0.08 mmol) of the resultant compound of Example 240 in 1.0 ml of dimethylformamide and 26 µL (0.24 mmol) of 4-methylmorpholine. The resulting solution was stirred at 0° C. for 1 h, concentrated in vacuo, partitioned between chloroform and aqueous $NaHCO_3$, dried over $Na_2SO_4$, and concentrated. The residue was purified by silica gel chromatography using 3% methanol in chloroform to provide 40 mg (65%) of the desired compound ($R_f$ 0.4, 10% methanol in chloroform) as a white solid, m.p. 205°–206° C. Mass spectrum: $(M+H)^+=737$.

EXAMPLE 245

2,4-Di-(N-((4-pyridinyl)carbonyl)-valinyl-amino)-1,5-diphenyl-3-hydroxypentane

Using the procedure of Example 163A but replacing nicotinyl chloride hydrochloride with isonicotinyl chloride hydrochloride and replacing valine benzyl ester p-toluenesulfonate with the resultant compound of Example 140 provided, after silica gel chromatography using 5% methanol in chloroform, the desired compound (90%, $R_f$ 0.3, 10% methanol in chloroform) as a white solid, m.p. 256°–258° C. Mass spectrum: $(M+H)^+=679$.

EXAMPLE 246

2,4-Di-(N-(3-pyridinyl)propanoyl)-valinyl-amino)-1,5-diphenyl-3-hydroxypentane

The resultant compound of Example 223A was coupled to the resultant compound of Example 140 using the carbodiimide coupling procedure described in Example 55 to provide after silica gel chromatography using 3% methanol in chloroform, the desired compound (75%, $R_f$ 0.2, 10% methanol in chloroform) as a white solid, 234°–235° C. Mass spectrum: $(M+H)^+=735$.

EXAMPLE 247

(2S,3R,4R,5S)-2,5-Di-(N-((3-pyridinyl) methoxycarbonyl)-valinyl-amino)-3,4-dihydroxy-1,6-diphenylhexane Using the procedure of Example 160D, the resultant compound of Example 161B was coupled to the resultant compound of Example 171 to provide, after silica gel chromatography using 5% methanol in chloroform, the desired compound ($R_f$ 0.25, 10% methanol in chloroform) as a white solid, m.p. 207°–208° C., in 32% yield. Mass spectrum: $(M+H)^+=769$.

Anal. Calcd for $C_{42}H_{52}N_6O_8 \cdot 1.25H_2O$: C, 63.74; H, 6.94; N, 10.62. Found: C, 63.70; H, 6.70; N, 10.54.

EXAMPLE 248

(2S,3R,4S,5S)-2,5-Di-(N-((2-(4-morpholinyl) ethyloxy)-carbonyl)-valinyl-amino)-3,4-dihydroxy-1,6-diphenylhexane The resultant compound of Example 165B was coupled to the resultant compound of Example 171 using the carbodiimide coupling procedure of Example 160D to provide, after silica gel chromatography using 5% methanol in chloroform, the desired compound ($R_f$ 0.21, 10% methanol in chloroform) as a white solid, m.p. 227°–230° C. (dec) in 47% yield. Mass spectrum: $(M+H)^+=813$.

Anal. Calcd for $C_{42}H_{64}N_6O_{10} \cdot 1.25H_2O$: C, 60.38; H, 8.02; N, 10.06. Found: C, 60.21; H, 7.78; N, 10.43.

EXAMPLE 249

(2S,3S,4R,5S)-2-(N-((t-Butyloxy)carbonyl)amino)-5-(N-((3-pyridinyl)methoxycarbonyl)-valinyl-amino)-3,4-dihydroxy-1,6-diphenylhexane Using the procedure of Example 160D, the resultant compound of Example 161B was coupled to the resultant compound of Example 212 to provide, after silica gel chromatography using 3% methanol in chloroform, the desired compound ($R_f$ 0.21, 5% methanol in chloroform) as a white solid, m.p. 175°–178° C., in 66% yield. Mass spectrum: $(M+H)^+=635$.

Anal. Calcd for $C_{35}H_{46}N_4O_2 \cdot 0.75H_2O$: C, 64.65; H, 7.38; N, 8.64. Found: C, 64.61; H, 7.16; N, 8.80.

EXAMPLE 250

Bis-(2-(N-(Cbz-valinyl)amino)-3-phenylpropyl) sulfone

The resultant compound of Example 155B was deprotected according to the procedure of Example 12 and coupled to Cbz-valine according to the procedure of Example 55. The crude mixture was diluted with ethyl acetate, washed sequentially with aqueous citric acid, water, aqueous $NaHCO_3$, and water. The solid in the organic layer was filtered, washed with ethyl acetate, and air-dried to a fine white powder, m.p. 259°–260° C. (dec) (67% yield). Mass spectrum: $(M+H)^+$=799.

Anal. Calcd for $C_{44}H_{54}N_4O_8S \cdot H_2O$: C, 64.69; H, 6.91; N, 6.86. Found: C, 64.42; H, 6.93; N, 7.51.

EXAMPLE 251

(2S,3R,4S,5S)-2,5-Di-(N-((N-Methyl-N-((2-pyridinyl)methyl)amino)sulfonyl)-valinyl-amino)-3,4-dihydroxy-1,6-diphenylhexane The resultant compound of Example 234C was coupled to (2S,3R,4S,5S)-2,5-diamino-3,4-dihydroxy-1,6-diphenylhexane using the carbodiimide coupling procedure of Example 55 to provide, after silica gel chromatography, the desired compound ($R_f$ 0.65, 10% methanol in chloroform) as a white solid, m.p. 91°–93° C. Mass spectrum: $(M+H)^+$=867.

Anal. Calcd for $C_{42}H_{58}N_8O_8S_2 \cdot H_2O$: C, 57.00; H, 6.83; N, 12.66. Found: C, 67.26; H, 8.30; N, 4.98.

EXAMPLE 252

(2S,3S,4S,5S)-2,5-Di-(N-((N-methyl-N-((2-pyridinyl)methyl)amino)sulfonyl)-valinyl-amino)-3,4-dihydroxy-1,6-diphenylhexane The resultant compound of Example 234C was coupled to (2S,3S,4S,5S)-2,5-diamino-3,4-dihydroxy-1,6-diphenylhexane using the carbodiimide coupling procedure of Example 55 to provide, after silica gel chromatography, the desired compound ($R_f$ 0.54, 10% methanol in chloroform) as a white solid, m.p. 75°–77° C. Mass spectrum: $(M+H)^+$=867.

EXAMPLE 253

(2S,3S,4S,5S,2'S,2"S)-2,5-Di-((2-hydroxy-3-methylpentanoyl)-amino)-3,4-dihydroxy-1,6-diphenylhexane L-2-Hydroxy-3-methylvaleric acid was coupled to the resultant compound of Example 171 using the diimide coupling procedure described in Example 55 to provide the desired compound ($R_f$ 0.23, 10% methanol in chloroform) as a white solid, m.p.226°–230° C.

Anal. Calcd for $C_{30}H_{44}N_2O_6 \cdot 0.5H_2O$: C, 67.01; H, 8.44; N, 5.21. Found: C, 67.26; N, 8.30; N, 4.98.

EXAMPLE 254

2-(N-(((1-Methyl)piperidin-3-yl)methoxycarbonyl)-valinyl-amino)-4-(Cbz-valinyl-amino)-1,5-diphenyl-3-hydroxypentane Using the procedures of Example 165 but replacing 4-(2-hydroxyethyl)morpholine with 3-(hydroxymethyl)-1-methylpiperidine provided the desired compound ($R_f$ 0.30, 10% methanol in chloroform) as a white solid, m.p. 162–163. Mass spectrum: $(M+H)^+$=758.

Anal. Calcd for $C_{43}H_{59}N_5O_7 \cdot 0.5H_2O$: C, 67.34; H, 7.88; N, 9.13. Found: C, 67.40; H, 8.03; N, 8.69.

EXAMPLE 255

2-(N-(((1-Methyl)piperidin-2-yl)methoxycarbonyl)-valinyl-amino)-4-(Cbz-valinyl-amino)-1,5-diphenyl-3-hydroxypentane Using the procedures of Example 165 but replacing 4-(2-hydroxyethyl) morpholine with 2-(hydroxymethyl)-1-methylpiperidine provided the desired compound ($R_f$ 0.40, 10% methanol in chloroform) as a white solid, m.p. 160–161. Mass spectrum: $(M+H)^+$=758.

Anal. Calcd for $C_{43}H_{59}N_5O_7 \cdot 0.5H_2O$: C, 67.34; H, 7.88; N, 9.13. Found: C, 67.15; H, 7.77; N, 8.91.

EXAMPLE 256

2,4-Di-(N-((2-(1-imidazolyl)acetyl)-valinyl-amino)-1,5-diphenyl-3-hydroxypentane Using the procedure of Example 190C but replacing the resultant compound of Example 173 with the resultant compound of Example 140 provided the desired compound as a white solid, m.p. >260. Mass spectrum: $(M+H)^+$=685.

Anal. Calcd for $C_{37}H_{48}N_8O_4 \cdot 2H_2O$: C, 61.65; H, 7.27; N, 15.54. Found: C, 60.47; H, 6.70; N, 15.30.

EXAMPLE 257

A. 2-(t-Butyloxycarbonyl)methyl-3-methylbutanoic Acid

The resultant compound of Example 235B was hydroyzed according to the procedure of Example 6D except that excess 30% hydrogen peroxide was included in the reaction mixture to provide the crude desired compound.

B. (2S,3S,4R,5S)-2-(N-(2-(t-Butyloxycarbonyl)methyl-3-methylbutanoyl)amino)-5-(N-((3-pyridinyl)methoxycarbonyl)-valinyl-amino)-3,4-dihydroxy-1,6-diphenylhexane The resultant compound of Example 257A was coupled to the resultant compound of Example 232 using the carbodiimide coupling procedure of Example 55 to provide, after silica gel chromatography using a gradient of 1–5% methanol in chloroform, the desired compound in 22% yield.

B. (2S,3S,4R,5S)-2-(N-(2-Carboxymethyl-3-methylbutanoyl)amino)-5-(N-((3-pyridinyl)methoxycarbonyl)-valinyl-amino)-3,4-dihydroxy-1,6-diphenylhexane Trifluoroacetate Salt The resultant compound of Example 257B (45 mg) was treated with 1.5 ml of 2:1 dichloromethane/trifluoroacetic acid. After 4 h at ambient temperature, the solution was concentrated in vacuo to provide 28 mg (55%) of the desired compound as an off-white solid, m.p. 208°–210° C.

EXAMPLE 258

2,4-Di-(N-(3-(2-pyridinyl)propanoyl)-valinyl-amino)-1,5-diphenyl-3-hydroxypentane Using the procedures of Example 223A and Example 223B but replacing 3-(3-pyridinyl)acrylic acid with 3-(2-pyridinyl)acrylic acid and replacing the resultant compound of Example 173 with the resultant compound of Example 140 provided, after silica gel chromatography using 3% methanol in chloroform, the desired compound (35%, $R_f$ 0.6, 10% methanol in chloroform) as a white solid, m.p. 216°–218° C. Mass spectrum: $(M+H)^+$=735

EXAMPLE 259

2,4-Di-(N-((N-benzylamino)carbonyl)-valinyl-amino)-1,5-diphenyl-3-hydroxypentane Using the procedure of Example 226 but replacing (2S,3R,4S,5S)-2,5-diamino-3,4-dihydroxy-1,6-diphenylhexane with the resultant compound of Example 140 and replacing t-butylisocyanate with benzylisocyanate provided, after silica gel chromatography using 3% methanol in chloroform, the desired compound (64%, $R_f$ 0.7, 10% methanol in chloroform) as a white solid, m.p. 238°–238.5° C. Mass spectrum: (M+H)$^+$=735

EXAMPLE 260

2,4-Di-(N-((N-((2-pyridinyl)methyl)amino)carbonyl)-valinyl-amino)-1,5-diphenyl-3-hydroxypentane A solution of 34 mg of triphosgene in 2 ml of tetrahydrofuran was cooled under $N_2$ atmosphere to −78° C. and treated over a period of 2 min with a precooled (−78° C.) solution of 80 mg of the resultant compound of Example 140 and 40 μl of 4-methylmorpholine in 1 ml of tetrahydrofuran. After 30 min, the solution was treated with a solution of 37 mg of 2-(aminomethyl)pyridine and 40 μl of 4-methylmorpholine in 1 ml of tetrahydrofuran. The resulting solution was allowed to warm to −10° C. over a 2 hour period, after which it was concentrated in vacuo. Silica gel chromatography of the residue using a gradient of 3% methanol in chloroform-4.5% methanol/4.5% isopropylamine in chloroform provided 80 mg (64%) of the desired compound ($R_f$ 0.46, 4.5% methanol/4% isopropylamine in chloroform) as a white solid, m.p. 198°–199° C. Mass spectrum: (M+H)$^+$=737.

EXAMPLE 261

2,4-Di-(N-((N-((3-pyridinyl)methyl)amino)carbonyl)-valinyl-amino)-1,5-diphenyl-3-hydroxypentane Using the procedure of Example 260 but replacing 2-(aminomethyl)pyridine with 3-(aminomethyl)pyridine provided, after silica gel chromatography using a gradient of 3% methanol in chloroform-4.5% methanol/4.5% isopropylamine in chloroform a 60% yield of the desired compound ($R_f$ 0.3, 4.5% methanol/4% isopropylamine in chloroform) as a white solid, m.p. 238°–239° C. Mass spectrum: (M+H)$^+$ =737.

Anal. Calcd for $C_{42}H_{52}N_6O_6 \cdot H_2O$: C, 66.82; H, 7.21; N, 11.13. Found: C, 67.07; H, 6.98; N, 11.12.

EXAMPLE 262

(2S,3S,4S,5S,2'S,2"S)-2,5-Di-((2-((methoxy)-methoxy)-3-methylpentanoyl)-amino)-3,4-dihydroxy-1,6-diphenylhexane Using the procedure of Example 253 but replacing L-2-hydroxy-3-methylvaleric acid with L-2-((methoxy)-methoxy)-3-methylvaleric acid provided, after silica gel chromatography using 20% ethyl acetate in hexane, the desired compound (88%, $R_f$ 0.18, 20% ethyl acetate in hexane) as a white solid, m.p. 190°–194° C. Mass spectrum: (M+H)$^+$=617.

EXAMPLE 263

3,6-Diamino-2,8-dimethyl-5-hydroxy-4,4-difluorononane

Using the procedures described in detail in Example 181, and replacing Boc-L-cyclohexylalaninal with Boc-L-leucinal provided the desired compound. Mass spectrum: M$^+$=238.

EXAMPLE 264

3,6-Bis-(Cbz-valinyl-amino)-2,8-dimethyl-5-hydroxy-4,4-difluorononane

Using the procedure described in Example 182, the product from Example 263 was coupled to Cbz-Val to give the desired compound (56%). Mass spectrum: (M+H)$^+$=705. $^1$H NMR (CDCl$_3$) δ0.82 (m, 12H), 3.90 (m, 1H), 4.02 (m, 1H), 4.30 (m, 1H), 4.55 (m, 1H), 5.02 (s, 4H), 5.80 (br d, 1H), 7.20 (br d, 1H), 7.35 (m, 10H), 7.70 (br d, 1H).

EXAMPLE 265

3,6-Bis-(Cbz-valinyl-amino)-2,8-dimethyl-5-oxo-4,4-difluorononane

Using the procedure described in Example 183, the product from Example 264 was oxidized to provide the desired product (93%). Mass spectrum: (M+H)$^+$=703. $^1$H NMR (CDCl$_3$): 50.8 (m, 1,12H), 3.90 (m, 1H), 4.02 (m, 1H), 4.65 (m, 1H), 4.80 (m, 1H), 5.05 (s, 4H), 7.35 (m, 12H), 7.95 (br d, 1H), 8.42 (br d, 1H).

EXAMPLE 266

A. 2-Oxazolidinone derivative of Ethyl 4(S)-amino-5-phenyl-2,2-difluoro-3-(R)-hydroxypentanoate Using the procedure described in Examples 181A and 181B but replacing Boc-L-cyclohexylalaninal with phenylalaninal provided the desired product. Mass spectrum: M$^+$=299.

B. 4(S)Benzyl-5(R)-(3'(3',3'-difluoro-2'-oxo-1'-phenyl-propyl))-2-oxazolidinone

The hydrolysis of the resultant compound of Example 266A by lithium hydroxide in aqueous dioxane provided the corresponding acid, which was condensed with N,O-dimethyl-hydroxylamine with EDAC to give the corresponding amide. The amide was dissolved in THF and reacted with 3 equivalents of benzylmagnesium chloride to give the desired compound (88%). Mass spectrum: M$^+$=345. $^1$H NMR (CDCl$_3$) δ2.82 (dd, 1H), 3.0 (dd, 1H), 4.07 (m, 2H), 4.15 (m, 1H), 4.70 (m, 1H), 7.15–7.38 (m, 10H).

C. 2,5-Diamino-1,6-diphenyl-3,3-difluoro-4-hydroxyhexane

Using the resultant compound from Example 266B and the procedures described in Example 181D, 181E, and 181F provided the desired compound. Mass spectrum: M$^+$=320.

EXAMPLE 267

2,5-Bis-(Cbz-valinyl-amino)-1,6-diphenyl-3,3-difluoro-4-hydroxyhexane

Using the resultant compound from Example 266C and the procedure described in Example 182, the desired product was obtained in 70% yield. Mass spectrum: (M+H)$^+$=787. $^1$H NMR (CDCl$_3$) δ0.60–0.80 (m, 12H), 5.02 (s, 4H), 6.05 (br d, 1H), 6.95, 1H), 7.10–7.35 (m, 10H), 7.50 (br d, 1H), 7.95 (br d, 1H).

EXAMPLE 268

2,5-Bis-(2-pyridyl-methoxycarbonyl-valinyl-amino)-1,6-diphenyl-3,3-difluoro-4-hydroxyhexane Using the resultant compound from Example 266C and the procedure described in Example 182, but replacing Cbz-Val with 2-pyridinyl-methoxycarbonyl-valine provided the desired compound in 74% yield. (M+H)$^+$=789, $^1$H NMR (CDCl$_3$) δ0.60–0.75 (m, 12H), 1.75 (m, 1H), 1.88 (m, 1H), 3.80 (m, 2H), 4.62 (m, 1H), 4.80 (m, 1H), 5.08 (s, 2H), 5.10 (s, 2H), 6.10 (br d, 1H), 7.05–7.40 (m, 15H), 7.50 (br d, 1H), 7.80 (m, 2H), 8.0 (br d, 1H), 8.52 (m, 2H).

EXAMPLE 269

5-(2-Pyridinyl-methoxycarbonyl-valinyl-amino)-2-amino-1,6-diphenyl-3,3-difluoro-4-hydroxyhexane Using the resultant compound from Example 266C and reacting with the p-nitrophenyl ester of 2-pyridinyl-methoxycarbonyl-valine in DMF provided the desired compound in 69% yield. Mass spectrum: (M+H)$^+$=555. $^1$H NMR (CDCl$_3$) δ0.90 (d, 3H), 1.0 (d, 3H), 2.15 (m, 1H), 2.45(m, 1H), 2.80–3.20 (m, 4H), 3.82 (m, 1H), 4.05 (m, 1H), 4.58 (m, 1H), 5.27 (s, 2H), 5.50 (br d, 1H), 6.50 (br d, 1H), 7.10–7.40 (m, 12H), 7.70 (m, 1H), 8.60 (d, 1H).

EXAMPLE 270

2-(t-Butylacetyl-amino)-5-(2-pyridinyl-methoxycarbonyl-valinyl-amino)-1,6-diphenyl-3,3-difluoro-4-hydroxyhexane Reaction of the resultant compound from Example 269 with t-butylacetyl chloride in dichloromethane and 1.1 equivalent of triethylamine provided the desired compound in 77% yield. Mass spectrum: (M+H)$^+$=653. $^1$H NMR (CDCl$_3$): δ0.80 (s, 9H), 0.82 (d, 3H), 0.93 (d, 3H), 1.83 (q, 2H), 2.12 (m, 1H), 2.70–3.20 (m, 4H), 3.80 (m, 1H), 3.95 (m, 1H), 4.55 (m, 1H), 4.80 (m, 1H), 5.20 (s,0.2H), 5.35 (br d, 1H), 6.50 (br d, 1H), 7.10–7.35 (m, 13H), 7.70 (m, 1H), 8.60 (br d, 1H).

EXAMPLE 271

2-(N-Propylsulfonylamino)-5-(2-pyridinyl-methoxycarbonyl-valinyl-amino)-3,3-difluoro-4-hydroxyhexane Reaction of the resultant compound from Example 269 and 1 equivalent of propane-sulfonyl chloride and 1.1 equivalent of triethylamine provided the desired product in 65% yield. Mass spectrum: (M+H)$^+$=661. $^1$H NMR (CDCl$_3$) δ0.80 (d, 3H), 0.88 (m, 2H), 0.95 (d, 3H), 1.10 (t, 3H), 2.0 (m, 3H), 2.40 (m, 2H), 2.85–3.15 (m, 4H), 3.30 (m, 1H), 3.50 (m, 1H), 3.95 (m, 1H), 4.90 (m, 1H), 5.25 (m, 3H), 6.12 (br d, 1H), 7.20 (m, 12H), 7.70 (m, 1H), 8.60 (m, 1H).

EXAMPLE 272

A. 4(S)-Benzyl-5(R)-(3'(3',3'-difluoro-2'-hydroxy-1'-phenyl-propyl)-2-oxazolidinone To a solution of 1 gm of the resultant compound from Example 266B in 20 ml of dry THF was added two equivalents of DIBAH in toluene at −78° C. After 1 hr, the reaction was quenched by careful addition of water. The reaction mixture was acidified with 1N HCl and extracted with EtOAc (3×5 ml), washed with satd. brine and dried with anhy. Na$_2$SO$_4$. Concentration and purification by SiO$_2$ column chromatography (20% EtOAc/CH$_2$Cl$_2$) provided 850 mg of pure product. Mass spectrum: M$^+$=347. $^1$H NMR (CDCl$_3$): δ2.05 (d, 1H), 2.80–3.10 (m, 4H), 4.20 (m, 1H), 4.30 (m, 1H), 4.70 (m, 1H), 5.0 (br s, 1H), 7.30 (m, 10H).

B. 5-Benzyloxycarbonylamino-3,3-difluoro-2,4-dihydroxy-1,6-diphenylhexane

To a solution of 100 mg of the resultant compound from Example 272A in 5 ml of dioxane and 5 ml of water was added 226 mg of barium hydroxide octahydrate. After refluxing for 3 hr and cooled to RT, the solution was filtered and concentrated in in vacuo. The crude material was dissolved in CH$_2$Cl$_2$ and 1.2 equivalent of Cbz-NOS was added and the mixture was stirred at RT overnight. Concentration and purification by SiO2 column chromatography (20% EtOAc/CH$_2$Cl$_2$) provided 120 mg of product. Mass spectrum: M$^+$=439.

EXAMPLE 273

5-Cbz-valinyl-amino-3,3-difluoro-2,4-dihydroxy-1,6-diphenylhexane

The resultant compound from Example 272B was deprotected by hydrogenolysis (Pd/C, H$_2$) and coupled to Cbz-Val-OH using the procedure described in Example 182 to provide the desired product (72%). Mass spectrum: (M+H)$^+$ =539. $^1$H NMR (CDCl$_3$): δ0.75 (d, 3H), 0.88 (d, 3H), 2.15 (m, 1H), 2.70–3.05 (m, 4H), 3.88 (m, 1H), 4.0–4.20 (m, 2H), 4.40 (m, 1H), 4.50 (m, 1H), 5.05 (s, 2H), 5.10 (d, 1H), 6.46 (br d, 1H), 7.30 (m, 15H).

EXAMPLE 274

5-Cbz-valinyl-amino-3,3-difluoro-1,6-diphenyl-4-hydroxy-2-oxo-hexane

Oxidation of the resultant compound from Example 273 with sodium dichromate in acetic acid provided the desired product. $^1$H NMR (CDCl$_3$): δ0.8 (d, 3H), 0.9 (d, 3H), 2.0 (m, 1H), 2.80 (m, 1H), 3.26 (m, 1H), 3.90 (m, 1H), 4.0 (br s, 3H), 5.0 (br s, 3H), 6.20 (br s, 1H), 7.25 (m, 15H).

EXAMPLE 275

A. 4(S)-Benzyl-5(R)-(3'(3',3'-difluoro-2'-methanesulfonyloxy-1'-phenyl-propyl)-2-oxazolidinone To a solution of 250 mg of the resultant product from Example 272A in 5 ml of CH$_2$Cl$_2$ was added 0.136 ml of triethylamine and 0.065 µl of methanesulfonyl chloride. After 2 hr at RT the mixture was poured into satd. brine and extracted with CH$_2$Cl$_2$ (3×30 ml), dried and concentrated. SiO$_2$ column chromatography (10% EtOAc/CH$_2$Cl$_2$) provided 203 mg of product. $^1$H NMR (CDCl$_3$): δ2.32 (s, 3H), 2.80–3.30 (m, 4H), 4.27 (m, 1H), 4.72 (m, 1H), 5.02 (br s 1H), 5.25 (m, 1H), 7.30 (m, 10H).

B. 4(S)-Benzyl-5(R)-(3'(3',3'-difluoro-1'-phenyl-trans-propenyl)-2-oxazolidinone To a solution of 200 mg of the resultant product from Example 275A in 10 ml of toluene as added 2 equivalent of DBU. After refluxing for 2 hr, cooled to RT the crude product was purified by SiO$_2$ column chromatography to provide 77 mg of product. $^1$H NMR (CDCl$_3$): δ2.80–3.05 (m, 2H), 4.15 (m, 1H), 4.50 (m, 1H), 5.10 (br s, 1H), 6.20 (m, 1H), 7.05 (m, 1H), 7.30 (m, 10H).

C. 4(S)-Benzyl-5(R)-(3'(3',3'-difluoro-1'-phenyl-propyl)-2-oxazolidinone

The resultant compound from Example 275B was dissolved in 2 ml of methanol and stirred under hydrogen with 10% Pd/C as catalyst. After 15 minutes, filtration and concentration provided the desired product (100%). $^1$H NMR (CDCl$_3$): δ2.30 (m, 2H), 2.80–3.00 (m, 4H), 4.20 (m, 1H), 4.32 (m, 1H), 7.30 (m, 10H).

D. 5-Benzyloxycarbonyl-valinyl-amino-3,3-difluoro-1,6-diphenyl-4-hydroxyhexane

Opening of the oxazolidinone ring of the resultant compound from Example 275C with barium hydroxide and coupling to Cbz-Val-OH using the procedure of Example 182 provided the desired product (70%). ¹H NMR (CDCl₃): δ0.80 (d, 3H), 0.90 (d, 3H), 2.10 (m, 3H), 2.70 (m, 2H), 3.0 (m, 2H), 3.70 (m, 2H), 3.95 (m, 1H), 4.30 (m, 1H), 5.10 (br s, 2H), 5.15 (br d, 1H), 6.45 (br d, 1H), 7.10–7.40 (m, 15H).

EXAMPLE 276

5-Benzyloxycarbonyl-valinyl-amino-3,3-difluoro-1, 6-diphenyl-4-oxo-hexane

Oxidation of the resultant compound from Example 275D using sodium dichromate in acetic acid provided the desired compound (70%). ¹H NMR (CDCl₃): δ0.82 (d, 3H), 0.90 (d, 3H), 2.05 (m, 1H), 2.35 (m, 2H), 2.80 (t, 2H), 2.90 (m, 1H), 3.30 (m, 1H), 3.90 (m, 1H), 5.10 (s, 2H), 5.12 (br d, 1H), 5.30 (m, 1H), 6.10 (br d, 1H), 7.10–7.35 (m, 15H).

EXAMPLE 277

5-Cbz-valinyl-amino-3,3-difluoro-4-hydroxy-1,6-diphenyl-2-isobutylcarbonyloxy-hexane To a solution of the resultant compound from Example 273 in CH₂Cl₂ was added 2 equivalents of triethylamine and 1.5 equivalents of isovaleryl chloride. After 2 hr at RT, the mixture was poured into dil. HCl, extraction with EtOAc (3×50 ml), washed with satd. NAHCO₃ and brine, dried and concentrated. Purification by SiO₂ column chromatography (10% EtOAc/CH₂Cl₂) provided the desired product.

EXAMPLE 278

5-Cbz-valinyl-amino-3,3-difluoro-4-hydroxy-1,6-diphenyl-2-isopropylamino-carbonyloxy-hexane To a solution of the resultant compound from Example 273 in CH₂Cl₂ was added 1.5 equivalent of isopropylisocyanate and excess DMAP. The solution was stirred at RT overnight. The reaction mixture was poured into dil. HCl and extracted with EtOAc (3×50 ml), washed with brine, dried and concentrated. Purification by SiO₂ column chromatography (15% EtOAc/CH₂Cl₂) provided the desired product.

EXAMPLE 279

5-Cbz-valinyl-amino-3,3-difluoro-4-hydroxy-1,6-diphenyl-2-methoxy-hexane

To the resultant compound of Example 272A was added 2.2 eq. of sodium hydride in DMF at 0° C., followed by the addition of methyl iodide. After 2 h at RT, conc. and purified the product by silica gel column chromatography. The resultant product was hydrolyzed with barium hydroxide to open the oxazolidinone ring and coupled to Cbz-Val-OH using the procedure described in Example 182, to give the desired product.

EXAMPLE 280

5-Cbz-valinyl-amino-3,3-difluoro-4-oxo-1,6-diphenyl-2-methoxy-hexane

The resultant compound of Example 279 was oxidized with Na₂Cr₂O₇ in acetic acid to provide the desired product.

EXAMPLE 281

A. N, N-Bis-(Cbz-valinyl)-(2R, 3R, 4R, 5R)-1,6-bis-(2'-pyridylthio)-2,5-diamino-3,4-O-isopropylidenehexanediol A mixture of 171 µL (1.23 mmol) of triethylamine, 137 mg (1.23 mmol) of 2-mercaptopyridine and 200 mg (0.308 mmol) of the resultant compound of Example 196A in 1.0 mL of dry DMF was stirred at ambient temperature overnight. The reaction mixture was concentrated under reduced pressure. The residue was purified by flash chromatography on a 1.5×42 cm silica gel column eluted with 50% ethyl acetate in hexane to give 211 mg (78.6% yield) of the title compound; FAB MS M/Z: 873 (M+H)⁺. The 300 MHz ¹H NMR spectrum was consistent with the assigned structure.

B. N,N-Bis-(Cbz-valinyl)-(2R, 3R, 4R, 5R)-1,6-bis (2'-pyridylthio)-2,5-diamino-3,4-hexanediol A solution of 200 mg (0.23 mmol) of the resultant compound of Example 281A in 7.0 mL of methanol containing 1 mL of 0.1N aqueous hydrochloric acid was stirred at 40° C. overnight. The solvent was evaporated under reduced pressure. The residue was dissolved in methylene chloride/methanol and the resultant solution was washed with aqueous sodium bicarbonate solution and brine, dried over anhydrous magnesium sulfate, filtered and concentrated under reduced pressure to give the title compound as a white powder; FAB MS M/Z: 833 (M+H)⁺. The 300 MHz ¹H NMR spectrum was consistent with the assigned structure. Analysis calculated for C₄₂H₅₂N₆O₈S₂: C, 60.58; H, 6.29; N, 10.10. Found: C, 60.15; H, 6.29; N, 9.97.

EXAMPLE 282

A. N, N-Bis-(Cbz-valinyl)-(2R, 3R, 4R, 5R)-1,6-bis-((1'-methyl-2'-imdazoyl)thio)-2,5-diamino-3,4-O-isopropylidenehexanediol To a solution of 196 mg (1.72 mmol) of 2-mercapto-1-methylimidazole and 280 mg (0.431 mmol) of the resultant compound of Example 196A in 1.5 mL of dry DMF was added 240 µL (1.72 mmol) of triethylamine. The resultant solution stirred at ambient temperature overnight. The reaction mixture was concentrated under reduced pressure. The residue was purified by flash chromatography on a 1.5×35 cm silica gel column eluted with 10% isopropyl alcohol in toluene to give 287 mg (81% yield) of the title compound; FAB MS M/Z: 879 (M+H)⁺. The 300 MHz ¹H NMR spectrum was consistent with the assigned structure.

B. N,N-Bis-(Cbz-valinyl)-(2R, 3R, 4R, 5R)-1,6-bis-((1'-methyl-2'-imdazoyl)thio)-2,5-diamino-3,4-hexanediol A solution of 280 mg (0.32 mmol) of the resultant compound of Example 282A in 7.0 mL of methanol containing 0.1 mL of concentrated aqueous hydrochloric acid was stirred at 40° C. for 40 h. The solvent was evaporated under reduced pressure and methanol was added to the residue. The methanol was evaporated and the residue was treated with aqueous sodium bicarbonate solution. The precipitate which formed was filtered to give 148 mg of the title compound; FAB MS M/Z: 839 (M+H)⁺, 861 (M+Na)⁺. ¹H NMR (d₆-DMSO) δ 0.79 (d, 6H), 0.84 (d, 6H), 2.00 (m, 2H), 3.12 (d, 4H), 3.50 (s, 6H), 3.97 (dd, 2H), 4.08 (br dd, 2H), 5.0 (q, 4H), 5.44 (br m, 2H), 6.89 (d, 2H), 7.19 (d, 2H), 7.23 (d, 2H), 7.34 (m, 6H), 7.70 (d, 2H).

EXAMPLE 283

A. N, N-Bis-(Cbz-valinyl)-(2R, 3R, 4R, 5R)-1,6-bis-(2'-pyrimidinylthio)-2,5-diamino-3,4-O-isopropylidenehexanediol A mixture of 185 µL (1.335 mmol) of triethylamine, 150 mg (1.335 mmol) of 2-mercaptopyrimidine (commercially available from Aldrich Chemical Co.) and 217 mg (0.333 mmol) of the resultant compound of Example 196A in 2.0 mL of dry DMF was stirred at ambient temperature overnight. The reaction mixture was concentrated under reduced pressure. The residue was purified by flash chromatography on a 1.5×35 cm silica gel column eluted with 10% isopropyl alcohol in toluene to give 219 mg (75% yield) of the title compound; FAB MS M/Z: 875 (M+H)$^+$. The 300 MHz $^1$H NMR spectrum was consistent with the assigned structure. Analysis calculated for $C_{43}H_{54}N_8O_8S_2$: C, 59.04; H, 6.18; N, 12.81. Found: C, 58.69; H, 6.20; N, 12.61.

B. N,N-Bis-(Cbz-valinyl)-(2R, 3R, 4R, 5R)-1,6-bis (2'-pyrimidinylthio)-2,5-diamino-3,4-hexanediol A solution of the resultant compound of Example 283A (205 mg, 0.234 mmol) in 10.0 mL of methanol containing 0.10 mL of concentrated aqueous hydrochloric acid was stirred at 40° C. for 7.5 h. The reaction mixture was stirred for approximately 64 h at ambient temperature. Additional methanolic hydrochloric acid (5 mL) was added and the reaction mixture was then stirred for 8 h at 40° C. The solvent was evaporated under reduced pressure and methanol was added to the residue. The methanol was evaporated. The residue was dissolved in chloroform and the resultant solution was washed with aqueous sodium bicarbonate solution and brine, dried over anhydrous magnesium sulfate, filtered and concentrated under reduced pressure to give 198 mg of the crude product. The crude product was purified by flash chromatography on a 1.5×37 cm silica gel column eluted with 5% methanol in methylene chloride to give 28 mg (14% yield) of the title compound; FAB MS M/Z: 835 (M+H)$^+$. The 300 MHz $^1$H NMR spectrum was consistent with the assigned structure. Analysis calculated for $C_{42}H_{52}N_6O_8S_2+H_2O$: C, 56.33; H, 6.10; N, 13.14. Found: C, 56.47; H, 5.89; N, 13.13.

EXAMPLE 284

A. N, N-Bis-(Cbz-valinyl)-(2R, 3R, 4R, 5R)-1,6-bis-(cyclohexylthio)-2,5-diamino-3,4-O-isopropylidenehexanediol A mixture of 190 µL (1.366 mmol) of triethylamine, 158 mg (1.23 mmol) of cyclohexylmercaptan and 222 mg (0.341 mmol) of the resultant compound of Example 196A in 3.0 mL of dry DMF was stirred at ambient temperature for 2 days. The reaction mixture was concentrated under reduced pressure. The residue was purified by flash chromatography on a 1.5×40 cm silica gel column eluted with 40% ethyl acetate in hexane to give 211 mg (78.6% yield) of the title compound; FAB MS M/Z: 883 (M+H)$^+$. The 300 MHz $^1$H NMR spectrum was consistent with the assigned structure.

Analysis calculated for $C_{47}H_{71}N_4O_8S_2$: C, 63.95; H, 7.94; N, 6.35. Found: C, 63.86; H, 8.00; N, 6.31.

B. N,N-Bis-(Cbz-valinyl)-(2R, 3R, 4R, 5R)-1,6-bis-(cyclohexylthio)-2,5-diamino-3,4-hexanediol A solution of the resultant compound of Example 284A (120 mg, 0.136 mmol) in 3.0 mL of trifluoroacetic acid was cooled in an ice bath. To the cooled solution was added 3 mL of water and the solution was stirred for 5 h at 0° C. The solvent was evaporated under reduced pressure. The residue was purified by flash chromatography on a 1.0×37 cm silica gel column eluted with 20% ethyl acetate in methylene chloride, followed by 40% ethyl acetate in methylene chloride to give the title compound; FAB MS M/Z: 843 (M+H)$^+$. The 300 MHz $^1$H NMR spectrum was consistent with the assigned structure. Analysis calculated for $C_{44}H_{66}N_6O_8S_2$: C, 62.71; H, 7.84; N, 6.65. Found: C, 62.69; H, 7.84; N, 6.64.

EXAMPLE 285

A. N, N-Bis-(Cbz-valinyl)-(2R, 3R, 4R, 5R)-1,6-bis-(4'-pyridylthio)-2,5-diamino-3,4-O-isopropylidenehexanediol A mixture of 204 µL (1.47 mmol) of triethylamine, 163 mg (1.47 mmol) of 4-mercaptopyridine and 239 mg (0.368 mmol) of the resultant compound of Example 196A, in 2.0 mL of dry DMF was stirred at 5° C. for 1 h and at ambient temperature for 4 h. The reaction mixture was concentrated under reduced pressure. The residue was purified by flash chromatography on a 1.5×43 cm silica gel column eluted with 5% methanol in methylene chloride to give 220 mg (68.6% yield) of the title compound; FAB MS M/Z: 873 (M+H)$^+$. The 300 MHz $^1$H NMR spectrum was consistent with the assigned structure. Analysis calculated for $C_{45}H_{56}N_6O_8S_2$: C, 61.86; H, 6.53; N, 9.62. Found: C, 61.49; H, 6.35; N, 9.57.

B. N,N-Bis-(Cbz-valinyl)-(2R, 3R, 4R, 5R)-1,6-bis-(4'-pyridylthio)-2,5-diamino-3,4-hexanediol A solution of the resultant compound of Example 285A, in 5.0 mL of methanol containing 40 µL of concentrated aqueous hydrochloric acid was stirred at 40° C. for 2 days. While the reaction mixture was stirring additional aliquots (total 80 µL) of concentrated hydrochloric acid were added. The reaction mixture was allowed to stir over the weekend at ambient temperature and then another drop of concentrated hydrochloric acid was added. After stirring for a total of 4.5 days the solvent was evaporated under reduced pressure. Methanol was added to the residue and evaporated off under reduced pressure. The residue was purified by flash chromatography on a 1.5×45 cm silica gel column eluted with 10% methanol in methylene chloride, followed by 20% methanol in methylene chloride The material obtained from the column was treated with 10 mL of methanol containing 0.10 mL of concentrated aqueous hydrochloric acid at 40° C. for 5.5 h. The solvent was evaporated under reduced pressure. Methanol was added to the residue and evaporated off under reduced pressure. The residue was dissolved in methylene chloride/methanol and the resultant solution was washed with dilute aqueous sodium bicarbonate solution, dried over anhydrous magnesium sulfate, filtered and concentrated under reduced pressure to give 13 mg (6.2% yield) of the title compound; FAB MS M/Z: 833 (M+H)$^+$. $^1$H NMR (CD$_3$OD) δ 0.91 (d, 6H), 0.93 (d, 6H), 2.01 (m, 2H), 3.20 (br m, 4H), 3.90 (d, 2H), 4.27 (m, 2H), 4.77 (m, 2H), 5.11 (s, 4H), 7.25–7.40 (m, 14H), 8.23 (d, 4H).

EXAMPLE 286

A. N, N-Bis-(Cbz-valinyl)-(2R, 3R, 4R, 5R)-1,6-bis-(t-butylthio)-2,5-diamino-3,4-O-isopropylidenehexanediol A solution of 157 mg (1.74 mmol) of t-butylmercaptan and 283 mg (0.435 mmol) of the resultant compound of Example 196A in 2.0 mL of dry DMF was cooled in an ice bath. To the cooled solution added 242 µL (1.74 mmol) of triethylamine. The resultant solution was allowed to warm slowly to ambient temperature and it was stirred at ambient temperature overnight. The reaction mixture was concentrated under reduced pressure. The residue was purified by flash chromatography on a 1.5×35 cm silica gel column eluted with 20% ethyl acetate in hexane, followed by 40% ethyl acetate in hexane to give 173 mg (48% yield) of the title compound; FAB MS M/Z: 831 (M+H)$^+$. The 300 MHz $^1$H NMR spectrum was consistent with the assigned structure. Analysis calculated for $C_{43}H_{66}N_4O_8S_2$: C, 62.17; H, 7.95; N, 6.74. Found: C, 62.34; H, 8.02; N, 6.74.

B. N,N-Bis-(Cbz-valinyl)-(2R, 3R, 4R, 5R)-1,6-bis-(t-butylthio)-2,5-diamino-3,4-hexanediol A solution of the resultant compound of Example 286B (173 mg, 0.208 mmol) in 3.0 mL of trifluoroacetic acid containing 0.4 mL of water was stirred at 0° C. for 4.5 h. The solvent was evaporated under reduced pressure. The residue was purified by flash chromatography on a 1.5×39 cm silica gel column eluted with 50% ethyl acetate in hexane to give 78 mg (47.5% yield) of the title compound; FAB MS M/Z: 791 (M+H)$^+$. The 300 MHz $^1$H NMR spectrum was consistent with the assigned structure. Analysis calculated for $C_{40}H_{62}N_4O_8S_2$: C, 60.76; H, 7.85; N, 7.09. Found: C, 60.50; H, 7.93; N, 7.03.

EXAMPLE 287

A. N, N-Bis-(Cbz-valinyl)-(2R, 3R, 4R, 5R)-1,6-bis-(ethylthio)-2,5-diamino-3,4-O-isopropylidenehexanediol A solution of 283 mg (0.435 mmol) of the resultant compound of Example 196A, in 2.0 mL of dry DMF was cooled in an ice bath. To the cooled solution was added 108 mg (1.74 mmol) of ethylmercaptan followed by 242 µL (1.74 mmol) of triethylamine. The resultant solution was stirred at 0° C. for 4.5 h, allowed to warm slowly to ambient temperature and it was stirred at ambient temperature overnight. The reaction mixture was concentrated under reduced pressure. The residue was purified by flash chromatography on a 1.5×37 cm silica gel column eluted with 50% ethyl acetate in hexane to give 116 mg (34.5% yield) of the title compound; FAB MS M/Z: 775 (M+H)$^+$. The 300 MHz $^1$H NMR spectrum was consistent with the assigned structure. Analysis calculated for $C_{39}H_{58}N_4O_8S_2$: C, 60.46; H, 7.49; N, 7.24. Found: C, 60.24; H, 7.33; N, 7.16.

B. N,N-Bis-(Cbz-valinyl)-(2R, 3R, 4R, 5R)-1,6-bis-(ethylthio)-2,5-diamino-3,4-hexanediol A solution of the resultant compound of Example 287A (116 mg, 0.15 mmol) in 3.0 mL of trifluoroacetic acid containing 0.3 mL of water was stirred at 0° C. for 2.5 h. The solvent was evaporated under reduced pressure. The residue was purified by flash chromatography on a 1.0×35 cm silica gel column eluted with 50% ethyl acetate in hexane to give the title compound; FAB MS M/Z: 735 (M+H)$^+$. The 300 MHz $^1$H NMR spectrum was consistent with the assigned structure. Analysis calculated for $C_{36}H_{54}N_4O_8S_2$: C, 58.86; H, 7.36; N, 7.63. Found: C, 58.58; H, 7.33; N, 7.52.

EXAMPLE 288

A. (6R,7R,8S,9S)-6,9-Di-((N-toluenesulfonyl)amino)-7,8-O-isopropylidenetetradecanediol To a solution of 1.175 g (5.715 mmol) of cuprous bromide-dimethylsufide complex in 8 mL of anhydrous, oxygen-free THF at −40° C. was added 4.57mL (11.43 mmol) of 2.5M n-butyl lithium. The solution was stirred for 0.5 h at −40° C. and then cooled to −60° C. A solution of (2S,3R,4R,5S)-1,2:5,6-diimino-3,4-O-isopropylidenehexanediol (703 mg, 1.43 mmol(Y. L. Merrer, et al, *Heterocycles*, 1987, 25, 541–548)) in ~16 mL of anhydrous, oxygen-free THF was added. The solution was allowed to warm slowly to approximately −25° C. and stirred for 4 h at that temperature. The reaction mixture was treated with 10% concentrated ammonium hydroxide in saturated ammonium chloride solution and the aqueous mixture was extracted with diethyl ether. The organic solution was washed with brine, dried over anhydrous magnesium sulfate and concentrated under reduced pressure. The residue was purified by flash chromatography on a 1.0×27 cm silica gel column eluted with 20% ethyl acetate in hexane to give 0.414 g (47.6% yield) of the title compound; DCI/NH$_3$ MS M/Z: 626 (M+NH$_4$)$^+$; The 300 MHz $^1$H NMR spectrum was consistent with the assigned structure.

B. N,N-Bis-(Cbz-valinyl)-(2R, 3R, 4S, 5S)-6,9-diamino-7,8-O-isopropylidenetetradecanediol The resultant compound of Example 288A, in 3 mL of anhydrous diethyl ether was added to ~75 mL of liquid ammonia and small pieces of sodium metal were added until a blue color persisted for 5 minutes. The reaction was quenched with ammonium chloride and the ammonia was evaporated. The residue was dissolved in diethyl ether and the ether solution was washed with dilute aqueous ammonium hydroxide and brine, dried over anhydrous sodium sulfate, filtered and concentrated under reduced pressure to give the intermediate 6,9-diamino compound. The diamine (159 mg, 0.53 mmol) was dissolved in 5 mL of THF and the THF solution was cooled in an ice bath. To the cooled solution was added 532 mg (2.12 mmol) of N-carbobenzyloxyvaline, followed by 406 mg (2.12 mmol) of N-ethyl-N'-(dimethylaminopropyl)carbodiimide and 295 µL (2.12 mmol) of triethylamine. The reaction mixture was allowed to gradually warm to ambient temperature and was stirred at ambient temperature overnight. The solvent which had evaporated from the reaction mixture was replaced with 5 mL of THF and the mixture was stirred for 2 h. The reaction mixture was then diluted with ethyl acetate and washed with saturated aqueous sodium bicarbonate solution and brine, dried over anhydrous magnesium sulfate, filtered and concentrated under reduced pressure. The residue was purified by flash chromatography on a 1.5×35 cm silica gel column eluted with 30% ethyl acetate to to give 83 mg (20% yield) of the title compound; DCI/NH$_3$ MS M/Z: 784 (M+NH$_4$)$^+$, 767 (M+H)$^+$; The 300 MHz $^1$H NMR spectrum is consistent with the assigned structure. Analysis calculated for $C_{43}H_{66}N_4O_8$: C, 67.36; H, 8.62; N, 7.31. Found: C, 67.68; H, 9.02; N, 7.27.

C. N,N-Bis-(Cbz-valinyl)-(6S, 7R, 8R, 9S)-6,9-diamino-7,8-tetradecanediol

A solution of the resultant compound of Example 288B (80 mg, 0.1 mmol) in 3.0 mL of trifluoroacetic acid containing 0.3 mL of water was stirred at 0° C. for 4.75 h. The solvent was evaporated under reduced pressure. The residue was purified by flash chromatography on a 1.0×22 cm silica gel column eluted with 50% ethyl acetate in hexane to give 51 mg (45% yield) of the title compound; $^1$H NMR (CDCl$_3$) δ 0.86 (t, 6H), 0.92 (d, 6H), 0.98 (d, 6H), 1.20–1.33 (br m, 12H), 1.51–1.61 (br m, 2H), 2.12–2.22 (m, 2H), 3.39 (br s, 1H), 3.55 (br s, 1H), 3.82–3.92 (m, 2H), 3.95 (dd, 2H), 5.10 (s, 4H), 5.10 (s, 4H), 5.20 (br d, 2H), 6.23 (d, 2H), 7.30–7.40 (m, 10H).Analysis calculated for $C_{40}H_{62}N_4O_8$: C, 66.12; H, 8.54; N, 7.71. Found: C, 66.04; H, 8.59; N, 7.70.

EXAMPLE 289

A. (2S,3R,4R,5S)-1,6-Diphenyl-2,5-di-((N-toluenesulfonyl)amino)-3,4-O-isopropylidenehexanediol To a stirred suspension of 411 mg (2.0 mmol) of CuBr-Me$_2$S in 2 mL of ether at 0 ° C. was added 3.08 ml (4.0 mmol) of 1.3M phenyllithium in ether/cyclohexane. After 30 minutes, a suspension of 246 mg (0.50 mmol) of (2S,3R, 4R,5S)-1,2:5,6-diimino-3,4-O-isopropylidene-hexanediol (703 mg, 1.43 mmol (Y. L. Merrer, et al, *Heterocycles,* 1987, 25, 541–548)) was added in 20 mL. After 80 minutes, the reaction mixture was quenched with 10% NH$_4$OH saturated with NH$_4$Cl. The ether layer was washed with brine, dried over magnesium sulfate, and concentrated under reduced pressure. Chromatography of the residue on silica gel with 7:3/hexane:EtOAc afforded 280 mg (86.4%) of the title compound. MS m/z 649 (M+H$^+$)

B. N,N-Bis-(Cbz-valinyl)-(2S, 3R, 4R, 5S)-1,6-diphenyl-2,5-diamino-3,4-hexanediol The resultant compound of Example 289A was converted to the title compound in a manner analogous to that described in Examples 288B and 288C.

EXAMPLE 290

A. N,N-Bis-(Cbz-valinyl)-(2S, 3R, 4R, 5S)-1,6-di-(4-(methyoxymethyloxy)phenyl)-2,5-diamino-3,4-hexanediol Using the procedures of Example 289, but subsituting 4-(methoxymethyloxy)phenyllithium for phenyllithium in Step A provided the desired product.

B. N,N-Bis-(Cbz-valinyl)-(2S, 3R, 4R, 5S)-1,6-di-(4-hydroxyphenyl)-2,5-diamino-3,4-hexanediol The resultant compound of Example 290A was hydrolyzed according to the procedure of Example 23B to provide the desired compound.

EXAMPLE 291

2,4-Bis-(N-(Cbz-isoleucyl)amino)-1,5-diphenyl-3-hydroxypentane

The resultant compound of Example 12 (100 mg, 0.37 mmol), N-benzyloxycarbonyl-isoleucine p-nitrophenyl ester (428 mg, 1.1 mmol) and triethylamine (210 µL) were combined with 0.5 mL of dry acetonitrile and stirred together at ambient temperature for 0.5 h. Dry THF (1.0 mL) was added and the resultant solution was stirred at ambient temperature overnight. The reaction mixture was then diluted with 5 mL of THF and 5 mL of 3M aqueous sodium hydroxide solution was added. The mixture was stirred at ambient temperature for 0.5 h and then it was extracted with 100 mL of methylene chloride. The organic solution was washed with 3×25 mL of 0.5M aqueous sodium hydroxide solution and brine, dried over anhydrous magnesium sulfate, filtered and concentrated under reduced pressure. The residue (319 mg) was dissolved in approximately 5 mL of chloroform and applied to a 1.0×40 cm column of 40 mesh silica gel. The column was eluted sequentially @ 5 p.s.i with 100 mL of chloroform, 100 mL of 0.5% methanol in chloroform and 100 mL of 1% methanol in chloroform to give 106 mg (37% yield) of the title compound: FAB MS M/Z: 765 (M+H)$^+$. The 300 MHz $^1$H NMR spectrum was consistent with the assigned structure. Analysis calculated for C$_{45}$H$_{56}$N$_4$O$_7$: C, 70.65; H, 7.38; N, 7.32. Found: C, 70.35; H, 7.52; N, 7.21.

EXAMPLE 292

2-(t-Butyloxycarbonylamino)-4-(N-(Cbz-isoleucyl)amino)-1,5-diphenyl-3-hydroxypentane The resultant compound of Example 11 (125 mg, 0.34 mmol), N-benzyloxycarbonyl-isoleucine p-nitrophenyl ester (196 mg, 0.51 mmol) and triethylamine (94 µL, 0.67 mmol) were combined with 1.0 mL of dry THF and stirred together at ambient temperature overnight. The reaction mixture was then heated at reflux temperature for 3 h. The cooled reaction mixture was then diluted with 5 mL of THF and 5 mL of 3M aqueous sodium hydroxide solution was added. The mixture was stirred at ambient temperature for approximately 0.5 h. and was then diluted with chloroform. The chloroform solution was washed with 3×25 mL of 0.5M aqueous sodium hydroxide solution and brine, dried over anhydrous magnesium sulfate, filtered and concentrated under reduced pressure. The residue (227 mg) was taken up in approximately 5 mL of chloroform and applied to a 1.0×45 cm column of 40 mesh silica gel. The column was eluted @ 5–10 p.s.i. sequentially with 100 mL of chloroform, 100 mL of 0.5% methanol in chloroform and 100 mL of 1% methanol in chloroform to give 169 mg (81% yield) of the title compound; FAB MS M/Z: 618 (M+H)$^+$. The 300 MHz $^1$H NMR spectrum was consistent with the assigned structure.

Analysis calculated for C$_{36}$H$_{47}$N$_3$O$_6$: C, 69.99; H, 7.67; N, 6.80. Found: C, 69.26; H, 7.52; N, 6.61.

EXAMPLE 293

A. 2,4-Bis-(N-(Cbz-valinyl)amino)-1,5-diphenyl-3-pentyl α-bromoacetate

The resultant compound of Example 70 (600 mg, 0.81 mmol) was dissolved in 8 mL of methylene chloride and 72 µL (0.9 mmol) of pyridine. The solution was cooled in an ice bath with stirring under a nitrogen atmosphere. α-Bromoacetyl bromide (181 mg, 0.9 mmol) was added in one portion and the ice bath was removed. The reaction mixture was stirred at ambient temperature for 3 h and then diluted with 150 mL of chloroform. The chloroform solution was washed with 150 mL of water, dried over anhydrous magnesium sulfate, filtered and concentrated under reduced pressure. The residue (644 mg) was taken up in a mixture of chloroform and methanol and adsorbed onto approximately 1.5 g of 40 mesh silica gel in vacuo @ 40° C. The silica gel with the product adsorbed onto it was applied to a 1.0×40 cm column of 40 mesh silica gel and the column was eluted @ ~5 p.s.i. sequentially with 100 mL of chloroform and 100 mL of 1% methanol in chloroform to give 378 mg (55% yield) of the title compound; FAB MS M/Z: 859 (M+H)$^+$. The 300 MHz $^1$H NMR spectrum was consistent with the assigned structure.

B. 2,4-Bis-(N-(Cbz-valinyl)amino)-1,5-diphenyl-3-pentyl (α-(4'-methyl-1'-piperazinyl)acetate The resultant compound of Example 293A (175 mg, 0.204 mmol) and 1-methylpiperazine (44 mg, 0.44 mmol) were combined with 4 mL of freshly distilled THF and the reaction mixture was stirred at ambient temperature under a nitrogen atmosphere for 2 h. The reaction mixture was then concentrated under reduced pressure. The residue (218 mg) was taken up in appromimately 3 mL of 5% methanol in methylene chloride and applied to a 0.6×40 cm column of 40 mesh silica gel. The column was eluted @ ~10 p.s.i. sequentially with 50 mL of methylene chloride and 50 mL of 5% methanol in methylene chloride to give 170 mg (96% yield) of product. The product was dissolved in methylene chloride/methanol and adsorbed onto ~1g of 40 mesh silica gel. The silica gel containing the adsorbed product was applied to a 0.6×45 cm column of 40 mesh silica gel and the column was eluted @ ~10 p.s.i sequentially with 50 mL of methylene chloride, 50 mL of 0.5% methanol in methylene chloride, 50 mL of 1% methanol in methylene chloride, 50 mL of 2% methanol in methylene chloride, 50 mL of 3% methanol in methylene chloride, 50 mL of 4% methanol in methylene chloride and 50 mL of 5% methanol in methylene chloride to give 144 mg (82% yield) of the title compound; FAB MS M/Z: 877 (M+H)$^+$. The 300 MHz $^1$H NMR spectrum was consistent with the assigned structure. Analysis calculated for $C_{50}H_{64}N_6O_8$: C, 68.47; H, 7.36; N, 9.58. Found: C, 68.32; H, 7.27; N, 9.54.

EXAMPLE 294

2,4-Bis-(N-(Cbz-valinyl)amino)-1,5-diphenyl-3-pentyl (α-1'-morpholinoacetate

The resultant compound of Example 293A (198 mg, 0.231 mmol), and morpholine (43 mg, 0.5 mmol) were combined with 4 mL of freshly distilled THF and the reaction mixture was stirred at ambient temperature under a nitrogen atmosphere for 4 h. A drop of triethylamine was added and the reaction mixture was concentrated under reduced pressure. The residue (241 mg) was dissolved in methanol/methylene chloride and adsorbed onto ~500 mg of 40 mesh silica gel. The silica gel containing the adsorbed product was applied to a 0.6×40 cm column of 40 mesh silica gel and the column was eluted @ ~10 p.s.i. sequentially with 50 mL of chloroform, 50 mL of 1% methanol in chloroform, 50 mL of 2% methanol in chloroform and 50 mL of 3% methanol in chloroform to give 186 mg (93% yield) of the title compound; FAB MS M/Z: 864 (M+H)$^+$. The 300 MHz $^1$H NMR spectrum was consistent with the assigned structure.

Analysis calculated for $C_{49}H_{61}N_5O_9$: C, 68.11; H, 7.12; N, 8.11. Found: C, 67.99; H, 7.14; N, 8.09.

EXAMPLE 295

A. 2,4-Bis-(N-(Cbz-valinyl)amino)-1,5-diphenyl-3-pentyl 3-(chloromethyl)benzoate The resultant compound of Example 70 (769 mg, 1.04 mmol) was combined with 3-(chloromethyl)benzoyl chloride (395 mg, 2.09 mmol) and pyridine (165 mg, 2.09 mmol) in 10 mL of freshly distilled methylene chloride. The reaction mixture was stirred at ambient temperature under nitrogen for approximately 65 h and then diluted with 150 mL of chloroform. The chloroform solution was washed with 75 mL of water, dried over anhydrous magnesium sulfate, filtered and concentrated under reduced pressure. The residue (1.59 g) was taken up in ~10 mL of methylene chloride and applied to a 1.5×45 cm column of 40 mesh silica gel. The column was eluted @ ~5 p.s.i. sequentially with 200 mL of methylene chloride, 200 mL of 0.5% methanol in methylene chloride and 200 mL of 1% methanol in methylene chloride to give 275 mg (30% yield) of the title compound; FAB MS M/Z: 889 (M+H)$^+$. The 300 MHz $^1$H NMR spectrum was consistent with the assigned structure.

B. 2,4-Bis-(N-(Cbz-valinyl)amino)-1,5-diphenyl-3-pentyl 3-((4'-methyl-1'-piperazinyl)methyl)benzoate The resultant compound of Example 295A (130 mg, 0.146 mmol) and 1-methylpiperazine (32 mg, 0.337 mmol) were combined with 4 mL of freshly distilled THF and the reaction mixture was stirred at ambient temperature under a nitrogen atmosphere for 2 h. The reaction mixture was then heated at reflux for 18 h under a nitrogen atmosphere and concentrated under reduced pressure. The residue (160 mg) was taken up in appromimately 2 mL of chloroform and applied to a 0.6×45 cm column of 40 mesh silica gel. The column was eluted @ 5–10 p.s.i. sequentially with 50 mL of methylene chloride, 50 mL of 1% methanol in methylene chloride, 50 mL of 2% methanol in methylene chloride, 50 mL of 3% methanol in methylene chloride, 50 mL of 4% methanol in methylene chloride and 50 mL of 5% methanol in methylene chloride to give 89 mg (60% yield) of the title compound; FAB MS M/Z: 953 (M+H)$^+$. The 300 MHz $^1$H NMR spectrum was consistent with the assigned structure. Analysis calculated for $C_{56}H_{68}N_6O_8$: C, 70.56; H, 7.19; N, 8.82. Found: C, 70.22; H, 7.13; N, 8.63.

EXAMPLE 296

2,4-Bis-(N-(Cbz-valinyl)amino)-1,5-diphenyl-3-pentyl 3-((1'-morpholino)methyl)benzoate The resultant compound of Example 295A (133 mg, 0.15 mmol), and morpholine (26 mg, 0.30 mmol) were combined with 4 mL of freshly distilled THF and the reaction mixture was heated at reflux under a nitrogen atmosphere for 17 h. The reaction mixture was concentrated under reduced pressure. The residue (170 mg) was taken up in appromimately 1 mL of chloroform and applied to a 0.6×45 cm column of 40 mesh silica gel. The column was eluted @ 10 p.s.i. sequentially with 50 mL of chloroform, 50 mL of 1% methanol in chloroform, 50 mL of 2% methanol in chloroform and 50 mL of 3% methanol in chloroform to give 84 mg (60% yield) of the title compound; FAB MS M/Z: 940 (M+H)$^+$. Analysis calculated for $C_{55}H_{65}N_5O_9+H_2O$: C, 68.94; H, 7.05; N, 7.31. Found: C, 69.15; H, 6.82; N, 7.27

EXAMPLE 297

A. 4-(Chloromethyl)benzoyl chloride

Benzoic acid (20.0 g, 117 mmol) was suspended in 100 mL of freshly distilled methylene chloride with stirring under a nitrogen atmosphere. Approximately 2 drops of DMF was added to the suspension, followed by the dropwise addition of oxalyl chloride (29.7 g, 234 mmol) over a 0.5 h period. The reaction mixture was stirred at ambient temperature for 17 h. The reaction mixture was then concentrated in vacuo @ 45°–50° C. Toluene (30 mL) was three times added to the residual oil and removed by azeotropic distillation. The oil was then distilled under reduced pressure to give 20.8 g (94% yield) of the title compound; b.p. 139°–149° C. (12 mm Hg); $^1$H NMR (CDCl3) d 4.63 (s, 2H), 7.54 (d, 2H), 8.12 (d, 2H).

B. 2,4-Bis-(N-(Cbz-valinyl)amino)-1,5-diphenyl-3-pentyl 4-(chloromethyl)benzoate The resultant compound of Example 70 (1.3 g, 1.76 mmol) was combined with 4-(chloromethyl)benzoyl chloride (1.0 g, 5.3 mmol) and pyridine (418 mg, 5.3 mmol) in 10 mL of freshly distilled methylene chloride. The reaction mixture was heated at reflux under nitrogen for approximately 10 h and then diluted with 150 mL of chloroform. The chloroform solution was washed with 75 mL of water, dried over anhydrous magnesium sulfate, filtered and concentrated under reduced pressure. The residue (2.1 g) was taken up in ~10 mL of chloroform and applied to a 1.8×45 cm column of 40 mesh silica gel. The column was eluted @ ~5 p.s.i. sequentially with 200 mL of methylene chloride, 250 mL of 0.5% methanol in methylene chloride and 600 mL of 1% methanol in methylene chloride to give 721 mg (46% yield) of the title compound; FAB MS M/Z: 889 (M+H)$^+$. The 300 MHz $^1$H NMR spectrum was consistent with the assigned structure.

C. 2,4-Bis-(N-(Cbz-valinyl)amino)-1,5-diphenyl-3-pentyl 4-((4'-methyl-1'-piperazinyl)methyl)benzoate The resultant compound of Example 297B (200 mg, 0.225 mmol) and 1-methylpiperazine (45 mg, 0.45 mmol) were combined with 5 mL of freshly distilled THF and the reaction mixture was heated at 45° C. under a nitrogen atmosphere for approximately 64 h. The reaction mixture was concentrated under reduced pressure. The residue (245 mg) was taken up in appromimately 2 mL of chloroform and applied to a 0.6×40 cm column of 40 mesh silica gel. The column was eluted @ 10 p.s.i. sequentially with 50 mL of chloroform and 50 mL of 1% methanol in methylene chloride to give 106 mg (37% yield) of the title compound; FAB MS M/Z: 953 (M+H)$^+$. Analysis calculated for $C_{56}H_{68}N_6O_8 + H_2O$: C, 69.25; H, 7.26; N, 8.65. Found: C, 69.06; H, 7.00; N, 8.60.

EXAMPLE 298

2,4-Bis-(N-(Cbz-valinyl)amino)-1,5-diphenyl-3-pentyl 4-((1'-morpholino)methyl)benzoate The resultant compound of Example 297B (200 mg, 0.225 mmol), and morpholine (39 mg, 0.45 mmol) were combined with 5 mL of freshly distilled THF and the reaction mixture was heated at 45° C. under a nitrogen atmosphere for approximately 64 h. The reaction mixture was concentrated under reduced pressure. The residue (249 mg) was taken up in appromimately 2 mL of chloroform and applied to a 0.6×45 cm column of 40 mesh silica gel. The column was eluted @ ~10 p.s.i. sequentially with 50 mL of 1% methanol in methylene chloride, 50 mL of 2% methanol in methylene chloride, 50 mL of 3% methanol in methylene chloride and 50 mL of 4% methanol in methylene chloride to give 163 mg (76% yield) of the title compound; FAB MS M/Z: 940 (M+H)$^+$. Analysis calculated for $C_{55}H_{65}N_5O_9 + H_2O$: C, 68.94; H, 7.05; N, 7.31. Found: C, 68.84; H, 6.80; N, 7.29.

EXAMPLE 299

A. 2,4-Bis(t-butyloxycarbonylamino)-1,5-diphenyl-3-pentanol

To a stirred solution of the resultant compound of Example 11 (1.0 g, 2.7 mmol) in 20 mL of dichloromethane was added 0.77 g of di-t-butyldicarbonate. After 1 hour, 4 drops of diisopropylethylamine was added, and after 30 minutes, the reaction mixture was concentrated under reduced pressure. Chromatrography of the residue on a 1.5×45 cm column of silica gel with 200 mL of chloroform and then 200 mL of 99:1/chloroform:methanol afforded 1.19 g (94%) of the title compound. DCI/IBU MS M/Z: 471 (M+H)$^+$. The 300 MHz $^1$H NMR was consistent with the assigned structure.

B. 2,4-Bis-(t-butyloxycarbonyl)amino-1,5-diphenyl-3-pentanone

Oxalyl chloride (380 mg, 3.0 mmol) was dissolved in 45 mL of freshly distilled methylene chloride and the solution was cooled to −78° C. under a nitrogen atmosphere. DMSO (469 mg, 6.0 mmol) was added to the stirred solution, followed 5 minutes later by a solution of 1.18 g (2.5 mmol) of the resultant compound of Example 299A, in 20 mL of methylene chloride. After the reaction mixture was stirred for 50 min at −78° C., 1.75 mL (12.5 mmol) of triethylamine was added. The reaction mixture was stirred for 5 min at −78° C. and then allowed to warm to ambient temperature and stirred at ambient temperature for 1 h. The reaction mixture was diluted with 100 mL of chloroform, washed with 100 mL of brine, dried over anhydrous magnesium sulfate, filtered and concentrated under reduced pressure. The residue was taken up in ~10 mL of methylene chloride and applied to a 1.0×45 cm column of silica gel. The column was eluted @ 5–10 p.s.i. with 100 mL of methylene chloride and 100 mL of 1% methanol in methylene chloride to give 1.02 g (87% yield) of the title compound; DCI/NH3 MS M/Z: 486 (M+NH$_4$)+, 469 (M+H)+.

C. 2,4-Bis-(t-butyloxycarbonylamino)-1,5-diphenyl-3-pentanone oxime

The resultant compound of Example 299B (217 mg, 0.46 mmol), hydroxylamine hydrochloride (48 mg, 0.69 mmol) and anhydrous pyridine (75 µL, 0.92 mmol) were added to 10 mL of methanol. The reaction mixture was stirred at ambient temperature under a nitrogen atmosphere for 18 h. Additional hydroxylamine hydrochloride (48 mg) and pyridine (75 µL) were added and the reaction mixture was stirred for 5 h. The reaction mixture was then concentrated under reduced pressure and the residue was dissolved in 100 mL of chloroform. The chloroform solution was washed with 50 mL of water, dried over anhydrous magnesium sulfate, filtered and concentrated under reduced pressure. The residue (250 mg) was taken up in ~2 mL of methylene chloride and applied to a 0.6×45 cm column of silica gel. The column was eluted sequentially with 50 mL of methylene chloride, 50 mL of 1% methanol in methylene chloride and 50 mL of 2% methanol in methylene chloride to give 160 mg (72% yield) of the title compound; DCI/NH3 MS M/Z: 501 (M+NH$_4$)$^+$, 484 (M+H)+. Analysis calculated for $C_{27}H_{37}N_3O_5 + 0.5H_2O$: C, 65.77; H, 7.77; N, 8.52. Found: C, 66.11; H, 7.50; N, 8.66.

EXAMPLE 300

2,4-Bis-(t-butyloxycarbonylamino)-1,5-diphenyl-3-aminopentane

The resultant compound of Example 299 (134 mg, 0.277 mmol), was dissolved in 20 mL of methanol. 10% Palladium on carbon (50 mg) and ammonium formate (350 mg, 5.5 mmol) were added and the reaction mixture was stirred at ambient temperature under one atmosphere of hydrogen for ~64 h. The reaction was incomplete at this time and 100 mg of 10% palladium on carbon and 200 mg ammonium formate were added. The reaction mixture was stirred at ambient temperature under one atmosphere of hydrogen for ~24 h. The catalyst was removed by filtration and the filtrate was concentrated under reduced pressure. The residue was dissolved in methanol and adsorbed onto ~500 mg of silica gel in vacuo @ 45° C. The silica gel was applied to a 0.6×40 cm of silica gel and eluted @ 10 p.s.i. with 50 mL of 2% methanol in methylene chloride, 50 mL of 3% methanol in methylene chloride, and 150 mL of 5% methanol in methylene chloride to give 20 mg (15% yield) of the title compound; DCI/NH$_3$ MS M/Z: 470 (M+H)$^+$; $^1$H NMR (CDCl$_3$) δ7.35–7.00 (m, 10H), 5.20 (d, 1H), 4.83 (d, 1H), 4.10 (m, 1H), 3.83 (m, 1H), 3.0–2.5 (m, 5H), 1.42 (s, 9H), 1.32 (s, 9H).

EXAMPLE 301

2,2-Bis-(2'-phenyl-1'-(t-butoxycarbonylamino)-1'-ethyl)oxirane

Approximately 3 mmol of diazomethane was generated by standard procedures from N-methyl-N-nitroso-p- toluenesulfonamide (sold by Aldrich Chemical Co. under the tradename Diazald®) and distilled directly into a solution of the resultant compound of Example 289B (100 mg, 0.21 mmol) in 2 mL of THF. The solution was then diluted with 10 mL of methanol and ~13 mL of diethyl ether. The reaction mixture was stirred at ambient temperature for 18 h. The reaction mixture was protected from moisture by a drying tube containing calcium chloride. The solution was concentrated under reduced pressure and the residue (106 mg) was taken up in ~1 mL of methylene chloride. The methylene chloride solution was applied to a 0.6×45 cm column of silica gel preequilibriated with hexane. The column was eluted @ 10 p.s.i sequentially with 50 mL of hexane, 50 mL of 5% ethyl acetate in hexane, 50 mL of 10% ethyl acetate in hexane, 50 mL of 15% ethyl acetate in hexane, 50 mL of 20% ethyl acetate in hexane, 50 mL of 25% ethyl acetate in hexane, and 50 mL of 5% methanol in methylene chloride to give 24.5 g (24% yield) of the title compound; DCI/isobutane MS M/Z: 483 (M+H)$^+$.

EXAMPLE 302

A. 2,4-Bis-(N-(Cbz-valinyl)amino)-1,5-diphenyl-3-pentanone

To a cold (−78° C.) solution of oxalyl chloride (93 mg, 0.73 mmol) in 11 mL of freshly distilled methylene chloride was added, with stirring, 103 μL (1.46 mmol) of DMSO. To this soltuion at −78° C. after stirring for 5 minutes was added a solution of the resultant compound of Example 70 (450 mg, 0.61 mmol) in 5.5 mL of methylene chloride/DMSO (10:1). The reaction mixture was stirred at −78° C. for ~50 min, triethylamine (426 μL, 3.0 mmol) was added and stirring was continued for 5 min at −78° C. The cold bath was removed and the reaction mixture was allowed to warm to ambient temperature. The reaction mixture was diluted with 150 mL of chloroform. The chloroform solution was washed with 100 mL of brine, dried over anhydrous magnesium sulfate, filtered and concentrated under reduced pressure. The residue was taken up in ~3 mL of chloroform and applied to a 1.0×45 cm column of silica gel. The column was eluted with 100 mL of chloroform and 100 mL of 0.5% methanol in chloroform to give 376 mg (84% yield) of the title compound; DCI/NH3 MS M/Z: 501 (M+NH$_4$)$^+$. The 300 MHz $^1$H NMR spectrum was consistent with the assigned structure.

B. 2,2-Bis-(2'-phenyl-1'-(N-(Cbz-valinyl)amino)-1'-ethyl)oxirane

The resultant compound of Example 302A (370 mg, 0.5 mmol) was suspended in 50 mL of methanol at ambient temperature. THF was added (30 mL) until a solution was formed. Excess diazomethane was generated by standard procedures from N-methyl-N-nitroso-p-toluenesulfonamide (sold by Aldrich Chemical Co. under the tradename Diazold®) and distilled (in ~50 mL of diethyl ether) directly into the solution of the ketone. The reaction mixture was stirred at ambient temperature for 17 h and then concentrated in vacuo at 40° C. The residue (410 mg) was taken up in 2 mL of chloroform and applied to a 1.0×45 cm column of silica gel preequilibrated with hexane. The column was eluted @~5 p.s.i. with 100 mL of methylene chloride, 100 mL of 1% methanol in methylene chloride, 100 mL of 2% methanol in methylene chloride and 100 mL of 3% methanol in methylene chloride to give 82 mg (22% yield) of the title compound; DCI/NH$_3$ MS M/Z: 749 (M+H)$^+$.

EXAMPLE 303

A. Dimethyl-2,4-bis(phenylmethyl)-3-oxoglutarate

Dimethyl 2,4-bis(phenylmethylene)-3-oxo-glutarate (630 mg, 1.8 mmol) (C. H. Chen, et al, *J. Org. Chem.*, 1981, 46, 2752–2757) was dissolved in about 100 mL of methanol and 250 mg of 10% palladium on carbon was added. The reaction mixture was shaken at ambient temperature under 4 atmospheres of hydrogen for about 12 h. The catalyst was removed by filtration and the filtrate was concentrated under reduced pressure. The residue (750 mg) was taken up in ~15 mL of methylene chloride and applied to a 1.0×45 cm column of silica gel. The column was eluted @ 5 p.s.i. with 150 mL of methylene chloride to give 374 mg (58% yield) of the title compound. The 300 MHz $^1$H NMR was consistent with the assigned structure.

B. Dimethyl-2,4-bis(phenylmethyl)-3-hydroxyglutarate

To a solution of the resultant compound of Example 303B (370 mg, 1.04 mmol) in 20 mL of methanol/THF (1:1) at ambient temperature under a nitrogen atmosphere was added 40 mg (1.04 mmol) of sodium borohydride. The reaction mixture was stirred at ambient temperature for 1 h and then concentrated under reduced pressure. The residue was co-evaporated with 2×10 mL of methanol. The residue (517 mg) was then taken up in methylene chloride and applied to a 1.0×45 cm column of silica gel. The column was eluted with 100 mL of methylene chloride, 100 mL of 0.5% methanol in methylene chloride and 100 mL of 1.0% methanol in methylene chloride to give two products. The title compound was recovered as the major product in 49% yield (182 mg); DCI/NH3 MS M/Z: 374 (M+NH$_4$)$^+$, 357 (M+H)+.

EXAMPLE 304

A. 2,4-Bis-(phenylmethyl)-3-hydroxy-glutaric acid

The resultant compound of Example 303B (120 mg, 0.337 mmol) and lithium hydroxide monohydrate (30 mg, 0.71 mmol) were added to THF/water (4:1) and the solution was stirred for ~20 h at ambient temperature under a nitrogen atmosphere. The reaction mixture was diluted with 20 mL of THF and adjusted to neutral pH with strongly acidic ion exchange resin HCR-S (commercially available from Nalco Co.). The mixture was filtered through a Millepore (0.45μ) filter and the filtrate was concentrated under reduced pressure to give 120 mg of the title compound; DCI/NH3 MS M/Z: 346 (M+NH$_4$)$^+$.

B. N,N'-Bis-(1'-benzyloxycarbonyl-2'-methyl-1'-propyl)-2,4-bis(phenylmethyl)-3-hydroxy-glutaramide To a stirred mixture of 2,4-bis(phenylmethyl)-3-hydroxy-glutaric acid (66 mg, 0.2 mmol) and valine benzyl ester (168 mg, 0.44 mmol) in DMF at 0° C. was added diethyl cyanophosphonate (67 mg, 0.44 mmol) followed by triethylamine (123 mg, 0.88 mmol). The reaction mixture was stirred at 0° C. under nitrogen for 0.5 h and then it was allowed to warm to ambient temperature. The reaction mixture was stirred at ambient temperature for 18 h and was then diluted with 100 mL of chloroform, washed with 100 mL of water, dried over anhydrous magnesium sulfate, filtered and concentrated under reduced pressure. The residue (1.6 g) was taken up in ~1 mL of methylene chloride and applied to a 0.6×45 cm column of silica gel. The column was eluted @ 10 p.s.i. with 100 mL of methylene chloride. The residue was then taken up in ~1 mL of methylene chloride and applied to a 0.6×40 cm column of silica gel. The column was eluted @ ~10 p.s.i. with 50 mL of methylene chloride, 50 mL of 1% methanol in methylene chloride and 2% methanol in methylene chloride to give 93 mg (65% yield) of the title compound; FAB MS M/Z: 707 (M+H)$^+$.

EXAMPLE 305

N,N'-Bis-(1'-benzyloxycarbonyl-2'-methyl-1'-propyl)
-2,3,4,5-tetrahydroxyadipamide Valine benzyl ester p-toluenesulfonate salt (10.6 g, 28 mmol) was partitioned between 200 mL of chloroform and 56 mL of 0.5M aqueous sodium hydroxide solution. The organic layer was separated and washed with 75 mL of brine and 75 mL of 5% aqueous sodium bicarbonate, dried over anhydrous magnesium sulfate, filtered and concentrated under reduced pressure. Acetonitrile (25 mL) and mannosaccharodilactone (W. N. Haworth, et al, *J. Chem. Soc.*, 1944, 217) (1.8 g, 10.3 mol) were added to the residue and the reaction mixture was heated at reflux under nitrogen for 10.5 h. The reaction mixture was allowed to cool to ambient temperature and stirred at ambient temperature for ~64 h. Acetonitrile (75 mL) was added followed by 25 mL of strongly acidic ion exchange resin (HCR-S) and the mixture was stirred at ambient temperature for 2 h. The resin was removed by filtration and the filtrate was concentrated under reduced pressure. The residue was taken up in ~25 mL of methylene chloride and applied to a 2.8×55 cm column of silica gel. The column was eluted @ ~5 p.s.i with 250 mL of methylene chloride and 1 L of 5% methanol in methylene chloride to give 5.26 g (86% yield) of the desired product. The product (267 mg) was further purified by chromatography. It was dissolved in ~1 mL of methylene chloride and applied to a 0.6×45 cm column of silica gel. The column was eluted @~10 p.s.i. With 50 mL of methylene chloride and 100 mL of 2% methanol in methylene chloride to give 212 mg of the title compound: EI MS m/z 589 (M+H$^+$); $^1$H NMR δ 0.87 (d, 6H), 0.93 (d, 6H), 2.18–2.30 (m, 2H), 4.05 (t, 2H), 4.14 (d, 2H), 4.25 (dd, 2H), 4.58 (dd, 2H), 4.67 (d, 2H), 5.12–5.24 (dd, 4H), 7.30–7.40 (m, 8H), 7.62 (d, 2H).

EXAMPLE 306

N,N'-Bis-(1'-benzyloxycarbonyl-2'-methyl-1'-propyl)
-3,4-dihydroxy-2,5-bis(phenylmethyl)adipamide A solution of 100 mg (0.68 mmol) of 2,3:4,5-dianhydro-D-iditol (R. S. Tipson, et al, Carbohydrate Research, 1968, 7, 232–243) in 5 mL of dichloromethane and 1 mL of DMSO was added to a solution of 208 mg (1.64 mmol) of oxalyl chloride in 10 mL of dichloromethane which had been treated with 257 mg (3.28 mmol) of DMSO at −78 ° C. After 15 minutes at this temperature 685 mg (6.8 mmol) of triethylamine was added and the resulting solution allowed to warm to room temperature. The resulting dialdehyde is purifed by chromatography on silica gel and then oxidized to dimethyl 2,3:4,5-diepoxyadipate according to the procedure of D. R. Williams, et al (Tetrahederon Letters, 1988, 5087–5090). The diepoxide is then treated with the cuprate reagent prepared from benzyl lithium and CuBr-Me$_2$S or CuCN in an ethereal solvent such as tetrahydrofuran or diethyl ether, to affored dimethyl 3,4-dihydroxy-2,5-bis(phenylmethyl)adipate. The resulting diol is then protected as the bis(t-butyldiphenylsilyl) ether by treatment with t-butyldiphenylsilyl chloride in DMF in the presence of imidazole. Saponification of the diester with LiOH in aqueous THF, followed by acidification and coupling to valine benzyl ester in the manner described in Example 304, followed by deprotection with tetrabutylammmonium fluoride in THF affords the title compound.

EXAMPLE 307

A. N,N'-Bis-(1'-benzyloxycarbonyl-2'-methyl-1'-propyl)-2.3.4.5-tetrahydroxyadipamide, 3,4-O-isopropylidene To a stirred solution of 5.00 g (8.49 mmol) of The resultant compound of Example 305, in 1000 mL of acetone was aded 3.3 mL of concentrated sulfuric acid. After 60 minutes at room temperature, the reaction mixture was diluted with 1 liter of dichloromethane and then neutralized with 8.3 mL of concentrated ammonium hydroxide. The precipitate was removed by filtration, the filtrate concentrated under reduced pressure, and the residue purified by chromatography on silica gel with a hexane/EtOAc gradient to afford 3.93 g (74%) of the desired product. $^1$H NMR (CDCl$_3$) δ 7.35 (s, 10H), 5.18 (abq, 4H), 4.58 (dd, 2H), 4.33 (m, 2H), 4.20 (m, 2H), 2.22 (m, 2H), 1.41 (s, 6H), 0.90 (d, 6H), 0.94 (d, 6H).

B. N,N'-Bis-(1'-benzyloxycarbonyl-2'-methyl-1'-propyl)-2,5-bis(trifluoromethylsulfonyloxy)-3,4,-dihydroxyadipamide, 3,4-O-isopropylidene To a stirred solution of 159 mg (0.253 mmol) of the resultant compound of Example 307A in 3 mL of dichloromethane at −15 ° C. was added 0.051 mL (0.63 mmol) of pyridine and then 0.094 mL (0.56 mmol) of triflic anhydride. After 2 h, the temperature had increased to −10° C., and the reaction mixture was diluted with 100 mL of dichloromethane, and washed with saturated aqueous sodium bicarbonate. The separated organic phase was dried over magnesium sulfate, filtered, and concentrated under reduced pressure. Chromatography of the residue on silica gel with 98:2/dichloromethane:methanol afforded 55 mg (24%) of the title compound. FAB MS m/z 893 (M+H)$^+$.

C. N,N'-Bis-(1'-benzyloxycarbonyl-2'-methyl-1'-propyl)-2,5-phenylthio-3,4-dihydroxyadipamide, 3, 4-0-isopropylidene To a stirred solution of 50 mg (0.056 mmol) of the resultant compound of Example 307B, in 5 mL of acetonitrile was simultaneously added 62 mg (0.56 mmol) of thiophenol and 28 mg (0.28 mmol) of triethylamine. After 30 minutes at room temperature, the reaction mixture was concentrated under reduced pressure. Chromatography of the residue on silica gel with 98:2/dichloromethane:methanol afforded 30 mg (66%) of the title compound. $^1$H NMR (CDCl$_3$) δ 7.5–7.15 (m, 22H), 5.16 (abq, 4H), 4.88 (s, 2H), 4.54 (dd, 2H); 3.84 (s, 2H), 2.15 (m, 2H), 1.47 (s, 6H), 0.78 (d, 12 H).

D. N,N'-Bis-(1'-benzyloxycarbonyl-2'-methyl-1'-propyl)-2,5-phenylthio-3,4-dihydroxyadipamide A stirred solution of 27 mg (0.033 mmol) of the resultant compound of Example 307C in 2 mL of 4:1/acetonitrile:10% aqeuous HCl was heated at 45 ° C. for 3 hours. The cooled reaction mixtures was diluted with 75 mL of dichloromethane, and then washed with 50 mL of water and then 25 mL of pH 6 phosphate buffer. The separated organic phase was dried over magnesium sulfate and then concentrated under reduced pressure. Chromatography of the residue on silica gel with 95:5 to 85:15/dichloromethane:EtOAc afforded 6.5 mg of the desired compound. $^1$H NMR (CDCl$_3$) δ 7.45–7.20 (m, 22H), 5.19 (abq, 4H), 4.52 (dd, 2H), 4.47 (dd, 2H), 3.92 (d, 2H), 3.88 (d, 2H), 2.19 (m, 2H), 0.80 (d, 6H), 0.78 (d, 6H).

EXAMPLE 308

2,4-Bis-(N-(Cbz-valinyl)amino)-1,5-diphenyl-3-pentyl 2-aminoacetate

To a stirred solution of 50 mg (0.058 mmol) of the resultant compound of Example 293A, in 1 mL of THF was added approximately ten equivalents of ammonia dissolved in THF. AFter 72 h, the reaction mixture was concentrated under reduced pressure. Chromatography of the residue on silica gel with a 97:3 to 93:7/dichloromethane:MeOH gradient afforded 6.6 mg (14%) of the title compound. FAB MS m/z 794 (M+H)$^+$. $^1$H NMR (CDCl$_3$) δ 7.4–7.1 (m, 20H), 5.08 (s, 4H), 0.81 (d, 3H), 0.76 (d, 3H), 0.66 (d 3H), 0.62 (d 3H).

EXAMPLE 309

1-(1'-(N-(Cbz-valinyl)amino)-2'-cyclohexyl-1'-ethyl)-1-(2"-(N-(Cbz-valinyl)amino-3"-methyl-1",1"-difluoro-1"-butyl)-oxirane To a solution of 16 mg (0.022 mmol) of the ketone product from Example 183 in 2 mL of THF was added 4 mL of an ethereal solution containing excess diazomethane. After 2 h at room temperature and 16 hours at –20° C., the solution was warmed to room temperature and concentrated under reduced pressure to afford 16 mg of the title compound. DCI/NH$_3$ MS, 757 (M+H$^+$), 774 (M+NH$_4$+). $^1$H NMR (CDCl$_3$) δ 7.37 (s, 5H), 7.34 (s, 5H), 5.98 (d 1H), 5.83 (d, 1H), 5.32 (d, 1H), 5.2–5.0 (m, 5H), 4.62–4.40 (m, 2 H), 4.03–3.90 (m, 2H), 2.94 (bs, 1H), 2.78 (bs, 1H), 2.40–0.80 (m).

EXAMPLE 310

N,N-Bis-(Cbz-valinyl)-(2S, 3S, 4S, 5S)-1,6-diphenyl-2,5-diamino-3,4-hexanediol

Oxidation of of 2,3:4,5-dianhydro-D-iditol (R. S. Tipson, et al, *Carbohydrate Research*, 1968, 7, 232–243) as described in Example 306, but substituting THF for the dichloromethane/DMSO mixture as solvent, affords a solution of the corresponding dialdehyde. This solution is then recooled to –78 ° C., and treated with four equivalents (relative to the iditol) of phenylmagnesium bromide. The reaction mixture is then quenched with a pH 7 phosphate buffer and extracted into ethyl acetate, dried over sodium sulfate, and concentrated under reduced pressure. The resulting diol is treated with benzyl isocyanate, in the presence of either DMAP or diisopropylethylamine, in an inert solvent, such as benzene or THF. The resulting bis-carbamate is then treated with 2 equivalents of NaH or potassium t-butoxide in THF. The resulting diol is then treated with hydrogen over a Pd catalyst in a solvent such as MeOH to afford (2S, 3S, 4S, 5S)-3,4-dihydroxy-1,6-diphenyl-hexane-2,5-diamine. This is then converted into the title compound by treatment with Cbz-valine p-nitrophenyl ester in THF in the presence of triethylamine.

EXAMPLE 311

2-(N-Benzyl-N-(benzyloxycarbonyl)amino)-5-(t-butyloxycarbonylamino)-1,6-diphenyl-3-hexene-3,4-oxide A solution of 160 mg (0.27 mmol) of the resultant compound of Example 17A and 117 mg (0.54 mmol) of 3-chloroperoxybenzoic acid in 1 ml of dichloromethane was stirred at ambient temperature for 2 days. The resulting solution was diluted with dichloromethane, washed sequentially with aqueous sodium bicarbonate and saturated brine, dried over MgSO$_4$, and concentrated. Silica gel chromatography of the residue using 10% ethyl acetate in hexane provided 150 mg (92%) of the desired compound (R$_f$ 0.50, 20% ethyl acetate in hexane) as an oil. Mass spectrum: (M+H)$^+$=607.

EXAMPLE 312

2-Amino-5-(t-butyloxycarbonylamino)-1,6-diphenyl-3-hexene-3,4-oxide

A mixture of the resultant compound of Example 311 (152 mg) and 50 mg of 10% palladium on carbon in 50 ml of methanol was shaken under 4 atmospheres of hydrogen for 1 day. The mixture was filtered and concentrated in vacuo to provide 92 mg (96%) of the desired compound. Mass spectrum: (M+H)$^+$=383.

EXAMPLE 313

2,5-Di-(t-butyloxycarbonylamino)-1,6-diphenyl-3-hexene-3,4-oxide

Using the procedure of Example 205 with the resultant compound of Example 312 provided the desired compound.

EXAMPLE 314

2,5-Di-(t-butyloxycarbonylamino)-1,6-diphenyl-3-hydroxyhexane

A solution of the resultant compound of Example 313 in tetrahydrofuran was treated at ambient temperature with 2 molar equivalents of lithium triethylborohydride (1.0M in tetrahydrofuran). After 2 h, the solution was quenched with citric acid, extracted with ether, washed with dilute aqueous NaOH and saturated brine, dried over Na$_2$SO$_4$, and concentrated. Silica gel chromatography provided the desired compound.

EXAMPLE 315

A. 4-Azido-2,5-di-(t-butyloxycarbonylamino)-1,6-diphenyl-3-hydroxyhexane

Using the procedure of Example 10C with the resultant compound of Example 314 provided the desired compound.

B. 4-Amino-2,5-di-(t-butyloxycarbonylamino)-1,6-diphenyl-3-hydroxyhexane

Using the procedure of Example 11 with the resultant compound of Example 315 provided the desired compound.

EXAMPLE 316

(2S,3R,4R,5S)-2,5-Di-(N-(quinoline-2-carbonyl)-valinyl-amino)-3,4-dihydroxy-1,6-diphenylhexane Quinaldic acid was coupled to the resultant compound of Example 173 using the carbodiimide coupling procedure of Example 55 to provide the desired compound.

EXAMPLE 317

(2S,3S,4S,5S)-2,5-Di-(N-(valinyl)amino)-3,4-dihydroxy-1,6-diphenylhexane

Using the procedure of Example 71C with the resultant compound of Example 210 provided the desired compound.

EXAMPLE 318

(2S,3S,4S,5S)-2,5-Di-(N-(quinoline-2-carbonyl)-valinyl-amino)-3,4-dihydroxy-1,6-diphenylhexane Quinaldic acid was coupled to the resultant compound of Example 317 using the carbodiimide coupling procedure of Example 55 to provide the desired compound.

EXAMPLE 319

(2S,3S,4R,5S)-2,5-Di-(N-(valinyl)amino)-3,4-dihydroxy-1,6-diphenylhexane

Using the procedure of Example 71C with the resultant compound of Example 209 provided the desired compound.

EXAMPLE 320

(2S,3S,4R,5S)-2,5-Di-(N-(quinoline-2-carbonyl)-valinyl-amino)-3,4-dihydroxy-1,6-diphenylhexane Quinaldic acid was coupled to the resultant compound of Example 319 using the carbodiimide coupling procedure of Example 55 to provide the desired compound.

EXAMPLE 321

(2S,3R,4R,5S)-2,5-Di-(N-(indole-2-carbonyl)-valinyl-amino)-3,4-dihydroxy-1,6-diphenylhexane Indole-2-carboxylic acid was coupled to the resultant compound of Example 173 using the carbodiimide coupling procedure of Example 55 to provide the desired compound.

EXAMPLE 322

(2S,3S,4S,5S)-2,5-Di-(N-(indole-2-carbonyl)-valinyl-amino)-3,4-dihydroxy-1,6-diphenylhexane Indole-2-carboxylic acid was coupled to the resultant compound of Example 317 using the carbodiimide coupling procedure of Example 55 to provide the desired compound.

EXAMPLE 323

(2S,3R,4S,5S)-2,5-Di-(N-(indole-2-carbonyl)-valinyl-amino)-3,4-dihydroxy-1,6-diphenylhexane Indole-2-carboxylic acid was coupled to the resultant compound of Example 319 using the carbodiimide coupling procedure of Example 55 to provide the desired compound.

EXAMPLE 324

(2S,3R,4R,5S,2'S,2"S)-2,5-Di-(N-(2-(1,2,3,4-tetrahydropyrrolo[3,4-b]indol-3-on-2-yl)-4-methylpentanoyl)-amino)-3,4-dihydroxy-1,6-diphenylhexane (1'S)-2-(1-Carboxy-3-methylbutyl)-1,2,3,4-tetrahydropyrrolo[3,4-b]indol-3-one lithium salt, prepared according to the procedure of Kempf et. al. (J. Org. Chem. 1990, 55, 1390) was coupled to the resultant compound of Example 171 using the carbodiimide coupling procedure of Example 160D to provide the desired compound.

EXAMPLE 325

(2S,3R,4R,5S,2'S,2"S)-2,5-Di-(N-(2-(1,2,3,4-tetrahydropyrrolo[3,4-b]indol-3-on-2-yl)-3-methylbutanoyl)-amino)-3,4-dihydroxy-1,6-diphenylhexane (1'S)-2-(1-Carboxy-2-methylpropyl)-1,2,3,4-tetrahydropyrrolo[3,4]-blindol-3-one lithium salt, prepared according to the procedure of Kempf et. al. (J. Org. Chem. 1990, 55, 1390) was coupled to the resultant compound of Example 171 using the carbodiimide coupling procedure of Example 160D to provide the desired compound.

EXAMPLE 326

(2S,3R,4R,5S)-2,5-Di-(N-(((t-butyloxy)carbonyl)methyl)-amino)-1,6-diphenyl-3,4-dihydroxyhexane-4-methylpentanoyl)amino)-3,4-dihydroxy-1,6-diphenylhexane Using the procedure of Example 201A but replacing L-valine methyl ester hydrochloride with the resultant compound of Example 171 and replacing benzyl bromoacetate with t-butylbromoacetate provided the desired compound.

EXAMPLE 327

A. N, N-Di-(N-(t-butyloxy)carbonyl)-(2S, 3R, 4R, 5S)-1,2:5,6-diimino-3,4-O-isopropylidenehexanediol Using the procedure of Example 205 but replacing (2S,3S,4S,5S)-2,5-diamino-3,4-dihydroxy-1,6-diphenylhexane with (2S,3R,4R, 5S)-1,2:5,6-diimino-3,4-O-isopropylidenehexanediol (Y. L. Merrer, et al, *Heterocycles*, 1987, 25, 541–548) provided the desired compound.

B. (2S,3R,4R,5S)-2,5-Di-(N-((t-butyloxy)carbonyl)amino-1,6-di-(2-formylphenyl)-3,4-O-isopropylidenehexanediol Using the procedure of Example 289A but replacing (2S,3R,4R,5S)-1,2:5,6-diimino-3,4-O-isopropylidenehexanediol with the resultant compound of Example 327A and replacing phenyllithium with lithium 1-(N-methyl-N-(dimethylaminoethyl)amino-1-(2-lithiophenyl)-methoxide (Tetrahedron Lett. 1983, 24, 5465) provided the desired compound.

C. (2S,3R,4R,5S)-2,5-Diamino-3,4-dihydroxy-1,6-di-(2-formylphenyl)-hexane Dihydrochloride Using the procedure of Example 12 with the resultant compound of Example 327B provided the desired compound.

EXAMPLE 328

(1R,2R,3'S,3"S)-1,2-bis-(1,2,3,4-tetrahydroisoquinolin-3-yl)-ethane

Using the procedure of Example 145A but replacing dihydrocinnamaldehyde and valine benzyl ester dihydrochloride with the resultant compound of Example 327C provided the desired compound.

EXAMPLE 329

(1R,2R,3'S,3"S)-1,2-Dihydroxy-1,2-bis-2-((t-butyl)amino)carbonyl-1,2,3,4-tetrahydroisoquinolin-3-yl)-ethane Using the procedure of Example 226 but replacing (2S,3R,4S,5S )-2,5-diamino-3,4-dihydroxy-1,6-diphenylhexane with the resultant compound of Example 328 provided the desired compound.

EXAMPLE 330

A. N-(t-Butyloxucarbonyl)-1,2,3,4-tetrahydroisoquinoline-3-carboxylic Acid

Using the procedure of Example 205 but replacing (2S,3S,4S,5S)-2,5-diamino-3,4-dihydroxy-1,6-diphenylhexane with 1,2,3,4-tetrahydroisoquinoline-2-carboxylic acid provided the desired compound.

B. N-(t-Butyloxycarbonyl)-1,2,3,4-tetrahydroisoquinoline-3-carboxylic Acid t-Butyl Amide The resultant compound of Example 330A was coupled to t-butylamine using the mixed anhydride coupling procedure described in Example 6F to provide the desired compound.

C. 1,2,3,4-Tetrahydroisoquinoline-3-carboxylic Acid
t-Butyl Amide Hydrochloride

The resultant compound of Example 330B was deprotected according to the procedure of Example 12 to provide the desired compound.

D. 2,2-Dimethoxy-1,3-bis-(3-((t-butyl)amino)
carbonyl-1,2,3,4-tetrahydroisoquinolin-2-yl)-
propane Using the procedure of Example 201A but replacing L-valine methyl ester hydrochloride with the resultant compound of Example 330C and replacing benzyl bromoacetate with 1,3-dibromo-2,2-dimethoxypropane (J. Org. Chem. 1981, 46, 2532) provided the desired compound.

E. 1,3-Bis-(3-((t-butyl)amino)carbonyl-1,2,3,4-
tetrahydroisoquinolin-2-yl)-propan-2-ol The resultant compound of Example 330D (0.05 mmol) was treated with 25 ml of 1:1 1N HCl/tetrahydrofuran. After being stirred for 16 h, the solution was concentrated in vacuo. The residue was taken up in methanol and treated with excess sodium borohydride. After 1 h, the solution was quenched with aqueous ammonium chloride, partitioned between chloroform and aqueous NaOH, dried over $Na_2SO_4$, and concentrated to provide the desired compound.

EXAMPLE 331

1,3-Bis-(3-((t-butyl)amino)carbonyl-
decahydroisoquinolin-2-yl)-propan-2-ol

Using the procedure of Example 211 with the resultant compound of Example 330E provided the desired compound.

EXAMPLE 332

A. (2S,3S)-2,3-O-Isopropylidene-1,4-bis-(3-((t-
butyl)amino)carbonyl-1,2,3,4-tetrahydroisoquinolin-
2-yl)-butan-2,3-diol Using the procedure of Examaple 201A but replacing L-valine methyl ester hydrochloride with the resultant compound of Example 330C and replacing benzyl bromoacetate with 2,3-isopropylidenethreitol 1,4-ditosylate provided the desired compound.

EXAMPLE 333

A. (2S,3S)-2,3-O-Isopropylidene-1,4-bis-(3-((t-
butyl)amino)carbonyl-decahydroisoquinolin-2-yl)-
butan-2,3-diol Using the procedure of Example 211 with the resultant compound of Example 332 provided the desired compound.

Fluorogenic Assay for Screening Inhibitors of HIV Protease

The inhibitory potency of the compounds of the invention can be determined by the following method.

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1M sodium chloride, 5 mM dithiothreitol, 0.5 mg/ml bovine serum albumin, 1.3 uM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The percent inhibition is 100−(1×(rate in presence of inhibitor)/(rate in absence of inhibitor)).

Fluorogenic substrate: Dabcyl-Ser-Gln-Asp-Tyr-Pro-Ile-Val-Gln-EDANS wherein DABCYL=4-(4-dimethylaminophenyl)azobenzoic acid and EDANS=5-((2-aminoethyl)amino)-naphthalene-1-sulfonic acid.

Compounds of the invention inhibit HIV-1 protease at concentrations between 0.01 nM and 500,000 nM. Table 3 shows the inhibitory potencies of specific compounds of the invention against HIV-1 protease.

TABLE 3

| Compound of Example | Percent Inhibition | Inhibitor Concentration (micromolar) |
|---|---|---|
| 12 | 75 | 50 |
| 34C | 95 | 270 |
| 35 | 68 | 50 |
| 43C | 94 | 270 |
| 55 | 37 | 0.01 |
| 59 | 50 | 0.01 |
| 62 | 100 | 270 |
| 65 | 79 | 0.1 |
| 66 | 95 | 0.1 |
| 68 | 51 | 0.91 |
| 70 | 75 | 0.01 |
| 160D | 47 | 0.005 |
| 161C | 59 | 0.005 |
| 162C | 63 | 0.005 |
| 163C | 59 | 0.0025 |
| 165C | 40 | 0.005 |
| 166C | 31 | 0.005 |
| 170B | 40 | 0.01 |
| 172B | 74 | 0.001 |
| 178 | 58 | 0.005 |
| 182 | 59 | 0.0025 |
| 183 | 70 | 0.001 |
| 202 | 82 | 0.1 |
| 203 | 62 | 0.01 |
| 206 | 44 | 0.01 |
| 209 | 56 | 0.001 |
| 210 | 65 | 0.001 |
| 211 | 67 | 0.1 |
| 213 | 86 | 0.005 |
| 214 | 73 | 0.005 |
| 215 | 81 | 0.001 |
| 216 | 84 | 0.001 |
| 217 | 78 | 0.001 |
| 218 | 45 | 0.001 |
| 219 | 68 | 0.001 |
| 220 | 62 | 0.001 |
| 221 | 53 | 0.05 |
| 222 | 78 | 0.1 |
| 223 | 38 | 0.001 |
| 224 | 62 | 0.005 |
| 225 | 74 | 0.005 |
| 228 | 44 | 0.002 |
| 229 | 78 | 0.001 |
| 230 | 69 | 0.001 |
| 231 | 67 | 0.005 |
| 233 | 68 | 0.01 |
| 235 | 45 | 0.01 |
| 237 | 69 | 0.001 |
| 238 | 35 | 0.1 |
| 239 | 53 | 0.1 |
| 240 | 52 | 0.01 |
| 241 | 63 | 0.01 |
| 242 | 31 | 0.01 |
| 243 | 53 | 0.005 |
| 244 | 33 | 0.001 |

TABLE 3-continued

| Compound of Example | Percent Inhibition | Inhibitor Concentration (micromolar) |
|---|---|---|
| 245 | 82 | 0.1 |
| 246 | 81 | 0.1 |
| 247 | 74 | 0.001 |
| 248 | 33 | 0.01 |
| 249 | 40 | 0.001 |
| 251 | 60 | 0.1 |
| 252 | 56 | 0.05 |
| 254 | 79 | 0.05 |
| 255 | 49 | 0.05 |
| 258 | 46 | 0.01 |
| 259 | 78 | 0.005 |
| 264 | 45 | 0.005 |
| 265 | 62 | 0.001 |
| 267 | 92 | 0.005 |
| 267 | 53 | 0.001 |
| 268 | 71 | 0.001 |
| 269 | 47 | 0.1 |
| 270 | 48 | 0.01 |
| 276 | 51 | 0.005 |
| 280 | 41 | 0.01 |
| 281 | 30 | 0.01 |
| 283 | 70 | 0.1 |
| 284 | 87 | 0.1 |
| 291 | 52 | 0.005 |
| 292 | 36 | 0.01 |

Antiviral Activity

The anti-HIV activity of the compounds of the invention can be determined by the following method.

A mixture of 0.1 ml ($2\times10^5$ cells/ml) of H9 cells and 0.1 ml (100 infectious units) of HIV-$1_{3B}$ was incubated on a shaker for 2 h at 37° C. The resulting culture was washed three times and resuspended into 2 ml of medium containing 10 ul of a compound of the invention in dimethylsulfoxide. The control culture was treated in an identical manner except no compound was added to the medium. Aliquots of culture supernatants were removed at 3 time points, usually 4, 7 and 10 days, and monitored for HIV-1 antigen EIA (HIVAG-1) (Paul, et al., J. Med. Virol., 22 357 (1987)). Cell viability was determined by trypan blue dye exclusion, and cells were refed with media containing compound (except for control wells which were refed with media only) at these time points. Per cent inhibition of HIV by the compound was determined by comparing HIV antigen levels in the supernatants of infected cells incubated with compound to supernatants from the control culture without compound. The $IC_{50}$ is the concentration of compound that gives 50% inhibition of HIV activity. The $LD_{50}$ is the concentration of compound at which 50% of the cells remain viable.

Table 4 shows the inhibitory potencies of compounds of the invention against HIV-1 in H9 cells:

TABLE 4

| Compound of Example | $IC_{50}$ (micromolar) | $LD_{50}$ (micromolar) |
|---|---|---|
| 55 | 0.17–0.24 | 20 |
| 70 | 0.3–0.8 | 120 |
| 160 | 0.3–0.8 | 15 |
| 161 | 0.6–1.1 | 20 |
| 162 | 0.6–1.0 | 25 |
| 163 | 0.6–1.1 | >100 |
| 165 | 0.5–1.0 | >100 |
| 166 | 6.1–9.4 | 21 |
| 169 | 6.2–11.2 | 54 |
| 172 | 0.12 | 11 |
| 174 | 1.1–2.7 | >100 |
| 175 | 0.75–1.1 | >100 |
| 206 | 2.3–4.5 | 25 |
| 209 | 0.015–0.027 | 60 |
| 210 | 0.05–0.07 | >100 |
| 213 | 0.54 | 30 |
| 215 | 0.10 | >100 |
| 216 | 0.04–0.1 | >100 |
| 218 | 0.42 | >100 |
| 219 | 0.05–0.1 | >100 |
| 220 | 0.09–0.18 | >100 |
| 225 | 0.27 | >100 |
| 237 | 0.4–1.6 | >100 |
| 241 | 2.4–5.0 | 75 |
| 242 | 4.50 | >100 |
| 244 | 0.5–1.0 | >100 |
| 247 | 0.25 | 180 |
| 248 | 1.2–7.5 | >100 |
| 249 | 0.3–0.9 | 45 |
| 268 | 0.11–0.22 | 25 |
| 269 | 3–6 | 130 |
| 270 | 4–15 | 35 |
| 286 | 2–6 | 20 |

Additionally a decrease in infectivity of HIV as a measure of anti-HIV activity of the compounds of the invention can be assessed as follows:

After incubation of the culture containing a compound of the invention as descrived above for approximately 6 days (range: 4–10 days), an aliquot (0.1 ml) of the supernatant was withdrawn, 5-fold dilutions were made in media, and these dilutions were then incubated with fresh H9 cells ($4\times10^5$ cells/ml) on a shaker for 2 hr at 37° C. The resulting cultures were washed three times, resuspended in 2 ml of medium with and without compound, and incubated and maintained as above. Production of virus in the culture supernatant was monitered at various time points using the Abbott HIV-1 antigen EIA. Loss of infectivity was determined by comparing HIV antigen end point dilutions of cultures with and without compound. In this manner, the compound of Example 70 reduced the HIV infectivity 25-fold.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl-substituted compound of formula I which has been acylated with a blocked or unblocked amino acid residue, a phosphate function, a hemisuccinate residue or a benzoyl group which is substituted on the phenyl ring with —$NR_{800}R_{801}$ wherein $R_{800}$ and $R_{801}$ are independently selected from hydrogen and loweralkyl or the group —$NR_{800}R_{801}$ forms a nitrogen containing heterocyclic ring. The amino acid esters of particular interest are glycine and lysine; however, other amino acid residues can also be used, including those wherein the amino acyl group is —C(O)CH$_2$NR$_{800}$R$_{801}$ wherein $R_{800}$ and $R_{801}$ are independently selected from hydrogen and loweralkyl or the group —$NR_{800}R_{801}$ forms a nitrogen containing heterocyclic ring. These esters serve as pro-drugs of the compounds of the present invention and serve to increase the solubility of these substances in the gastrointestinal tract. These esters also serve to increase solubility for intravenous administration of the compounds. These pro-drugs are metabolized in vivo to provide the hydroxyl-substituted compound of formula I. The preparation of the pro-drug esters is carried out by reacting a hydroxyl-substituted compound of formula I with an activated amino acyl, phosphoryl, hemisuccinyl or substituted benzoyl derivative as defined above. The resulting product is then deprotected to provide the desired pro-drug ester.

The compounds of the present invention are useful for the treatment or prophylaxis of diseases caused by retroviruses in mammals (especially humans) and are particularly useful for the treatment or prophylaxis of acquired immune deficiency syndrome or an HIV infection.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, by aerosols, rectally, or topically in dosage unit formulations containing conventional nontoxic pharmaceutically acceptable carriers, adjuvants, and vehicles as desired. Topical administration may also involve the use of sublingual dosage forms, transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, ganciclovir, dideoxycytidine, trisodium phosphonoformate, HPA-23, eflornithine, Peptide T, Reticulose (nucleophosphoprotein), zidovudine (AZT), ansamycin LM 427, trimetrexate, UA001, ribavirin, alpha interferon and acyclovir. Immunomodulators that can be administered in combination with a compound of the present invention include bropirimine, Ampligen, anti-human alpha interferon antibody, colony stimulating factor, CL246,738, Imreg-1, Imreg-2, diethyldithiocarbamate, interleukin-2, alpha-interferon, inosine pranobex, methionine enkephalin, muramyl-tripeptide, TP-5, erythropoietin, naltrexone and tumor necrosis factor. Other antiinfective agents that can be administered in combination with a compound of the present invention include pentamidine isethionate. Any of a variety of HIV or AIDS vaccines can be used in combination with a compound of the present invention.

It will be understood that agents which can be combined with the compounds of the present invention for the treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:
1. A compound of the formula:

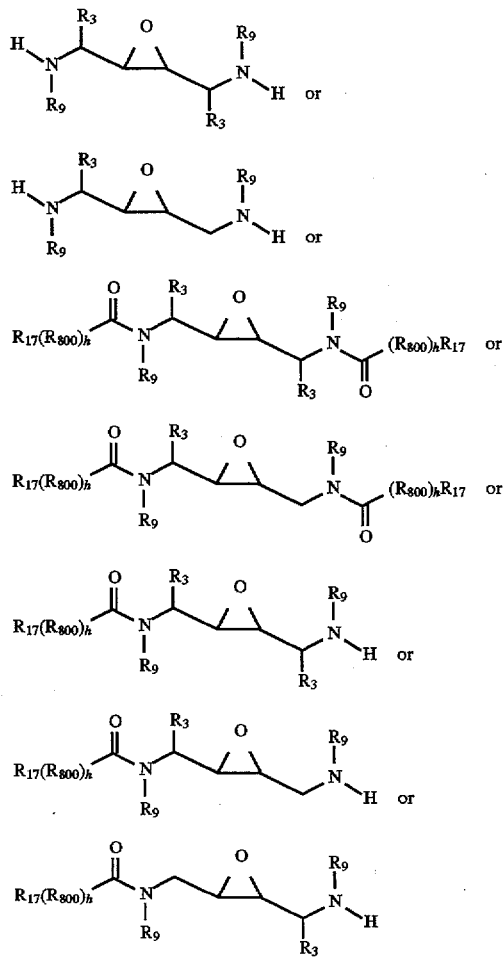

wherein at each occurrence $R_3$ is independently selected from the group consisting of
(i) $C_1$-to-$C_6$-loweralkyl,
(ii) aryl,
(iii) (aryl)-$C_1$-to-$C_6$-alkyl,
(iv) $C_3$-to-$C_7$-cycloalkyl and
(v) $C_3$-to-$C_7$-cycloalkyl-$C_1$-to-$C_6$-alkyl $R_9$ is independently selected at each occurrence from the group consisting of hydrogen and aryl-$C_1$-to-$C_6$-alkyl;

$R_{17}$ at each occurrence is independently selected from the group consisting of $C_1$-to-$C_6$-loweralkyl, aryl and aryl-$C_1$-to-$C_6$-alkyl;

$R_{800}$ is —O—;

and at each occurrence h is independently selected from the group consisting of 0 and 1;

wherein at each occurrence aryl is independently selected from phenyl, naphthyl, tetrahydronaphthyl, indanyl, tetrafluorophenyl and pentafluorophenyl and wherein the phenyl, naphthyl, tetrahydronaphthyl and indanyl rings are unsubstituted or substituted with one, two or three substitutents independently selected from the group consisting of $C_1$-to-$C_6$-loweralkyl, halo-$C_1$-to-$C_6$-alkyl, $C_1$-to-$C_6$-alkoxy, $C_1$-to-$C_6$-thioalkoxy, amino, $C_1$-to-$C_6$-alkylamino, di-$C_1$-to-$C_6$-alkylamino, hydroxy, halo, mercapto, nitro, carboxaldehyde, carboxy, carbo-$C_1$-to-$C_6$-alkoxy and carboxamide;

or a pharmaceutically acceptable salt thereof.

2. A compound according to claim 1 of the formula:

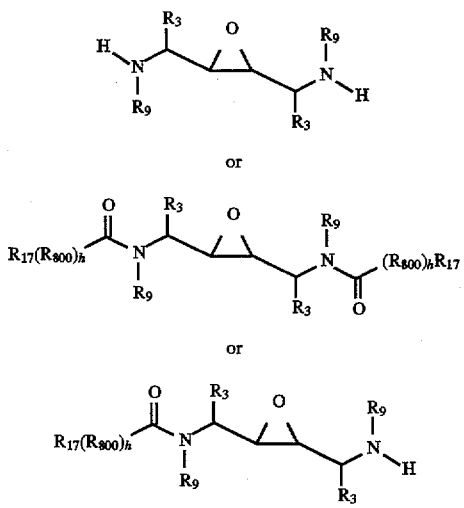

wherein at each occurrence $R_3$ is independently selected from the group consisting of $C_1$-to-$C_6$-loweralkyl, $C_3$-to-$C_7$-cycloalkyl, $C_3$-to-$C_7$-cycloalkyl-$C_1$-to-$C_6$-alkyl, aryl and aryl-$C_1$-to-$C_6$-alkyl;

$R_9$ is independently selected at each occurrence from the group consisting of hydrogen and aryl-$C_1$-to-$C_6$-alkyl;

$R_{17}$ at each occurrence is independently selected from the group consisting of $C_1$-to-$C_6$-loweralkyl, aryl and aryl-$C_1$-to-$C_6$-alkyl;

$R_{800}$ is —O—;

and at each occurrence h is independently selected from the group consisting of 0 and 1;

or a pharmaceutically acceptable salt thereof.

3. A compound according to claim 1 of the formula:

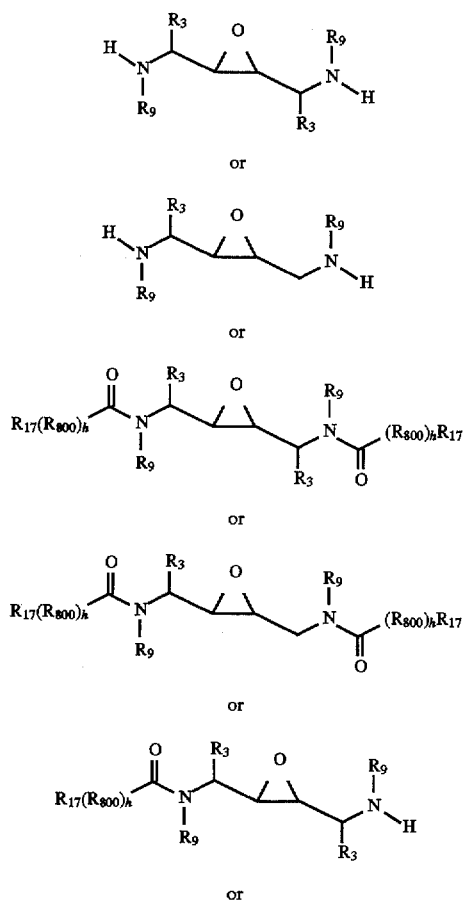

or

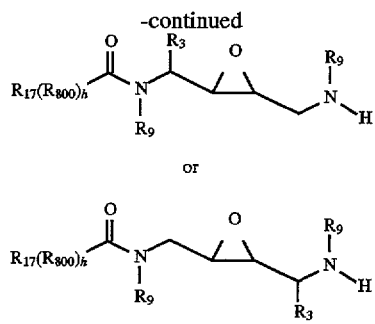

or wherein at each occurrence $R_3$ is independently selected from the group consisting of aryl-$C_1$-to-$C_6$-alkyl;

$R_9$ is independently selected at each occurrence from the group consisting of hydrogen and aryl-$C_1$-to-$C_6$-alkyl;

$R_{17}$ at each occurrence is independently selected from the group consisting of $C_1$-to-$C_6$-loweralkyl, aryl and aryl$C_1$-to-$C_6$-alkyl;

$R_{800}$ is —O—;

and at each occurrence h is independently selected from the group consisting of 0 and 1;

or a pharmaceutically acceptable salt thereof.

4. A compound selected from the group consisting of:

2-(N-benzyl-N-(benzyloxycarbonyl)amino)-5-(t-butyloxycarbonylamino)-1,6-diphenyl-3-hexene-3,4-oxide;

2-amino-5-(t-butyloxycarbonylamino)-1,6-diphenyl-3-hexene-3,4-oxide; and 2,5-di-(t-butyloxycarbonylamino)-1,6-diphenyl-3-hexene-3,4-oxide.

* * * * *